US009062015B2

(12) United States Patent
Stieber et al.

(10) Patent No.: US 9,062,015 B2
(45) Date of Patent: Jun. 23, 2015

(54) INHIBITORS OF SPHINGOSINE KINASE

(75) Inventors: Frank Stieber, Einhausen (DE); Dirk Wienke, Darmstadt (DE)

(73) Assignee: Merck Patent GmbH, Darmstadt (DE)

(*) Notice: Subject to any disclaimer, the term of this patent is extended or adjusted under 35 U.S.C. 154(b) by 227 days.

(21) Appl. No.: 13/515,598

(22) PCT Filed: Nov. 22, 2010

(86) PCT No.: PCT/EP2010/007057
§ 371 (c)(1),
(2), (4) Date: Jun. 13, 2012

(87) PCT Pub. No.: WO2011/072791
PCT Pub. Date: Jun. 23, 2011

(65) Prior Publication Data
US 2012/0252789 A1    Oct. 4, 2012

(30) Foreign Application Priority Data

Dec. 14, 2009  (EP) .................................... 09015422
Dec. 18, 2009  (EP) .................................... 09015754

(51) Int. Cl.
| | |
|---|---|
| C07D 401/04 | (2006.01) |
| C07D 401/14 | (2006.01) |
| A61K 31/444 | (2006.01) |
| A61K 31/496 | (2006.01) |
| A61P 19/02 | (2006.01) |
| C07D 295/088 | (2006.01) |
| C07D 213/61 | (2006.01) |
| C07D 213/65 | (2006.01) |
| C07D 213/74 | (2006.01) |
| C07D 239/42 | (2006.01) |
| C07D 241/20 | (2006.01) |
| C07D 251/22 | (2006.01) |
| C07D 295/033 | (2006.01) |
| C07D 295/096 | (2006.01) |
| C07D 403/04 | (2006.01) |
| C07D 413/14 | (2006.01) |
| C07F 5/02 | (2006.01) |

(52) U.S. Cl.
CPC .......... *C07D 295/088* (2013.01); *C07D 401/04* (2013.01); *A61K 31/444* (2013.01); *C07B 2200/05* (2013.01); *C07D 213/61* (2013.01); *C07D 213/65* (2013.01); *C07D 213/74* (2013.01); *C07D 239/42* (2013.01); *C07D 241/20* (2013.01); *C07D 251/22* (2013.01); *C07D 295/033* (2013.01); *C07D 295/096* (2013.01); *C07D 401/14* (2013.01); *C07D 403/04* (2013.01); *C07D 413/14* (2013.01); *C07F 5/025* (2013.01)

(58) Field of Classification Search
CPC .. C07D 401/04; C07D 401/14; A61K 31/444; A61K 31/496

USPC .............. 546/193; 544/360, 364; 514/253.01, 514/318, 218; 540/575
See application file for complete search history.

(56) References Cited

U.S. PATENT DOCUMENTS

| | | | | |
|---|---|---|---|---|
| 6,340,759 | B1 * | 1/2002 | Ueno et al. ..................... | 544/358 |
| 6,790,844 | B2 * | 9/2004 | Ueno et al. ..................... | 514/183 |
| 6,875,761 | B2 * | 4/2005 | Ueno et al. ..................... | 514/183 |
| 7,250,510 | B2 * | 7/2007 | Organ et al. ................... | 544/225 |
| 2007/0032531 | A1 | 2/2007 | Smith et al. | |
| 2009/0030012 | A1 | 1/2009 | Adams et al. | |
| 2010/0137315 | A1 | 6/2010 | Smith et al. | |
| 2011/0106241 | A1 | 5/2011 | Lynch et al. | |

FOREIGN PATENT DOCUMENTS

| | | |
|---|---|---|
| WO | 2006/138660 A2 | 12/2006 |
| WO | 2007/100610 A2 | 9/2007 |
| WO | 2009/146112 A1 | 12/2009 |

OTHER PUBLICATIONS

Cecil Textbook of Medicine, edited by Bennet, J.C., and Plum F., 20th edition, vol. 1, 1004-101 O, 1996.*
Mass, R. D., Int. J. Radiation Oncology Bio. Phys.vol. 58(3): 932-940, 2004.*
Fabbro et al. Pharmacology & therapeutics 93, 79-98, 2002.*
Cohen et al., Current Opinion in Chemical Biology, 3,459-465, 1999.*
Freshney et al.,Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Ferrara, N, Oncology, 69 Suppl. 3, 11-16, 2005.*
Jain et al., Nature Clinical Practice Oncology, 3(1), 24-40, 2006,.*
Gautschi et al., Clin. Cancer Res., 14(6), 1639-1648, 2008.*
Mountzios et al., Cancer Treatments Reviews, 34, 175-182, 2008.*
Qiu Y., Oncogene 19, 5651-5661,2000.*
Wolff Manfred E. "Burger's Medicinal Chemistry, 5ed, Part 1", John Wiley & Sons, 1995, pp. 975-977.*
Banker, G.S. et al, "Modern Pharmaceutices, 3ed.", Marcel Dekker, New York. 1996, pp. 451 and 596.*
Pyne et al. Cancer Res 2011;71:6576-6582.*
Zoorob, H. H., et al., "Reactivity of 2-Cinnamoyl-5,6,7,8-tetrahydronaphthalene Towards Ethyl Cyanoacetate, Cyanoacetamide & Some Reactions with the Adducts Formed," Indian Journal of Chemistry, Section B: Organic Chemistry Including Medicinal Chemistry, Jan. 1978, vol. 16B, pp. 53-56; Cited in International Search Report, dated Feb. 7, 2011, issued in corresponding PCT/EP2010/007057.
International Search Report, dated Feb. 7, 2011, issued in corresponding PCT/EP2010/007057.

* cited by examiner

*Primary Examiner* — Venkataraman Balasubramanian
(74) *Attorney, Agent, or Firm* — Millen, White, Zelano & Branigan, P.C.

(57) ABSTRACT

The present invention relates to compounds of the formula (I), in which $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $M_1$, $M_2$, $M_3$, $M_4$, $Y_1$, $Y_2$, V, W, n, m and o have the meanings given in Claim 1, and physiologically acceptable salts, derivatives, prodrugs, solvates, tautomers and stereoisomers thereof, including mixtures thereof in all ratios, for use in the treatment of diseases which are influenced by inhibition of Sph kinase 1.

22 Claims, No Drawings

INHIBITORS OF SPHINGOSINE KINASE

TECHNICAL AREA

The present invention relates to inhibitors of sphingosine kinase and physiologically acceptable salts, derivatives, prodrugs, solvates, tautomers and stereoisomers thereof, including mixtures thereof in all ratios, for use in the treatment of diseases which are influenced by inhibition of Sph kinase 1.

BACKGROUND OF THE INVENTION

The invention was based on the object of finding novel compounds having valuable properties, in particular those which can be used for the preparation of medicaments.

The present invention relates to compounds and to the use of compounds for the treatment of diseases which are associated with an increase in the sphingosine phosphate level, furthermore to pharmaceutical compositions which comprise these compounds.

In detail, the present invention relates to compounds of the formula (I), which preferably inhibit the enzyme sphingosine kinase 1, which regulates the sphingosine phosphate level by phosphorylation of sphingosine, to compositions which comprise these compounds, and to methods for the use thereof for the treatment of diseases and complaints, such as cancer, tumour formation, growth and spread, arteriosclerosis, eye diseases, choroidal neovascularisation and diabetic retinopathy, inflammatory diseases, arthritis, neurodegeneration, restenosis, heart diseases, wound healing or transplant rejection. In particular, the compounds according to the invention are suitable for the therapy of cancer diseases.

Sphingosine phosphate belongs to the molecule family of the sphingolipids, which, besides their role as structural building blocks of cell membranes, also exert important functions as extra- and intracellular signal molecules. Sphingosine phosphate (S1P) is formed in the cell from sphingomyelin, which initially breaks down to form ceramide and sphingosine, and the latter is phosphorylated by sphingosine kinases. Of the two sphingosine kinases identified to date, sphingosine kinase 1 (SphK1) is ascribed the greater importance in the formation of S1P in the serum (Zemann et al., 2006 Blood Vol 107 page 1454). While ceramide and sphingosine induce cell death and cell growth inhibition (Kolesnick 2002, J Clin Invest Vol 110, page 3; Ogretmen et al. 2004 Nat Rev Cancer Vol 4, page 604), sphingosine phosphate has an opposite effect on the cell and increases the resistance to apoptosis, cell growth and the discharge of messenger substances, which promote perfusion of the tissue and thus also of tumours (Cuvilier et al. 1996, Nature Vol 381, page 800; Perez et al. 1997, Nat Med Vol 3, page 1228). The ratio of ceramide and sphingosine on the one hand and S1P on the other is consequently decisive for cell growth, and inhibition of SphK 1 can thus not only suppress the formation of the growth-promoting sphingosine phosphate, but also increase the cellular concentration of the growth-inhibiting molecules ceramide and sphingosine.

A multiplicity of cellular effects which are triggered by S1P is promoted by secretion of S1P and binding thereof to date 5 different G-protein-coupled receptors (known as $S1P_{1-5}$). Signal propagation in turn takes place via various G-proteins ($G_i$, $G_q$, $G_{12/13}$), meaning that a number of different cellular signalling pathways, such as, for example, ERK or PI3K, which are particularly important in cancer formation and growth, are activated. In addition, an increasing number of publications shows that S1P is an important factor in tumoral angiogenesis. Angiogenesis is an important process in tumour growth, by means of which blood vessels are reformed starting from already existing ones and the supply of the tumour with nutrients is thus ensured. For this reason, inhibition of angiogenesis is an important starting point for cancer and tumour therapy. (Folkman, 2007, Nature Reviews Drug Discovery Vol. 6, page 273-286). S1P stimulates chemotactic movement of endothelial cells and induces differentiation to give multicellular structures, both early steps in the formation of new blood vessels (Lee et al. 1999 Biochem Biophys Res Commun Vol 264 page 325; Argraves et al. 2004 J Biol Chem Vol 279 page 50580). In addition, S1P promotes the migration of endothelial precursor cells originating from bone marrow to neovascular initiation sites (Annabi et al. 2003 Exp Hematology Vol 31 page 640) and transactivates the receptor of VEGF, one of the most important proangiogenic factors, in particular in tumour biology (Tanimoto et al. 2002 J Biol Chem Vol 277 page 42997; Endo et al. 2002 J Biol Chem Vol 277 page 23747). Direct evidence of the activity of S1P in tumour angiogenesis has been provided by experiments with an antibody which binds specifically to S1P. The S1P antibody inhibited the migration and vascularisation of endothelial cells in vitro, blocked the S1P-dependent secretion of proangiogenic factors, such as VEGF, IL-8 and IL-6, in vitro and in vivo and significantly reduced the growth of tumour models of the breast, lung and ovaries in mouse xenograft experiments (Visentin 2006 Cancer Cell Vol 9 page 225).

In addition, S1P also has intracellular functions, such as, for example, the activation of the transcription factor NF-κB, which plays a major role in apoptosis resistance of cancer cells (Xia et al. 2002 J Biol Chem Vol 277 page 7996). However, the intracellular interaction partners of S1P have not yet been identified.

It follows from this that, in contrast to a likewise conceivable intervention with the cancer-promoting action of S1P by pharmacological blockade of the extracellular receptors, inhibition of the enzyme SphK1, which is responsible for S1P formation, has the advantage of thus also suppressing the intracellular activities of S1P. This approach is supported by investigations by Xia et al. (2000 Curr Biol Vol 10 page 1527), which show that non-tumorigenic fibroblasts are transformed by ectopic expression of SphK1 and can form tumours in mice. SphK1 can thus be classified as an oncogene. In various expression studies, increased SphK1-mRNA concentrations in tumour tissues of the brain, breast, lung, ovaries, stomach, uterus, kidneys and small and large intestine have been observed compared with healthy tissue (French et al. 2003 Cancer Research Vol. 63 page 5962; Johnson et al. 2005 J Histochem Cytochem Vol 53 page 1159; Van Brocklyn et al. 2005 J Neuropathol Exp Neurol Vol 64 page 695). In addition, increased expression of SphK1 correlates with a worse prognosis in patients with glioblastoma multiforme (Van Brocklyn et al. 2005 J Neuropathol Exp Neurol Vol 64 page 695).

SphK1 has an important role in the modulation of the apoptosis of cancer cells induced by chemotherapeutic agents. Thus, overexpression of SphK1 increases the resistance of breast cancer, prostate cancer and leukaemia cells to chemotherapeutic agents, such as anthracyclines, docetaxel, camptothecin or doxorubicin (Nava et al. 2002 Exp Cell Res Vol 281 page 115; Pchejetski 2005 Cancer Res Vol 65 page 11667; Bonhoure 2006 Leukemia Vol 20 page 95). It has been shown that the increased presence of SphK1 results in a shift in the ceramide/S1P equilibrium towards S1P, which promotes apoptosis resistance. A possible mechanism here is the inhibition of the mitochondrial cytochrome C discharge by SphK1, which normally represents an early event in programmed cell death (Cuvilier et al. 2001 Blood Vol 98 page 2828; Bonhoure 2006 Leukemia Vol 20 page 95).

Conversely, specific blockade of SphK1 expression by means of siRNA in tumour cell models of various indications, such as leukaemia, breast cancer, glioblastoma or prostate cancer, enables apoptosis to be triggered or the effect of chemotherapeutic agents to be increased (Bonhoure 2006 Leukemia Vol 20 page 95; Taha et al. 2004 J Biol Chem Vol 279 page 20546; Taha et al. 2006 FASEB J Vol 20 page 482; Van Brocklyn et al. 2005 J Neuropathol Exp Neurol Vol 64 page 695; Pchejetski 2005 Cancer Res Vol 65 page 11667).

It has been shown in a mouse model that overexpression of SphK1 triggers degenerative changes of cardiomyocytes and myocardial fibrosis, which increased with increasing age of the experimental animals. A function of the S1P signalling pathway in heart diseases is also supported by the fact that the formation of cardiovascular fibroses is strongly inhibited in mice in which the expression of the S1P3 receptor has been specifically suppressed (Takuwa 2008 Biochimica and Biophysica Acta in press). S1P also has a role in the differentiation of fibroblasts to give myofibroblasts and thus in the formation and progression of fibrotic diseases in other organs, such as, for example, the lung (Kono et al. 2007 Am J Respir Cell Mol Biol page 395).

It has been found that the compounds according to the invention cause specific inhibition of sphingosine kinase 1, but not of sphingosine kinase 2. The compounds according to the invention preferably exhibit an advantageous biological activity which can be detected in the tests described herein, for example. In such tests, the compounds according to the invention exhibit and cause an inhibiting effect, which is usually documented by $IC_{50}$ values in a suitable range, preferably in the micromolar range and more preferably in the nanomolar range.

In general, all solid and non-solid tumours can be treated with the compounds of the formula (I), such as, for example, monocytic leukaemia, brain, urogenital, lymph system, stomach, laryngeal, ovarian and lung carcinoma, including lung adenocarcinoma and small-cell lung carcinoma. Further examples include prostate, pancreatic and breast carcinoma.

As discussed herein, effects of the compound according to the invention are relevant for various diseases. Accordingly, the compounds according to the invention are useful in the prophylaxis and/or treatment of diseases which are influenced by inhibition of SphK1.

The present invention therefore relates to compounds according to the invention as medicaments and/or medicament active ingredients in the treatment and/or prophylaxis of the said diseases and to the use of compounds according to the invention for the preparation of a pharmaceutical agent for the treatment and/or prophylaxis of the said diseases, and also to a method for the treatment of the said diseases comprising the administration of one or more compounds according to the invention to a patient in need of such an administration.

The host or patient can belong to any mammalian species, for example a primate species, particularly humans; rodents, including mice, rats and hamsters, rabbits, horses, cows, dogs, cats, etc. Animal models are of interest for experimental investigations, where they represent a model for the treatment of human disease.

The sensitivity of a particular cell to treatment with the compounds according to the invention can be determined by in vitro tests. Typically, a culture of the cell is combined with a compound according to the invention at various concentrations for a period of time which is sufficient to enable the active agents to lower the intra-cellular S1P concentration and in addition to block the secretion of angiogenesis-promoting substances or to induce cell death. For testing in vitro, use can be made of cultivated cells from a biopsy sample or established cancer cell lines in which SphK1 is expressed.

The dose varies depending on the specific compound used, the specific disease, the patient status, etc. A therapeutic dose is typically sufficient to considerably reduce the undesired cell population in the target tissue, while the viability of the patient is maintained. The treatment is generally continued until a considerable reduction has occurred, for example at least about 50% reduction in the cell burden, and can be continued until essentially no undesired cells can be detected in the body.

Use

As described in the introduction, SphK1, S1P and the cell surface receptors $S1P_{1-5}$ thereof are involved in a multiplicity of physiological and pathophysiological processes. For this reason, it can be expected that the inhibition of SphK1 by the substances described here can be utilised for therapeutic purposes in various diseases.

The formation of S1P by SphK1 and the associated shift in the ceramide/S1P equilibrium results, as stated above, in the cells proliferating to a greater extent and becoming more resistant to apoptotic stimuli. A general function of SphK1 can be derived therefrom in hyperproliferative diseases, such as cancer, psoriasis, restenosis and arteriosclerosis. The compounds of the formula I on which this invention is based and which inhibit SphK1 and thus regulate and/or modulate the S1P level, compositions which comprise these compounds, and the methods described can thus be employed for the treatment of these diseases. In general, all solid and non-solid tumours can be treated with the compounds of the formula X, such as, for example, monocytic leukaemia, brain, urogenital, lymph system, stomach, laryngeal ovarian and lung carcinoma, including lung adenocarcinoma and small-cell lung carcinoma. Further examples include bowel, prostate, pancreatic and breast carcinoma.

Besides the function in cell growth, S1P also plays a role in the neoformation of blood vessels (angiogenesis). In many disease processes, angiogenesis is either causally at the centre of the disease or has a worsening effect on the progression of the disease. In cancer events, for example, angiogenesis results in the tumour being enlarging and possibly spreading into other organs. Further diseases in which angiogenesis plays an important role are psoriasis, arthrosis, arteriosclerosis and eye diseases, such as diabetic retinopathy, age-induced macular degeneration, rubeosis iridis or neovascular glaucoma. The compounds of the formula I on which this invention is based and which inhibit SphK1 and thus regulate and/or modulate the S1P level, compositions which comprise these compounds, and the methods described can thus be employed for the treatment of these diseases.

Furthermore, SphK1 and S1P influence the proliferation, differentiation, migration and secretion of immune cells (Rosen and Goetzl 2005 Nat Rev Immunol Vol 5 page 560) and are thus involved in various functions of the immune system and in inflammatory processes. Stimulation of the immune system increases the formation and discharge of S1P in mast cells, blood platelet cells and some mononuclear phagocytes (Stunff et al. 2004 J Cell Biochem Vol 92 page 882; Olivera and Rivera 2005 j Immunol Vol 174 page 1153). The activity of SphK1 is greatly increased, in particular, by factors such as tumour necrosis factor (TNF) and crosslinking of IgG receptors (Stunff et al. 2004 J Cell Biochem Vol 92 page 882; Delon et al. 2004 J Biol Chem Vol 279 page 44763). In addition, it has been shown that SphK1 and S1P are important for the TNF-dependent formation of pro-inflammatory enzymes, such as cyclooxygenase-2 (COX-2) and nitric oxide synthase (NOS) (Pettus et al. 2003 FASEB J Vol 17 page 1411; Kwon et al. 2001 J Biol Chem Vol 276 page 10627-33). The compounds of the formula I on which this invention is based and which inhibit SphK1 and thus regulate and/or modulate the S1P level, compositions which comprise these compounds, and the methods described can thus be employed for the treatment of inflammation-induced diseases, such as arthrosis, arteriosclerosis, psoriasis, multiple sclerosis, chronic inflammatory bowel diseases (Crohn's disease, colitis ulcerosa) asthma and other allergic diseases.

The compounds of the formula (I) can furthermore be used for the isolation and investigation of the activity or expression of Sph kinase. In addition, they are particularly suitable for use in diagnostic methods for diseases in connection with unregulated or disturbed Sph kinase activity.

It can be shown that the compounds according to the invention have an anti-proliferative action in vivo in a xenotransplant tumour model. The compounds according to the invention are administered to a patient having a hyperproliferative disease, for example to inhibit tumour growth, to reduce inflammation associated with a lymphoproliferative disease, to inhibit transplant rejection or neurological damage due to tissue repair, etc. The present compounds are suitable for prophylactic or therapeutic purposes. As used herein, the term "treatment" is used to refer to both prevention of diseases and treatment of pre-existing conditions. The prevention of proliferation is achieved by administration of the compounds according to the invention prior to the development of overt disease, for example to prevent the growth of tumours, prevent metastatic growth, diminish restenosis associated with cardiovascular surgery, etc. Alternatively, the compounds are used for the treatment of ongoing diseases by stabilising or improving the clinical symptoms of the patient.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow the active agents to induce cell death or to inhibit migration, usually between about one hour and one week. In vitro testing can be carried out using cultivated cells from a biopsy sample. The viable cells remaining after the treatment are then counted.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

For the identification of a signal transduction pathway and for detection of interactions between various signal transduction pathways, various scientists have developed suitable models or model systems, for example cell culture models (for example Khwaja et al., EMBO, 1997, 16, 2783-93) and models of transgenic animals (for example White et al., Oncogene, 2001, 20, 7064-7072). For the determination of certain stages in the signal transduction cascade, interacting compounds can be utilised in order to modulate the signal (for example Stephens et al., Biochemical J., 2000, 351, 95-105). The compounds according to the invention can also be used as reagents for testing kinase-dependent signal transduction pathways in animals and/or cell culture models or in the clinical diseases mentioned in this application.

For the identification of a signal transduction pathway and for detection of interactions between various signal transduction pathways, various scientists have developed suitable models or model systems, for example cell culture models (for example Khwaja et al., EMBO, 1997, 16, 2783-93) and models of transgenic animals (for example White et al., Oncogene, 2001, 20, 7064-7072). For the determination of certain stages in the signal transduction cascade, interacting compounds can be utilised in order to modulate the signal (for example Stephens et al., Biochemical J., 2000, 351, 95-105). The compounds according to the invention can also be used as reagents for testing kinase-dependent signal transduction pathways in animals and/or cell culture models or in the clinical diseases mentioned in this application.

Measurement of the kinase activity is a technique which is well known to the person skilled in the art. Generic test systems for the determination of the kinase activity using substrates, for example histone (for example Alessi et al., FEBS Lett. 1996, 399, 3, pages 333-338) or the basic myelin protein, are described in the literature (for example Campos-González, R. and Glenney, Jr., J. R. 1992, J. Biol. Chem. 267, page 14535).

For the identification of kinase inhibitors, various assay systems are available. In scintillation proximity assay (Sorg et al., J. of Biomolecular Screening, 2002, 7, 11-19) and flash-plate assay, the radioactive phosphorylation of a protein, peptide or, in the case of SphK1, a lipid as substrate using gamma-ATP is measured. In the presence of an inhibitory compound, a decreased radioactive signal, or none at all, is detectable. Furthermore, homogeneous time-resolved fluorescence resonance energy transfer (HTR-FRET) and fluorescence polarisation (FP) technologies are suitable as assay methods (Sills et al., J. of Biomolecular Screening, 2002, 191-214).

Another non-radioactive ELISA assay method uses a specific antibody against S1P for the quantification of S1P (assay system from Echelon).

There are many diseases associated with deregulation of cellular proliferation and cell death (apoptosis). The conditions of interest include, but are not limited to, the following. The compounds according to the invention are suitable for the treatment of various conditions where there is proliferation and/or migration of smooth muscle cells and/or inflammatory cells into the intimal layer of a vessel, resulting in restricted blood flow through that vessel, for example in the case of neointimal occlusive lesions. Occlusive graft vascular diseases of interest include atherosclerosis, coronary vascular disease after grafting, vein graft stenosis, peri-anastomatic prosthetic restenosis, restenosis after angioplasty or stent placement, and the like.

PRIOR ART

WO 2003/077921 describes azinylaminoazoles as protein kinase inhibitors.

WO 2003/078423 describes compositions which are suitable as protein kinase inhibitors.

WO 2003/078426 and WO 2003/078427 describe azolylaminoazines as protein kinase inhibitors.

WO 2004/043925 describes 3-substituted 6-arylpyridines which act as ligands of C5a receptors.

WO 2004/058149 describes 1-(amino)indanes and (1,2-dihydro-3-amino)benzofurans, benzothophenes and indoles as ADG receptor agonists.

WO 2007/100610 describes pyridine, pyrimidine and pyrazine derivatives as CXCR3 receptor modulators.

SUMMARY OF THE INVENTION

The invention relates to compounds of the formula (I)

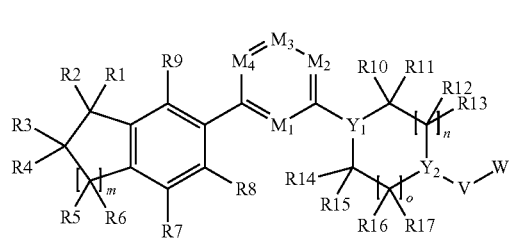

(I)

in which, in each case independently of one another:
$R^1, R^2, R^3, R^4, R^5, R^6, R^7, R^8, R^9, R^{10}, R^{11}, R^{12}, R^{13}, R^{14}, R^{15}, R^{16}, R^{17}$ denote H, D (deuterium), A, $OR^{18}$, CN, F, Cl and $NR^{18}R^{18'}$;
  where $R^1$ and $R^2$, $R^3$ and $R^4$, $R^5$ and $R^6$, $R^{10}$ and $R^{11}$, $R^{12}$ and $R^{13}$, $R^{14}$ and $R^{15}$, $R^{16}$ and $R^{17}$ together may in each case also form =O (carbonyl oxygen);
  where $R^9$ and $R^1$, $R^1$ and $R^2$, $R^2$ and $R^3$, $R^3$ and $R^4$, $R^4$ and $R^5$, $R^5$ and $R^6$, $R^6$ and $R^7$, $R^7$ and $R^8$, $R^{10}$ and $R^{11}$, $R^{11}$ and $R^{12}$, $R^{12}$ and $R^{13}$, $R^{14}$ and $R^{15}$, $R^{15}$ and $R^{16}$, $R^{16}$ and $R^{17}$ together may in each case also form cyclic alkyl having 3, 4, 5, 6 or 7 C atoms or Het having 3, 4, 5, 6 or 7 ring atoms;
  where $R^{10}$ and $R^{19}$, if $Y_1$=$CR^{19}$, $R^{11}$ and $R^{12}$, $R^{13}$ and $R^{19}$, if $Y_2$=$CR^{19}$, $R^{14}$ and $R^{19}$, if $Y_1$=$CR^{19}$, $R^{15}$ and $R^{16}$, $R^{17}$ and $R^{19}$, if $Y_2$=$CR^{19}$, together may in each case also form a C=C double bond with the single bond and the C atoms to which they are attached;
$R^{18}, R^{18'}$ denote H, D or A;
$R^{19}, R^{19'}$ denote H, D, A, $OR^{18}$, $NR^{18}R^{18'}$, F, Cl, Br, CN or Het;
$M_1, M_2, M_3, M_4$ denote $CR^{19}$ or N;
$Y_1, Y_2$ denote $CR^{19}$ or N;
V denotes $C(R^{19})(R^{19'})$, $NR^{19}$ or is absent;
W denotes $[C(R^{19})(R^{19'})]_pZ$, CO—$[C(R^{19})(R^{19'})]_pZ$, $[C(R^{19})(R^{19'})]_pN(R^{19})$—Z, CO—$N(R^{19})$—$[C(R^{19})(R^{19'})]_pZ$, $N(R^{19})$—CO—$[C(R^{19})(R^{19'})]_pZ$, CO—O—$[C(R^{19})(R^{19'})]_pZ$, $C(O)OR^{18}$, $OR^{18}$, H or D;
  where V, W and $Y_2$ together may in each case also form cyclic alkyl having 3, 4, 5, 6 or 7 C atoms, in which 1, 2, 3, 4, 5, 6 or 7H atoms may preferably be replaced by F, Cl, Br, CN and/or OH, $OR^{19}$, $OC(O)R^{19}$, $NR^{19}C(O)OZ$, $C(O)OR^{19}$, $C(O)N(R^{19})(R^{19'})$ or $N(R^{19})(R^{19'})$, or Het having 3, 4, 5, 6 or 7 ring atoms, where Het preferably represents a saturated, unsaturated or aromatic heterocycle having 1 to 4 N, O and/or S atoms, which may be unsubstituted or mono-, di- or trisubstituted by Hal, F, Cl, Br, CN, A, $OR^{18}$, W, $SR^{18}$, $NO_2$, $N(R^{19})(R^{19'})$, $NR^{18}COOZ$, OCONHZ, $NR^{18}SO_2Z$, $SO_2N(R^{18})Z$, $S(O)_mZ$, COZ, CHO, COZ, =S, =NH, =NA, oxy (—$O^-$) and/or =O (carbonyl oxygen);
Z denotes Het, Ar or A;
A denotes unbranched or branched alkyl having 1, 2, 3, 4, 5, 6, 7, 8, 9 or 10 C atoms, in which 1, 2, 3, 4, 5, 6 or 7H atoms may be replaced by F, Cl, Br, CN and/or OH, $OR^{19}$, $OC(O)R^{19}$, $NR^{19}C(O)OZ$, $C(O)OR^{19}$, $C(O)N(R^{19'})(R^{19'})$ or $N(R^{19})(R^{19'})$;
  and/or in which one or two $CH_2$ groups may be replaced by O, S, SO, $SO_2$, CO, COO, $NR^{18}$, $NR^{18}CO$, $CONR^{18}$, cyclic alkyl having 3, 4, 5, 6 or 7 C atoms, CH=CH and/or CH=CH groups;
  or cyclic alkyl having 3, 4, 5, 6 or 7 C atoms, in which 1, 2, 3, 4, 5, 6 or 7 H atoms may preferably be replaced by F, Cl, Br, CN and/or OH, $OR^{19}$, $OC(O)R^{19}$, $NR^{19}C(O)OZ$, $C(O)OR^{19}$, $C(O)N(R^{19})(R^{19'})$ or $N(R^{19})(R^{19'})$;
Ar denotes phenyl, naphthyl or biphenyl, each of which is mono-, di- or trisubstituted by Hal, F, Cl, Br, CN, A, $OR^{18}$, W, $SR^{18}$, $NO_2$, $N(R^{19})(R^{19'})$, $NR^{18}COOZ$, OCONHZ, $NR^{18}SO_2Z$, $SO_2N(R^{18})Z$, $S(O)_mZ$, COZ, CHO, COZ,
Het in each case, independently of one another, denotes a mono-, bi- or tri-cyclic saturated, unsaturated or aromatic heterocycle having 1 to 4 N, O and/or S atoms, which may be unsubstituted or mono-, di- or trisubstituted by Hal, F, Cl, Br, CN, A, $OR^{18}$, W, $SR^{18}$, $NO_2$, $N(R^{19})(R^{19'})$, $NR^{18}COOZ$, OCONHZ, $NR^{18}SO_2Z$, $SO_2N(R^{18})Z$, $S(O)_mZ$, COZ, CHO, COZ, =S, =NH, =NA, oxy (—$O^-$) and/or =O (carbonyl oxygen),
m denotes 1, 2 or 3,
n, o denote 0, 1 or 2,
p denotes 0, 1, 2, 3 or 4
with the proviso that compounds of the formula (I) in which
  (a) V is absent, and
  (b) W=C(O)—$CH_2$-Het
and physiologically acceptable salts, derivatives, prodrugs, solvates, tautomers and stereoisomers thereof, including mixtures thereof in all ratios.

The invention furthermore relates to preferred, in each case independent embodiments of compounds of the formula (I), in which in each case, independently of one another:

Preferred embodiment (A): $R^1, R^2, R^3, R^4, R^5, R^6, R^7, R^8, R^9, R^{10}, R^{11}, R^{12}, R^{13}, R^{14}, R^{15}, R^{16}, R^{17}$ denote H, D, A, $OR^{18}$ or $NR^{18}R^{18'}$;
  where $R^1$ and $R^2$, $R^3$ and $R^4$, $R^5$ and $R^6$, $R^{10}$ and $R^{11}$, $R^{12}$ and $R^{13}$, $R^{14}$ and $R^{15}$, $R^{16}$ and $R^{17}$ together may in each case also form =O (carbonyl oxygen);
  where $R^9$ and $R^1$, $R^1$ and $R^2$, $R^2$ and $R^3$, $R^3$ and $R^4$, $R^4$ and $R^5$, $R^5$ and $R^6$, $R^6$ and $R^7$, $R^7$ and $R^8$, $R^{10}$ and $R^{11}$, $R^{11}$ and $R^{12}$, $R^{12}$ and $R^{13}$, $R^{14}$ and $R^{15}$, $R^{15}$ and $R^{16}$, $R^{16}$ and $R^{17}$ together may in each case also form cyclic alkyl having 3, 4, 5, 6 or 7 C atoms or Het having 3, 4, 5, 6 or 7 ring atoms;

Preferred embodiment (B): $R^{19}, R^{19'}$ denote H, A, $OR^{18}$, F;

Preferred embodiment (C): $M_1, M_2, M_3, M_4$ denote $CR^{19}$;

Preferred embodiment (D): $M_1$ denotes N, and $M_2, M_3, M_4$ denote $CR^{19}$;

Preferred embodiment (E): $M_2$ denotes N, and $M_1, M_3, M_4$ denote $CR^{19}$;

Preferred embodiment (F): $M_4$ denotes N, and $M_1, M_2, M_3$ denote $CR^{19}$;

Preferred embodiment (G): $M_1, M_2$ denote N, and $M_3, M_4$ denote $CR^{19}$;

Preferred embodiment (H): $M_1, M_3$ denote N, and $M_2, M_4$ denote $CR^{19}$;

Preferred embodiment (J): $M_1$, $M_4$ denote N, and $M_2$, $M_3$ denote $CR^{19}$;

Preferred embodiment (K): $M_1$, $M_2$, $M_4$ denote N, and $M_3$ denotes $CR^{19}$;

Preferred embodiment (L): $Y_1$, $Y_2$ denote N;

Preferred embodiment (M): $Y_1$ denotes N, and $Y_2$ denotes $CR^{19}$;

Preferred embodiment (N): $Y_1$ denotes $CR^{19}$ and $Y_2$ denotes N;

Preferred embodiment (O): W denotes $[C(R^{19})(R^{19'})]_pZ$, CO—$[C(R^{19})(R^{19'})]_pZ$, CO—O—$[C(R^{19})(R^{19'})]_pZ$, $[C(R^{19})(R^{19'})]_pN(R^{19})$—Z, $N(R^{19})$—CO—$[C(R^{19})(R^{19'})]_pZ$, $C(O)OR^{18}$, $OR^{18}$ or H;

Preferred embodiment (P): Z denotes Het or A;

Preferred embodiment (O): m denotes 1 or 2;

Preferred embodiment (R): n, o denote 0, 1 or 2;

Preferred embodiment (S): p denotes 0, 1 or 2;

and in each case physiologically acceptable salts, derivatives, prodrugs, solvates, tautomers and stereoisomers thereof, including mixtures thereof in all ratios.

In a preferred embodiment, the invention furthermore relates to compounds of the formula (I) and preferred embodiments described here, in which in each case, independently of one another:

$R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ denote H, D, A, $OR^{18}$ or $NR^{18}R^{18'}$;

where $R^1$ and $R^2$, $R^3$ and $R^4$, $R^5$ and $R^6$, $R^{10}$ and $R^{11}$, $R^{12}$ and $R^{13}$, $R^{14}$ and $R^{15}$, $R^{16}$ and $R^{17}$ together may in each case also form =O (carbonyl oxygen);

where $R^9$ and $R^1$, $R^1$ and $R^2$, $R^2$ and $R^3$, $R^3$ and $R^4$, $R^4$ and $R^5$, $R^5$ and $R^6$, $R^6$ and $R^7$, $R^7$ and $R^8$, $R^{10}$ and $R^{11}$, $R^{11}$ and $R^{12}$, $R^{12}$ and $R^{13}$, $R^{14}$ and $R^{15}$, $R^{15}$ and $R^{16}$, $R^{16}$ and $R^{17}$ together may in each case also form cyclic alkyl having 3, 4, 5, 6 or 7 C atoms or Het having 3, 4, 5, 6 or 7 ring atoms;

$R^{19}$, $R^{19'}$ denote H, A, $OR^{18}$, F;

$M_1$, $M_2$, $M_3$, $M_4$ denote $CR^{19}$, or $M_1$ denotes N, and $M_2$, $M_3$, $M_4$ denote $CR^{19}$, or $M_2$ denotes N, and $M_1$, $M_3$, $M_4$ denote $CR^{19}$, or $M_4$ denotes N, and $M_1$, $M_2$, $M_3$ denote $CR^{19}$, or $M_1$, $M_2$ denote N, and $M_3$, $M_4$ denote $CR^{19}$, or $M_1$, $M_3$ denote N, and $M_2$, $M_4$ denote $CR^{19}$, or $M_1$, $M_4$ denote N, and $M_2$, $M_3$ denote $CR^{19}$, or $M_1$, $M_2$, $M_4$ denote N, and $M_3$ denotes $CR^{19}$;

$Y_1$, $Y_2$ denote N, or $Y_1$ denotes N, and $Y_2$ denotes $CR^{19}$, or $Y_1$ denotes $CR^{19}$ and $Y_2$ denotes N;

W denotes $[C(R^{19})(R^{19'})]_pZ$, CO—$[C(R^{19})(R^{19'})]_pZ$, CO—O—$[C(R^{19})(R^{19'})]_pZ$, $[C(R^{19})(R^{19'})]_pN(R^{19})$—Z, $N(R^{19})$—CO—$[C(R^{19})(R^{19'})]_pZ$, $C(O)OR^{18}$, $OR^{18}$ or H;

Z denotes Het or A;

m denotes 1 or 2;

n, o denote 0, 1 or 2;

p denotes 0, 1 or 2;

and physiologically acceptable salts, derivatives, prodrugs, solvates, tautomers and stereoisomers thereof, including mixtures thereof in all ratios.

The invention furthermore relates to compounds selected from the group consisting of:

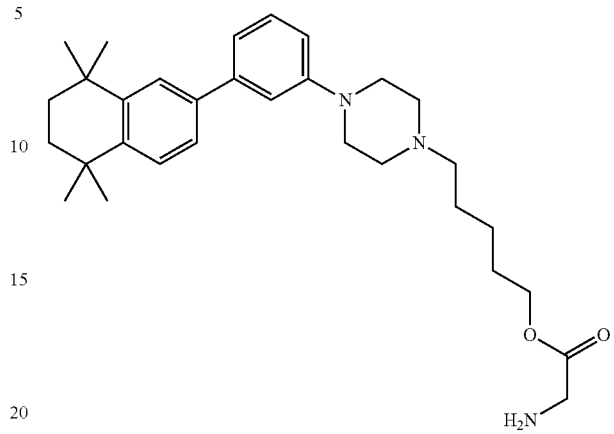

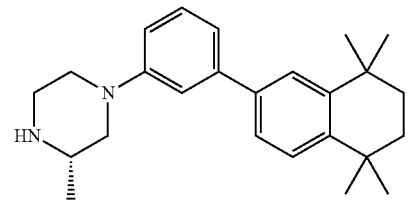

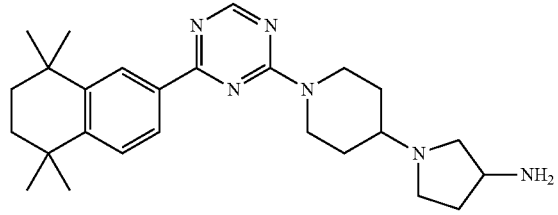

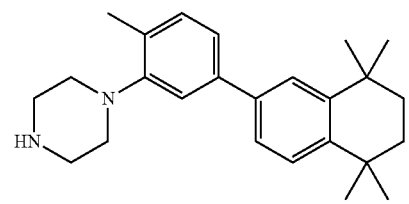

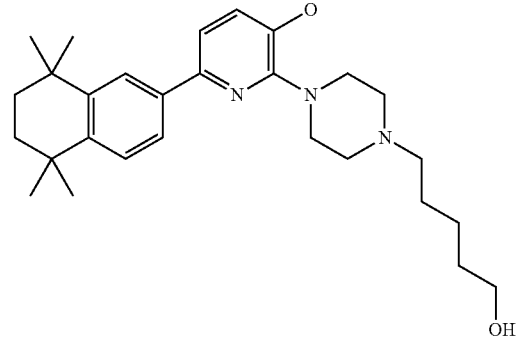

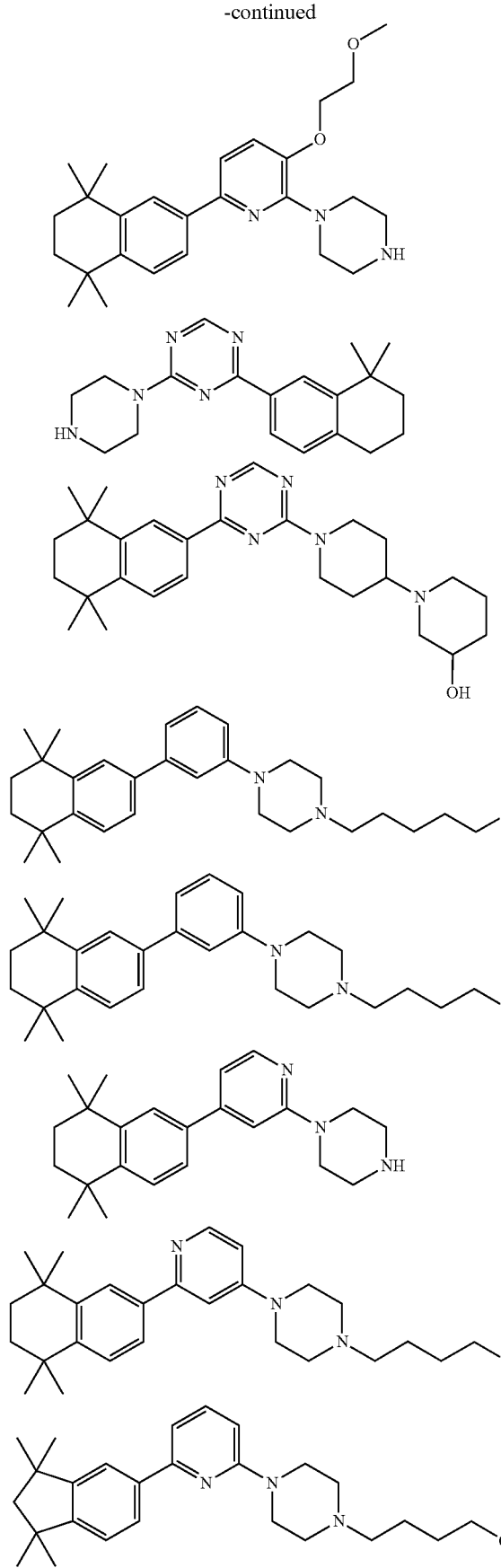
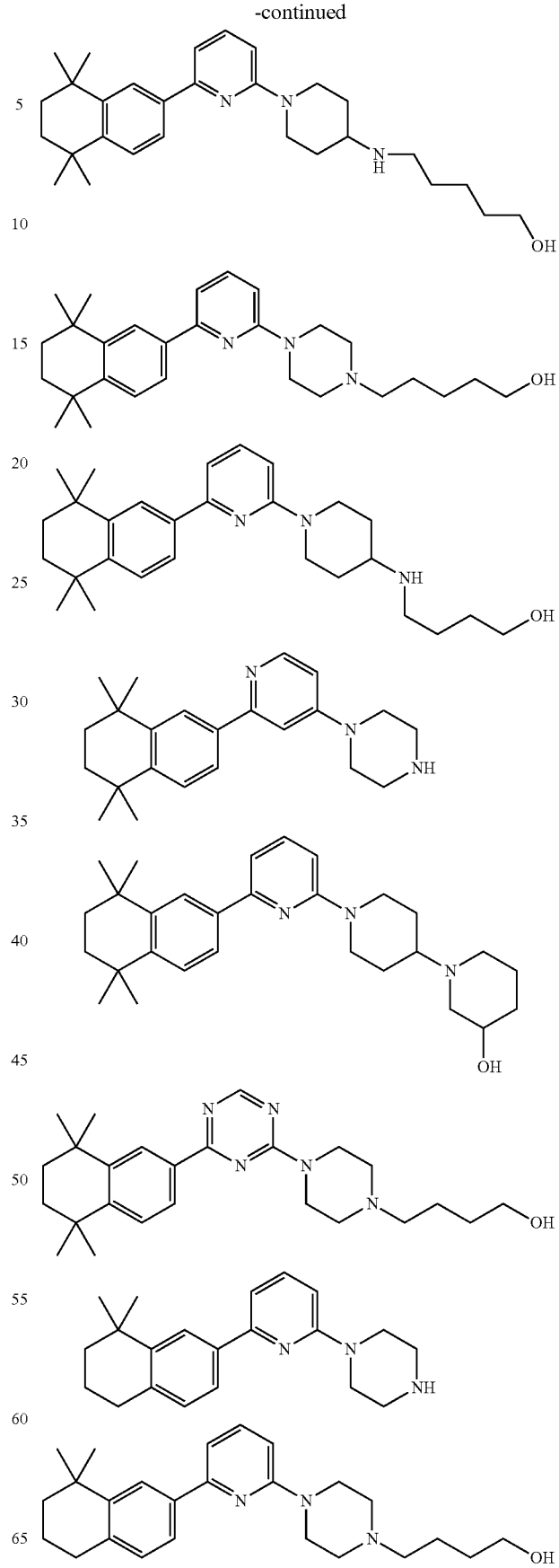

-continued
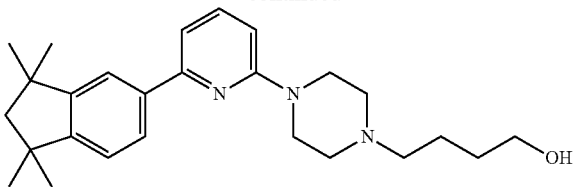
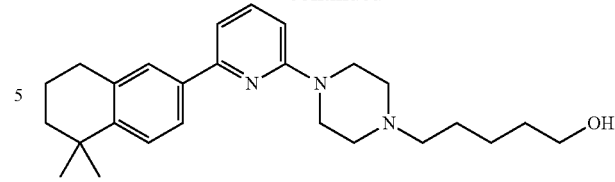
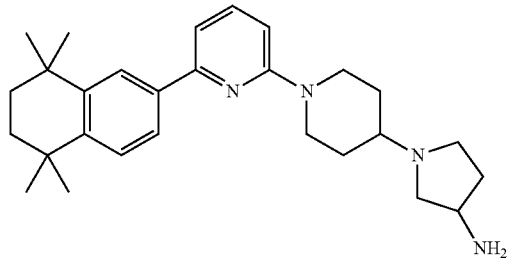
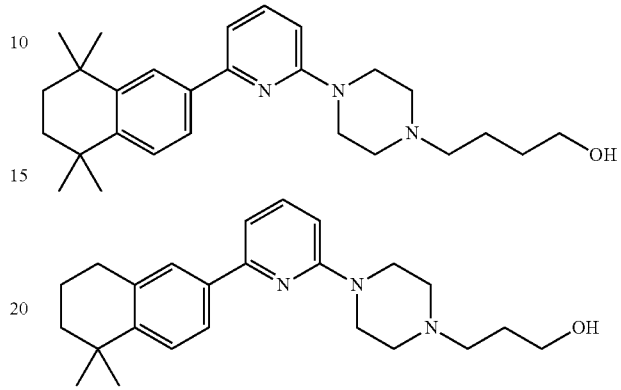
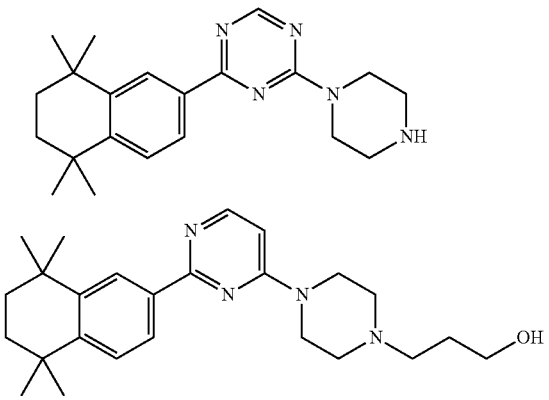
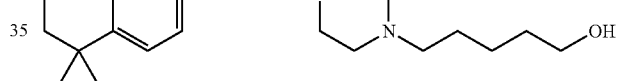
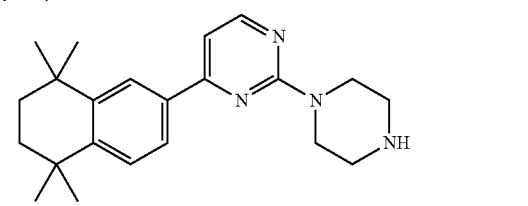
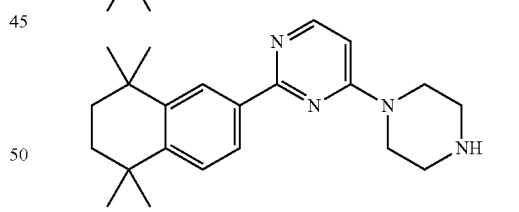
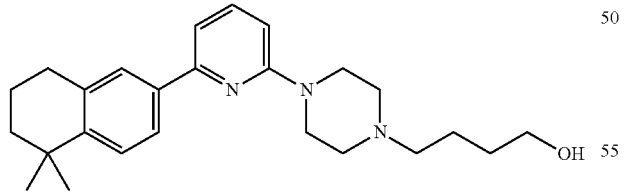
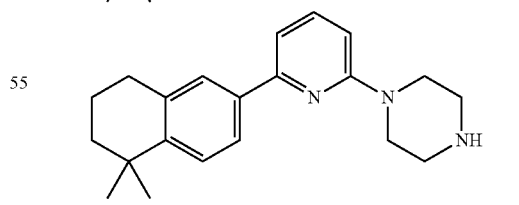
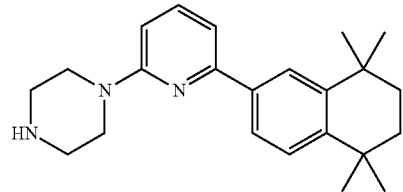
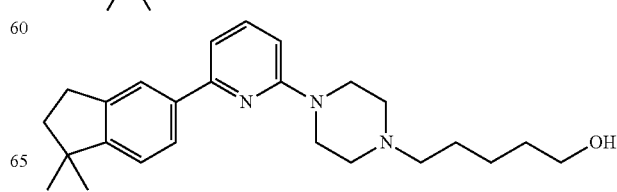

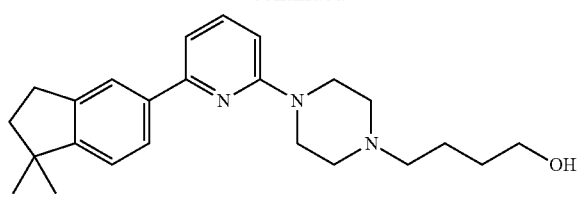
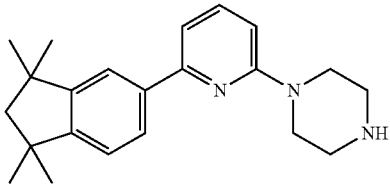
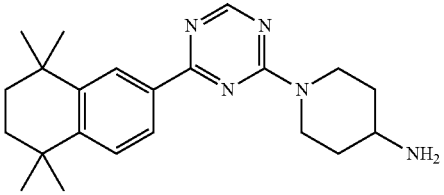
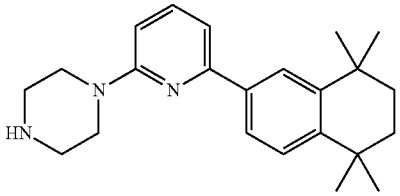
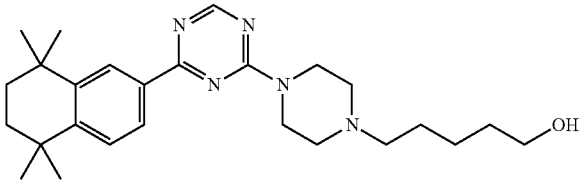
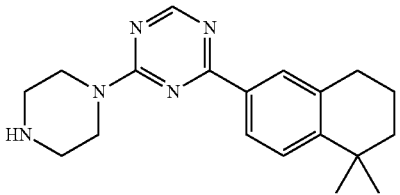
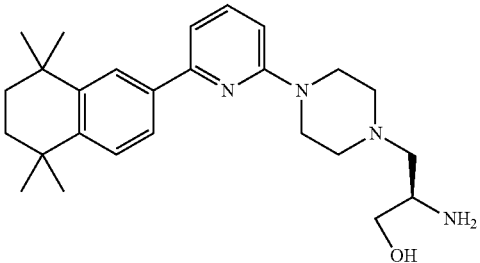
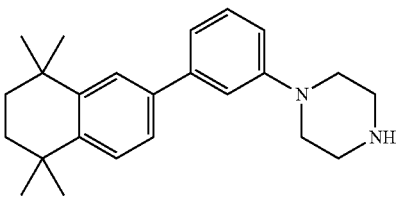
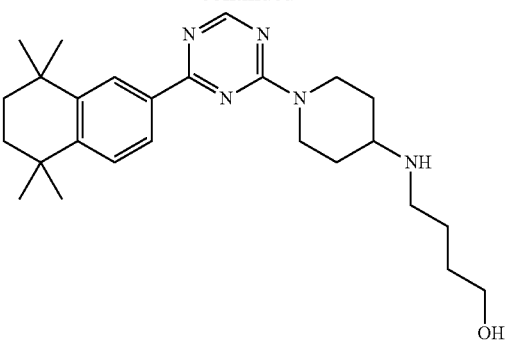
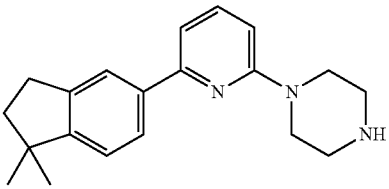
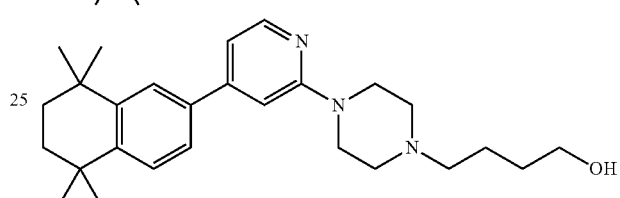
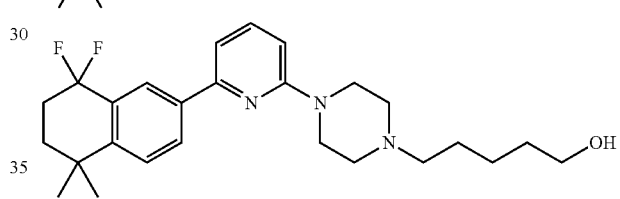
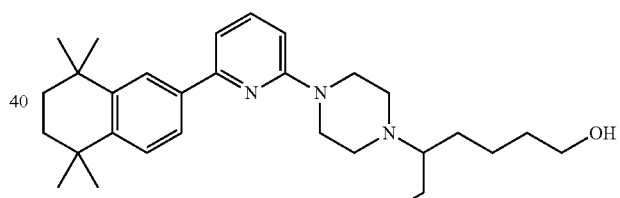
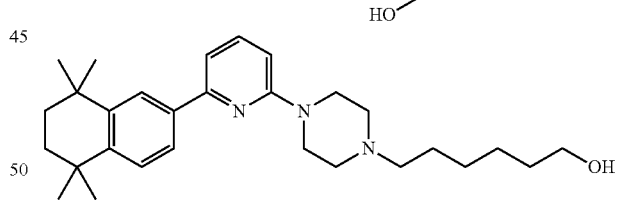
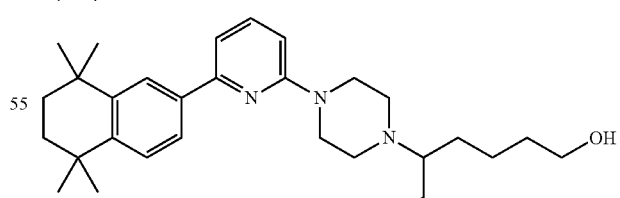
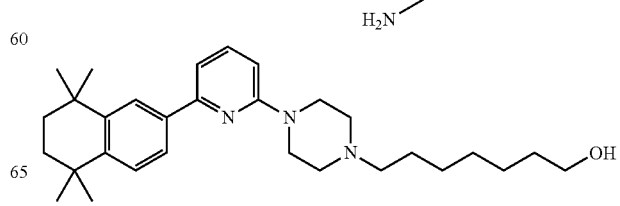

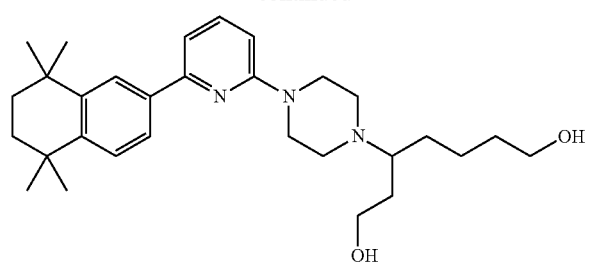
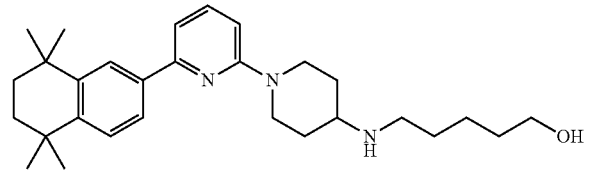
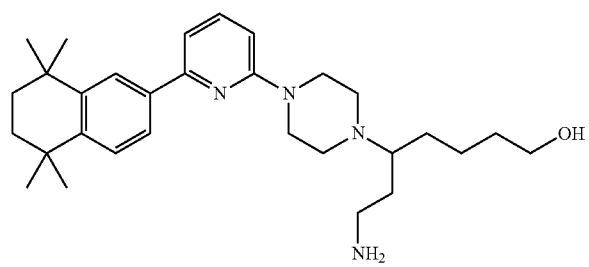
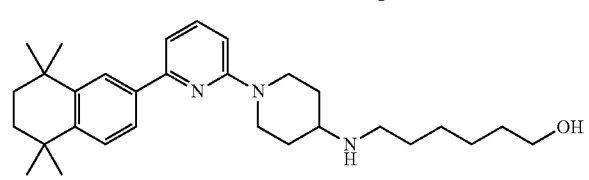
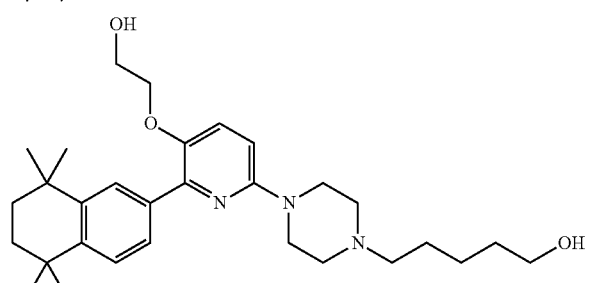
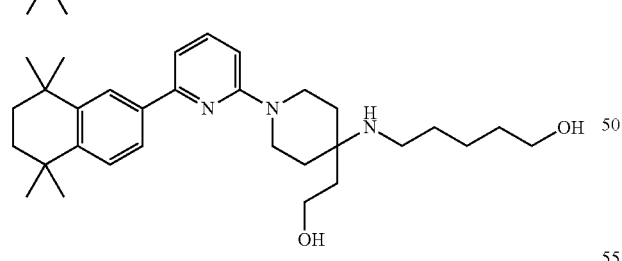
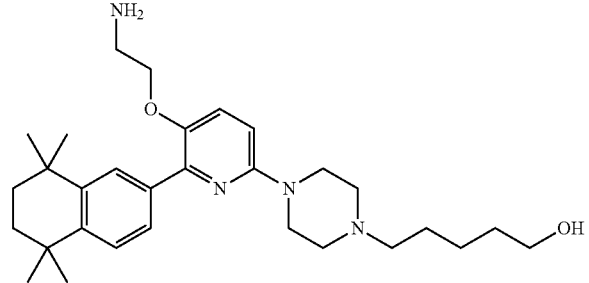
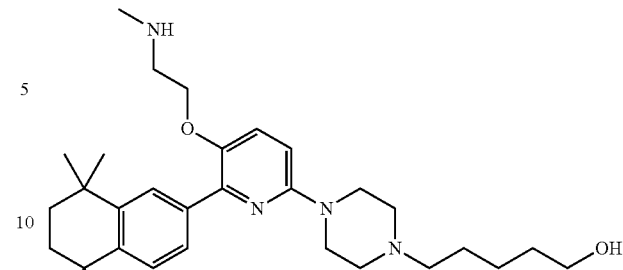

-continued
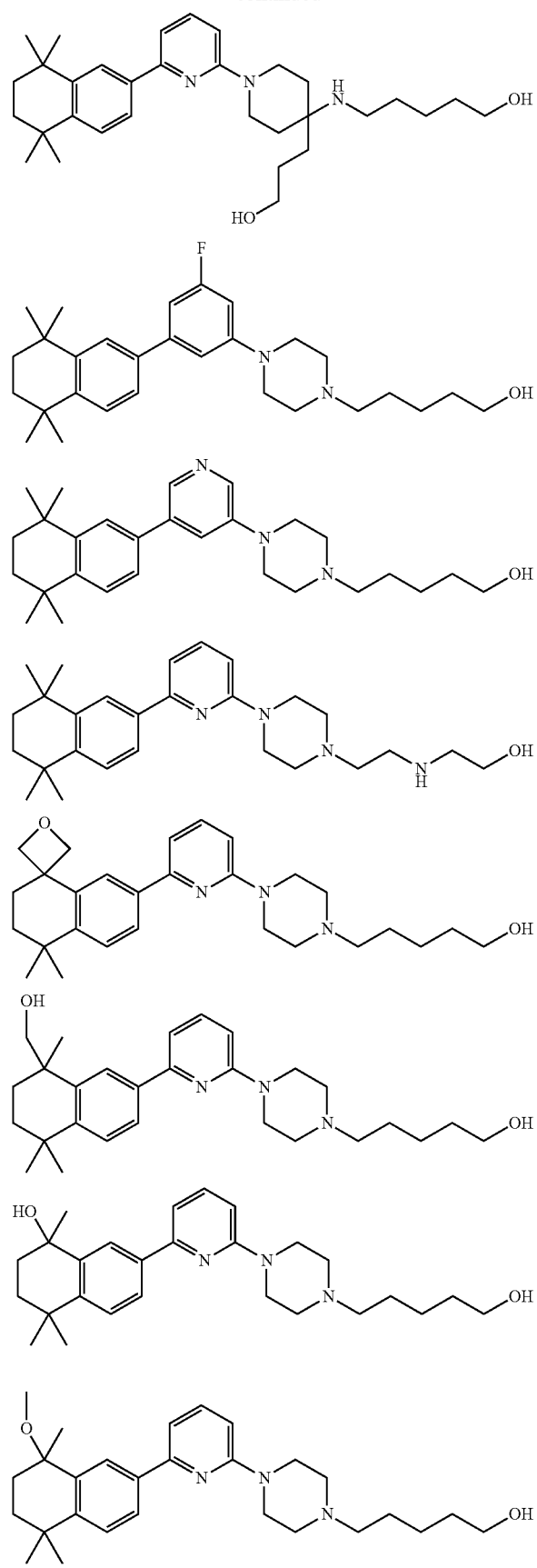
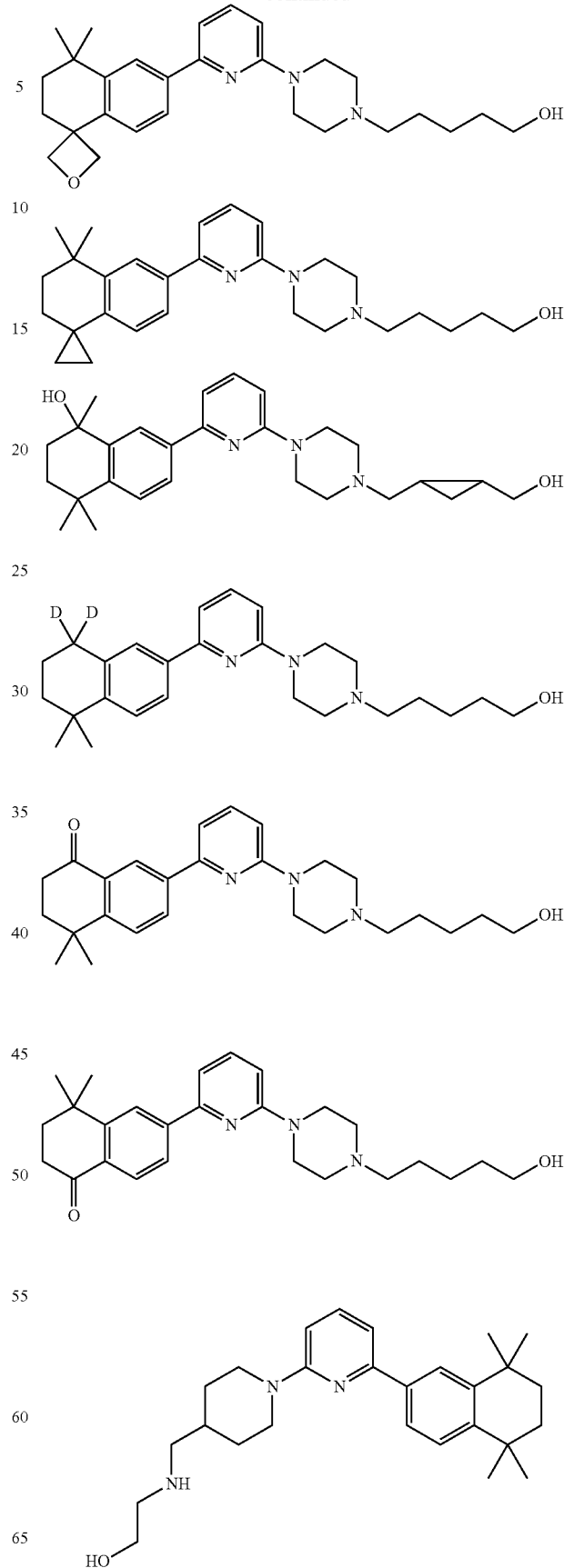

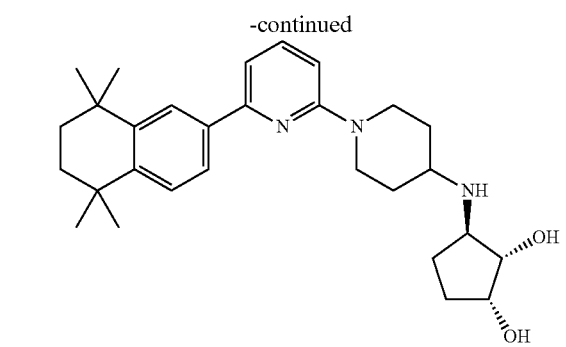
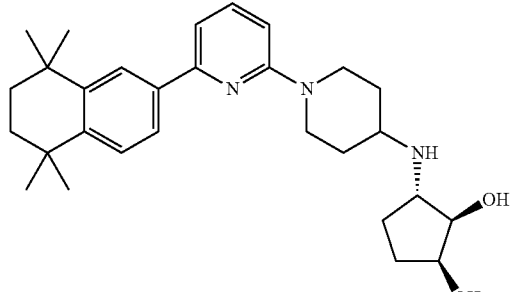
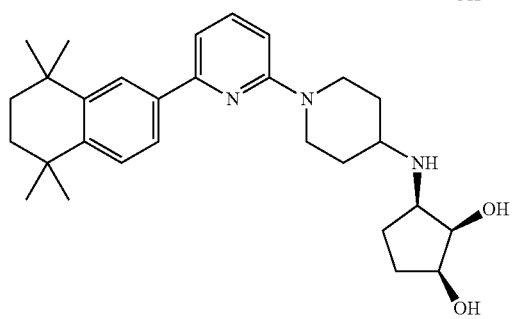
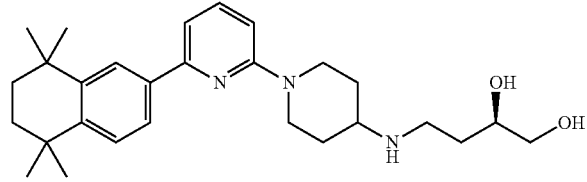
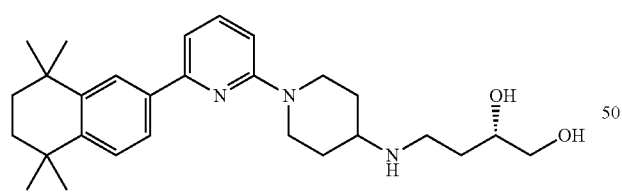
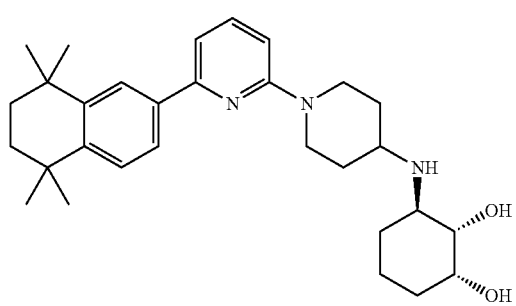
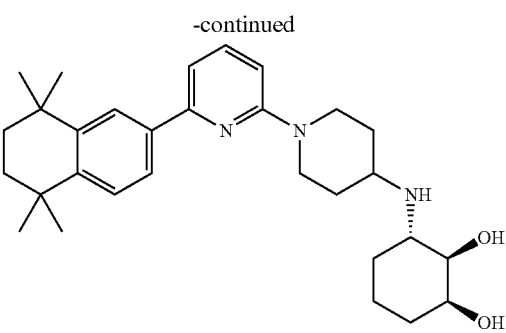
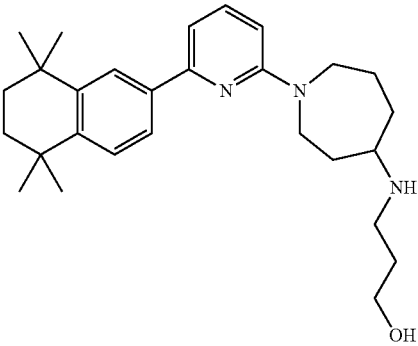
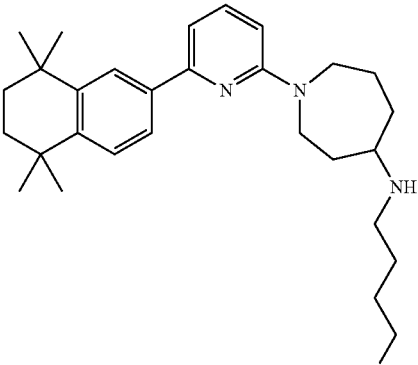
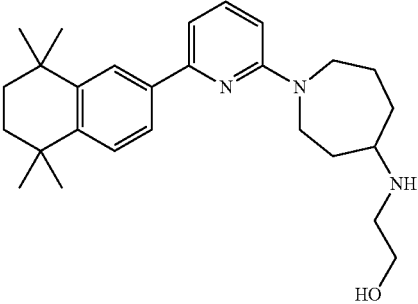
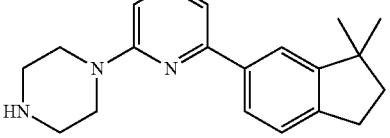
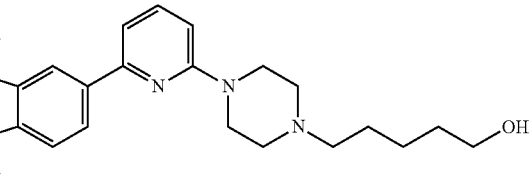

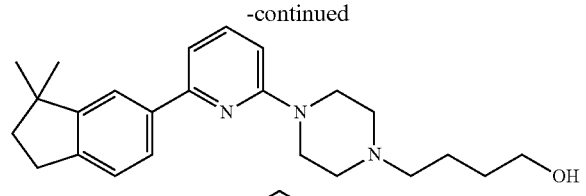
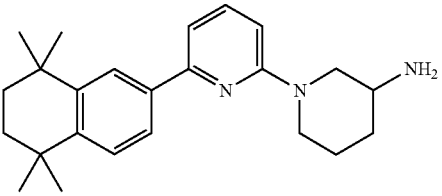
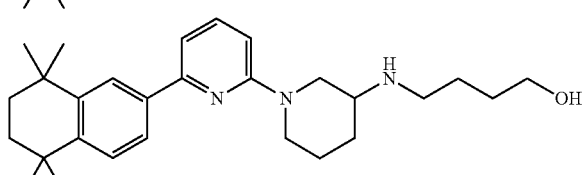
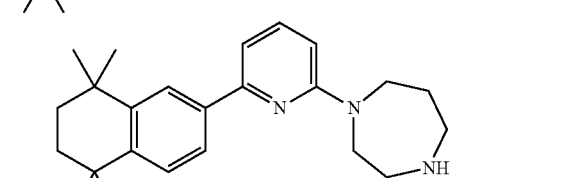
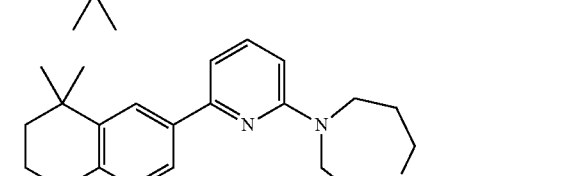
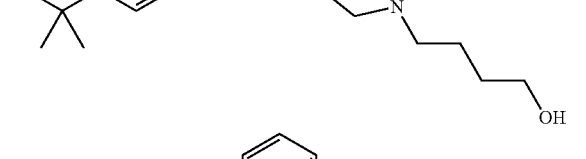
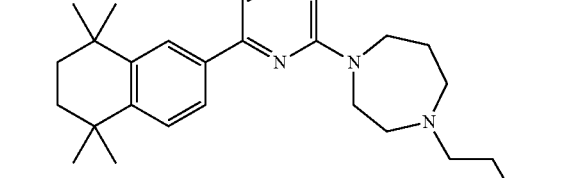

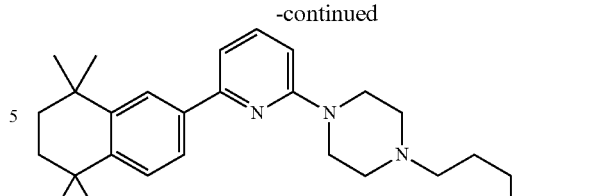
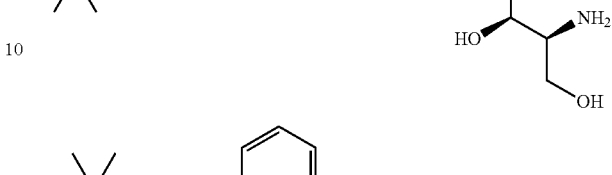
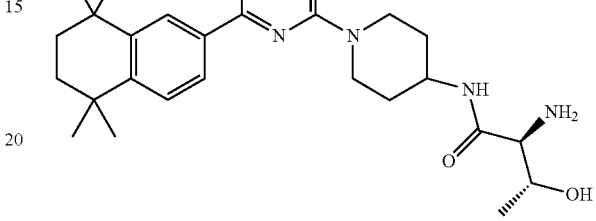
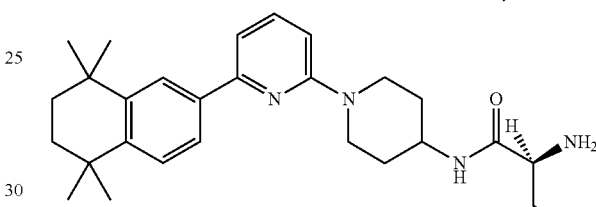
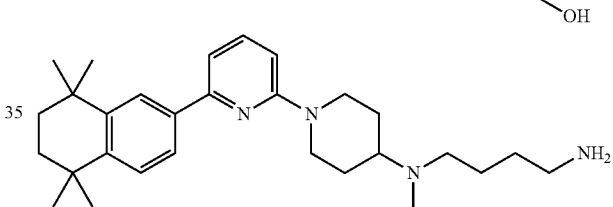
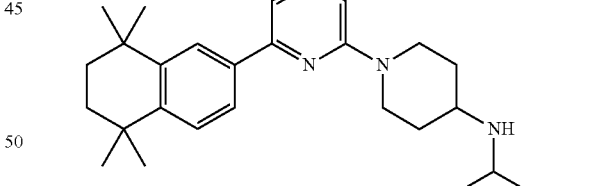
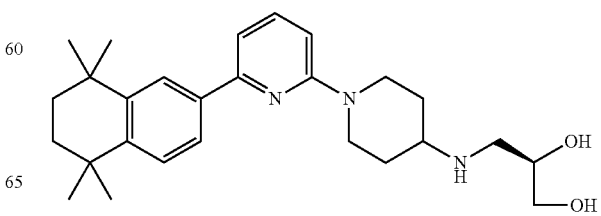

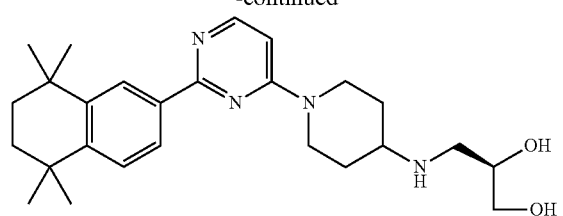
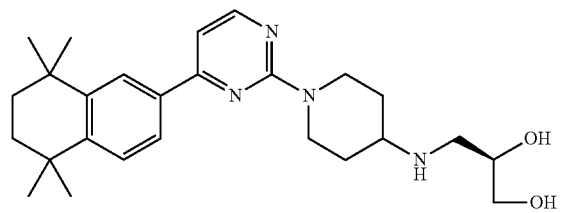
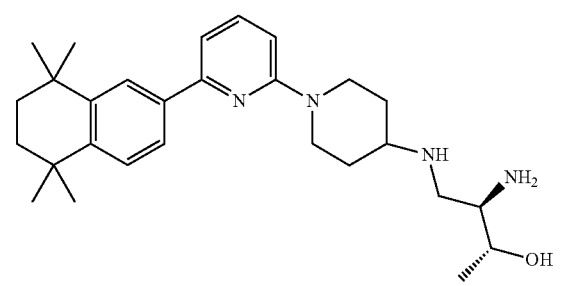
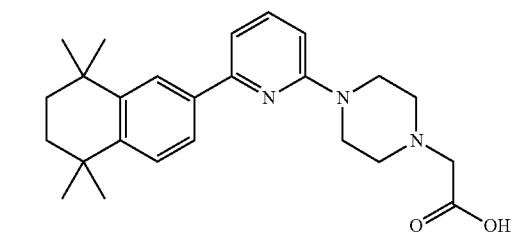
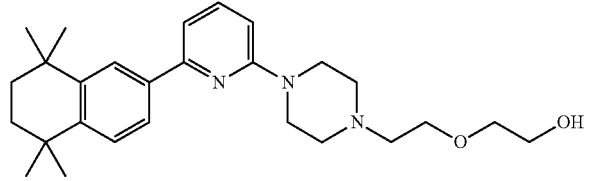
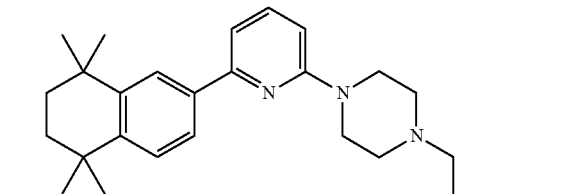
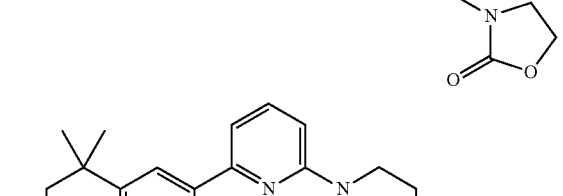
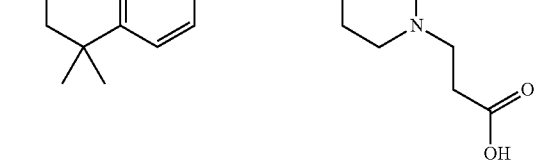
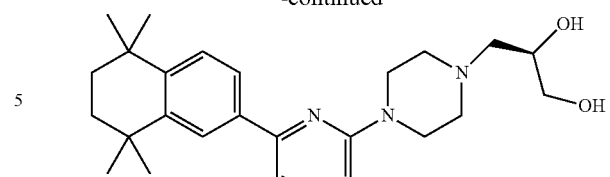
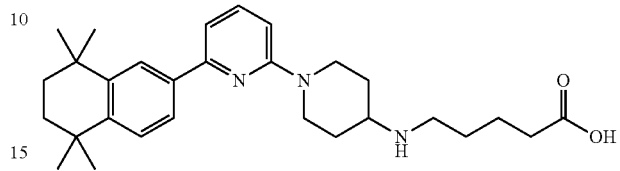
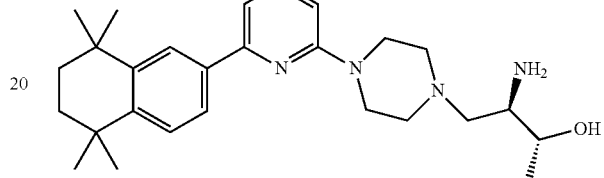
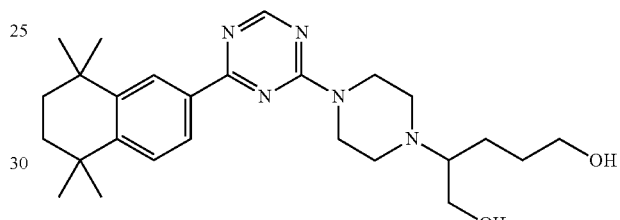
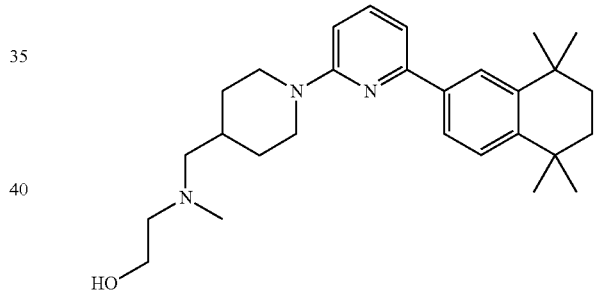
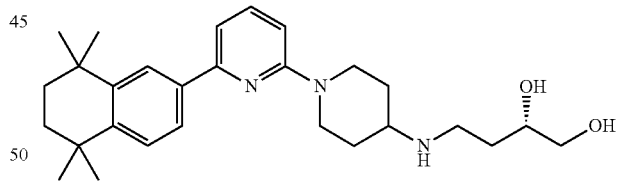
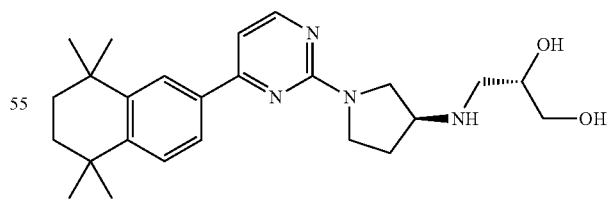
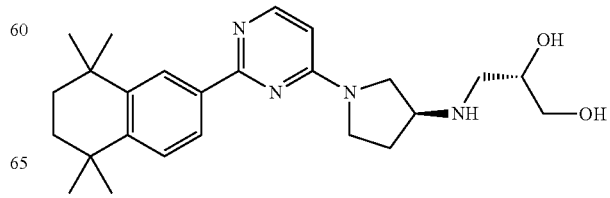

-continued

29
-continued
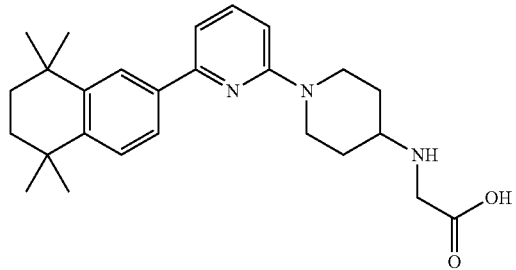
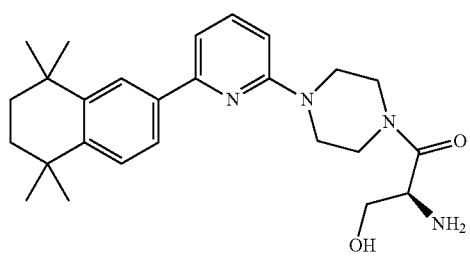
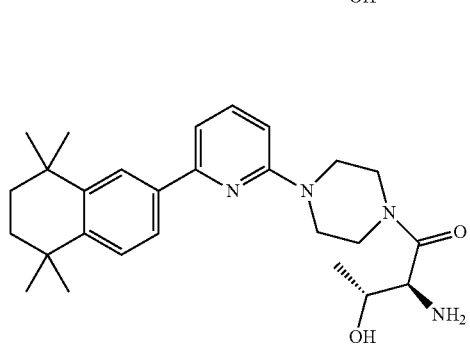
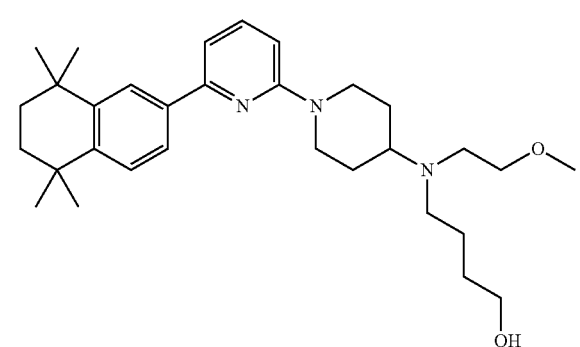
30
-continued
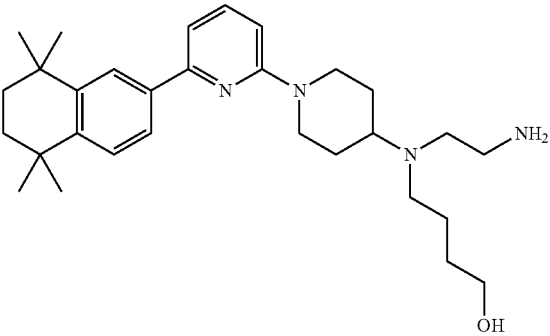
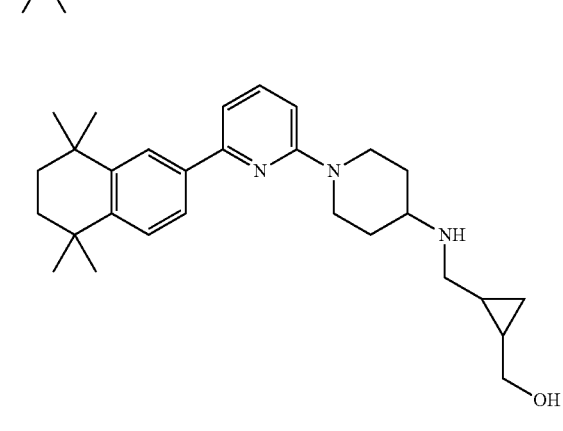
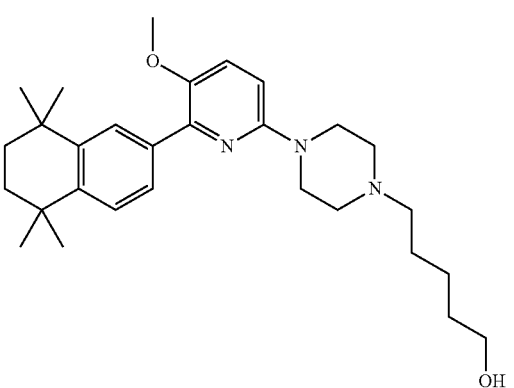

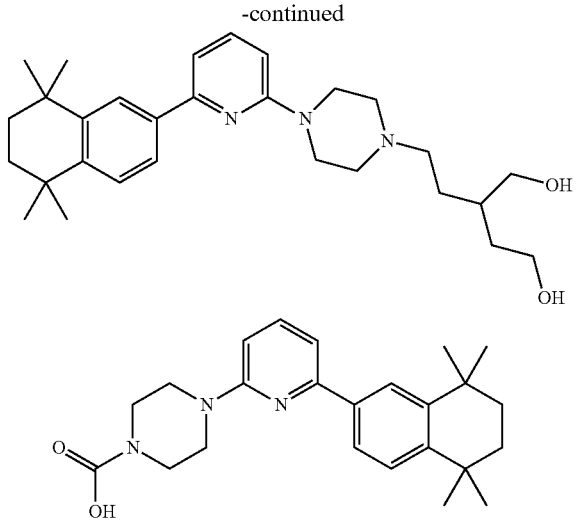
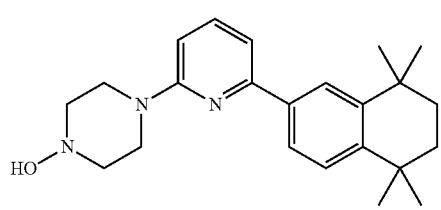
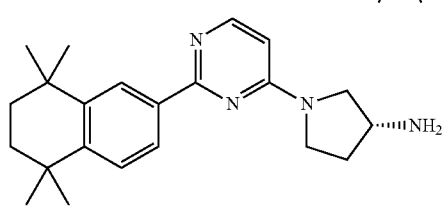
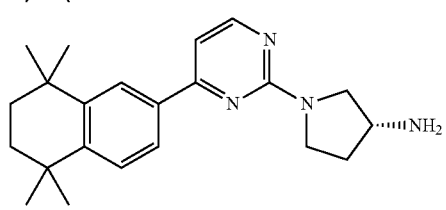
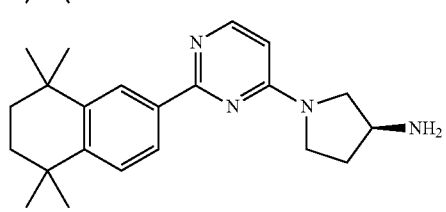
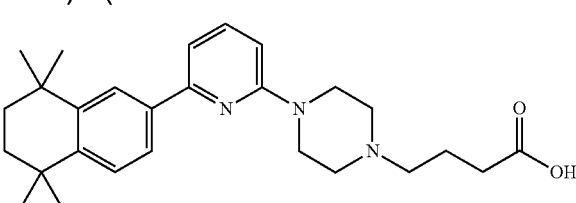
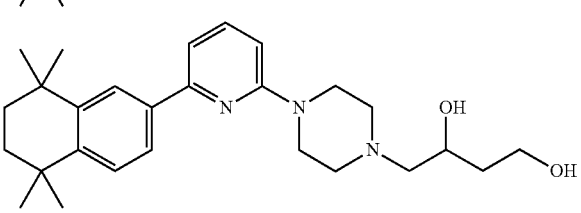
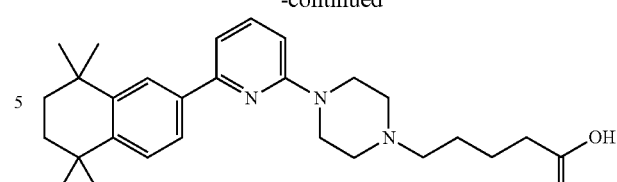
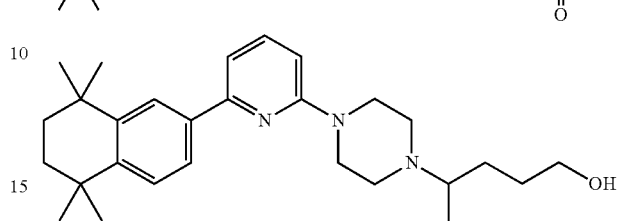
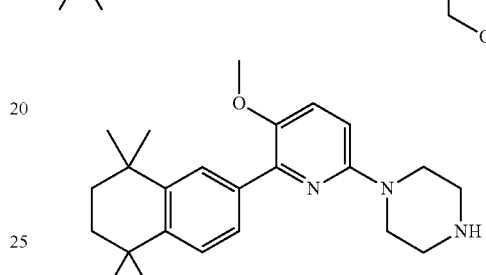
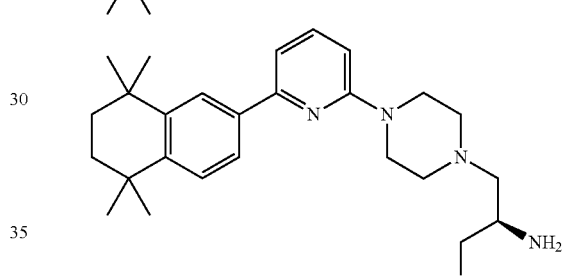
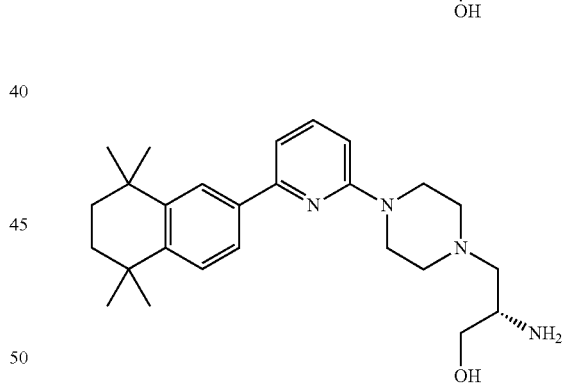
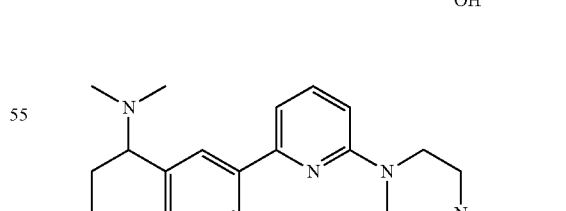
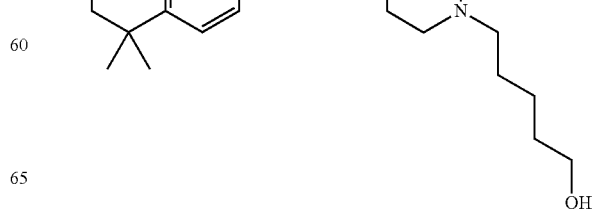

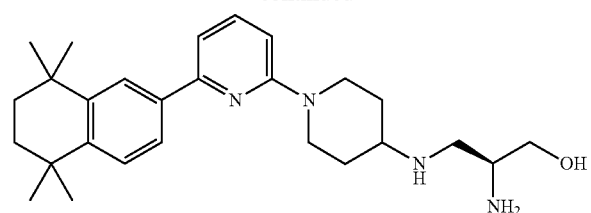
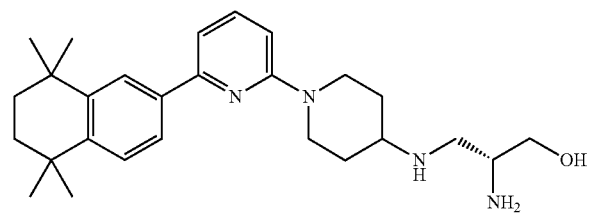
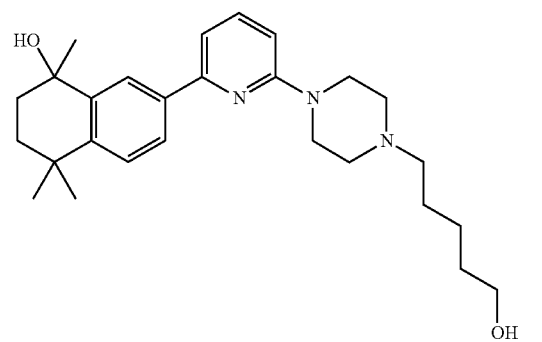
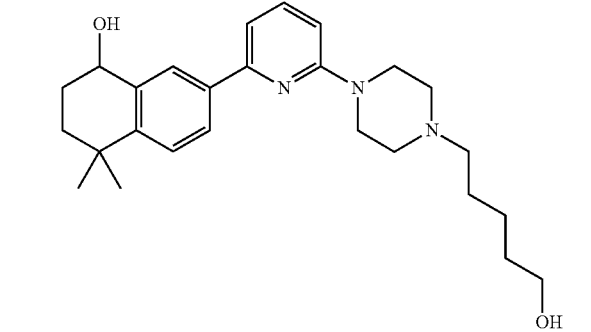
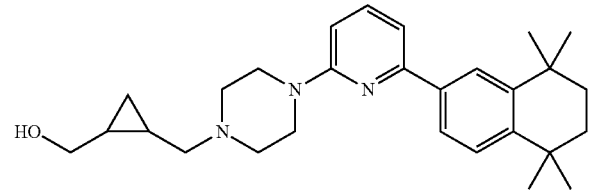
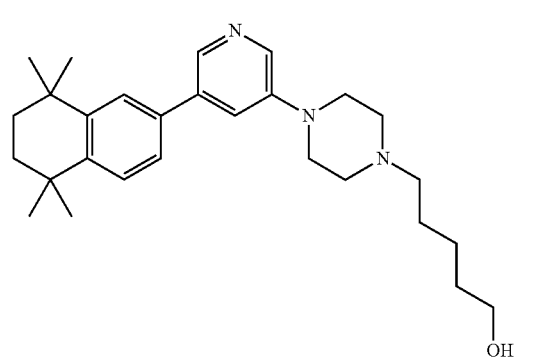
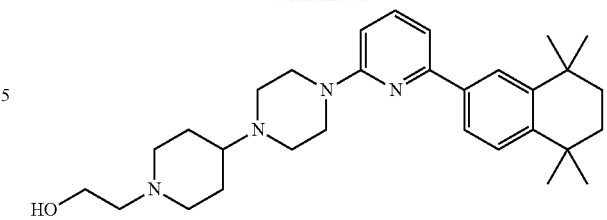
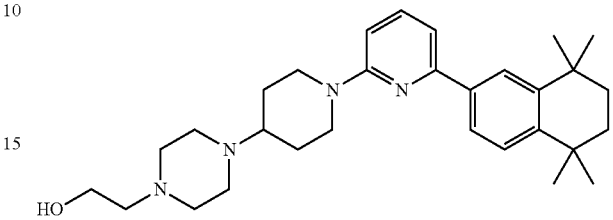
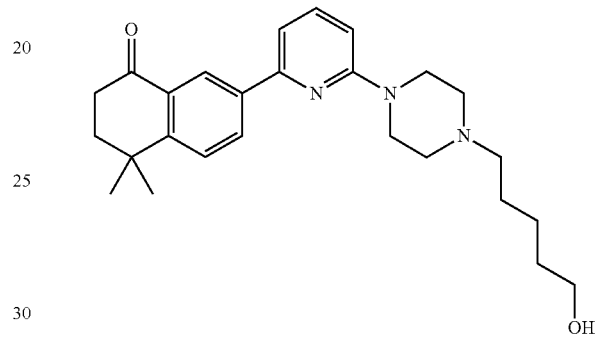
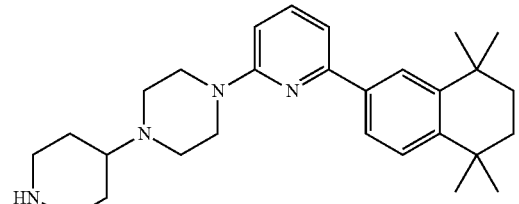
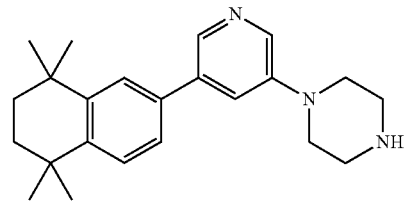
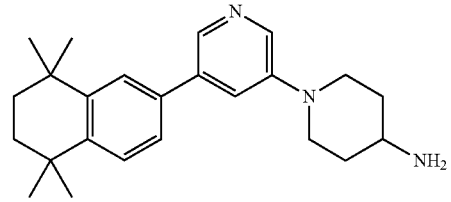
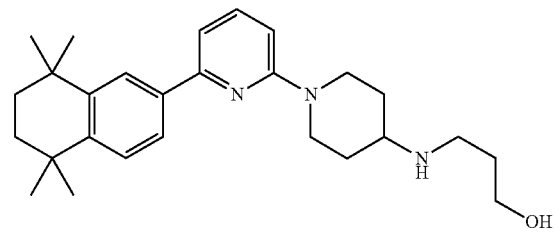

35
-continued
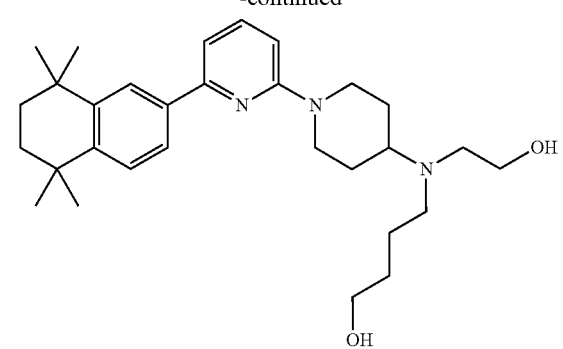
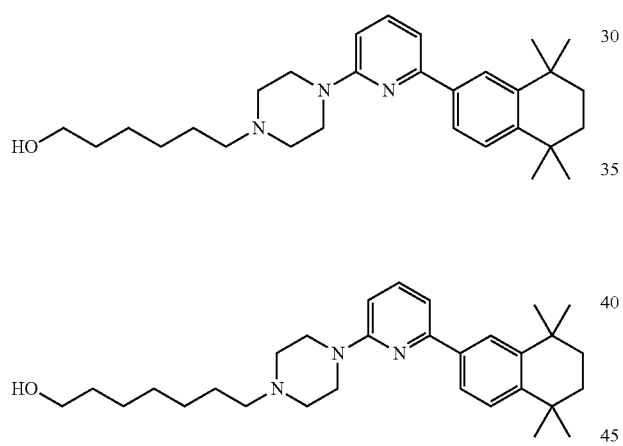
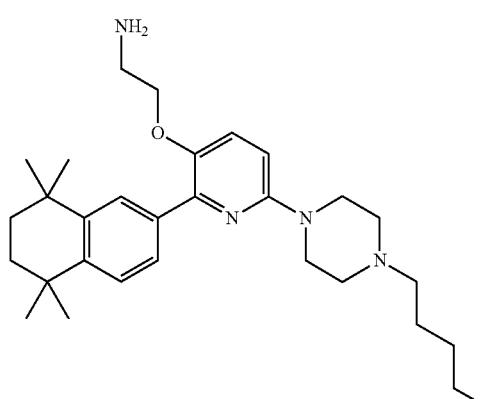
36
-continued
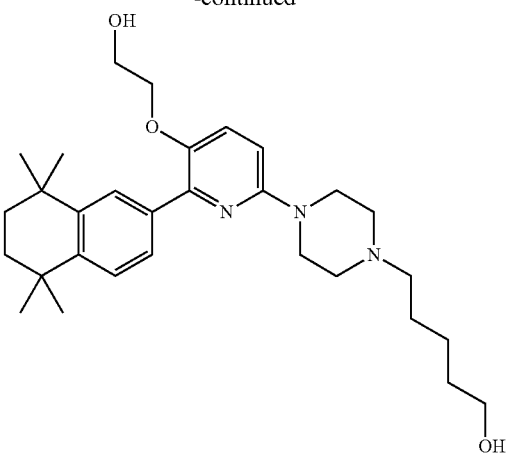
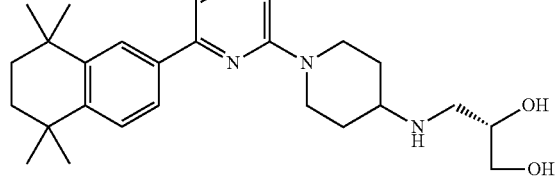
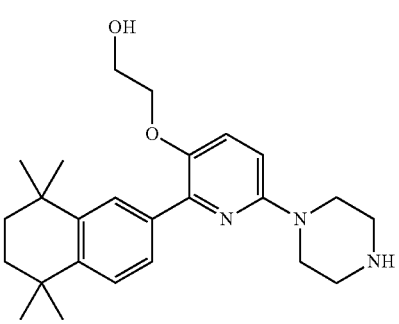
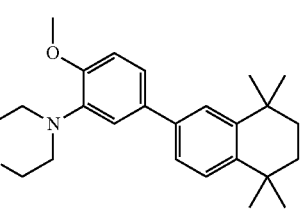

| 37 -continued | 38 -continued |
|---|---|
| 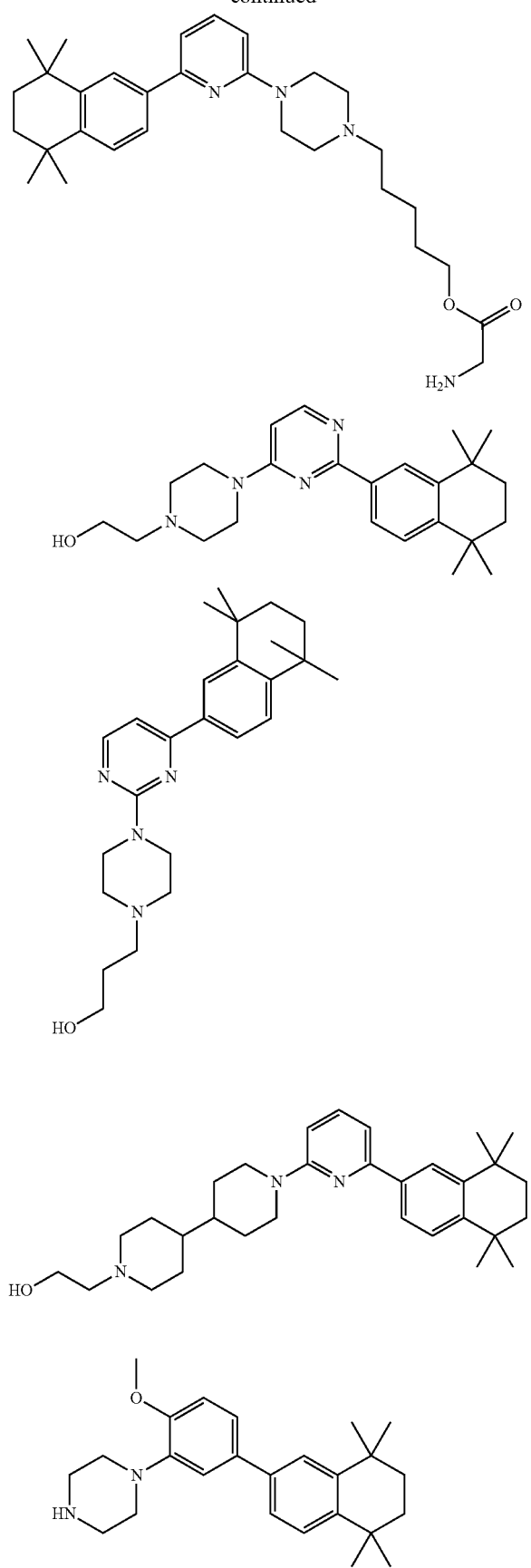 | 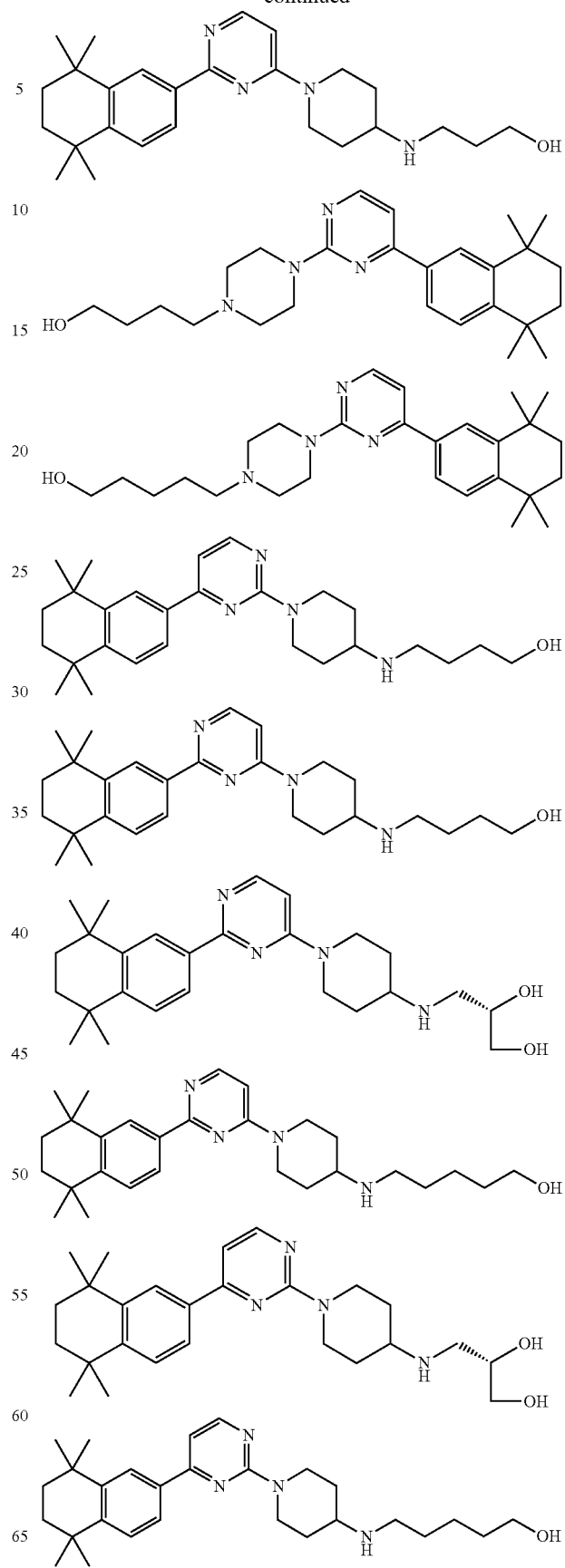 |

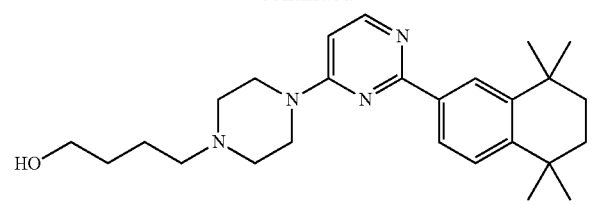
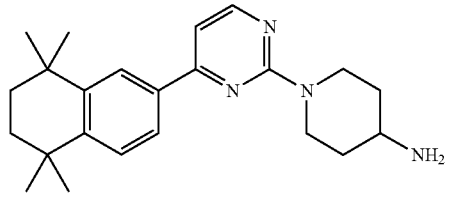
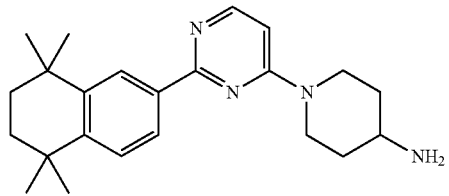
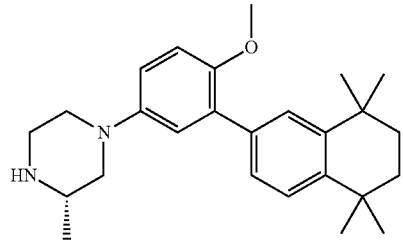
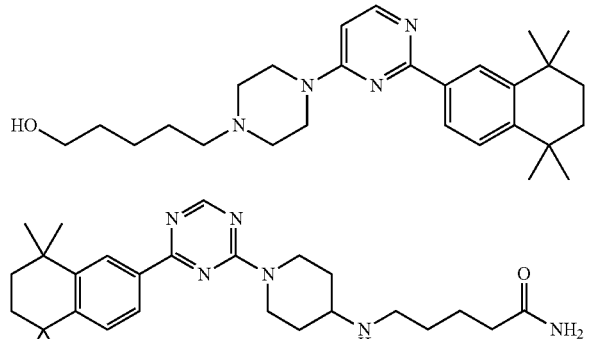
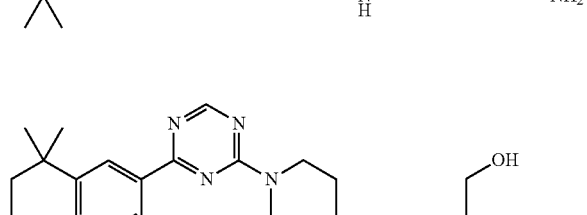
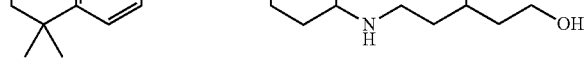
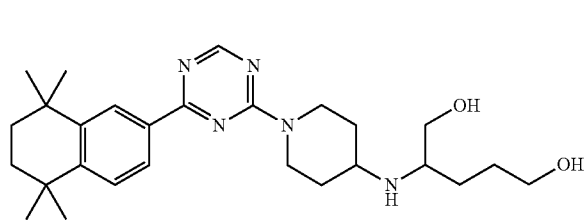
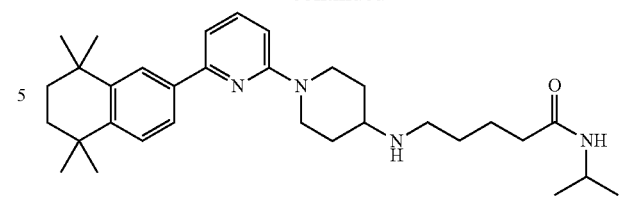
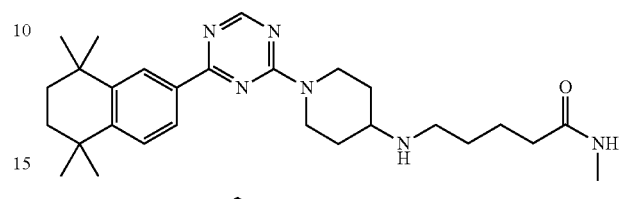
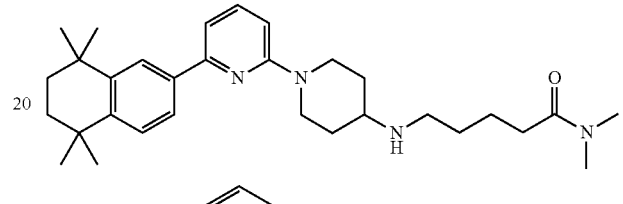
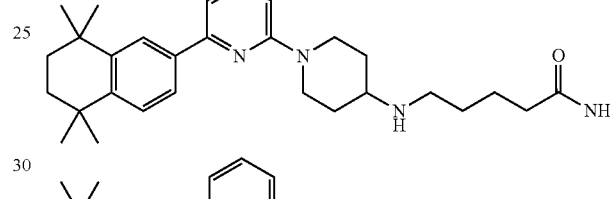
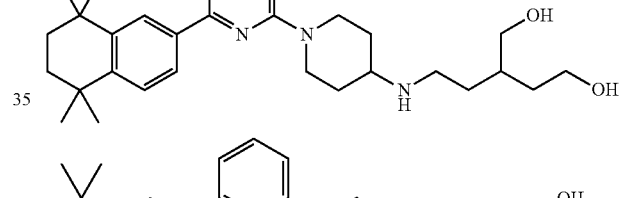
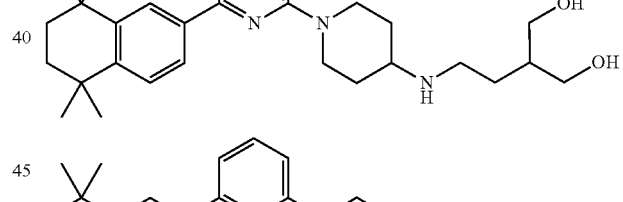
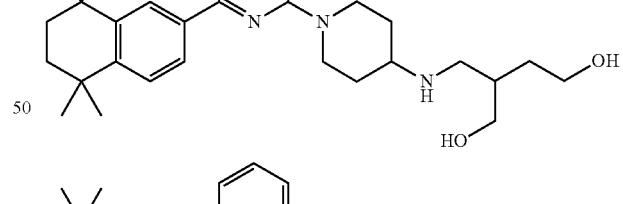
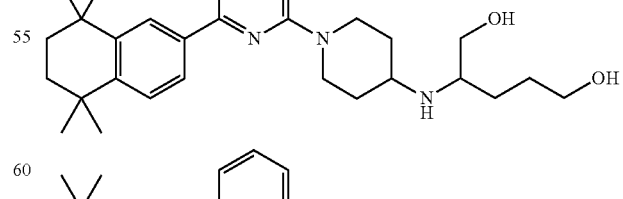
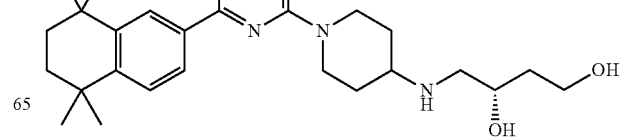

41
-continued
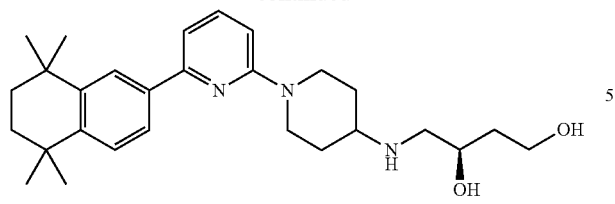
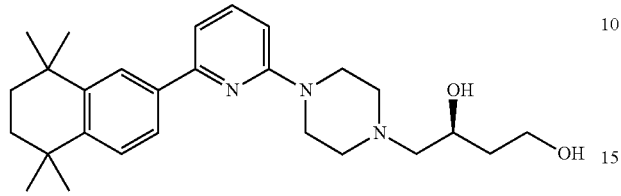
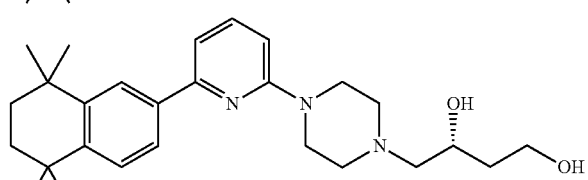
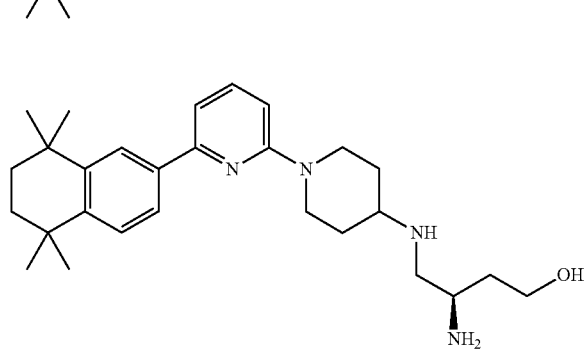
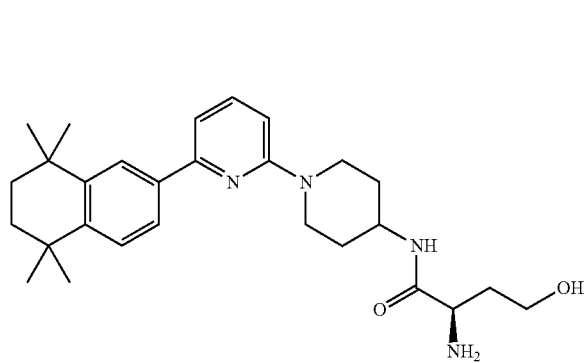
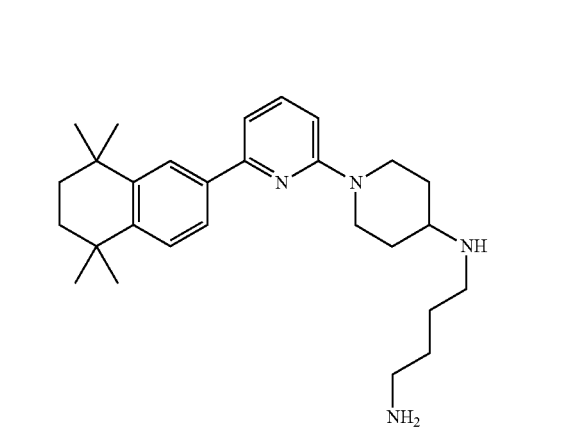
42
-continued
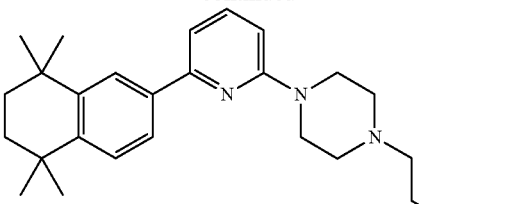
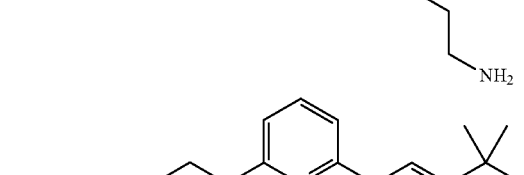
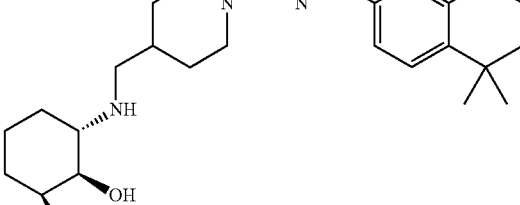
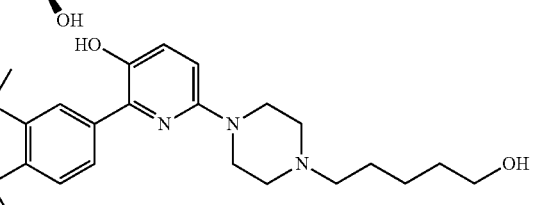
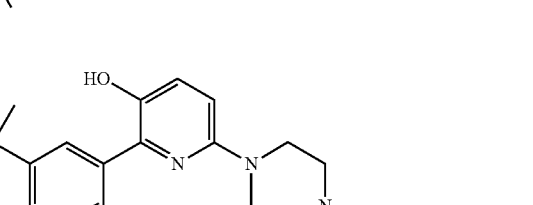
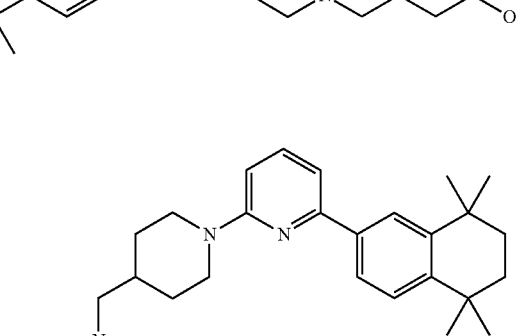
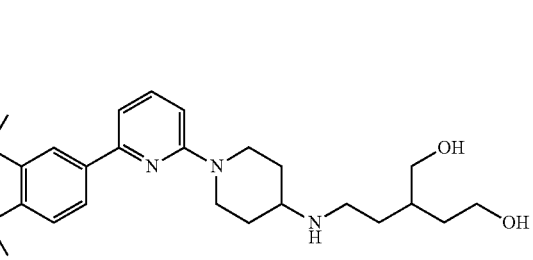

43
-continued
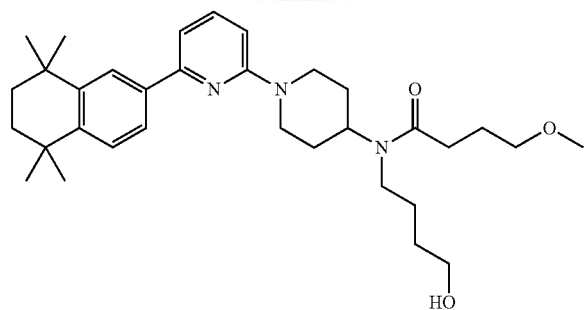
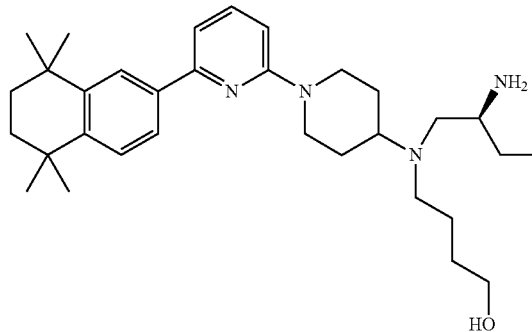
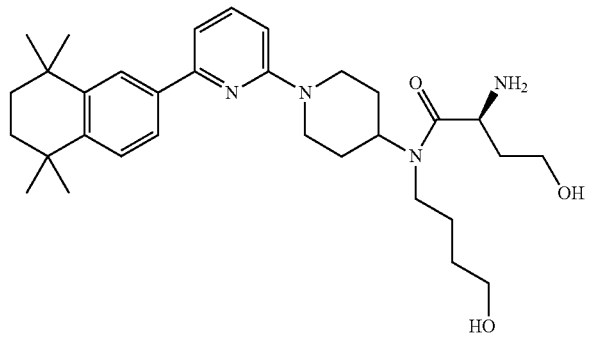
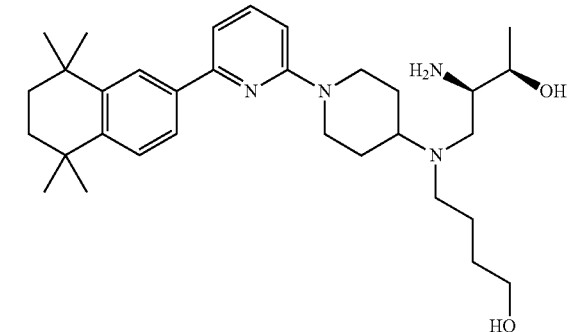
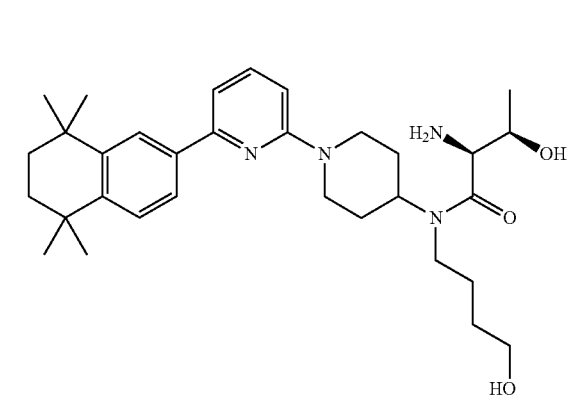
44
-continued

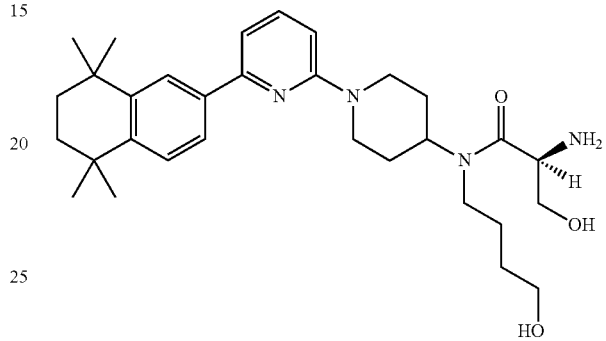
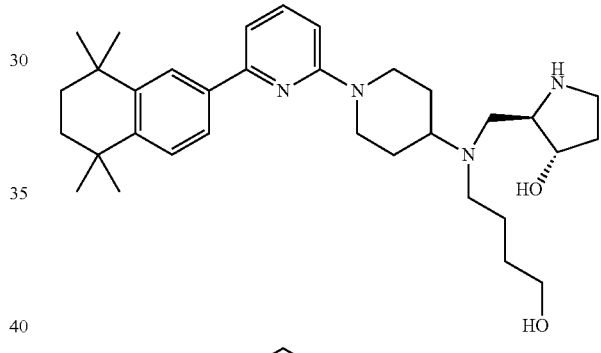
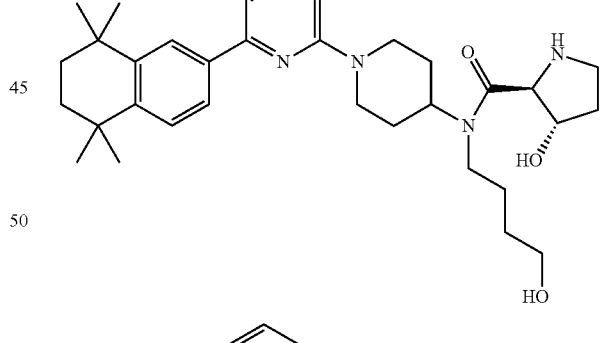
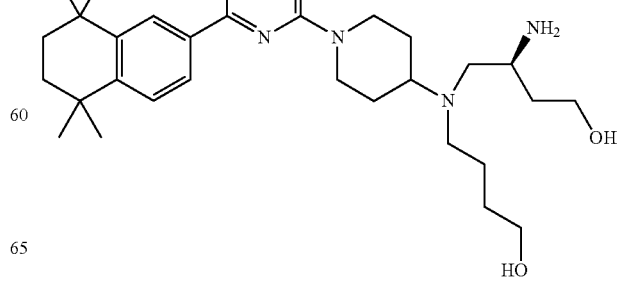

-continued

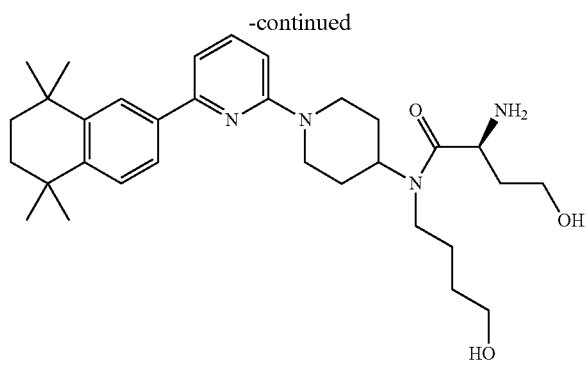

and physiologically acceptable salts, derivatives, prodrugs, solvates, tautomers and stereoisomers thereof, including mixtures thereof in all ratios.

The invention also relates to the precursors of the compounds of the formula (I), to medicaments which comprise these compounds, and to the use thereof for the treatment of diseases as described for the compounds of the formula (I).

Compounds of the formula (I) are also taken to mean the hydrates and solvates of these compounds, furthermore pharmaceutically usable derivatives.

The invention also relates to the optically active forms (stereoisomers), the enantiomers, the racemates, the diastereomers and the hydrates and solvates of these compounds. Solvates of the compounds are taken to mean adductions of inert solvent molecules onto the compounds which form owing to their mutual attractive force. Solvates are, for example, mono- or dihydrates or alcoholates.

Pharmaceutically usable derivatives are taken to mean, for example, so-called prodrug compounds.

Prodrug derivatives are taken to mean compounds of the formula (I) which have been modified by means of, for example, alkyl or acyl groups, amino acids, sugars or oligopeptides and which are rapidly cleaved in the organism to form the effective compounds according to the invention.

These also include biodegradable polymer derivatives of the compounds according to the invention, as described, for example, in Int. J. Pharm. 115, 61-67 (1995).

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:

improved treatment, healing, prevention or elimination of a disease, syndrome, condition, complaint, disorder or side effects or also the reduction in the advance of a disease, complaint or disorder.

The term "therapeutically effective amount" also encompasses the amounts which are effective for increasing normal physiological function.

The invention also relates to the use of mixtures of the compounds of the formula I, for example mixtures of two diastereomers, for example in the ratio 1:1, 1:2, 1:3, 1:4, 1:5, 1:10, 1:100 or 1:1000. These are particularly preferably mixtures of stereoisomeric compounds.

The invention furthermore relates to a process for the preparation of compounds of the formula (I) and preferred embodiments described here and disclosed compounds and physiologically acceptable salts, derivatives, prodrugs, solvates, tautomers and stereoisomers thereof, characterised in that (a) a compound of the formula (II)

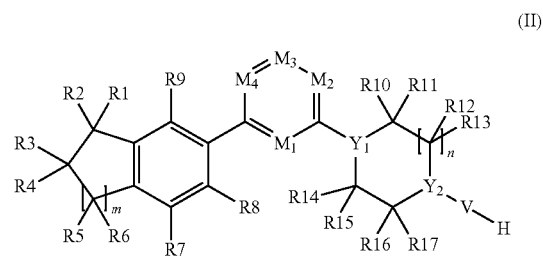

in which $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $M_1$, $M_2$, $M_3$, $M_4$, $Y_1$, $Y_2$, V, n, m and o have the meanings indicated herein, is reacted with a compound of the formula (III)

L-W                (III)

in which W has the meaning indicated herein and L denotes Cl, Br, I or a free or reactively functionally modified OH group, or (b) a compound of the formula (IV)

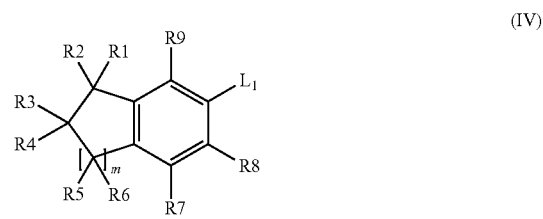

in which $R^1$, $R^2$, $R^3$, $R^4$, $R^5$, $R^6$, $R^7$, $R^8$, $R^9$ and m have the meanings indicated herein and $L_1$ denotes $B(OH)_2$ or $B(OR)_2$, where $B(OR)_2$ is a cyclic or linear boronic acid alkyl ester, is reacted with a compound of the formula (V)

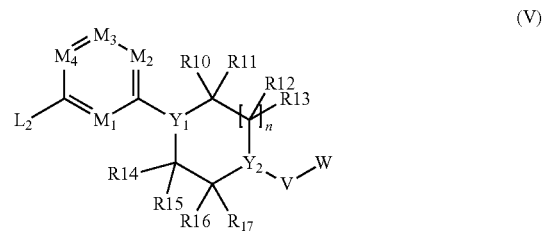

in which $R^{10}$, $R^{11}$, $R^{12}$, $R^{13}$, $R^{14}$, $R^{15}$, $R^{16}$, $R^{17}$, $M_1$, $M_2$, $M_3$, $M_4$, $Y_1$, $Y_2$, V, W, n, and o have the meanings indicated herein and $L_2$ denotes Cl, Br or I, or (c) they are liberated from one of their functional derivatives (for example containing protecting groups) by treatment with an acidic, basic, solvolysing or hydrogenolysing agent, and/or a base or acid of the formula (I) is converted into one of its salts.

The expression "carbamoyl" means "aminocarbonyl" and vice versa.

A denotes alkyl, is unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, further preferably, for example, trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

Cyclic alkyl (cycloalkyl) preferably denotes cyclopropyl, cyclobutyl, cylopentyl, cyclohexyl or cycloheptyl.

Ar denotes, for example, phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino) phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, o-, m- or p-methylsulfanylphenyl, o-, m- or p-cyanophenyl, o-, m- or p-carboxyphenyl, o-, m- or p-methoxycarbonylphenyl, o-, m- or p-formylphenyl, o-, m- or p-acetylphenyl, o-, m- or p-aminosulfonylphenyl, o-, m- or p-(morpholin-4-ylcarbonyl)phenyl, o-, m- or p-(morpholin-4-ylcarbonyl)phenyl, o-, m- or p-(3-oxomorpholin-4-yl)phenyl, o-, m- or p-(piperidinylcarbonyl)phenyl, o-, m- or p-[2-(morpholin-4-yl)ethoxy]phenyl, o-, m- or p-[3-(N,N-diethylamino)propoxy]phenyl, o-, m- or p-[3-(3-diethylaminopropyl)ureido]phenyl, o-, m- or p-(3-diethylaminopropoxycarbonylamino)phenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Irrespective of further substitutions, Het denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, indazolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4- or -5-yl, 2,1,3-benzoxadiazol-5-yl or dibenzofuranyl.

The heterocyclic radicals may also be partially or fully hydrogenated.

Irrespective of further substitutions, Het can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, further preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxo-methylenedioxy)phenyl or also 3,4-dihydro-2H-1,5-benzodioxepin-6- or -7-yl, furthermore preferably 2,3-dihydrobenzofuranyl, 2,3-dihydro-2-oxofuranyl, 3,4-dihydro-2-oxo-1H-quinazolinyl, 2,3-dihydrobenzoxazolyl, 2-oxo-2,3-dihydrobenzoxazolyl, 2,3-dihydrobenzimidazolyl, 1,3-dihydroindole, 2-oxo-1,3-dihydroindole or 2-oxo-2,3-dihydrobenzimidazolyl.

Hal preferably denotes F, Cl or Br, but also I, particularly preferably F or Cl.

Throughout the invention, all radicals which occur more than once may be identical or different, i.e. are independent of one another.

The compounds of the formula (I) may have one or more chiral centres and can therefore occur in various stereoisomeric forms. The formula (I) encompasses all these forms.

Accordingly, the invention relates, in particular, to the compounds of the formula (I), and the use thereof, in which at least one of the said radicals has one of the preferred meanings indicated above.

The compounds of the formula (I) and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

The starting compounds of the formulae (II), (III), (IV) and (V) are generally known. If they are novel, however, they can be prepared by methods known per se.

The reaction to give the compounds of the formula (I) is generally carried out in the presence of an acid-binding agent, preferably an organic base, such as DIPEA, triethylamine, dimethylaniline, pyridine or quinoline.

The addition of an alkali or alkaline earth metal hydroxide, carbonate or bicarbonate or another salt of a weak acid of the alkali or alkaline earth metals, preferably of potassium, sodium, calcium or caesium, may also be favourable.

Depending on the conditions used, the reaction time is between a few minutes and 14 days, the reaction temperature is between about −30° and 140°, normally between −10° and 90°, in particular between about 0° and about 70°.

Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to acetonitrile, dichloromethane and/or DMF.

Furthermore, free amino groups can be acylated in a conventional manner using an acid chloride or anhydride or alkylated using an unsubstituted or substituted alkyl halide, advantageously in an inert solvent, such as dichloromethane or THF, and/or in the presence of a base, such as triethylamine or pyridine, at temperatures between −60 and +30°.

The compounds of the formula (I) can furthermore be obtained by liberating them from their functional derivatives (for example containing protecting groups) by solvolysis, in particular hydrolysis, or by hydrogenolysis.

Preferred starting materials for the solvolysis or hydrogenolysis are those which contain corresponding protected amino and/or hydroxyl groups instead of one or more free amino and/or hydroxyl groups, preferably those which carry an amino-protecting group instead of an H atom bonded to an N atom, for example those which conform to the formula (I), but contain an NHR' group (in which R' is an amino-protecting group, for example BOC or CBZ) instead of an NH$_2$ group.

Preference is furthermore given to starting materials which carry a hydroxyl-protecting group instead of the H atom of a hydroxyl group, for example those which conform to the formula (I), but contain an R"O-alkyl group (in which R" is a hydroxyl-protecting group) instead of a hydroxyalkyl group.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxycarbonyl, ethoxycarbonyl, 2,2,2-trichloroethoxycarbonyl, BOC and 2-iodoethoxycarbonyl; aralkoxycarbonyl, such as CBZ ("carbobenzoxy"), 4-methoxybenzyloxycarbonyl and FMOC; and arylsulfonyl, such as Mtr, Pbf and Pmc. Preferred amino-protecting groups are BOC and Mtr, furthermore CBZ, Fmoc, benzyl and acetyl.

The term "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, tert-butoxycarbonyl, benzyl, p-nitrobenzoyl, p-toluenesulfonyl, tert-butyl and acetyl, where benzyl and tert-butyl are particularly preferred. The COOH groups in aspartic acid and glutamic acid are preferably protected in the form of their tert-butyl esters (for example Asp(OBut)).

The compounds of the formula (I) are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50°, preferably between 15 and 30° (room temperature).

The BOC, OBut, Pbf, Pmc and Mtr groups can, for example, preferably be cleaved off using TFA in dichloromethane or using approximately 3 to 5N HCl in dioxane at 15-30°, and the FMOC group can be cleaved off using an approximately 5 to 50% solution of dimethylamine, diethylamine or piperidine in DMF at 15-30°.

Hydrogenolytically removable protecting groups (for example CBZ or benzyl) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or ethers, such as THF. The hydrogenolysis is generally carried out at temperatures between about 0 and 100° and pressures between about 1 and 200 bar, preferably at 20-30° and 1-10 bar. Hydrogenolysis of the CBZ group succeeds well, for example, on 5 to 10% Pd/C in methanol or THF or using ammonium formate (instead of hydrogen) on Pd/C in methanol/DMF at 20-30°.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula (I) are for the most part prepared by conventional methods. If the compound of the formula (I) contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula (I) are likewise included. In the case of certain compounds of the formula (I), acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula (I) include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glutamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as $(C_1-C_4)$alkyl halides, for example methyl, ethyl, isopropyl and tert-butyl chloride, bromide and iodide; di$(C_1-C_4)$ alkyl sulfates, for example dimethyl, diethyl and diamyl sulfate; $(C_{10}-C_{18})$alkyl halides, for example decyl, dodecyl, lauryl, myristyl and stearyl chloride, bromide and iodide; and aryl$(C_1-C_4)$alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, phosphate, stearate, sulfate, sulfosalicylate, tartrate, thiomalate, tosylate and tromethamine, but this is not intended to represent a restriction.

Particular preference is given to hydrochloride, dihydrochloride, hydrobromide, maleate, mesylate, phosphate, sulfate and succinate.

The acid-addition salts of basic compounds of the formula (I) are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula (I) are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula (I) in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The invention furthermore relates to medicaments comprising one or more compounds of the formula (I) and preferred embodiments described here and disclosed compounds, where compounds of the formula (I) in which (a) V is absent and (b) W=C(O)—CH$_2$-Het are not excluded, and physiologically acceptable salts, derivatives, prodrugs, solvates, tautomers and stereoisomers thereof, including mixtures thereof in all ratios.

The invention furthermore relates to medicaments comprising one or more compounds of the formula (I) and preferred embodiments described here and disclosed compounds, where compounds of the formula (I) in which (a) V is absent and (b) W=C(O)—CH$_2$-Het, are not excluded, and physiologically acceptable salts, derivatives, prodrugs, solvates, tautomers and stereoisomers thereof, including mixtures thereof in all ratios, for use in the treatment of diseases which are influenced by inhibition of Sph kinase 1 by the compounds of the formula (I) and the embodiments described here and disclosed compounds. A corresponding use for the preparation of a medicament for the treatment and/or prophylaxis of the above-mentioned complaints is intended to be included.

In a preferred embodiment, medicaments comprising one or more compounds of the formula (I) and preferred embodiments described here and disclosed compounds, where compounds of the formula (I) in which (a) V is absent and (b) W=C(O)—CH$_2$-Het, are excluded, and physiologically acceptable salts, derivatives, prodrugs, solvates, tautomers and stereoisomers thereof, including mixtures thereof in all ratios, are furthermore claimed.

In a preferred embodiment, medicaments comprising one or more compounds of the formula (I) and preferred embodiments described here and disclosed compounds, where compounds of the formula (I) in which (a) V is absent and (b) W=C(O)—CH$_2$-Het, are excluded, and physiologically acceptable salts, derivatives, prodrugs, solvates, tautomers and stereoisomers thereof, including mixtures thereof in all ratios, are furthermore claimed for use in the treatment of diseases which are influenced by inhibition of Sph kinase 1 by the compounds of the formula (I) and the embodiments described here and disclosed compounds. A corresponding use for the preparation of a medicament for the treatment and/or prophylaxis of the above-mentioned complaints is intended to be included.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or drypressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula (I) and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula (I) and salts, solvates and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula (I) depends on a number of factors, including, for example, the age and weight, the precise condition that requires treatment, and its severity, the nature of the formulation and the method of administration, and is ultimately determined by the treating doctor or vet. However, an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to pharmaceutical composition comprising a therapeutically effective amount of at least one compound of the formula (I) and the preferred embodiments described here and disclosed compounds.

In a preferred embodiment, a pharmaceutical composition as described here is claimed comprising at least one additional compound selected from the group consisting of physiologically acceptable extenders, adjuvants, additives, diluents, excipients and/or additional pharmaceutically active substance, apart from the compounds of the formula (I) and the preferred embodiments described here and disclosed compounds.

The invention also relates to a kit comprising a therapeutically effective amount of at least one compound of the formula (I) and the preferred embodiments described here and disclosed compounds and/or at least one pharmaceutical composition as described here and a therapeutically effective amount of at least one further pharmacologically active substance, apart from the compounds of the formula (I) and the preferred embodiments described here and disclosed compounds.

The kit comprises suitable containers, such as boxes, individual bottles, bags or ampoules. The set may, for example, comprise separate ampoules, each containing an effective amount of a compound of the formula (I) and/or pharmaceutically usable derivatives, solvates, tautomers and stereoisomers thereof, including mixtures thereof in all ratios, and an effective amount of a further medicament active ingredient in dissolved or lyophilised form.

Use

The present compounds are suitable as pharmaceutical active ingredients for mammals, especially for humans, in the treatment of sphingosine kinase-induced diseases. These diseases include the proliferation of tumour cells, pathological neovascularisation (or angiogenesis) which promotes the growth of solid tumours, ocular neovascularisation (diabetic retinopathy, age-induced macular degeneration and the like) and inflammation (psoriasis, rheumatoid arthritis and the like).

The present invention encompasses the use of the compounds of the formula (I) and/or physiologically acceptable salts and solvates thereof for the preparation of a medicament for the treatment or prevention of cancer. Preferred carcinomas for the treatment originate from the group cerebral carcinoma, urogenital tract carcinoma, carcinoma of the lymphatic system, stomach carcinoma, laryngeal carcinoma and lung carcinoma. A further group of preferred forms of cancer are monocytic leukaemia, lung adenocarcinoma, small-cell lung carcinomas, prostate cancer, intestinal cancer, pancreatic cancer, ovarian carcinoma, renal cancer, liver carcinoma, glioblastomas and breast carcinoma.

Likewise encompassed is the use of the compounds according to the invention and/or physiologically acceptable salts and solvates thereof for the preparation of a medicament for the treatment or prevention of a disease in which angiogenesis is implicated.

Such a disease in which angiogenesis is implicated is an ocular disease, such as retinal vascularisation, diabetic retinopathy, age-induced macular degeneration and the like.

The use of compounds of the formula (I) and/or physiologically acceptable salts and solvates thereof for the preparation of a medicament for the treatment or prevention of inflammatory diseases also falls within the scope of the present invention. Examples of such inflammatory diseases include rheumatoid arthritis, psoriasis, contact dermatitis, delayed hypersensitivity reaction and the like.

Also encompassed is the use of the compounds of the formula (I) and/or physiologically acceptable salts and solvates thereof for the preparation of a medicament for the treatment or prevention of a disease or condition in a mammal, in which to this method a therapeutically effective amount of a compound according to the invention is administered to a sick mammal in need of such treatment. The therapeutic amount varies according to the specific disease and can be determined by the person skilled in the art without undue effort.

The present invention also encompasses the use of compounds of the formula (I) and/or physiologically acceptable salts and solvates thereof for the preparation of a medicament for the treatment or prevention of retinal vascularisation.

Methods for the treatment or prevention of ocular diseases, such as diabetic retinopathy and age-induced macular degeneration, are likewise part of the invention. The use for the treatment or prevention of inflammatory diseases, such as rheumatoid arthritis, psoriasis, contact dermatitis and delayed hypersensitivity reaction, as well as the treatment or prevention of bone pathologies from the group osteosarcoma, osteoarthritis and rickets, likewise falls within the scope of the present invention.

Besides the compounds of the formula (I), precursors thereof can also be used for the treatment of the said diseases.

The compounds of the formula (I) can be administered to patients for the treatment of cancer, in particular fast-growing tumours.

The invention thus relates to the use of compounds of the formula (I), and pharmaceutically usable derivatives, solvates, tautomers and stereoisomers thereof, including mixtures thereof in all ratios, for the preparation of a medicament for the treatment of diseases in which the inhibition, regulation and/or modulation of kinase signal transduction plays a role.

Preference is given here to Sph kinase.

Preference is given to the use of compounds of the formula (I), and pharmaceutically usable derivatives, solvates, tautomers and stereoisomers thereof, including mixtures thereof in all ratios, for the preparation of a medicament for the treatment of diseases which are influenced by inhibition of SphK1 by the compounds of the formula (I) and the preferred embodiments described here and disclosed compounds.

The diseases to be treated are preferably selected from the group hyperproliferative disease, inflammatory disease, angiogenic disease.

The hyperproliferative disease is preferably selected from the group cancer (tumour disease), atherosclerosis, restenosis, proliferative disease of the mesangial cells, psoriasis.

The tumour disease is preferably selected from the group tumour of the squamous epithelium, the bladder, the stomach, the kidneys, of head and neck, the oesophagus, the cervix, the thyroid, the intestine, the liver, the brain, the prostate, the urogenital tract, the lymphatic system, the stomach, the larynx, the lung, the skin, monocytic leukaemia, lung adenocarcinoma, small-cell lung carcinoma, pancreatic cancer, glioblastoma, breast carcinoma, acute myeloid leukaemia, chronic myeloid leukaemia, acute lymphatic leukaemia, chronic lymphatic leukaemia, Hodgkin's lymphoma, non-Hodgkin's lymphoma.

The proliferative disease of the mesangial cells is preferably selected from the group glomerulonephritis, diabetic nephropathy, malignant nephrosclerosis, thrombotic microangiopathy syndrome, transplant rejection, glomerulopathy.

The inflammatory disease is preferably selected from the group inflammatory bowel disease, arthritis, atherosclersosis, asthma, allergies, inflammatory kidney diseases, multiple sclerosis, chronic obstructive pulmonary disease, inflammatory skin diseases, pardontal diseases, psoriasis, T-cell-promoted immune disease.

The inflammatory bowel disease is preferably selected from the group ulcerative colitis, Crohn's disease, non-specific colitis.

The T-cell-promoted immune disease is preferably selected from the group allergic encephalomyelitis, allergic neuritis, transplant rejection, graft-versus-host reaction, myocarditis, thyroiditis, nephritis, systemic lupus erythematosus, insulin-dependent diabetes mellitus.

The arthritis disease is preferably selected from the group rheumatoid arthritis, osteoarthritis, Caplan's syndrome, Felty's syndrome, Sjogren's syndrome, spondylitis ankylosans, Still's disease, chondrocalcinosis, metabolic arthritis, rheumatic fever, Reiter's disease, Wissler's syndrome.

The inflammatory kidney disease is preferably selected from the group glomerulonephritis, glomerular injury, nephrotic syndrome, interstitial nephritis, lupus nephritis, Goodpasture's syndrome, Wegener's granulomatosis, renal vasculitis, IgA nephropathy, idiopatic glomerular disease.

The inflammatory skin disease is preferably selected from the group psoriasis, atopic dermatitis, contact sensitivity, acne.

The angiogenic disease is preferably selected from the group diabetic retinopathy, arthritis, cancer, psoriasis, Kaposi's sarcoma, haemangioma, myocardial angiogenesis, atherosclerotic plaque neovascularisation, angiogenic eye diseases, choroidal neovascularisation, retrolental fibroplasia, macular degeneration, corneal transplant rejection, rubeosis iridis, neuroscular glaucoma, Oster Webber syndrome.

The invention furthermore relates to medicaments comprising one or more compounds of the formula (I) and preferred embodiments described here and disclosed compounds, where compounds of the formula (I) in which (a) V is absent and (b) W=C(O)—CH$_2$-Het, are not excluded, and physiologically acceptable salts, derivatives, prodrugs, solvates, tautomers and stereoisomers thereof, including mixtures thereof in all ratios, for use in the treatment of diseases which are influenced by inhibition of Sph kinase 1 by the compounds of the formula (I) and the preferred embodiments described here and disclosed compounds, where the diseases to be treated are selected from the group consisting of: "hyperproliferative disease, inflammatory disease, angiogenic disease, fibrotic disease of the lung, kidney, liver and the heart, cancer (tumour disease), atherosclerosis, restenosis, proliferative disease of the mesangial cells, psoriasis, tumour of the squamous epithelium, the bladder, the stomach, the kidneys, of head and neck, the oesophagus, the cervix, the thyroid, the intestine, the liver, the brain, the prostate, the urogenital tract, the lymphatic system, the stomach, the larynx, the lung, the skin, monocytic leukaemia, lung adenocarcinoma, small-cell lung carcinoma, pancreatic cancer, glioblastoma, breast carcinoma, acute myeloid leukaemia, chronic myeloid leukaemia, acute lymphatic leukaemia, chronic lymphatic leukaemia, Hodgkin's lymphoma, non-Hodgkin's lymphoma, glomerulonephritis, diabetic nephropathy, malignant nephrosclerosis, thrombotic microangiopathy syndrome, transplant rejection, glomerulopathy, inflammatory bowel disease, arthritis, asthma, allergies, inflammatory kidney diseases, multiple sclerosis, chronic obstructive pulmonary disease, inflammatory skin diseases, pardontal diseases, T-cell-promoted immune disease, ulcerative colitis, Crohn's disease, non-specific colitis, allergic encephalomyelitis, allergic neuritis, transplant rejection, graft-versus-host reaction, myocarditis, thyroiditis, nephritis, systemic lupus erythematosus, insulin-dependent diabetes mellitus, rheumatoid arthritis, osteoarthritis, Caplan's syndrome, Felty's syndrome, Sjogren's syndrome, spondylitis ankylosans, Still's disease, chondrocalcinosis, metabolic arthritis, rheumatic fever, Reiter's disease, Wissler's syndrome, glomerulonephritis, glomerular injury, nephrotic syndrome, interstitial nephritis, lupus nephritis, Good-pasture's syndrome, Wegener's granulomatosis, renal vasculitis, IgA nephropathy, idiopatic glomerular disease, atopic dermatitis, contact sensitivity, acne, diabetic retinopathy, Kaposi's sarcoma, haemangioma, myocardial angiogenesis, atherosclerotic plaque neovascularisation, angiogenic eye diseases, choroidal neovascularisation, retrolental fibroplasia, macular degeneration, corneal transplant rejection, rubeosis iridis, neuroscular glaucoma, Oster Webber syndrome". A corresponding use for the preparation of a medicament for the treatment and/or prophylaxis of the above-mentioned complaints and also a method for the treatment of the said diseases comprising the administration of one or more compounds of the formula (I) and the preferred embodiments described here and disclosed compounds to a patient in need of such an administration are also intended to be covered here.

In a preferred embodiment, medicaments are furthermore claimed which comprise one or more compounds of the formula (I) and preferred embodiments described here and disclosed compounds, where compounds of the formula (I) in which (a) V is absent and (b) W=C(O)—CH$_2$-Het, are excluded, and physiologically acceptable salts, derivatives, prodrugs, solvates, tautomers and stereoisomers thereof, including mixtures thereof in all ratios, for use in the treatment of diseases which are influenced by inhibition of Sph kinase 1 by the compounds of the formula (I) and the preferred embodiments described here and disclosed compounds, where the diseases to be treated are selected from the group consisting of: "hyperproliferative disease, inflammatory disease, angiogenic disease, fibrotic disease of the lung, kidney, liver and the heart, cancer (tumour disease), atherosclerosis, restenosis, proliferative disease of the mesangial cells, psoriasis, tumour of the squamous epithelium, the bladder, the stomach, the kidneys, of head and neck, the oesophagus, the cervix, the thyroid, the intestine, the liver, the brain, the prostate, the urogenital tract, the lymphatic system, the stomach, the larynx, the lung, the skin, monocytic leukaemia, lung adenocarcinoma, small-cell lung carcinoma, pancreatic cancer, glioblastoma, breast carcinoma, acute myeloid leukaemia, chronic myeloid leukaemia, acute lymphatic leukaemia, chronic lymphatic leukaemia, Hodgkin's lymphoma, non-Hodgkin's lymphoma, glomerulonephritis, diabetic nephropathy, malignant nephrosclerosis, thrombotic microangiopathy syndrome, transplant rejection, glomerulopathy, inflammatory bowel disease, arthritis, asthma, allergies, inflammatory kidney diseases, multiple sclerosis, chronic obstructive pulmonary disease, inflammatory skin diseases, pardontal diseases, T-cell-promoted immune disease, ulcerative colitis, Crohn's disease, non-specific colitis, allergic encephalomyelitis, allergic neuritis, transplant rejection, graft-versus-host reaction, myocarditis, thyroiditis, nephritis, systemic lupus erythematosus, insulin-dependent diabetes mellitus, rheumatoid arthritis, osteoarthritis, Caplan's syndrome, Felty's syndrome, Sjogren's syndrome, spondylitis ankylosans, Still's disease, chondrocalcinosis, metabolic arthritis, rheumatic fever, Reiter's disease, Wissler's syndrome, glomerulonephritis, glomerular injury, nephrotic syndrome, interstitial nephritis, lupus nephritis, Goodpasture's syndrome, Wegener's granulomatosis, renal vasculitis, IgA nephropathy, idiopatic glomerular disease, atopic dermatitis, contact sensitivity, acne, diabetic retinopathy, Kaposi's sarcoma, haemangioma, myocardial angiogenesis, atherosclerotic plaque neovascularisation, angiogenic eye diseases, choroidal neovascularisation, retrolental fibroplasia, macular degeneration, corneal transplant rejection, rubeosis iridis, neuroscular glaucoma, Oster Webber syndrome". A corresponding use for the preparation of a medicament for the treatment and/or prophylaxis of the above-mentioned complaints and also a method for the treatment of the said diseases comprising the administration of one or more compounds of the formula (I) and the preferred embodiments described here and disclosed compounds to a patient in need of such an administration are also intended to be included here.

In a preferred embodiment, a medicament of this type comprises at least one additional pharmacologically active substance (therapeutic agent, medicament, ingredient).

In a furthermore preferred embodiment, the medicament is used before and/or during and/or after treatment with at least one additional pharmacologically active substance.

The disclosed compounds of the formula I can be administered in combination with other known therapeutic agents (pharmacologically active substances), including anticancer agents. As used here, the term "anticancer agent" relates to any agent which is administered to a patient with cancer for the purposes of treating the cancer.

The anti-cancer treatment defined herein may be applied as a sole therapy or may involve, in addition to the compound of the invention, conventional surgery or radiotherapy or chemotherapy. Such chemotherapy may include one or more of the following categories of anti-tumour agents:

(i) antiproliferative/antineoplastic/DNA-damaging agents and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside, hydroxyurea and gemcitabine); antitumour antibiotics (for example anthracyclines, like adriamycin, bleomycin, doxorubicin, daunomycin, epirubicin, idarubicin, mitomycin-C, dactinomycin and mithramycin); antimitotic agents (for example vinca alkaloids, like vincristine, vinblastine, vindesine and vinorelbine, and taxoids, like taxol and taxotere); topoisomerase inhibitors (for example epipodophyllotoxins, like etoposide and teniposide, amsacrine, topotecan, irinotecan and camptothecin) and cell-differentiating agents (for example all-trans-retinoic acid, 13-cis-retinoic acid and fenretinide);

(ii) cytostatic agents, such as antioestrogens (for example tamoxifen, toremifene, raloxifene, droloxifene and iodoxyfene), oestrogen receptor downregulators (for example fulvestrant), antiandrogens (for example bicalutamide, flutamide, nilutamide and cyproterone acetate), LHRH antagonists or LHRH agonists (for example goserelin, leuprorelin and buserelin), progesterones (for example megestrol acetate), aromatase inhibitors (for example as anastrozole, letrozole, vorazole and exemestane) and inhibitors of 5α-reductase, such as finasteride;

(iii) agents which inhibit cancer cell invasion (for example metallo-proteinase inhibitors, like marimastat, and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors, such as N-(3-chloro-4-fluorophenyl)-7-methoxy-6-(3-morpholinopropoxy) quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy) quinazolin-4-amine (Cl 1033)), for example inhibitors of the platelet-derived growth factor family and for example inhibitors of the hepatocyte growth factor family;

(v) antiangiogenic agents, such as those which inhibit the effects of vascular endothelial growth factor, (for example the anti-vascular endothelial cell growth factor antibody bevacizumab [Avastin™], compounds such as those disclosed in published international patent applications WO 97/22596, WO 97/30035, WO 97/32856 and WO 98/13354) and compounds that work by other mechanisms (for example linomide, inhibitors of integrin αvβ3 function and angiostatin);

(vi) vessel-damaging agents, such as combretastatin A4 and compounds disclosed in international patent applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-Ras antisense;

(viii) gene therapy approaches, including, for example, approaches for replacement of aberrant genes, such as aberrant p53 or aberrant BRCA1 or BRCA2, GDEPT (gene-directed enzyme pro-drug therapy) approaches, such as those using cytosine deaminase, thymidine kinase or a bacterial nitroreductase enzyme, and approaches for increasing patient tolerance to chemotherapy or radiotherapy, such as multi-drug resistance gene therapy; and (ix) immunotherapy approaches, including, for example, ex-vivo and in-vivo approaches for increasing the immunogenicity of patient tumour cells, such as transfection with cytokines, such as interleukin 2, interleukin 4 or granulocyte-macrophage colony stimulating factor, approaches for decreasing T-cell anergy, approaches using transfected immune cells, such as cytokine-transfected dendritic cells, approaches using cytokine-transfected tumour cell lines, and approaches using anti-idiotypic antibodies.

The medicaments from Table 1 below are preferably, but not exclusively, combined with the compounds of the formula (I).

TABLE 1

| | | |
|---|---|---|
| Alkylating agents | Cyclophosphamide | Lomustine |
| | Busulfan | Procarbazine |
| | Ifosfamide | Altretamine |
| | Melphalan | Estramustine phosphate |
| | Hexamethylmelamine | Mechloroethamine |
| | Thiotepa | Streptozocin |
| | chloroambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin (Aetema) |
| | Carboxyphthalatoplatinum | Satraplatin (Johnson Matthey) |
| | Tetraplatin | BBR-3464 (Hoffrnann-La Roche) |
| | Ormiplatin | SM-11355 (Sumitomo) |
| | Iproplatin | AP-5280 (Access) |
| Antimetabolites | Azacytidine | Tomudex |
| | Gemcitabine | Trimetrexate |
| | Capecitabine | Deoxycoformycin |
| | 5-fluorouracil | Fludarabine |
| | Floxuridine | Pentostatin |
| | 2-chlorodesoxyadenosine | Raltitrexed |
| | 6-Mercaptopurine | Hydroxyurea |
| | 6-Thioguanine | Decitabine (SuperGen) |
| | Cytarabine | Clofarabine (Bioenvision) |
| | 2-fluorodesoxycytidine | Irofulven (MGI Pharrna) |
| | Methotrexate | DMDC (Hoffmann-La Roche) |
| | Idatrexate | Ethynylcytidine (Taiho) |
| Topoisomerase inhibitors | Amsacrine | Rubitecan (SuperGen) |
| | Epirubicin | Exatecan mesylate (Daiichi) |
| | Etoposide | Quinamed (ChemGenex) |
| | Teniposide or mitoxantrone | Gimatecan (Sigma-Tau) |
| | Irinotecan (CPT-11) | Diflomotecan (Beaufour-Ipsen) |
| | 7-ethyl-10-hydroxycamptothecin | TAS-103 (Taiho) |
| | Topotecan | Elsamitrucin (Spectrum) |
| | Dexrazoxanet (TopoTarget) | J-107088 (Merck & Co) |
| | Pixantrone (Novuspharrna) | BNP-1350 (BioNumerik) |
| | Rebeccamycin analogue (Exelixis) | CKD-602 (Chong Kun Dang) |
| | BBR-3576 (Novuspharrna) | KW-2170 (Kyowa Hakko) |
| Antitumour antibiotics | Dactinomycin (Actinomycin D) | Amonafide |
| | Doxorubicin (Adriamycin) | Azonafide |
| | Deoxyrubicin | Anthrapyrazole |
| | Valrubicin | Oxantrazole |
| | Daunorubicin (Daunomycin) | Losoxantrone |
| | Epirubicin | Bleomycin sulfate (Blenoxan) |
| | Therarubicin | Bleomycinic acid |
| | Idarubicin | Bleomycin A |
| | Rubidazon | Bleomycin B |
| | Plicamycinp | Mitomycin C |
| | Porfiromycin | MEN-10755 (Menarini) |
| | Cyanomorpholinodoxorubicin | GPX-100 (Gem Pharmaceuticals |
| | Mitoxantron (Novantron) | |
| Antimitotic agents | Paclitaxel | SB 408075 (GlaxoSmithKline) |
| | Docetaxel | E7010 (Abbott) |
| | Colchicine | PG-TXL (Cell Therapeutics) |
| | Vinblastine | IDN 5109 (Bayer) |
| | Vincristine | A 105972 (Abbott) |
| | Vinorelbine | A 204197 (Abbott) |
| | Vindesine | LU 223651 (BASF) |
| | Dolastatin 10 (NCI) | D 24851 (ASTA Medica) |
| | Rhizoxin (Fujisawa) | ER-86526 (Eisai) |
| | Mivobulin (Warner-Lambert) | Combretastatin A4 (BMS) |
| | Cemadotin (BASF) | Isohomohalichondrin-B |
| | RPR 109881A (Aventis) | (PharmaMar) |
| | TXD 258 (Aventis) | ZD 6126 (AstraZeneca) |
| | Epothilone B (Novartis) | PEG-Paclitaxel (Enzon) |
| | T 900607 (Tularik) | AZ10992 (Asahi) |
| | T 138067 (Tularik) | !DN-5109 (Indena) |
| | Cryptophycin 52 (Eli Lilly) | AVLB (Prescient NeuroPharmaMar) |
| | Vinflunine (Fabre) | Azaepothilon B (BMS) |
| | Auristatin PE (Teikoku Hormorone) | BNP-7787 (BioNumerik) |
| | BMS 247550 (BMS) | CA-4-prodrug (OXiGENE) |
| | BMS 184476 (BMS) | Dolastatin-10 (NrH) |
| | BMS 188797 (BMS) | CA-4 (OXiGENE) |
| | Taxoprexin (Protarga) | |
| Aromatase inhibitors | Aminoglutethimide | Exemestan |
| | Letrozole | Atamestan (BioMedicines) |
| | Anastrazole | YM-511 (Yamanouchi) |
| | Formestan | |

TABLE 1-continued

| | | |
|---|---|---|
| Thymidylate synthase inhibitors | Pemetrexed (Eli Lilly) ZD-9331 (BTG) | Nolatrexed (Eximias) CoFactor ™ (BioKeys) |
| DNA antagonists | Trabectedin (PharmaMar) Glufosfamide (Baxter International) Albumin + 32P (Isotope Solutions) Thymectacin (NewBiotics) Edotreotid (Novartis) | Mafosfamide (Baxter International) Apaziquone (Spectrum Pharmaceuticals) O6-benzylguanine (Paligent) |
| Farnesyl transferase inhibitors | Arglabin (NuOncology Labs) Ionafarnib (Schering-Plough) BAY-43-9006 (Bayer) | Tipifarnib (Johnson & Johnson Perillyl alcohol (DOR BioPharma) |
| Pump inhibitors | CBT-1 (CBA Pharma) Tariquidar (Xenova) MS-209 (Schering AG) | Zosuquidar trihydrochloride (Eli Lilly) Biricodar dicitrate (Vertex) |
| Histone acetyl transferase inhibitors | Tacedinaline (Pfizer) SAHA (Aton Pharma) MS-275 (Schering AG) | Pivaloyloxymethyl butyrate (Titan) Depsipeptide (Fujisawa) |
| Metalloproteinase inhibitors | Neovastat (Aeterna Laboratories) Marimastat (British Biotech) | CMT-3 (CollaGenex) BMS-275291 (Celltech) |
| Ribonucleoside reductase inhibitors | Gallium maltolate (Titan) Triapin (Vion) | Tezacitabine (Aventis) Didox (Molecules for Health) |
| TNF-alpha agonists/ antagonists | Virulizin (Lorus Therapeutics) CDC-394 (Celgene) | Revimid (Celgene) |
| Endothelin-A receptor antagonists | Atrasentan (Abbot) ZD-4054 (AstraZeneca) | YM-598 (Yamanouchi) |
| Retinoic acid receptor agonists | Fenretinide (Johnson & Johnson) LGD-1550 (Ligand) | Alitretinoin (Ligand) |
| Immunomodulators | Interferon Oncophage (Antigenics) GMK (Progenics) Adenocarcinoma vaccine (Biomira) CTP-37 (AVI BioPharma) JRX-2 (Immuno-Rx) PEP-005 (Peplin Biotech) Synchrovax vaccines (CTL Immuno) Melanoma vaccine (CTL Immuno) p21-RAS vaccine (GemVax) | Dexosome therapy (Anosys) Pentrix (Australian Cancer Technology) JSF-154 (Tragen) Cancer vaccine (Intercell) Norelin (Biostar) BLP-25 (Biomira) MGV (Progenics) !3-Alethin (Dovetail) CLL-Thera (Vasogen) |
| Hormonal and antihormonal agents | Oestrogens Conjugated oestrogens Ethynyloestradiol chlorotrianisene Idenestrol Hydroxyprogesterone caproate Medroxyprogesterone Testosterone Testosterone propionate Fluoxymesterone Methyltestosterone Diethylstilbestrol Megestrol Tamoxifen Toremofin Dexamethasone | Prednisone Methylprednisolone Prednisolone Aminoglutethimide Leuprolide Goserelin Leuporelin Bicalutamide Flutamide Octreotide Nilutamide Mitotan P-04 (Novogen) 2-Methoxyoestradiol (EntreMed) Arzoxifen (Eli Lilly) |
| Photodynamic agents | Talaporfin (Light Sciences) Theralux (Theratechnologies) Motexafin-Gadolinium (Pharmacyclics) | Pd-Bacteriopheophorbid (Yeda) Lutetium-Texaphyrin (Pharmacyclics) Hypericin |
| Tyrosine kinase inhibitors | Imatinib (Novartis) Leflunomide(Sugen/Pharmacia) ZDI839 (AstraZeneca) Erlotinib (Oncogene Science) Canertjnib (Pfizer) Squalamine (Genaera) SU5416 (Pharmacia) SU6668 (Pharmacia) ZD4190 (AstraZeneca) ZD6474 (AstraZeneca) Vatalanib (Novartis) PKI166 (Novartis) GW2016 (GlaxoSmithKline) EKB-509 (Wyeth) EKB-569 (Wyeth) | Kahalide F (PharmaMar) CEP-701 (Cephalon) CEP-751 (Cephalon) MLN518 (Millenium) PKC412 (Novartis) Phenoxodiol O Trastuzumab (Genentech) C225 (ImClone) rhu-Mab (Genentech) MDX-H210 (Medarex) 2C4 (Genentech) MDX-447 (Medarex) ABX-EGF (Abgenix) IMC-1C11 (ImClone) |

TABLE 1-continued

| | | |
|---|---|---|
| Various agents | SR-27897 (CCK-A inhibitor, Sanofi-Synthelabo) | BCX-1777 (PNP inhibitor, BioCryst) |
| | Tocladesine (cyclic AMP agonist, Ribapharm) | Ranpirnase (ribonuclease stimulant, Alfacell) |
| | Alvocidib (CDK inhibitor, Aventis) | Galarubicin (RNA synthesis inhibitor, Dong-A) |
| | CV-247 (COX-2 inhibitor, Ivy Medical) | Tirapazamine (reducing agent, SRI International) |
| | P54 (COX-2 inhibitor, Phytopharm) | N-Acetylcysteine (reducing agent, Zambon) |
| | CapCell ™ (CYP450 stimulant, Bavarian Nordic) | R-Flurbiprofen (NF-kappaB inhibitor, Encore) |
| | GCS-IOO (gal3 antagonist, GlycoGenesys) | 3CPA (NF-kappaB inhibitor, Active Biotech) |
| | G17DT immunogen (gastrin inhibitor, Aphton) | Seocalcitol (vitamin D receptor agonist, Leo) |
| | Efaproxiral (oxygenator, Allos Therapeutics) | 131-I-TM-601 (DNA antagonist, TransMolecular) |
| | PI-88 (heparanase inhibitor, Progen) | Eflornithin (ODC inhibitor, ILEX Oncology) |
| | Tesmilifen (histamine antagonist, YM BioSciences) | Minodronic acid (osteoclast inhibitor, Yamanouchi) |
| | Histamine (histamine H2 receptor agonist, Maxim) | Indisulam (p53 stimulant, Eisai) |
| | Tiazofurin (IMPDH inhibitor, Ribapharm) | Aplidin (PPT inhibitor, PharmaMar) |
| | Cilengitide (integrin antagonist Merck KGaA) | Rituximab (CD20 antibody, Genentech) |
| | SR-31747 (IL-1 antagonist, Sanofi-Synthelabo) | Gemtuzumab (CD33 antibody, Wyeth Ayerst) |
| | CCI-779 (mTOR kinase inhibitor, Wyeth) | PG2 (haematopoiesis promoter, Pharmagenesis) |
| | Exisulind (PDE-V inhibitor, Cell Pathways) | Immunol ™ (triclosan mouthwash, Endo) |
| | CP-461 (PDE-V inhibitor, Cell Pathways) | Triacetyluridine (uridine prodrug, Wellstat) |
| | AG-2037 (GART inhibitor, Pfizer) | SN-4071 (sarcoma agent, Signature BioScience) |
| | WX-UK1 (plasminogen activator inhibitor, Wilex) | TransMID-107 ™ (immunotoxin, KS Biomedix) |
| | PBI-1402 (PMN stimulant, ProMetic LifeSciences) | PCK-3145 (apoptosis promote Procyon) |
| | Bortezomib (proteasome inhibitor Millennium) | Doranidazole (apoptosis promoter, Pola) |
| | SRL-172 (T-cell stimulant, SR Pharma) | CHS-828 (cytotoxic agent, Leo) |
| | TLK-286 (glutathione-S transferase inhibitor, Telik) | trans-Retinic acid (differentiator, NIH) |
| | PT-100 (growth factor agonist, Point Therapeutics) | MX6 (apoptosis promoter, MAXIA) |
| | Midostaurin (PKC inhibitor, Novartis) | Apomine (apoptosis promoter, ILEX Oncology) |
| | Bryostatin-1 (PKC stimulant, GPC Biotech) | Urocidin (apoptosis promoter, Bioniche) |
| | CDA-II (apoptosis promoter, Everlife) | Ro-31-7453 (apoptosis promoter, La Roche) |
| | SDX-101 (apoptosis promoter, Salmedix) | Brostallicin (apoptosis promoter, Pharmacia) |
| | Ceflatonin (apoptosis promoter, ChemGenex) | |
| Alkylating agents | Cyclophosphamide | Lomustine |
| | Busulfan | Procarbazine |
| | Ifosfamide | Altretamine |
| | Melphalan | Estramustine phosphate |
| | Hexamethylmelamine | Mechloroethamine |
| | Thiotepa | Streptozocin |
| | chloroambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin (Aetema) |
| | Carboxyphthalatoplatinum | Satraplatin (Johnson Matthey) |
| | Tetraplatin | BBR-3464 (Hoffrnann-La Roche) |
| | Ormiplatin | SM-11355 (Sumitomo) |
| | Iproplatin | AP-5280 (Access) |
| Antimetabolites | Azacytidine | Tomudex |
| | Gemcitabine | Trimetrexate |
| | Capecitabine | Deoxycoformycin |
| | 5-fluorouracil | Fludarabine |
| | Floxuridine | Pentostatin |
| | 2-chlorodesoxyadenosine | Raltitrexed |

TABLE 1-continued

| | | |
|---|---|---|
| | 6-Mercaptopurine | Hydroxyurea |
| | 6-Thioguanine | Decitabine (SuperGen) |
| | Cytarabine | Clofarabine (Bioenvision) |
| | 2-fluorodesoxycytidine | Irofulven (MGI Pharma) |
| | Methotrexate | DMDC (Hoffmann-La Roche) |
| | Idatrexate | Ethynylcytidine (Taiho) |
| Topoisomerase inhibitors | Amsacrine | Rubitecan (SuperGen) |
| | Epirubicin | Exatecan mesylate (Daiichi) |
| | Etoposide | Quinamed (ChemGenex) |
| | Teniposide or mitoxantrone | Gimatecan (Sigma-Tau) |
| | Irinotecan (CPT-11) | Diflomotecan (Beaufour-Ipsen) |
| | 7-ethyl-10-hydroxycamptothecin | TAS-103 (Taiho) |
| | Topotecan | Elsamitrucin (Spectrum) |
| | Dexrazoxanet (TopoTarget) | J-107088 (Merck & Co) |
| | Pixantrone (Novuspharrna) | BNP-1350 (BioNumerik) |
| | Rebeccamycin analogue (Exelixis) | CKD-602 (Chong Kun Dang) |
| | | KW-2170 (Kyowa Hakko) |
| | BBR-3576 (Novuspharrna) | |
| Antitumour antibiotics | Dactinomycin (Actinomycin D) | Amonafide |
| | Doxorubicin (Adriamycin) | Azonafide |
| | Deoxyrubicin | Anthrapyrazole |
| | Valrubicin | Oxantrazole |
| | Daunorubicin (Daunomycin) | Losoxantrone |
| | Epirubicin | Bleomycin sulfate (Blenoxan) |
| | Therarubicin | Bleomycinic acid |
| | Idarubicin | Bleomycin A |
| | Rubidazon | Bleomycin B |
| | Plicamycinp | Mitomycin C |
| | Porfiromycin | MEN-10755 (Menarini) |
| | Cyanomorpholinodoxorubicin | GPX-100 (Gem Pharmaceuticals) |
| | Mitoxantron (Novantron) | |
| Antimitotic agents | Paclitaxel | SB 408075 (GlaxoSmithKline) |
| | Docetaxel | E7010 (Abbott) |
| | Colchicine | PG-TXL (Cell Therapeutics) |
| | Vinblastine | IDN 5109 (Bayer) |
| | Vincristine | A 105972 (Abbott) |
| | Vinorelbine | A 204197 (Abbott) |
| | Vindesine | LU 223651 (BASF) |
| | Dolastatin 10 (NCI) | D 24851 (ASTA Medica) |
| | Rhizoxin (Fujisawa) | ER-86526 (Eisai) |
| | Mivobulin (Warner-Lambert) | Combretastatin A4 (BMS) |
| | Cemadotin (BASF) | Isohomohalichondrin-B |
| | RPR 109881A (Aventis) | (PharmaMar) |
| | TXD 258 (Aventis) | ZD 6126 (AstraZeneca) |
| | Epothilone B (Novartis) | PEG-Paclitaxel (Enzon) |
| | T 900607 (Tularik) | AZ10992 (Asahi) |
| | T 138067 (Tularik) | !DN-5109 (Indena) |
| | Cryptophycin 52 (Eli Lilly) | AVLB (Prescient NeuroPharma) |
| | Vinflunine (Fabre) | Azaepothilon B (BMS) |
| | Auristatin PE (Teikoku Hormone) | BNP-7787 (BioNumerik) |
| | BMS 247550 (BMS) | CA-4-prodrug (OXiGENE) |
| | BMS 184476 (BMS) | Dolastatin-10 (NrH) |
| | BMS 188797 (BMS) | CA-4 (OXiGENE) |
| | Taxoprexin (Protarga) | |
| Aromatase inhibitors | Aminoglutethimide | Exemestan |
| | Letrozole | Atamestan (BioMedicines) |
| | Anastrazole | YM-511 (Yamanouchi) |
| | Formestan | |
| Thymidylate synthase inhibitors | Pemetrexed (Eli Lilly) | Nolatrexed (Eximias) |
| | ZD-9331 (BTG) | CoFactor ™ (BioKeys) |
| DNA antagonists | Trabectedin (PharmaMar) | Mafosfamide (Baxter International) |
| | Glufosfamide (Baxter International) | Apaziquone (Spectrum Pharmaceuticals) |
| | Albumin + 32P (Isotope Solutions) | O6-benzylguanine (Paligent) |
| | Thymectacin (NewBiotics) | |
| | Edotreotid (Novartis) | |
| Farnesyl transferase inhibitors | Arglabin (NuOncology Labs) | Tipifarnib (Johnson & Johnson |
| | Ionafarnib (Schering-Plough) | Perillyl alcohol (DOR BioPharma) |
| | BAY-43-9006 (Bayer) | |
| Pump inhibitors | CBT-1 (CBA Pharma) | Zosuquidar trihydrochloride (Eli Lilly) |
| | Tariquidar (Xenova) | |
| | MS-209 (Schering AG) | Biricodar dicitrate (Vertex) |
| Histone acetyl transferase inhibitors | Tacedinaline (Pfizer) | Pivaloyloxymethyl butyrate (Titan) |
| | SAHA (Aton Pharma) | Depsipeptide (Fujisawa) |
| | MS-275 (Schering AG) | |

TABLE 1-continued

| | | |
|---|---|---|
| Metalloproteinase inhibitors | Neovastat (Aeterna Laboratories) Marimastat (British Biotech) | CMT-3 (CollaGenex) BMS-275291 (Celltech) |
| Ribonucleoside reductase inhibitors | Gallium maltolate (Titan) Triapin (Vion) | Tezacitabine (Aventis) Didox (Molecules for Health) |
| TNF-alpha agonists/antagonists | Virulizin (Lorus Therapeutics) CDC-394 (Celgene) | Revimid (Celgene) |
| Endothelin-A receptor antagonists | Atrasentan (Abbot) ZD-4054 (AstraZeneca) | YM-598 (Yamanouchi) |
| Retinoic acid receptor agonists | Fenretinide (Johnson & Johnson LGD-1550 (Ligand) | Alitretinoin (Ligand) |
| Immunomodulators | Interferon Oncophage (Antigenics) GMK (Progenics) Adenocarcinoma vaccine (Biomira) CTP-37 (AVI BioPharma) JRX-2 (Immuno-Rx) PEP-005 (Peplin Biotech) Synchrovax vaccines (CTL Immuno) Melanoma vaccine (CTL Immuno) p21-RAS vaccine (GemVax) | Dexosome therapy (Anosys) Pentrix (Australian Cancer Technology) JSF-154 (Tragen) Cancer vaccine (Intercell) Norelin (Biostar) BLP-25 (Biomira) MGV (Progenics) !3-Alethin (Dovetail) CLL-Thera (Vasogen) |
| Hormonal and antihormonal agents | Oestrogens Conjugated oestrogens Ethynyloestradiol chlorotrianisene Idenestrol Hydroxyprogesterone caproate Medroxyprogesterone Testosterone Testosterone propionate Fluoxymesterone Methyltestosterone Diethylstilbestrol Megestrol Tamoxifen Toremofin Dexamethasone | Prednisone Methylprednisolone Prednisolone Aminoglutethimide Leuprolide Goserelin Leuporelin Bicalutamide Flutamide Octreotide Nilutamide Mitotan P-04 (Novogen) 2-Methoxyoestradiol (EntreMed) Arzoxifen (Eli Lilly) |
| Photodynamic agents | Talaporfin (Light Sciences) Theralux (Theratechnologies) Motexafin-Gadolinium (Pharmacyclics) | Pd-Bacteriopheophorbid (Yeda) Lutetium-Texaphyrin (Pharmacyclics) Hypericin |
| Tyrosine kinase inhibitors | Imatinib (Novartis) Leflunomide(Sugen/Pharmacia) ZDI839 (AstraZeneca) Erlotinib (Oncogene Science) Canertjnib (Pfizer) Squalamine (Genaera) SU5416 (Pharmacia) SU6668 (Pharmacia) ZD4190 (AstraZeneca) ZD6474 (AstraZeneca) Vatalanib (Novartis) PKI166 (Novartis) GW2016 (GlaxoSmithKline) EKB-509 (Wyeth) EKB-569 (Wyeth) | Kahalide F (PharmaMar) CEP-701 (Cephalon) CEP-751 (Cephalon) MLN518 (Millenium) PKC412 (Novartis) Phenoxodiol O Trastuzumab (Genentech) C225 (ImClone) rhu-Mab (Genentech) MDX-H210 (Medarex) 2C4 (Genentech) MDX-447 (Medarex) ABX-EGF (Abgenix) IMC-1C11 (ImClone) |
| Various agents | SR-27897 (CCK-A inhibitor, Sanofi-Synthelabo) Tocladesine (cyclic AMP agonist, Ribapharm) Alvocidib (CDK inhibitor, Aventis) CV-247 (COX-2 inhibitor, Ivy Medical) P54 (COX-2 inhibitor, Phytopharm) CapCell ™ (CYP450 stimulant Bavarian Nordic) GCS-IOO (gal3 antagonist, GlycoGenesys) G17DT immunogen (gastrin inhibitor, Aphton) Efaproxiral (oxygenator, Allos Therapeutics) | BCX-1777 (PNP inhibitor, BioCryst) Ranpirnase (ribonuclease stimulant, Alfacell) Galarubicin (RNA synthesis inhibitor, Dong-A) Tirapazamine (reducing agent, SRI International) N-Acetylcysteine (reducing agent, Zambon) R-Flurbiprofen (NF-kappaB inhibitor, Encore) 3CPA (NF-kappaB inhibitor, Active Biotech) Seocalcitol (vitamin D receptor agonist, Leo) 131-I-TM-601 (DNA antagonist, TransMolecular) |

TABLE 1-continued

| | |
|---|---|
| PI-88 (heparanase inhibitor, Progen) | Eflornithin (ODC inhibitor, ILEX Oncology) |
| Tesmilifen (histamine antagonist YM BioSciences) | Minodronic acid (osteoclast inhibitor, Yamanouchi) |
| Histamine (histamine H2 receptor agonist, Maxim) | Indisulam (p53 stimulant, Eisai) |
| | Aplidin (PPT inhibitor, PharmaMar) |
| Tiazofurin (IMPDH inhibitor, Ribapharm) | Rituximab (CD20 antibody, Genentech) |
| Cilengitide (integrin antagonist, Merck KGaA) | Gemtuzumab (CD33 antibody, Wyeth Ayerst) |
| SR-31747 (1L-1 antagonist, Sanofi-Synthelabo) | PG2 (haematopoiesis promoter Pharmagenesis) |
| CCI-779 (mTOR kinase inhibitor, Wyeth) | Immunol ™ (triclosan mouthwash, Endo) |
| Exisulind (PDE-V inhibitor, Cell Pathways) | Triacetyluridine (uridine prodrug, Wellstat) |
| CP-461 (PDE-V inhibitor, Cell Pathways) | SN-4071 (sarcoma agent, Signature BioScience) |
| AG-2037 (GART inhibitor, Pfizer) | TransMID-107 ™ (immunotoxin, KS Biomedix) |
| WX-UK1 (plasminogen activator inhibitor, Wilex) | PCK-3145 (apoptosis promoter Procyon) |
| PBI-1402 (PMN stimulant, ProMetic LifeSciences) | Doranidazole (apoptosis promoter, Pola) |
| Bortezomib (proteasome inhibitor, Millennium) | CHS-828 (cytotoxic agent, Leo) |
| SRL-172 (T-cell stimulant, SR Pharma) | trans-Retinic acid (differentiator NIH) |
| TLK-286 (glutathione-S transferase inhibitor, Telik) | MX6 (apoptosis promoter, MAX |
| PT-100 (growth factor agonist, Point Therapeutics) | Apomine (apoptosis promoter, LEX Oncology) |
| Midostaurin (PKC inhibitor, Novartis) | Urocidin (apoptosis promoter, Bioniche) |
| Bryostatin-1 (PKC stimulant, GPC Biotech) | Ro-31-7453 (apoptosis promoter, La Roche) |
| CDA-II (apoptosis promoter, Everlife) | Brostallicin (apoptosis promoter, Pharmacia) |
| SDX-101 (apoptosis promoter Salmedix) | |
| Ceflatonin (apoptosis promoter ChemGenex) | |

A combined treatment of this type can be achieved with the aid of simultaneous, consecutive or separate dispensing of the individual components of the treatment. Combination products of this type employ the compounds according to the invention.

The invention furthermore relates to compounds selected from the group consisting of:

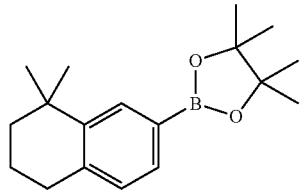

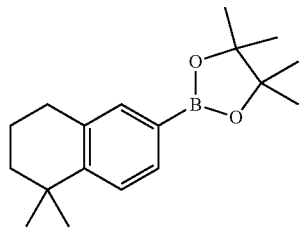

-continued

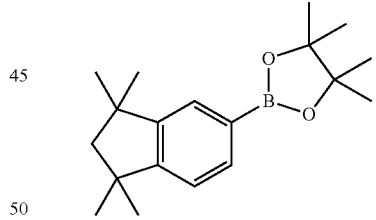

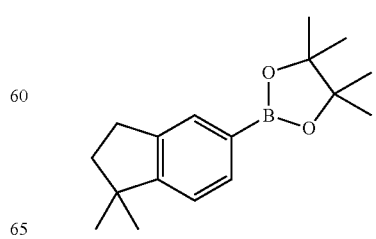

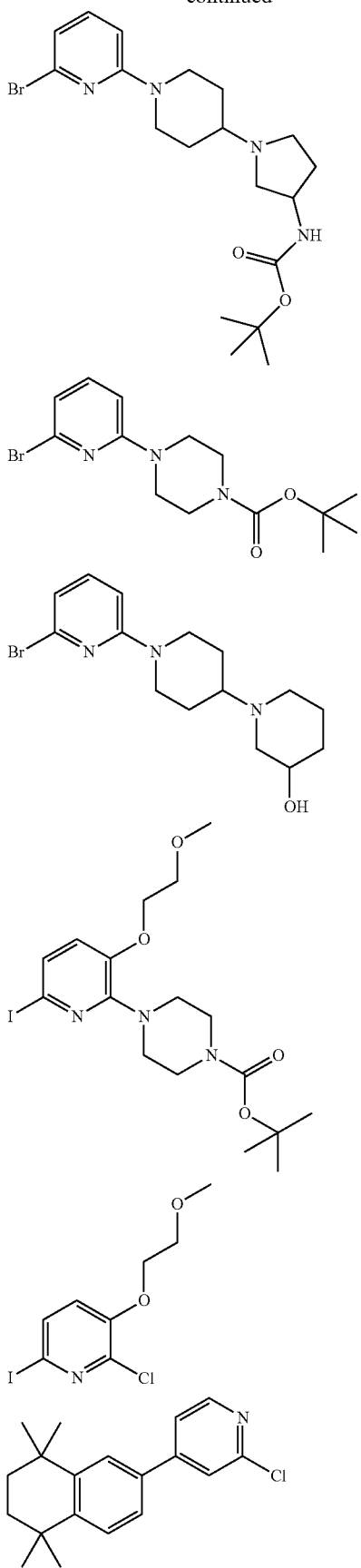
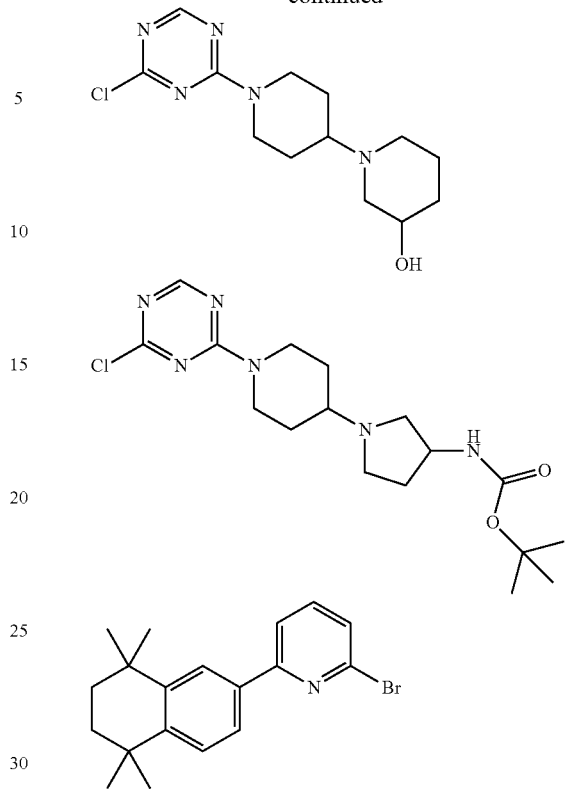

Even without further comments, it is assumed that a person skilled in the art will be able to utilise the above description in the broadest scope. The preferred embodiments should therefore merely be regarded as descriptive disclosure which is absolutely not limiting in any way.

Above and below, all temperatures are indicated in ° C. In the following examples, "conventional work-up" means: if necessary, the solvent is removed, water is added if necessary, the pH is adjusted, if necessary, to values between 2 and 10, depending on the constitution of the end product, the mixture is extracted with ethyl acetate or dichloromethane, the phases are separated, the organic phase is washed with saturated NaHCO$_3$ solution, optionally with water and saturated NaCl solution, the organic phase is dried over sodium sulfate, filtered and evaporated, and the product is purified by chromatography on silica gel, by preparative HPLC and/or by crystallisation. The purified compounds are optionally freeze-dried.

Mass spectrometry (MS): EI (electron impact ionisation) M$^+$
  FAB (fast atom bombardment) (M+H)$^+$
  ESI (electrospray ionisation) (M+H)$^+$
  APCI-MS (atmospheric pressure chemical ionisation mass spectrometry) (M+H)$^+$
HPLC Methods:
Method A:
Gradient: 4.2 min
Flow rate: 2 ml/min 99:01-0:100 water+0.1% (vol.) of TFA: acetonitrile+0.1% (vol.) of TFA
  0.0 to 0.2 min: 99:01
  0.2 to 3.8 min: 99:01→0:100
  3.8 to 4.2 min: 0:100
Column: Chromolith Performance RP18e; 100 mm long, internal diameter 3 mm
Wavelength: 220 nm Method B:
Flow rate: 2.75 ml/min 90:10-0:100 water+0.01% (vol.) of TFA:acetonitrile+0.01% (vol.) of TFA
0.0 to 3.5 min: 90:10→0:100
3.5 to 4.3 min: 0:100
Column: Chromolith SpeedRod RP18e; 50 mm long, internal diameter 4.6 mm
Wavelength: 220 nm
Method C:
Flow rate: 2.4 ml/min 85:15-0:100 water+0.05% (vol.) of AQcOH:acetonitrile+0.05% (vol.) of AcOH
0.0 to 2.8 min: 85:15→0:100
2.8 to 3.3 min: 0:100
Column: Chromolith SpeedRod RP18e; 50 mm long, internal diameter 4.6 mm
Wavelength: 220 nm List of abbreviations and acronyms:

AcOH acetic acid, anh. anhydrous, atm atmosphere(s), BOC tert-butoxycarbonyl CDI 1,1'-carbonyldiimidazole, conc. concentrated, d day(s), decomp. decomposition, DMAC N,N-dimethylacetamide, DMPU 1,3-dimethyl-3,4,5,6-tetrahydro-2(1H)-pyrimidinone, DMF N,N-dimethylformamide, DMSO dimethyl sulfoxide, DPPA diphenylphosphoryl azide, EDCI 1-(3-dimethylaminopropyl)-3-ethylcarbodiimide, EtOAc ethyl acetate, EtOH ethanol (100%), Et$_2$O diethyl ether, Et$_3$N triethylamine, h hour(s), MeOH methanol, pet. ether petroleum ether (boiling range 30-60° C.), temp. temperature, THF tetrahydrofuran, TFA trifluoroAcOH, Tf trifluoromethanesulfonyl, RT room temperature.

The contents of all cited references are incorporated in entirety by way of reference here. The invention is explained in greater detail by the following examples, but without being restricted thereto.

EXAMPLES

I. Synthesis of Selected Compounds of the Invention

The following compounds were synthesised and characterised. However, the preparation and characterisation of these compounds in another manner is part of the knowledge of the person skilled in the art.

FS101: 4-[6-(5,5,8,8-Tetramethyl-5,6,7,8-tetrahydronaphthalen-2-yl)pyridin-2-yl]-piperazine-1-carboxylic acid tert-butyl ester

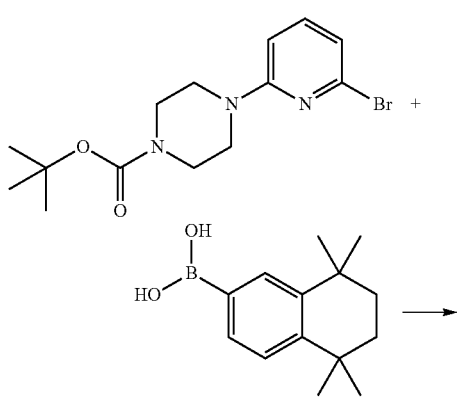

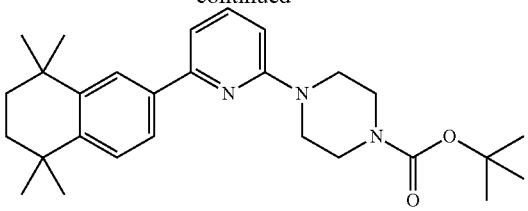

150 mg (0.44 mmol) of 4-(6-bromopyridin-2-yl)piperazine-1-carboxylic acid tert-butyl ester, 112 mg (0.48 mmol) of 5,5,8,8-tetramethyl-5,6,7,8-tetrahydronaphthalen-2-ylboronic acid and 202 mg (0.88 mmol) of tripotassium phosphate monohydrate are suspended in 6 ml of ethylene glycol monomethyl ether, degassed a number of times, and 25 mg (0.04 mmol) of bis(triphenylphosphine)-palladium(II) dichloride are added under nitrogen atmosphere. The reaction mixture is stirred at 80° C. for 16 h, cooled to RT, and 20 ml of water are added. This mixture is extracted three times with ethyl acetate, dried over Na$_2$SO$_4$ and evaporated. The crude product is purified by means of flash chromatography on silica gel.

220 mg oil, Rt.=3.75 min (method A), LCMS: 450 (M+H).

FS102: 4-[6-(5,5-Dimethyl-5,6,7,8-tetrahydronaphthalen-2-yl)pyridin-2-yl]-piperazine-1-carboxylic acid tert-butyl ester 500 mg (1.46 mmol) of 4-(6-bromopyridin-2-yl)piperazine-1-carboxylic acid tert-butyl ester, 460 mg (1.61 mmol) of 2-(5,5-dimethyl-5,6,7,8-tetrahydronaphthalen-2-yl)-4,4,5,5-tetramethyl-1,3,2-dioxaborolane and 620 mg (2.92 mmol) of tripotassium phosphate trihydrate are suspended in 10 ml of ethylene glycol monomethyl ether, degassed a number of times, and 82 mg (0.04 mmol) of bis(triphenylphosphine)palladium(II) dichloride are added under nitrogen atmosphere. The reaction mixture is treated in an ultrasound bath for 10 min, subsequently irradiated in the microwave at 100° C. for 90 min, 50 ml of water and 50 ml of ethyl acetate are added, and the mixture is filtered. The residue is discarded. The organic phase of the filtrate is separated off, and the aqueous phase is extracted three times with ethyl acetate. The combined organic phases are dried over Na₂SO₄ and evaporated. The crude product is purified by means of flash chromatography on silica gel.

482 mg oil, Rt.=3.93 min (method B), LCMS: 422 (M+H).

FS103: 4-[2-(5,5,8,8-Tetramethyl-5,6,7,8-tetrahydronaphthalen-2-yl)-pyrimidin-4-yl]piperazine-1-carboxylic acid tert-butyl ester

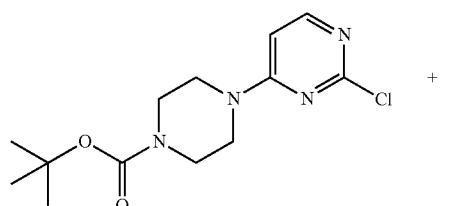

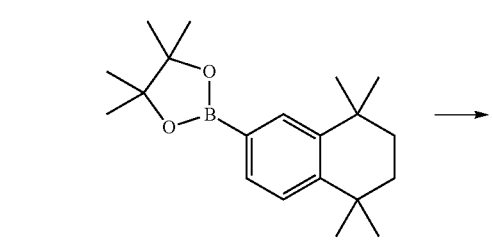

2.6 ml of toluene/ethanol (4:1) and 335 µl of 2N potassium carbonate solution are added to 100 mg (0.33 mmol) of 4-(2-chloropyrimidin-4-yl)piperazine-1-carboxylic acid tert-butyl ester (preparation analogous to US 2005/176722) and 147 mg (0.47 mmol) of 4,4,5,5-tetramethyl-2-(5,5,8,8-tetramethyl-5,6,7,8-tetrahydronaphthalen-2-yl)-1,3,2-dioxaborolane. The reaction mixture is degassed a number of times, 16 mg (0.01 mmol) of tetrakis(triphenylphosphine)palladium(0) are added under nitrogen atmosphere, the mixture is treated in an ultrasound bath for 10 min and subsequently irradiated in the microwave at 140° C. for 10 min. Water and dichloromethane are added to the reaction mixture. The organic phase is separated off, and the aqueous phase is extracted three times with ethyl acetate. The combined organic phases are dried over Na₂SO₄ and evaporated. The crude product is purified by means of flash chromatography on silica gel.

81 mg, white solid, Rt.=3.31 min (method A), LCMS: 451 (M+H).

FS104: 4-[4-(5,5,8,8-Tetramethyl-5,6,7,8-tetrahydronaphthalen-2-yl)-pyrimidin-2-yl]piperazine-1-carboxylic acid tert-butyl ester

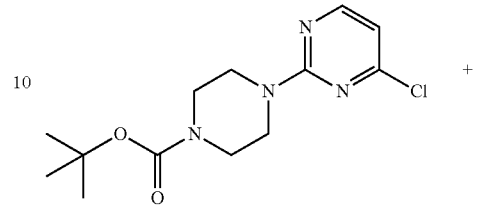

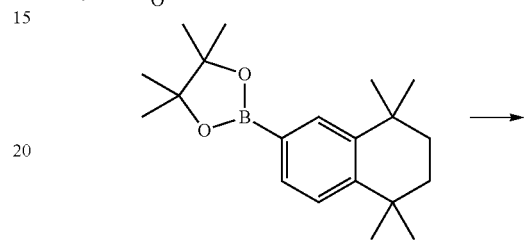

The preparation is carried out analogously to FS 103 starting from 4-(4-chloropyrimidin-2-yl)piperazine-1-carboxylic acid tert-butyl ester (preparation analogous to US 2005/176722) and 4,4,5,5-tetramethyl-2-(5,5,8,8-tetramethyl-5,6,7,8-tetrahydronaphthalen-2-yl)-1,3,2-dioxaborolane.

120 mg, white solid, Rt.=3.71 min (method A), LCMS: 451 (M+H).

FS105: 6'-(5,5,8,8-Tetramethyl-5,6,7,8-tetrahydronaphthalen-2-yl)-2,3,5,6-tetrahydro-1,2'-bipyrazinyl-4-carboxylic acid tert-butyl ester

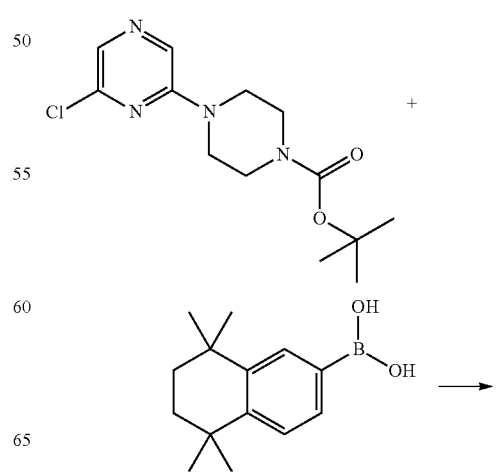

81
-continued

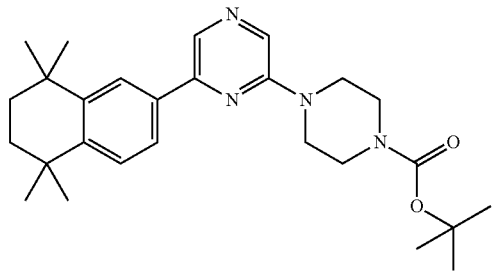

The preparation is carried out analogously to FS 102 starting from 6'-chloro-2,3,5,6-tetrahydro-1,2'-bipyrazinyl-4-carboxylic acid tert-butyl ester (preparation analogous to US 2005/176722) and 5,5,8,8-tetramethyl-5,6,7,8-tetrahydronaphthalen-2-ylboronic acid.

700 mg, yellow oil, Rt.=4.06 min (method A), LCMS: 451 (M+H).

FS106: 4-[4-(5,5,8,8-Tetramethyl-5,6,7,8-tetrahydronaphthalen-2-yl)-1,3,5-triazin-2-yl]piperazine-1-carboxylic acid tert-butyl ester

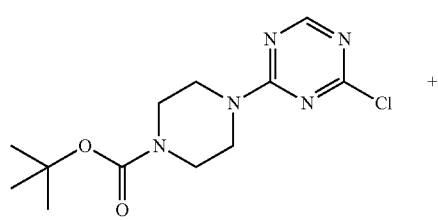

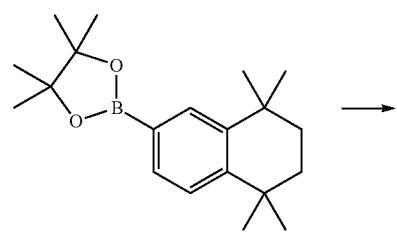

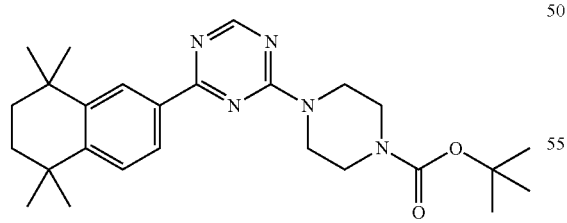

The preparation is carried out analogously to FS 102 starting from 4-(4-chloro-1,3,5-triazin-2-yl)piperazine-1-carboxylic acid tert-butyl ester (preparation analogous to US 2005/59668) and 4,4,5,5-tetramethyl-2-(5,5,8,8-tetramethyl-5,6,7,8-tetrahydronaphthalen-2-yl)-1,3,2-dioxaborolane.

213 mg, colourless oil, Rt.=3.82 min (method A), LCMS: 452 (M+H).

82
FS107: 4-[6-(8,8-Dimethyl-5,6,7,8-tetrahydronaphthalen-2-yl)pyridin-2-yl]piperazine-1-carboxylic acid tert-butyl ester

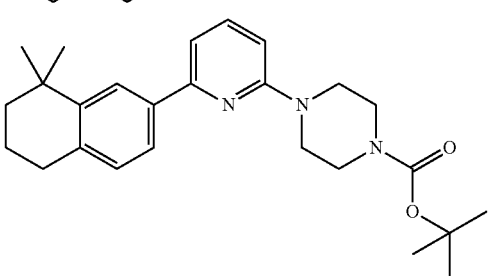

The preparation is carried out analogously to FS 102 starting from 4-(6-bromopyridin-2-yl)piperazine-1-carboxylic acid tert-butyl ester (US 2005/176722) and 2-(8,8-dimethyl-5,6,7,8-tetrahydronaphthalen-2-yl)-4,4,5,5-tetramethyl-1,3,2-dioxaborolane.

747 mg, yellow oil, Rt.=3.88 min (method B), LCMS: 422 (M+H).

$^1$H NMR (400 MHz, DMSO/deuterated TFA) δ 8.00 (dd, J=8.8, 7.6, 1H), 7.79 (d, J=1.5, 1H), 7.55 (dd, J=7.9, 1.7, 1H), 7.27-7.17 (m, 3H), 3.82-3.70 (m, 4H), 3.63-3.50 (m, 4H), 2.82 (t, J=6.1, 2H), 1.86-1.77 (m, 2H), 1.72-1.66 (m, 2H), 1.45 (s, 9H), 1.34 (s, 6H).

FS108: 4-[6-(1,1,3,3-Tetramethylindan-5-yl)pyridin-2-yl]piperazine-1-carboxylic acid tert-butyl ester

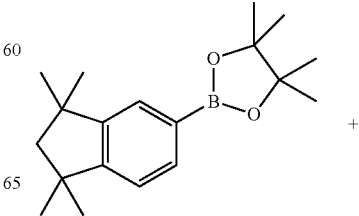

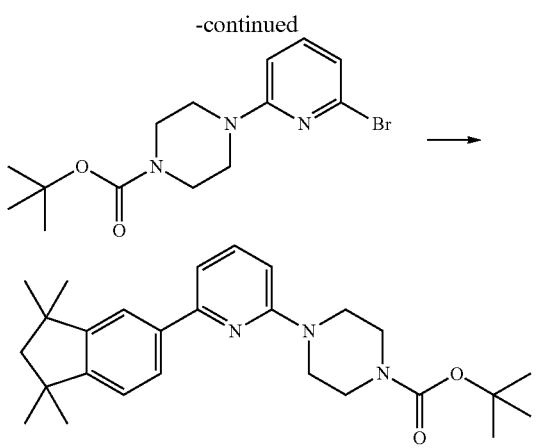

The preparation is carried out analogously to FS 102 starting from 4-(6-bromopyridin-2-yl)piperazine-1-carboxylic acid tert-butyl ester (US 2005/176722) and 4,4,5,5-tetramethyl-2-(1,1,3,3-tetramethylindan-5-yl)-1,3,2-dioxaborolane.

219 mg, colourless oil, Rt.=3.27 min (method B), LCMS: 436 (M+H).

$^1$H NMR (500 MHz, DMSO/deuterated TFA) δ 8.06 (dd, J=9.1, 7.4, 1H), 7.65 (dd, J=7.9, 1.7, 1H), 7.58 (d, J=1.6, 1H), 7.38 (d, J=7.9, 1H), 7.31 (d, J=9.1, 1H), 7.19 (d, J=7.3, 1H), 3.82-3.76 (m, 4H), 3.63-3.57 (m, 4H), 1.99 (d, J=1.7, 2H), 1.46 (s, 9H), 1.34 (t, J=14.1, 12H).

FS109: 4-[2-(5,5,8,8-Tetramethyl-5,6,7,8-tetrahydronaphthalen-2-yl)pyridin-4-yl]piperazine-1-carboxylic acid tert-butyl ester

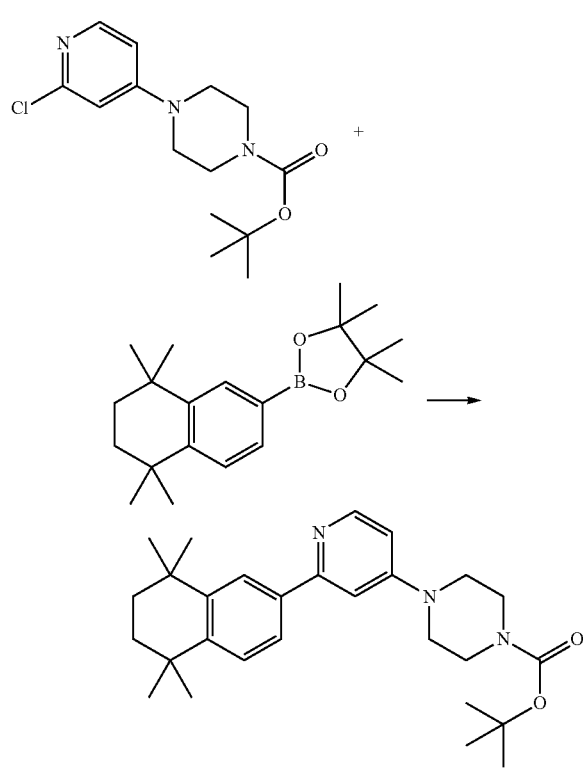

202 mg (0.68 mmol) of 4-(2-chloropyridin-4-yl)piperazine-1-carboxylic acid tert-butyl ester, 256 mg (0.81 mmol) of 4,4,5,5-tetramethyl-2-(5,5,8,8-tetramethyl-5,6,7,8-tetrahydronaphthalen-2-yl)-1,3,2-dioxaborolane and 187 mg (1.36 mmol) of potassium carbonate are dissolved in 6 ml of acetonitrile and 650 μl of water. The reaction mixture is degassed a number of times, 78 mg (0.07 mmol) of tetrakis(triphenylphosphine)palladium are added under nitrogen atmosphere, the mixture is irradiated in the microwave at 120° C. for 90 min, subsequently diluted with water and extracted three times with ethyl acetate. The combined organic phases are dried over Na$_2$SO$_4$ and evaporated. The crude product is purified by column chromatography on RP silica gel.

196 mg oil, Rt.=2.93 min (method B), LCMS: 450 (M+H).

FS110: 4-[6-(1,1-Dimethylindan-5-yl)pyridin-2-yl]piperazine-1-carboxylic acid tert-butyl ester

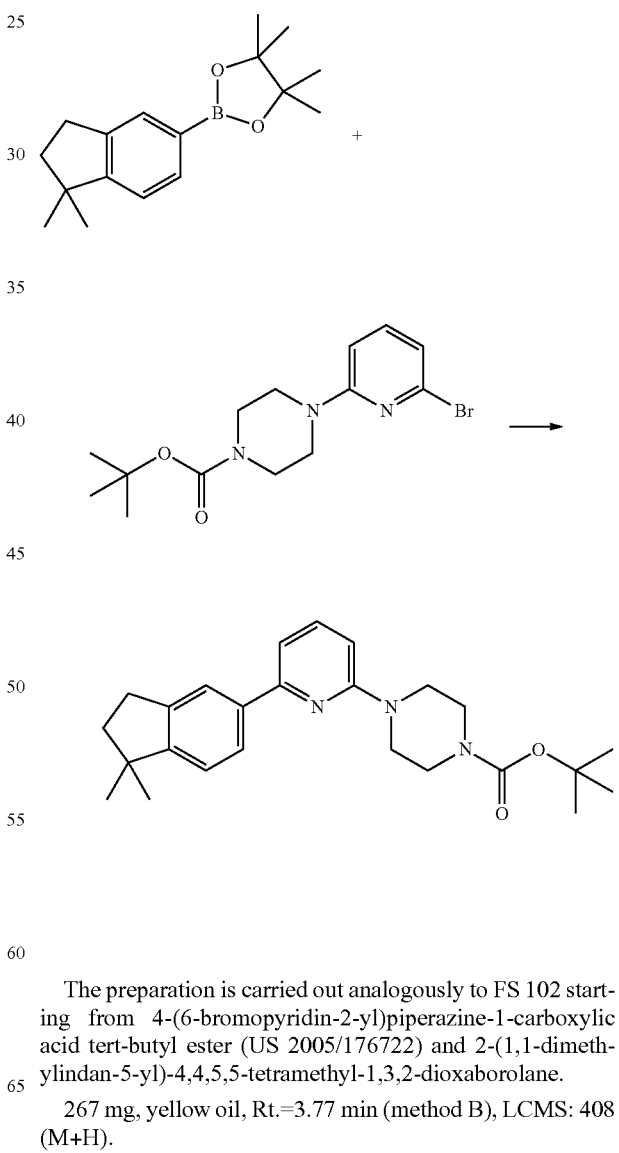

The preparation is carried out analogously to FS 102 starting from 4-(6-bromopyridin-2-yl)piperazine-1-carboxylic acid tert-butyl ester (US 2005/176722) and 2-(1,1-dimethylindan-5-yl)-4,4,5,5-tetramethyl-1,3,2-dioxaborolane.

267 mg, yellow oil, Rt.=3.77 min (method B), LCMS: 408 (M+H).

FS111: 4-[3-(5,5,8,8-Tetramethyl-5,6,7,8-tetrahydronaphthalen-2-yl)phenyl]piperazine-1-carboxylic acid tert-butyl ester

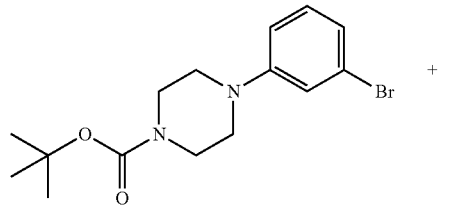

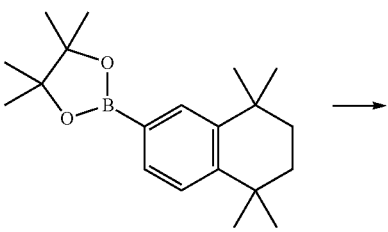

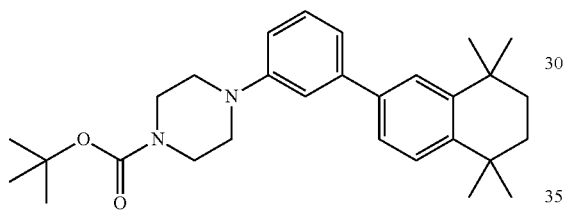

The preparation is carried out analogously to FS 102 starting from 4-(3-bromophenyl)piperazine-1-carboxylic acid tert-butyl ester (WO2007/97937) and 4,4,5,5-tetramethyl-2-(5,5,8,8-tetramethyl-5,6,7,8-tetrahydronaphthalen-2-yl)-1,3,2-dioxaborolane.

554 mg, yellow oil, Rt.=4.24 min (method B).

$^1$H NMR (400 MHz, DMSO/deuterated TFA) δ 7.96 (s, 1H), 7.76 (d, J=7.5, 1H), 7.70-7.60 (m, 3H), 7.51-7.44 (m, 2H), 3.79 (d, J=36.9, 8H), 1.72 (s, 4H), 1.48 (s, 9H), 1.33 (d, J=20.2, 12H).

FS112: 4-[4-(5,5-Dimethyl-5,6,7,8-tetrahydronaphthalen-2-yl)-1,3,5-triazin-2-yl]-piperazine-1-carboxylic acid tert-butyl ester

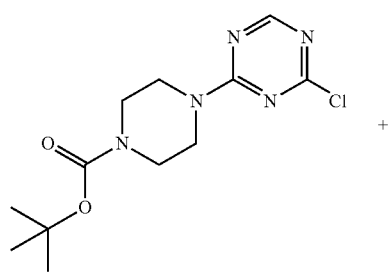

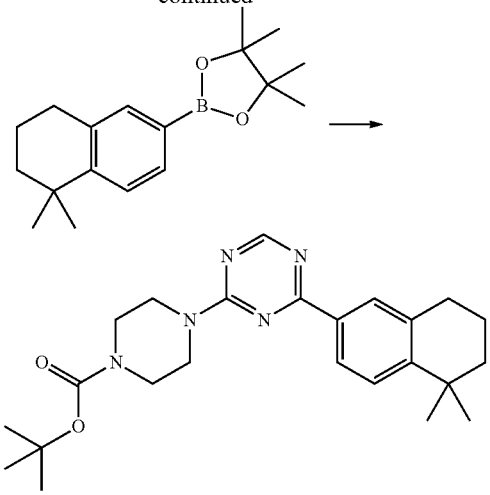

The preparation is carried out analogously to FS 102 starting from 4-(4-chloro-1,3,5-triazin-2-yl)piperazine-1-carboxylic acid tert-butyl ester (US 2005/59668) and 2-(5,5-dimethyl-5,6,7,8-tetrahydronaphthalen-2-yl)-4,4,5,5-tetramethyl-1,3,2-dioxaborolane.

62 mg, colourless oil, Rt.=3.78 min (method A), LCMS: 424 (M+H).

FS113: 4-[4-(8,8-Dimethyl-5,6,7,8-tetrahydronaphthalen-2-yl)-1,3,5-triazin-2-yl]-piperazine-1-carboxylic acid tert-butyl ester

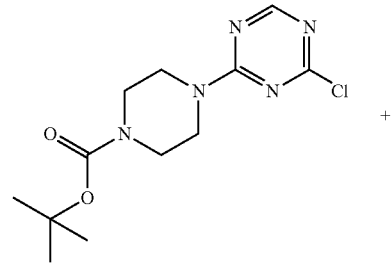

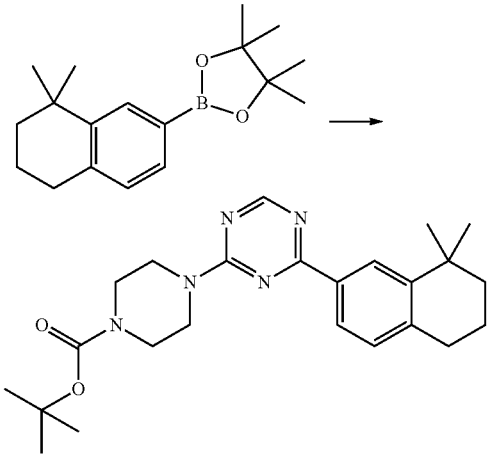

The preparation is carried out analogously to FS 102 starting from 4-(4-chloro-1,3,5-triazin-2-yl)piperazine-1-carboxylic acid tert-butyl ester (US 2005/59668) and 2-(8,8- dimethyl-5,6,7,8-tetrahydronaphthalen-2-yl)-4,4,5,5-tetramethyl-1,3,2-dioxaborolane.

55 mg, yellow oil, Rt.=4.13 min (method A), LCMS: 424 (M+H).

FS114: 1-[2-Methyl-5-(5,5,8,8-tetramethyl-5,6,7,8-tetrahydronaphthalen-2-yl)-phenyl]piperazine

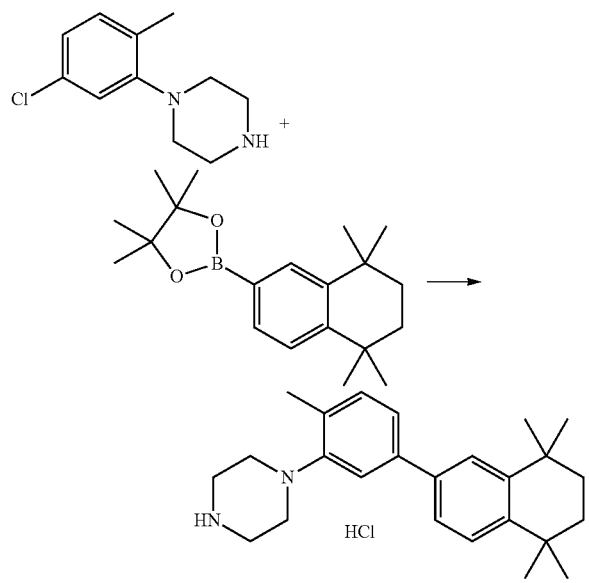

100 mg (0.48 mmol) of 1-(5-chloro-2-methylphenyl)piperazine and 300 mg (0.95 mmol) and of 4,4,5,5-tetramethyl-2-(5,5,8,8-tetramethyl-5,6,7,8-tetrahydronaphthalen-2-yl)-1,3,2-dioxaborolane are dissolved in 2 ml of THF, 302 mg (1.43 mmol) of potassium phosphate, 3 mg of palladium acetate and 11 mg of 2-dicylcohexylphosphino-2',4',6'-tri-i-propyl-1,1'-biphenyl are added. The reaction mixture is degassed a number of times and stirred at 120° C. under nitrogen atmosphere for 4 h, subsequently diluted with water and extracted three times with ethyl acetate. The combined organic phases are dried over $Na_2SO_4$ and evaporated. The crude product is purified by means of preparative HPLC and converted into the hydrochloride using methanolic HCl.

6 mg beige solid, Rt.=3.33 min (method A), LCMS: 363 (M+H).

$^1$H NMR (400 MHz, DMSO/deuterated TFA) δ 7.50 (d, J=1.7, 1H), 7.42-7.33 (m, 2H), 7.27 (s, 2H), 7.21 (s, 1H), 3.35-3.26 (m, 4H), 3.20-3.12 (m, 4H), 2.32 (s, 3H), 1.69 (s, 4H), 1.30 (d, J=14.3, 12H).

FS115: (S)-3-Methyl-1-[3-(5,5,8,8-tetramethyl-5,6,7,8-tetrahydronaphthalen-2-yl)-phenyl]piperazine

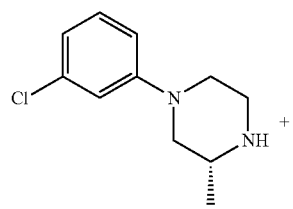

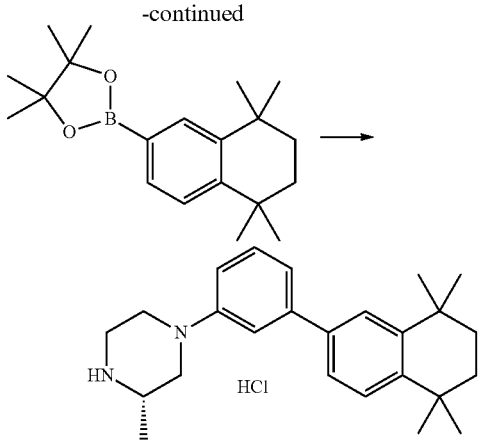

The preparation is carried out analogously to FS 114.

49 mg, beige solid, Rt.=3.21 min (method A), LCMS: 363 (M+H).

$^1$H NMR (400 MHz, DMSO/deuterated TFA) δ 7.52 (s, 1H), 7.42-7.31 (m, 3H), 7.21 (s, 1H), 7.13 (d, J=7.8, 1H), 7.02 (dd, J=8.2, 1.9, 1H), 3.87 (t, J=14.4, 2H), 3.45 (d, J=12.4, 2H), 3.29-3.17 (m, 1H), 3.08 (t, J=11.1, 1H), 2.86 (dd, J=12.9, 10.7, 1H), 1.70 (s, 4H), 1.39-1.27 (m, 15H).

FS116: (S)-1-[4-Methoxy-3-(5,5,8,8-tetramethyl-5,6,7,8-tetrahydronaphthalen-2-yl)-phenyl]-3-methylpiperazine

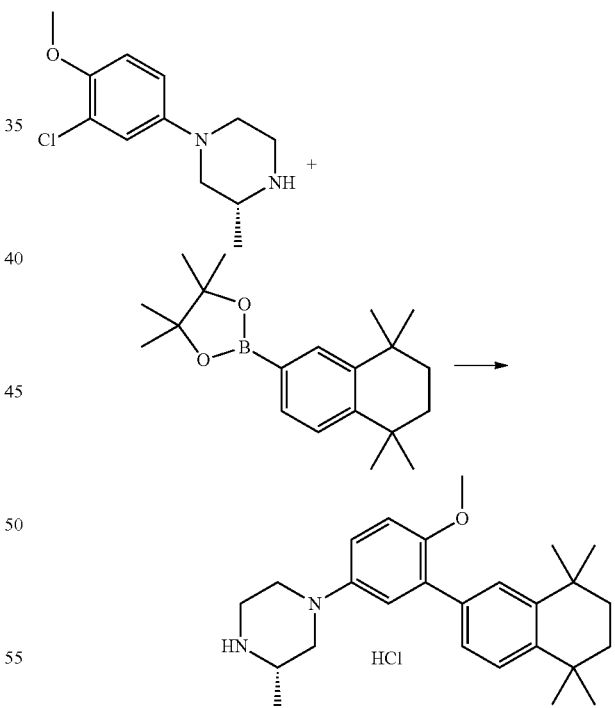

The preparation is carried out analogously to FS 114. Product is in the form of the hydrochloride.

8 mg, beige solid, Rt.=3.14 min (method A), LCMS: 393 (M+H).

$^1$H NMR (500 MHz, DMSO/deuterated TFA) δ 7.49 (d, J=1.7, 1H), 7.37 (d, J=8.2, 1H), 7.27 (dd, J=8.2, 1.8, 1H), 7.23-7.15 (m, 2H), 7.10 (d, J=8.8, 1H), 3.82-3.72 (m, 5H), 3.57 (ddd, J=25.4, 16.2, 7.7, 2H), 3.39-3.25 (m, 2H), 3.15-3.06 (m, 1H), 1.72 (s, 4H), 1.37-1.28 (m, 15H).

FS117: {1-[2-(5,5,8,8-Tetramethyl-5,6,7,8-tetrahydronaphthalen-2-yl)pyrimidin-4-yl]-piperidin-4-yl}carbamic acid tert-butyl ester

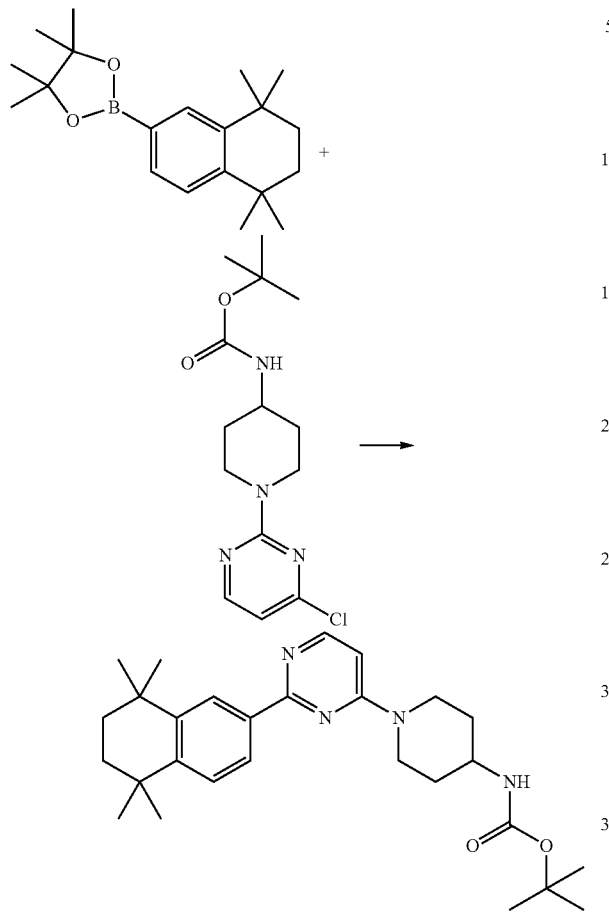

The preparation is carried out analogously to FS103.

Yield: 454 mg, colourless oil. Rt.=3.21 min (method A), LCMS: 465 (M+H).

1H NMR (500 MHz, DMSO/deuterated TFA) δ 8.14 (d, J=7.5 Hz, 1H), 8.03 (d, J=2.0 Hz, 1H), 7.84 (dd, J=8.4, 2.0 Hz, 1H), 7.44 (d, J=8.4 Hz, 1H), 6.98 (d, J=7.6 Hz, 1H), 4.80 (d, J=13.6 Hz, 1H), 4.08 (d, J=14.0 Hz, 1H), 3.91 (q, J=7.1 Hz, 1H), 3.63 (s, 1H), 3.40-3.27 (m, 2H), 1.88 (d, J=10.1 Hz, 2H), 1.60 (s, 4H), 1.49-1.36 (m, 2H), 1.30 (s, 9H), 1.20 (d, J=21.8 Hz, 12H).

FS118: {1-[4-(5,5,8,8-Tetramethyl-5,6,7,8-tetrahydronaphthalen-2-yl)pyrimidin-2-yl]-piperidin-4-yl}carbamic acid tert-butyl ester

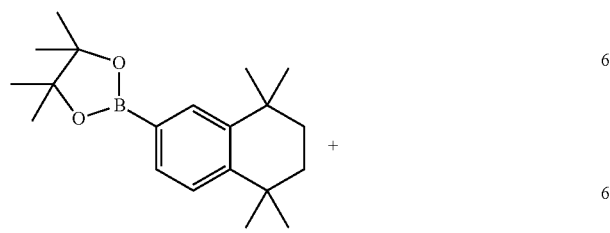

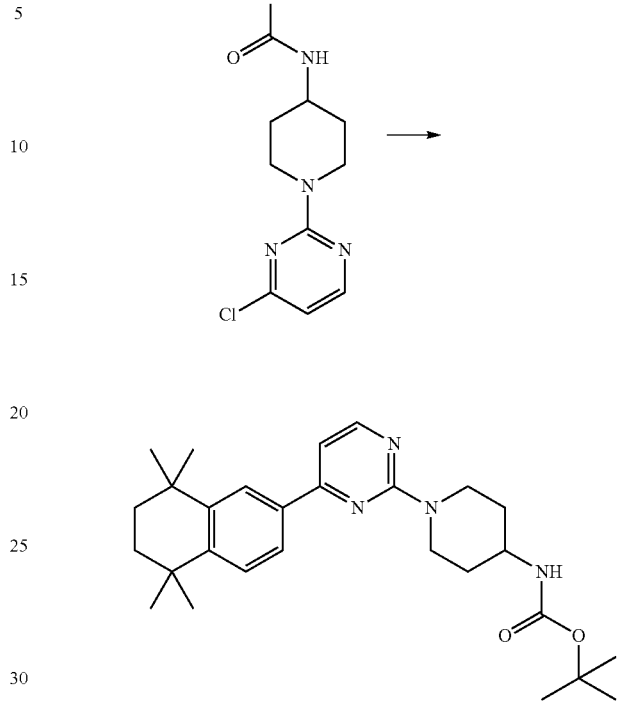

The preparation is carried out analogously to FS103.

Yield: 516 mg, colourless oil. Rt.=3.47 min (method A), LCMS: 465 (M+H).

1H NMR (500 MHz, DMSO/deuterated TFA) δ 8.38 (d, J=6.7 Hz, 1H), 8.19 (d, J=1.8 Hz, 1H), 8.00 (dd, J=8.3, 1.6 Hz, 1H), 7.58 (dd, J=18.5, 11.1 Hz, 2H), 4.51 (s, 2H), 3.75 (s, 1H), 3.48 (dd, J=17.9, 6.9 Hz, 2H), 2.10-1.97 (m, 2H), 1.74 (s, 4H), 1.60 (ddd, J=17.4, 13.7, 6.5 Hz, 2H), 1.44 (s, 9H), 1.34 (d, J=17.8 Hz, 12H).

FS119: 2-[6-(5,5,8,8-Tetramethyl-5,6,7,8-tetrahydronaphthalen-2-yl)-3',4',5',6',3",4",5",6"-octahydro-2'H,2"H-[2,1';4',4"]terpyridin-1"-yl]ethanol

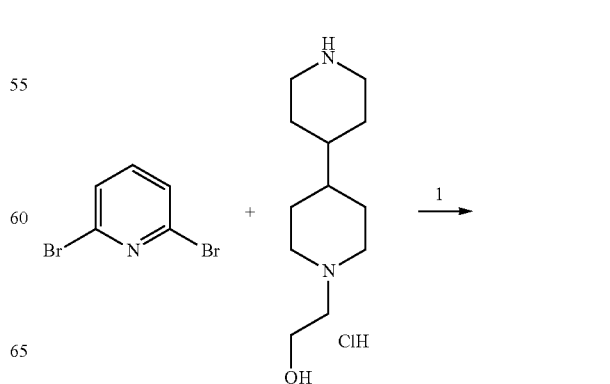

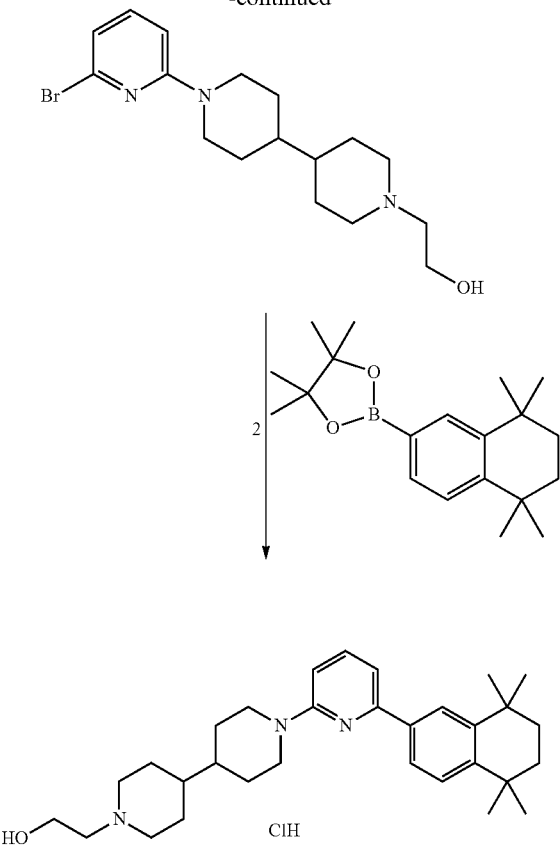

and 364 mg of potassium carbonate are suspended in 5 ml of NMP and stirred at 100° C. for 18 h. The mixture is subsequently filtered, sat. sodium carbonate solution is added to the filtrate, and the precipitate formed is filtered off with suction. The crude product is dried and reacted further directly.

176 mg, yellowish solid, Rt.=2.41 min (method A), LCMS: 369 (M+H)

Step 2

100 mg (0.27 mmol) of 2-(6-bromo-3',4',5',6',3",4",5",6"-octahydro-2'H,2"H-[2,1';4',4"]terpyridin-1"-yl)ethanol, 85 mg (0.27 mmol) of 4,4,5,5-tetramethyl-2-(5,5,8,8-tetramethyl-5,6,7,8-tetrahydronaphthalen-2-yl)-1,3,2-dioxaborolane and 27 mg (0.33 mmol) of sodium hydrogencarbonate are dissolved in 10 ml of DMF and 3 ml of water, degassed, and 7 mg of bis(triphenylphosphine)palladium(II) chloride are added under nitrogen atmosphere. The reaction mixture is stirred at 80° C. for 18 h, subsequently diluted with 20 ml of water, extracted with 2*20 ml of ethyl acetate and dried over sodium sulfate. The solvent is removed in a rotary evaporator, and the crude product is purified by means of prep HPLC. The product is converted into the hydrochloride using methanolic HCl.

Yield: 20 mg, yellow, viscous oil. Rt.=2.69 min (method A), LCMS: 476 (M+H).

$^1$H NMR (500 MHz, DMSO/deuterated TFA) δ 7.93 (dd, J=9.1, 7.4 Hz, 1H), 7.58 (d, J=1.8 Hz, 1H), 7.49 (d, J=8.2 Hz, 1H), 7.42 (dd, J=8.2, 1.9 Hz, 1H), 7.25 (d, J=9.2 Hz, 1H), 7.01 (d, J=7.3 Hz, 1H), 4.28 (d, J=13.4 Hz, 2H), 3.77-3.69 (m, 2H), 3.53 (d, J=13.2 Hz, 2H), 3.27-3.06 (m, 4H), 2.86 (t, J=11.8 Hz, 2H), 1.84 (t, J=10.3 Hz, 4H), 1.68 (s, 4H), 1.63-1.29 (m, 6H), 1.27 (d, J=10.4 Hz, 12H).

Step 1

223 mg (0.94 mmol) of 2,6-dibromopyridine, 234 mg (0.94 mmol) of 2-(4,4'-bipiperidinyl-1-yl)ethanol hydrochloride FS120: 1-[2-Methoxy-5-(5,5,8,8-tetramethyl-5,6,7,8-tetrahydronaphthalen-2-yl)phenyl]-piperazine

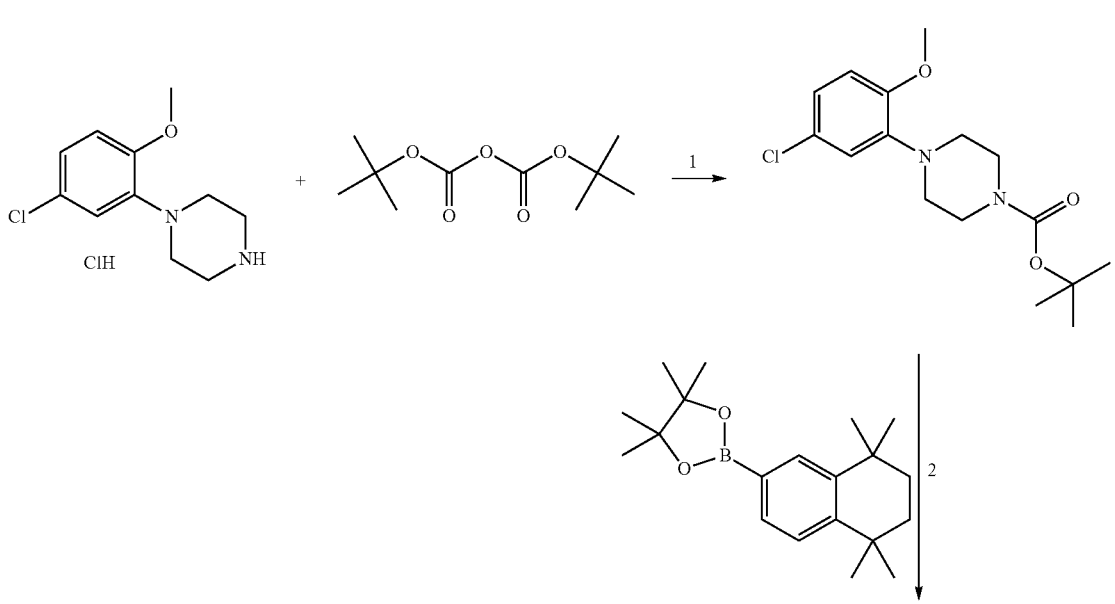

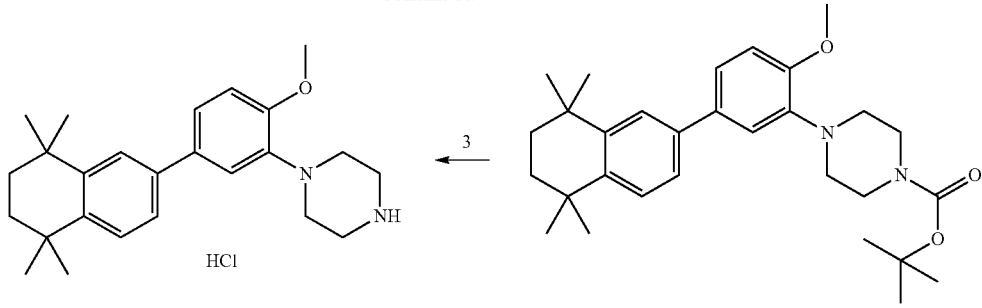

Step 1

500 mg (1.9 mmol) of 1-(5-chloro-2-methoxyphenyl)piperazine hydrochloride is dissolved in 15 ml of DMF, 316 μl (2.28 mmol) of triethylamine are added, and the mixture is stirred for 5 min. A solution of 447 μl (2.09 mmol) of di-tert-butyl dicarbonate is subsequently added dropwise, and the mixture is stirred at room temperature for 18 h. The reaction mixture is evaporated, dichloromethane is added, the mixture is extracted, dried and evaporated. The crude product was reacted further without further purification.

Rt.=3.26 min (method A), LCMS: 327 (M+H).

Step 2

The reaction with 4,4,5,5-tetramethyl-2-(5,5,8,8-tetramethyl-5,6,7,8-tetrahydronaphthalen-2-yl)-1,3,2-dioxaborolane is carried out analogously to FS114.

Rt.=3.47 min (method A), LCMS: 479 (M+H).

Step 3

The protecting group is cleaved off analogously to FS201. The product is in the form of the hydrochloride.

Yield: 25 mg, yellow, viscous oil. Rt.=3.12 min (method A), LCMS: 379 (M+H).

$^1$H NMR (500 MHz, DMSO/deuterated TFA) 7.46 (d, J=1.7 Hz, 1H), 7.37-7.28 (m, 3H), 7.23 (d, J=2.1 Hz, 1H), 7.05 (d, J=8.5 Hz, 1H), 3.85 (s, 3H), 3.41 (d, J=5.6 Hz, 4H), 3.34 (d, J=5.4 Hz, 4H), 1.66 (s, 4H), 1.26 (d, J=19.7 Hz, 12H).

FS121: 2-[6-piperazin-1-yl-2-(5,5,8,8-tetramethyl-5,6,7,8-tetrahydronaphthalen-2-yl)-pyridin-3-yloxy]ethanol

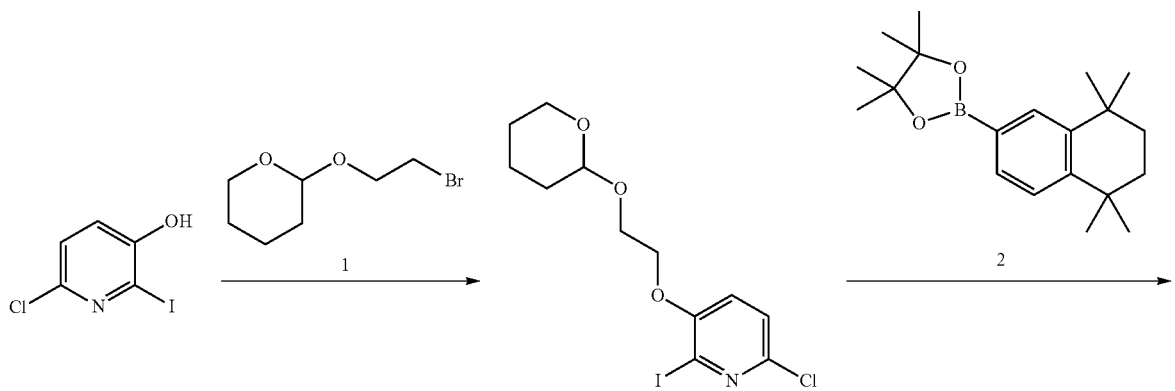

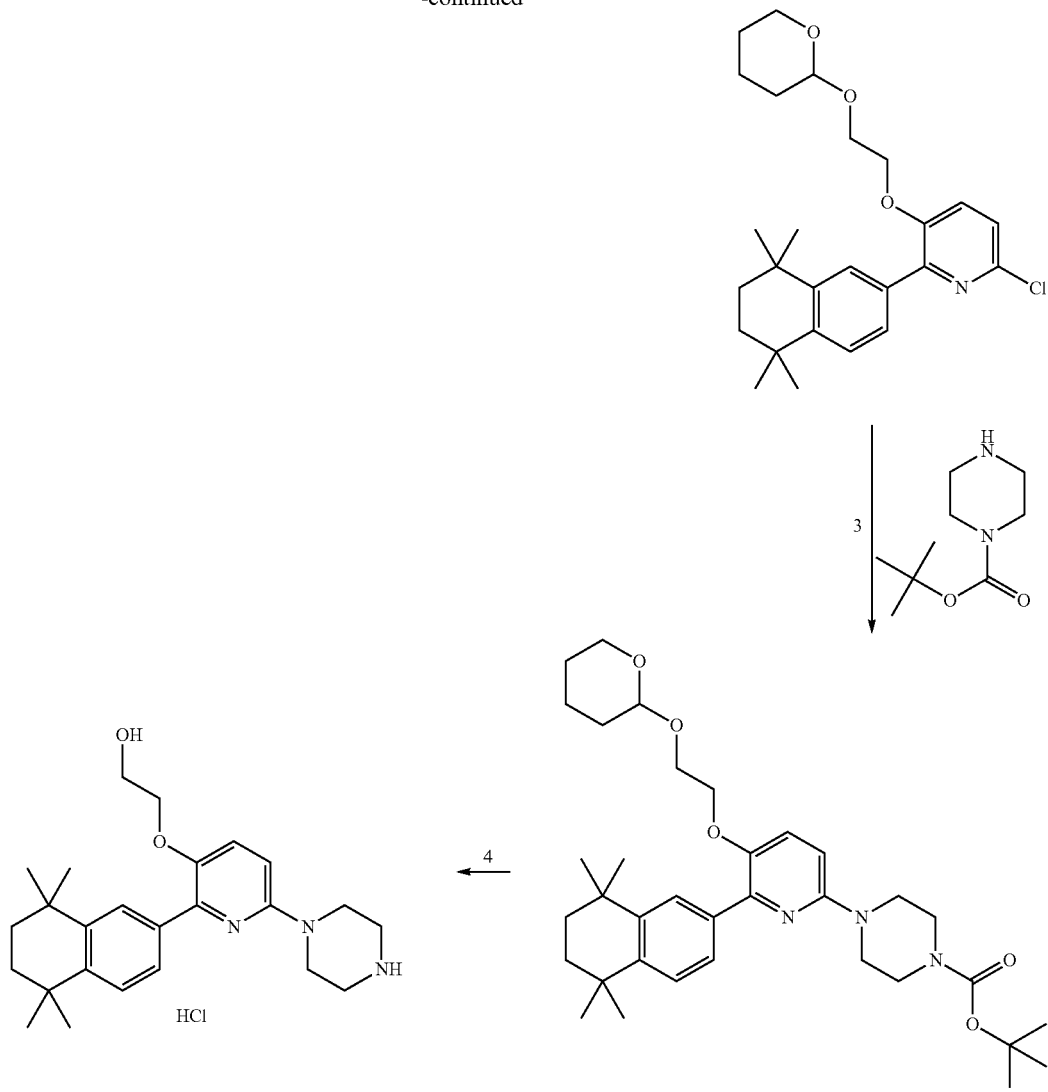

Step 1

500 mg (1.96 mmol) of 6-chloro-2-iodopyridin-3-ol and 700 mg (2.15 mmol) of caesium carbonate are suspended in DMF, and 325 μl (2.15 mmol) of 2-(2-bromoethoxy)tetrahydro-2H-pyran are added. The reaction mixture is stirred at RT for 18 h, water is subsequently added, and the mixture is extracted a number of times with ethyl acetate, dried and evaporated. The crude product is reacted further directly.

Yield: 846 mg. Rt.=3.11 min (method A), LCMS: 384 (M+H).

Step 2

The Suzuki reaction with 4,4,5,5-tetramethyl-2-(5,5,8,8-tetramethyl-5,6,7,8-tetrahydronaphthalen-2-yl)-1,3,2-dioxaborolane is carried out analogously to FS102.

Yield: 46 mg. Rt.=4.15 min (method A), LCMS: 444/446 (M+H).

Step 3

46 mg (0.104 mmol) of 6-chloro-3-[2-(tetrahydropyran-2-yloxy)ethoxy]-2-(5,5,8,8-tetramethyl-5,6,7,8-tetrahydronaphthalen-2-yl)pyridine was weighed out with 39 mg (0.207 mmol) of tert-butyl 1-piperazinecarboxylate and dissolved in 1 ml of toluene. The reaction mixture was degassed and added with 10 mg of tris(dibenzylideneacetone)dipalladium(0), 7 mg of rac-2,2'-bis(diphenylphosphino)-1,1'-binapthyl and 23 mg of potassium tert-butoxide. The reaction mixture was degassed again, and the reaction mixture was stirred at 90° C. under nitrogen atmosphere for 18 h. After cooling, ether was added, and the mixture was washed with water, dried and stripped off to dryness. The residue was reacted further directly without further purification.

Step 4

The protecting groups are cleaved off analogously to FS201. The product is in the form of the hydrochloride.

Yield: 19 mg, white solid. Rt.=2.68 min (method A), LCMS: 410 (M+H).

$^1$H NMR (500 MHz, DMSO/deuterated TFA) δ 7.94 (d, J=1.8 Hz, 1H), 7.79 (d, J=9.3 Hz, 1H), 7.65 (dd, J=8.2, 1.8 Hz, 1H), 7.41 (d, J=8.3 Hz, 1H), 7.08 (d, J=9.3 Hz, 1H), 4.08 (t, J=5.0 Hz, 2H), 3.80-3.68 (m, 6H), 3.32-3.22 (m, 4H), 1.70 (s, 4H), 1.29 (d, J=6.5 Hz, 12H).

FS121: 2-{2-[6-piperazin-1-yl-2-(5,5,8,8-tetramethyl-5,6,7,8-tetrahydronaphthalen-2-yl)-pyridin-3-yloxy]ethyl}isoindole-1,3-dione

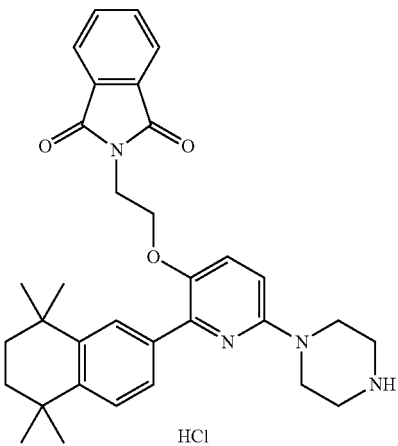 [SMILES: CC1(C)CCC(C)(C)c2cc(-c3nc(N4CCNCC4)ccc3OCCN3C(=O)c4ccccc4C3=O)ccc21 ; Cl]

The preparation is carried out analogously to FS120. The product is in the form of the hydrochloride.
Yield: 74 mg. Rt.=3.09 min (method A), LCMS: 539 (M+H).

FS122: 5'-(5,5,8,8-Tetramethyl-5,6,7,8-tetrahydronaphthalen-2-yl)-3,4,5,6-tetrahydro-2H-1,3'-bipyridinyl-4-ylamine Step 1

The Suzuki reaction was carried out analogously to STI102.
Yield: 1.6 g. Rt.=3.88 min (method A), LCMS: 344/346 (M+H).

Step 2

The reaction is carried out analogously to step 3 of FS120. The crude product is reacted further directly.

Step 3

The protecting group is cleaved off analogously to FS201. The product is in the form of the hydrochloride.
Yield: 6 mg. Rt.=2.51 min (method A), LCMS: 364 (M+H).
$^1$H NMR (400 MHz, DMSO/deuterated TFA) δ 8.53 (d, J=1.0 Hz, 1H), 8.47 (d, J=2.5 Hz, 1H), 8.21 (dd, J=2.5, 1.5 Hz, 1H), 7.73 (d, J=1.9 Hz, 1H), 7.60-7.56 (m, 1H), 7.52 (d, J=8.3 Hz, 1H), 4.17 (d, J=13.2 Hz, 2H), 3.43-3.34 (m, 1H), 3.16-3.06 (m, 2H), 2.06 (d, J=10.2 Hz, 2H), 1.76-1.60 (m, 6H), 1.33 (d, J=19.8 Hz, 12H).

FS123: 1-[5-(5,5,8,8-Tetramethyl-5,6,7,8-tetrahydronaphthalen-2-yl)pyridin-3-yl]-piperazine

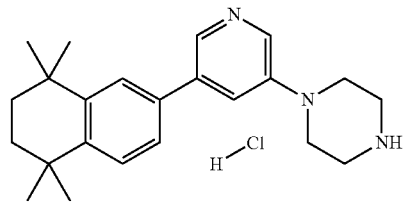

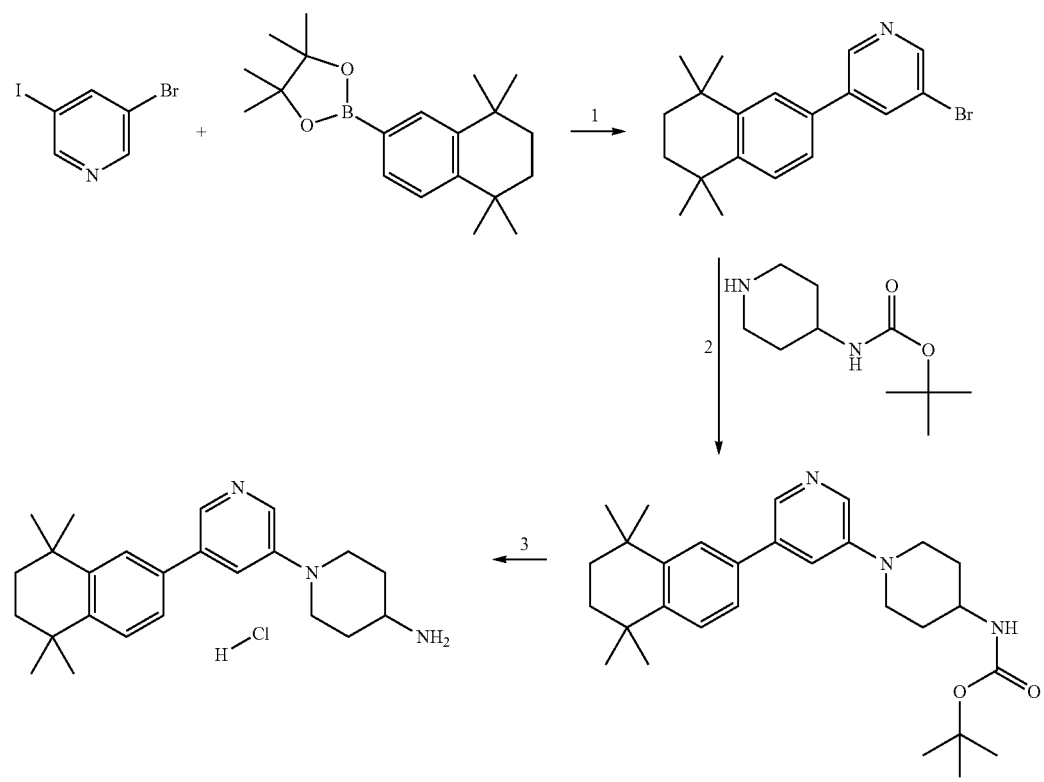

The preparation is carried out analogously to FS122. The product is in the form of the hydrochloride.

Yield: 35 mg. Rt.=2.48 min (method A), LCMS: 350 (M+H).

$^1$H NMR (400 MHz, DMSO/deuterated TFA) δ 8.63 (d, J=1.2 Hz, 1H), 8.52 (d, J=2.5 Hz, 1H), 8.27 (d, J=1.6 Hz, 1H), 7.75 (d, J=2.0 Hz, 1H), 7.60 (dd, J=8.3, 2.0 Hz, 1H), 7.52 (d, J=8.3 Hz, 1H), 3.85-3.73 (m, 4H), 3.38-3.26 (m, 4H), 1.71 (s, 4H), 1.33 (d, J=20.5 Hz, 12H).

FS124: 1-Piperidin-4-yl-4-[6-(5,5,8,8-tetramethyl-5,6,7,8-tetrahydronaphthalen-2-yl)-pyridin-2-yl]piperazine

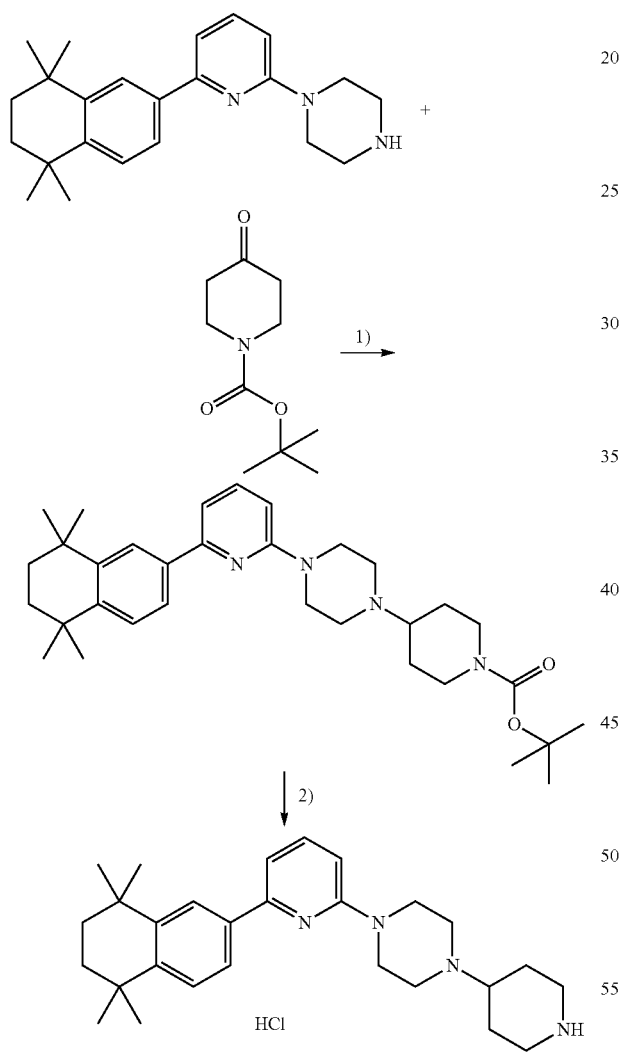

Step 1

The reductive amination is carried out analogously to FS501.

Yield: 420 mg. Rt.=3.32 min (method A), LCMS: 533 (M+H).

Step 2

The protecting group is cleaved off analogously to FS201. The product is in the form of the hydrochloride.

Yield: 370 mg. Rt.=2.78 min (method A), LCMS: 433 (M+H).

$^1$H NMR (500 MHz, DMSO/deuterated TFA) δ 7.90 (dd, J=8.7, 7.6 Hz, 1H), 7.73 (d, J=1.9 Hz, 1H), 7.55 (dd, J=8.2, 1.9 Hz, 1H), 7.45 (d, J=8.3 Hz, 1H), 7.18 (dd, J=16.5, 8.1 Hz, 2H), 3.80-3.73 (m, 1H), 3.35-3.62 (m, 6H), 3.23-3.15 (m, 1H), 3.01-2.87 (m, 3H), 2.29 (d, J=12.5 Hz, 2H), 1.99-1.81 (m, 3H), 1.67 (s, 4H), 1.65-1.56 (m, 1H), 1.26 (d, J=14.3 Hz, 12H).

FS125: 1-[5-Methoxy-6-(5,5,8,8-tetramethyl-5,6,7,8-tetrahydronaphthalen-2-yl)-pyridin-2-yl]piperazine

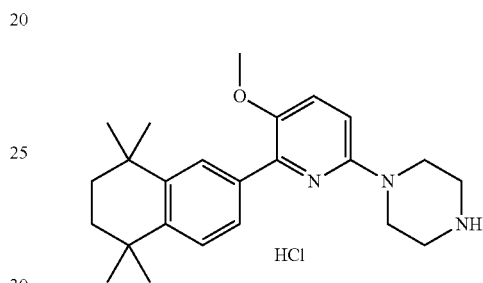

The preparation is carried out analogously to FS120. The product is in the form of the hydrochloride.

Yield: 12 mg. Rt.=2.99 min (method A), LCMS: 380 (M+H).

$^1$H NMR (400 MHz, DMSO/deuterated TFA) δ 7.84 (d, J=1.8 Hz, 1H), 7.61 (dd, J=8.3, 1.8 Hz, 1H), 7.52 (d, J=9.1 Hz, 1H), 7.34 (d, J=8.3 Hz, 1H), 6.90 (d, J=9.0 Hz, 1H), 3.77 (s, 3H), 3.72-3.61 (m, 4H), 3.18 (d, J=10.3 Hz, 4H), 1.67 (s, 4H), 1.27 (s, 12H).

FS126: 6'-(5,5,8,8-Tetramethyl-5,6,7,8-tetrahydronaphthalen-2-yl)-3,4,5,6-tetrahydro-2H-1,2'-bipyridinyl-4-ol

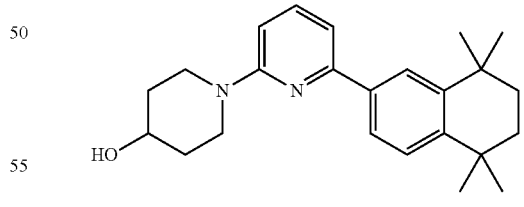

The preparation is carried out analogously to FS119.

Yield: 6 mg. Rt.=2.87 min (method A), LCMS: 365 (M+H).

$^1$H NMR (500 MHz, DMSO/deuterated TFA) δ 7.95 (dd, J=9.2, 7.3 Hz, 1H), 7.61 (d, J=1.9 Hz, 1H), 7.50 (d, J=8.2 Hz, 1H), 7.45 (dd, J=8.2, 1.9 Hz, 1H), 7.29 (d, J=9.1 Hz, 1H), 7.03 (d, J=7.3 Hz, 1H), 3.99-3.83 (m, 3H), 3.58-3.49 (m, 2H), 1.94-1.84 (m, 2H), 1.68 (s, 4H), 1.63-1.54 (m, 2H), 1.28 (d, J=11.5 Hz, 12H).

FS127: 6'-(5,5,8,8-Tetramethyl-5,6,7,8-tetrahydronaphthalen-2-yl)-3,4,5,6-tetrahydro-2H-1,2'-bipyridinyl-4-carboxylic acid

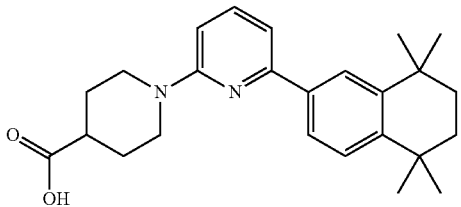 [SMILES: CC1(C)CCC(C)(C)c2cc(-c3cccc(N4CCC(C(=O)O)CC4)n3)ccc21]

The preparation is carried out analogously to FS119. The ethyl ester was subsequently cleaved using lithium hydroxide solution in THF to give the target compound.

Yield: 11 mg. Rt.=2.94 min (method A), LCMS: 393 (M+H).

$^1$H NMR (500 MHz, DMSO/deuterated TFA): δ 7.97 (dd, J=9.1, 7.4 Hz, 1H), 7.62 (d, J=1.9 Hz, 1H), 7.50 (d, J=8.2 Hz, 1H), 7.46 (dd, J=8.2, 1.9 Hz, 1H), 7.30 (d, J=9.2 Hz, 1H), 7.05 (d, J=7.2 Hz, 1H), 4.15 (d, J=13.6 Hz, 2H), 3.36 (dd, J=18.0, 7.0 Hz, 2H), 2.64 (ddd, J=14.7, 10.4, 4.1 Hz, 1H), 2.01 (dd, J=13.7, 3.3 Hz, 2H), 1.81-1.71 (m, 2H), 1.68 (s, 4H), 1.28 (d, J=11.7 Hz, 12H).

FS201: 1-[6-(5,5,8,8-Tetramethyl-5,6,7,8-tetrahydronaphthalen-2-yl)pyridin-2-yl]-piperazine

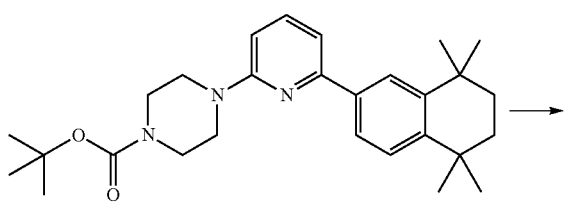

115 mg (0.26 mmol) of 4-[6-(5,5,8,8-tetramethyl-5,6,7,8-tetrahydronaphthalen-2-yl)pyridin-2-yl]piperazine-1-carboxylic acid tert-butyl ester are dissolved in 5 ml of dioxane, 2.5 ml of 4N HCl in dioxane are added, and the mixture is stirred at RT for 15 h. The reaction mixture is evaporated, water is added to the residue, the mixture is rendered basic using 1 N NaOH and extracted with ethyl acetate. The organic phase is dried over Na$_2$SO$_4$ and evaporated. The crude product is purified by means of preparative HPLC, 1.25 M HCl in methanol is added to the residue, and the mixture is evaporated.

26 mg, white solid. Product is the hydrochloride.

Rt.=3.08 min (method A), LCMS: 350 (M+H).

$^1$H NMR (400 MHz, DMSO/deuterated TFA) δ 7.97 (t, J=8.1, 1H), 7.82 (d, J=1.5, 1H), 7.65 (dd, J=8.2, 1.4 1H), 7.51 (d, J=8.2, 1H), 7.25 (dd, J=25.3, 8.1, 2H), 3.97 (b, 4H), 3.35 (b, 4H), 1.73 (s, 4H), 1.39-1.14 (m, 12H).

FS202: 1-[6-(5,5-Dimethyl-5,6,7,8-tetrahydronaphthalen-2-yl)pyridin-2-yl]-piperazine

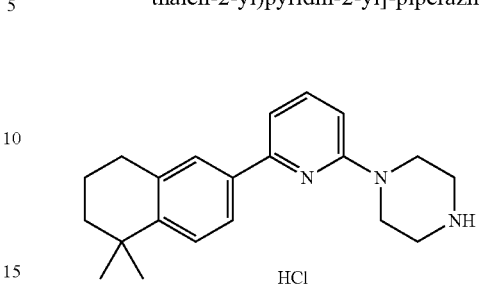

The above compound is prepared analogously to FS201 starting from 4-[6-(5,5-dimethyl-5,6,7,8-tetrahydronaphthalen-2-yl)pyridin-2-yl]piperazine-1-carboxylic acid tert-butyl ester. Product is the hydrochloride.

Yield: 318 mg, beige solid. Rt.=2.52 min (method B), LCMS: 322 (M+H).

$^1$H NMR (500 MHz, DMSO/deuterated TFA) δ 7.92-7.87 (m, 1H), 7.70 (dd, J=8.2, 1.5, 1H), 7.61 (d, J=0.8, 1H), 7.51 (d, J=8.2, 1H), 7.27 (d, J=7.4, 1H), 7.12 (d, J=8.7, 1H), 3.95-3.90 (m, 4H), 3.34-3.29 (m, 4H), 2.84 (t, J=6.2, 2H), 1.85-1.78 (m, 2H), 1.72-1.67 (m, 2H), 1.30 (s, 6H).

FS203: 4-piperazin-1-yl-2-(5,5,8,8-tetramethyl-5,6,7,8-tetrahydronaphthalen-2-yl)pyrimidine

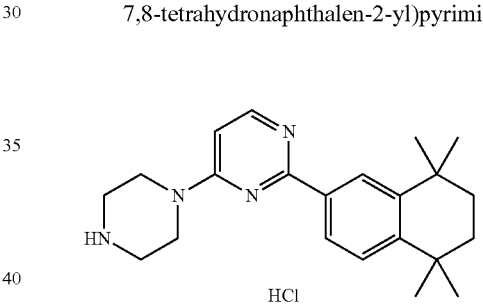

The above compound is prepared analogously to FS201 starting from 4-[2-(5,5,8,8-tetramethyl-5,6,7,8-tetrahydronaphthalen-2-yl)pyrimidin-4-yl]piperazine-1-carboxylic acid tert-butyl ester. Product is the hydrochloride.

Yield: 36 mg, white solid. Rt.=2.48 min (method A), LCMS: 351 (M+H).

$^1$H NMR (500 MHz, DMSO/deuterated TFA) δ 8.51 (d, J=7.5, 1H), 8.20 (d, J=1.9, 1H), 8.02 (dd, J=8.4, 1.8, 1H), 7.60 (d, J=8.4, 1H), 7.26 (d, J=7.5, 1H), 4.23 (d, J=139.4, 4H), 3.41-3.35 (m, 4H), 1.73 (s, 4H), 1.33 (d, J=21.6, 12H).

FS204: 2-piperazin-1-yl-4-(5,5,8,8-tetramethyl-5,6,7,8-tetrahydronaphthalen-2-yl)pyrimidine

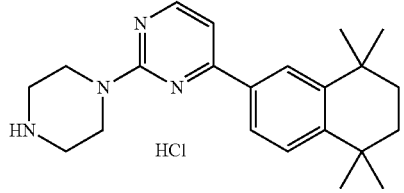 [SMILES: CC1(C)CCC(C)(C)c2cc(-c3ccnc(N4CCNCC4)n3)ccc21 ; Cl]

The above compound is prepared analogously to FS201 starting from 4-[4-(5,5,8,8-tetramethyl-5,6,7,8-tetrahydronaphthalen-2-yl)pyrimidin-2-yl]piperazine-1-carboxylic acid tert-butyl ester. Product is the hydrochloride.

Yield: 50 mg, white solid. Rt.=2.97 min (method A), LCMS: 351 (M+H).

$^1$H NMR (400 MHz, DMSO/deuterated TFA) δ 8.52 (d, J=5.8, 1H), 8.13 (d, J=1.9, 1H), 7.94 (dd, J=8.3, 1.9, 1H), 7.49 (dd, J=9.5, 7.1, 2H), 4.18-4.11 (m, 4H), 3.37-3.28 (m, 4H), 1.72 (s, 4H), 1.33 (d, J=16.2, 12H).

FS205: 6'-(5,5,8,8-Tetramethyl-5,6,7,8-tetrahydronaphthalen-2-yl)-3,4,5,6-tetrahydro-2H-1,2'-bipyrazinyl

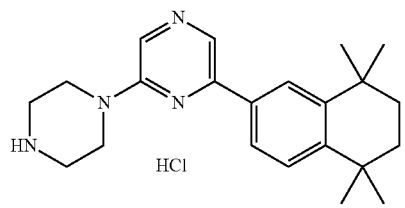 [SMILES: CC1(C)CCC(C)(C)c2cc(-c3cncc(N4CCNCC4)n3)ccc21 ; Cl]

The above compound is prepared analogously to FS201 starting from 6'-(5,5,8,8-tetramethyl-5,6,7,8-tetrahydronaphthalen-2-yl)-2,3,5,6-tetrahydro-1,2'-bipyrazinyl-4-carboxylic acid tert-butyl ester. Product is the hydrochloride.

Yield: 602 mg, yellow solid. Rt.=2.85 min (method A), LCMS: 351 (M+H).

$^1$H NMR (500 MHz, DMSO/deuterated TFA) δ 8.60 (s, 1H), 8.40 (s, 1H), 8.02 (d, J=1.8, 1H), 7.83 (dd, J=8.3, 1.9, 1H), 7.47 (d, J=8.3, 1H), 4.02-3.90 (m, 4H), 3.36-3.21 (m, 4H), 1.70 (s, 4H), 1.31 (d, J=21.7, 12H).

FS206: 2-piperazin-1-yl-4-(5,5,8,8-tetramethyl-5,6,7,8-tetrahydronaphthalen-2-yl)-1,3,5-triazine

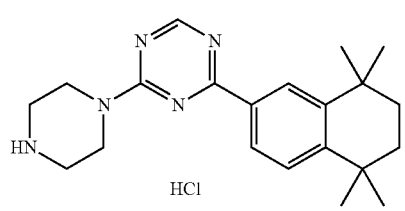 [SMILES: CC1(C)CCC(C)(C)c2cc(-c3ncnc(N4CCNCC4)n3)ccc21 ; Cl]

The above compound is prepared analogously to FS201 starting from 4-[4-(5,5,8,8-tetramethyl-5,6,7,8-tetrahydronaphthalen-2-yl)-1,3,5-triazin-2-yl]piperazine-1-carboxylic acid tert-butyl ester. Product is the hydrochloride.

Yield: 115 mg, white solid. Rt.=2.78 min (method A), LCMS: 352 (M+H).

$^1$H NMR (400 MHz, DMSO/deuterated TFA) δ 9.00 (s, 1H), 8.34 (d, J=2.0, 1H), 8.14 (dd, J=8.4, 2.0, 1H), 7.58 (d, J=8.4, 1H), 4.28 (d, J=37.1, 4H), 3.36 (s, 4H), 1.73 (s, 4H), 1.33 (d, J=14.1, 12H).

FS207: 1-[6-(8,8-Dimethyl-5,6,7,8-tetrahydronaphthalen-2-yl)pyridin-2-yl]piperazine

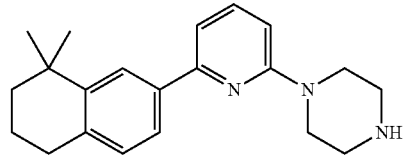 [SMILES: CC1(C)CCCc2ccc(-c3cccc(N4CCNCC4)n3)cc21]

The above compound is prepared analogously to FS201 starting from 4-[6-(8,8-dimethyl-5,6,7,8-tetrahydronaphthalen-2-yl)pyridin-2-yl]piperazine-1-carboxylic acid tert-butyl ester.

Yield: 470 mg, oil. Rt.=2.53 min (method B), LCMS: 322 (M+H).

$^1$H NMR (400 MHz, DMSO/deuterated TFA) δ 7.92 (d, J=1.5, 1H), 7.88-7.82 (m, 1H), 7.67 (dd, J=7.9, 1.7, 1H), 7.30 (d, J=7.5, 1H), 7.18 (d, J=8.0, 1H), 7.08 (d, J=8.6, 1H), 3.96-3.85 (m, 4H), 3.36-3.27 (m, 4H), 2.80 (t, J=6.2, 2H), 1.84-1.76 (m, 2H), 1.73-1.66 (m, 2H), 1.33 (s, 6H).

FS208: 1-[6-(1,1,3,3-Tetramethylindan-5-yl)pyridin-2-yl]piperazine

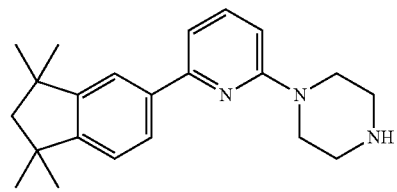 [SMILES: CC1(C)CC(C)(C)c2cc(-c3cccc(N4CCNCC4)n3)ccc21]

The above compound is prepared analogously to FS201 starting from 4-[6-(1,1,3,3-tetramethylindan-5-yl)pyridin-2-yl]piperazine-1-carboxylic acid tert-butyl ester.

Yield: 169 mg, oil. Rt.=2.73 min (method B), LCMS: 336 (M+H).

$^1$H NMR (400 MHz, DMSO/deuterated TFA) δ 7.98 (dd, J=8.8, 7.5, 1H), 7.73 (dd, J=7.9, 1.7, 1H), 7.64 (d, J=1.5, 1H), 7.34 (d, J=7.9, 1H), 7.28 (d, J=7.3, 1H), 7.23 (d, J=8.8, 1H), 4.00-3.94 (m, 4H), 3.38-3.32 (m, 4H), 1.98 (s, 2H), 1.36 (d, J=9.2, 12H).

FS209: 1-[2-(5,5,8,8-Tetramethyl-5,6,7,8-tetrahydronaphthalen-2-yl)pyridin-4-yl]-piperazine

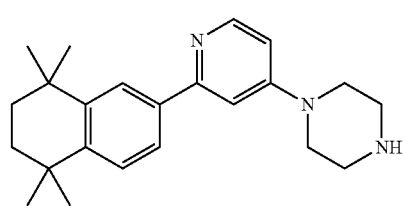 [SMILES: CC1(C)CCC(C)(C)c2cc(-c3cc(N4CCNCC4)ccn3)ccc21]

The above compound is prepared analogously to FS201 starting from 4-[2-(5,5,8,8-tetramethyl-5,6,7,8-tetrahydronaphthalen-2-yl)pyridin-4-yl]piperazine-1-carboxylic acid tert-butyl ester.

Yield: 86 mg, viscous oil. Rt.=1.97 min (method B), LCMS: 350 (M+H).

$^1$H NMR (400 MHz, DMSO/deuterated TFA) δ 8.34 (d, J=7.1, 1H), 7.76 (s, 1H), 7.64 (d, J=8.4, 1H), 7.56 (d, J=8.1, 1H), 7.41 (d, J=2.6, 1H), 7.23 (dd, J=7.4, 2.2, 1H), 4.04-3.94 (m, 4H), 3.37-3.23 (m, 4H), 1.68 (s, 4H), 1.30 (d, J=15.9, 12H).

FS210: 1-[6-(1,1-Dimethylindan-5-yl)pyridin-2-yl]piperazine

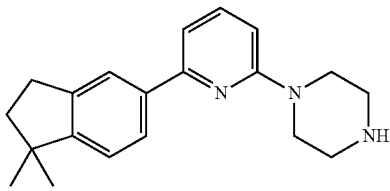

The above compound is prepared analogously to FS201 starting from 4-[6-(1,1-dimethylindan-5-yl)pyridin-2-yl]piperazine-1-carboxylic acid tert-butyl ester.

Yield: 192 mg, yellow oil. Rt.=1.72 min (method B), LCMS: 308 (M+H).

$^1$H NMR (400 MHz, DMSO/deuterated TFA) $^1$H NMR (400 MHz, DMSO) δ 7.90 (dd, J=8.8, 7.6, 1H), 7.67-7.60 (m, 2H), 7.27 (d, J=7.8, 1H), 7.19 (d, J=7.4, 1H), 7.14 (d, J=8.8, 1H), 3.93-3.83 (m, 4H), 3.31-3.22 (m, 4H), 2.90 (t, J=7.2, 2H), 1.90 (t, J=7.2, 2H), 1.21 (s, 7H).

FS211: 1-[3-(5,5,8,8-Tetramethyl-5,6,7,8-tetrahydronaphthalen-2-yl)phenyl]-piperazine

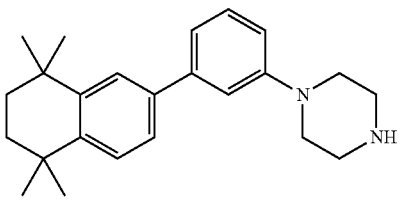 [SMILES: CC1(C)CCC(C)(C)c2cc(-c3cccc(N4CCNCC4)c3)ccc21]

The above compound is prepared analogously to FS201 starting from 4-[3-(5,5,8,8-tetramethyl-5,6,7,8-tetrahydronaphthalen-2-yl)phenyl]piperazine-1-carboxylic acid tert-butyl ester.

Yield: 423 mg, yellow oil. Rt.=2.81 min (method B), LCMS: 349 (M+H).

$^1$H NMR (400 MHz, DMSO/deuterated TFA) δ 7.54 (s, 1H), 7.41-7.33 (m, 3H), 7.22 (s, 1H), 7.16 (d, J=7.7, 1H), 7.02 (dd, J=8.2, 1.9, 1H), 3.53-3.46 (m, 4H), 3.36-3.30 (m, 4H), 1.71 (s, 4H), 1.31 (d, J=15.2, 12H).

FS212: 2-(5,5-Dimethyl-5,6,7,8-tetrahydronaphthalen-2-yl)-4-piperazin-1-yl-1,3,5-triazine

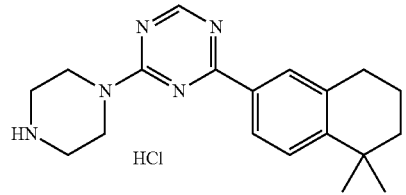 [SMILES: CC1(C)CCCc2cc(-c3ncnc(N4CCNCC4)n3)ccc21 ; Cl]

The above compound is prepared analogously to FS201 starting from 4-[4-(5,5-dimethyl-5,6,7,8-tetrahydronaphthalen-2-yl)-1,3,5-triazin-2-yl]piperazine-1-carboxylic acid tert-butyl ester. The product is in the form of the hydrochloride.

Yield: 250 mg, colourless oil. Rt.=2.78 min (method A), LCMS: 352 (M+H).

$^1$H NMR (500 MHz, DMSO/deuterated TFA) δ 8.92 (s, 1H), 8.13 (d, J=8.3, 1H), 8.08 (s, 1H), 7.58 (d, J=8.4, 1H), 4.26 (d, J=49.0, 4H), 3.35 (s, 4H), 2.86 (t, J=6.2, 2H), 1.87-1.79 (m, 2H), 1.71 (dd, J=7.5, 3.9, 2H), 1.31 (s, 6H).

FS213: 2-(8,8-Dimethyl-5,6,7,8-tetrahydronaphthalen-2-yl)-4-piperazin-1-yl-1,3,5-triazine

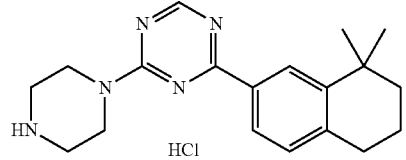 [SMILES: CC1(C)CCCc2ccc(-c3ncnc(N4CCNCC4)n3)cc21 ; Cl]

The above compound is prepared analogously to FS201 starting from 4-[4-(8,8-dimethyl-5,6,7,8-tetrahydronaphthalen-2-yl)-1,3,5-triazin-2-yl]piperazine-1-carboxylic acid tert-butyl ester. The product is in the form of the hydrochloride.

Yield: 7 mg, beige solid. Rt.=2.61 min (method A), LCMS: 324 (M+H).

$^1$H NMR (400 MHz, DMSO/deuterated TFA) δ 8.90 (s, 1H), 8.14 (dd, J=8.3, 1.9, 1H), 8.08 (s, 1H), 7.58 (d, J=8.3, 1H), 4.23 (d, J=39.9, 4H), 3.33 (s, 4H), 2.85 (t, J=6.1, 2H), 1.87-1.77 (m, 2H), 1.75-1.65 (m, 2H), 1.31 (s, 6H).

FS214: 1-{1-[4-(5,5,8,8-Tetramethyl-5,6,7,8-tetrahydronaphthalen-2-yl)-1,3,5-triazin-2-yl]piperidin-4-yl}pyrrolidin-3-ylamine

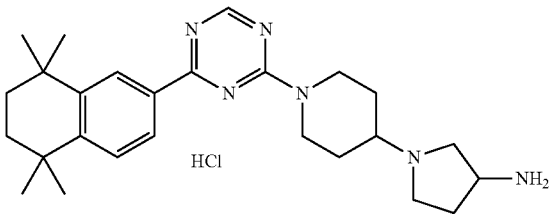 [SMILES: CC1(C)CCC(C)(C)c2cc(-c3ncnc(N4CCC(N5CCC(N)C5)CC4)n3)ccc21 ; Cl]

The above compound is prepared analogously to FS201 starting from (1-{1-[4-(5,5,8,8-tetramethyl-5,6,7,8-tetrahydronaphthalen-2-yl)-1,3,5-triazin-2-yl]piperidin-4-yl}pyrrolidin-3-yl)carbamic acid tert-butyl ester. The product is in the form of the hydrochloride.

Yield: 7 mg, beige solid. Rt.=2.26 min (method B), LCMS: 435 (M+H).

$^1$H NMR (400 MHz, DMSO/deuterated TFA) 8.86 (s, 1H), 8.30 (d, J=1.6, 1H), 8.10 (dd, J=8.4, 1.7, 1H), 7.55 (d, J=8.4, 1H), 5.06 (d, J=12.4, 1H), 4.90 (d, J=13.3, 1H), 3.98 (s, 2H), 3.77-3.08 (m, 7H), 2.27 (b, 2H), 2.18-1.94 (m, 1H), 1.77-1.60 (m, 6H), 1.31 (d, J=9.6, 12H).

FS215: 1-[2-(5,5,8,8-Tetramethyl-5,6,7,8-tetrahydronaphthalen-2-yl)pyrimidin-4-yl]-piperidin-4-ylamine

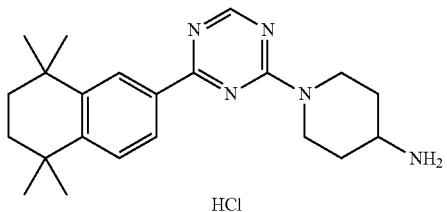 [SMILES: CC1(C)CCC(C)(C)c2cc(-c3ncnc(N4CCC(N)CC4)n3)ccc21 ; Cl]

The above compound is prepared analogously to FS201 starting {1-[2-(5,5,8,8-tetramethyl-5,6,7,8-tetrahydronaphthalen-2-yl)pyrimidin-4-yl]piperidin-4-yl}carbamic acid tert-butyl ester. The product is in the form of the hydrochloride.

Yield: 391 mg, white solid. Rt.=2.43 min (method A), LCMS: 365 (M+H).

$^1$H NMR (500 MHz, DMSO/deuterated TFA) δ 8.38 (d, J=7.5 Hz, 1H), 8.19 (d, J=2.0 Hz, 1H), 8.01 (dd, J=8.4, 2.0 Hz, 1H), 7.59 (d, J=8.4 Hz, 1H), 7.20 (d, J=7.6 Hz, 1H), 5.20 (d, J=12.6 Hz, 1H), 4.39 (d, J=13.1 Hz, 1H), 3.58-3.50 (m, 1H), 3.46 (t, J=11.3 Hz, 1H), 3.31 (t, J=12.3 Hz, 1H), 2.20 (b, 2H), 1.74 (s, 4H), 1.60-1.75 (m, 2H), 1.34 (d, J=22.3 Hz, 12H).

FS216: 1-[4-(5,5,8,8-Tetramethyl-5,6,7,8-tetrahydronaphthalen-2-yl)pyrimidin-2-yl]-piperidin-4-ylamine

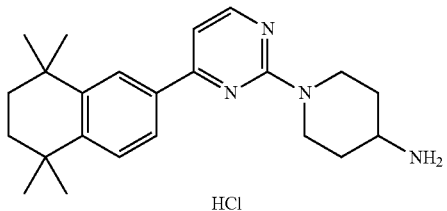 [SMILES: CC1(C)CCC(C)(C)c2cc(-c3ccnc(N4CCC(N)CC4)n3)ccc21 ; Cl]

The above compound is prepared analogously to FS201 {1-[4-(5,5,8,8-tetramethyl-5,6,7,8-tetrahydronaphthalen-2-yl)pyrimidin-2-yl]piperidin-4-yl}carbamic acid tert-butyl ester. The product is in the form of the hydrochloride.

Yield: 437 mg, white solid. Rt.=2.72 min (method A), LCMS: 365 (M+H).

$^1$H NMR (500 MHz, DMSO/deuterated TFA) δ 8.24 (d, J=6.7 Hz, 1H), 8.05 (d, J=1.8 Hz, 1H), 7.86 (dd, J=8.4, 1.8 Hz, 1H), 7.40-7.45 (m, 2H), 4.60 (b, 2H), 3.42-3.32 (m, 1H), 3.25 (t, J=11.9 Hz, 2H), 2.09 (d, J=10.3 Hz, 2H), 1.71-1.58 (m, 6H), 1.21 (d, J=16.6 Hz, 12H).

FS217: (S)-1-[2-(5,5,8,8-Tetramethyl-5,6,7,8-tetrahydronaphthalen-2-yl)-pyrimidin-4-yl]pyrrolidin-3-ylamine

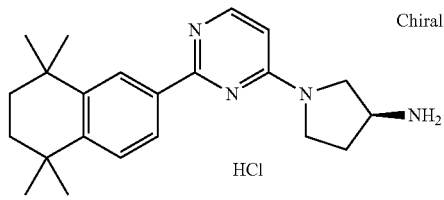 [SMILES: CC1(C)CCC(C)(C)c2cc(-c3nccc(N4CC[C@H](N)C4)n3)ccc21 ; Cl]

The above compound is prepared analogously to FS203. Product is the hydrochloride.

Yield: 333 mg, white solid. Rt.=2.38 min (method A), LCMS: 351 (M+H).

$^1$H NMR (500 MHz, DMSO/deuterated TFA) δ 8.42 (t, J=7.3 Hz, 1H), 8.24 (dd, J=3.9, 2.1 Hz, 1H), 8.06-7.98 (m, 1H), 7.62 (dd, J=8.4, 4.5 Hz, 1H), 6.95 (dd, J=14.0, 7.4 Hz, 1H), 4.19-3.75 (m, 5H), 2.54-2.36 (m, 1H), 2.35-2.18 (m, 1H), 1.73 (s, 4H), 1.42-1.30 (m, 12H).

FS218: (R)-1-[4-(5,5,8,8-Tetramethyl-5,6,7,8-tetrahydronaphthalen-2-yl)-pyrimidin-2-yl]pyrrolidin-3-ylamine

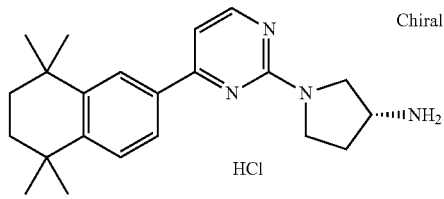 [SMILES: CC1(C)CCC(C)(C)c2cc(-c3ccnc(N4CC[C@@H](N)C4)n3)ccc21 ; Cl]

The above compound is prepared analogously to FS203. Product is the hydrochloride.

Yield: 207 mg, white solid. Rt.=2.59 min (method A), LCMS: 351 (M+H).

$^1$H NMR (500 MHz, DMSO/deuterated TFA) δ 8.51 (d, J=6.6 Hz, 1H), 8.22 (t, J=5.0 Hz, 1H), 7.99 (d, J=8.1 Hz, 1H), 7.67 (d, J=6.6 Hz, 1H), 7.53 (d, J=8.3 Hz, 1H), 4.17-3.58 (m, 5H), 2.49-2.09 (m, 2H), 1.68 (s, 4H), 1.29 (d, J=20.1 Hz, 12H).

FS219: (R)-1-[2-(5,5,8,8-Tetramethyl-5,6,7,8-tetrahydronaphthalen-2-yl)-pyrimidin-4-yl]pyrrolidin-3-ylamine

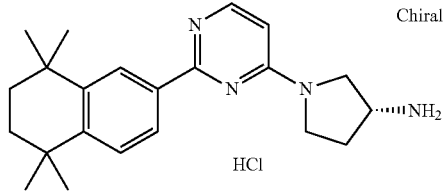 [SMILES: CC1(C)CCC(C)(C)c2cc(-c3nccc(N4CC[C@@H](N)C4)n3)ccc21 ; Cl]

The above compound is prepared analogously to FS203. Product is in the form of the hydrochloride.
Yield: 347 mg, solid. Rt.=2.38 min (method A), LCMS: 351 (M+H).
¹H NMR (500 MHz, DMSO/deuterated TFA) δ 8.37 (t, J=7.5 Hz, 1H), 8.20 (dd, J=4.0, 2.1 Hz, 1H), 7.98 (ddd, J=10.6, 8.4, 2.0 Hz, 1H), 7.57 (dd, J=8.4, 4.3 Hz, 1H), 6.90 (dd, J=15.7, 7.4 Hz, 1H), 4.15-3.72 (m, 5H), 2.51-2.15 (m, 2H), 1.70 (s, 4H), 1.35-1.27 (m, 12H).

FS220: Piperidin-4-yl-[6-(5,5,8,8-tetramethyl-5,6,7,8-tetrahydronaphthalen-2-yl)pyridin-2-yl]amine

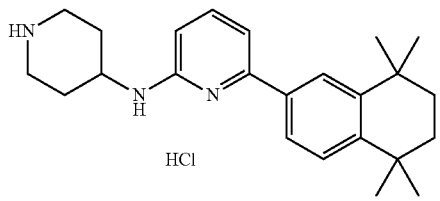 [SMILES: CC1(C)CCC(C)(C)c2cc(-c3cccc(NC4CCNCC4)n3)ccc21 ; Cl]

The above compound is prepared analogously to FS203. Product is in the form of the hydrochloride.
Yield: 360 mg, solid. Rt.=2.54 min (method A), LCMS: 364 (M+H).
¹H NMR (400 MHz, DMSO/deuterated TFA): δ 8.02 (t, J=8.2 Hz, 1H), 7.74 (s, 1H), 7.58-7.49 (m, 2H), 7.21-7.10 (m, 2H), 4.12-3.99 (m, 1H), 3.40 (d, J=13.1 Hz, 2H), 3.13-2.97 (m, 2H), 2.15 (d, J=11.0 Hz, 2H), 1.87-1.73 (m, 2H), 1.69 (s, 4H), 1.30 (d, J=15.5 Hz, 12H).

FS301: 3-{4-[6-(5,5,8,8-Tetramethyl-5,6,7,8-tetrahydronaphthalen-2-yl)pyridin-2-yl]-piperazin-1-yl}propan-1-ol

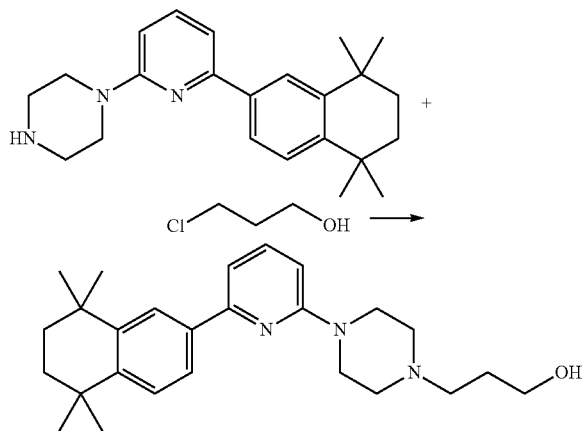

88 mg (0.25 mmol) of 1-[6-(5,5,8,8-tetramethyl-5,6,7,8-tetrahydronaphthalen-2-yl)pyridin-2-yl]piperazine are irradiated in the microwave at 140° C. for 2 h with 42 μl (0.50 mmol) of 3-chloropropan-1-ol in 2 ml of ethanol and 70 μl (0.50 mmol) of triethylamine. The reaction mixture is evaporated and purified by means of preparative HPLC.
Yield: 53 mg, beige solid. Rt.=2.61 min (method B), LCMS: 408 (M+H).
¹H NMR (500 MHz, DMSO/deuterated TFA) δ 7.90 (t, J=8.1, 1H), 7.86 (s, 1H), 7.68 (d, J=8.2, 1H), 7.48 (d, J=8.3, 1H), 7.29 (d, J=7.5, 1H), 7.15 (d, J=8.7, 1H), 4.54 (d, J=12.9, 2H), 3.71 (d, J=11.0, 2H), 3.58 (t, J=5.8, 2H), 3.45 (t, J=12.5, 2H), 3.32-3.27 (m, 2H), 3.27-3.17 (m, 2H), 1.92 (td, J=11.5, 5.8, 2H), 1.72 (s, 4H), 1.32 (d, J=16.6, 12H).

FS302: 3-{4-[6-(5,5-Dimethyl-5,6,7,8-tetrahydronaphthalen-2-yl)pyridin-2-yl]-piperazin-1-yl}propan-1-ol

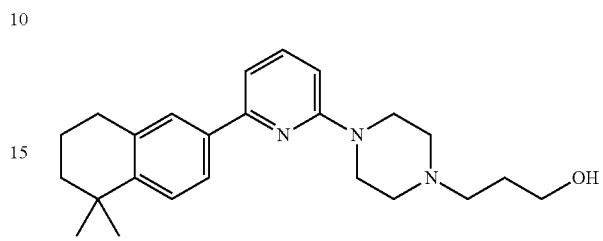

The preparation is carried out analogously to FS301.
Yield: 37 mg, white solid. Rt.=2.63 min (method B), LCMS: 380 (M+H).
¹H NMR (500 MHz, DMSO/deuterated TFA) δ 7.93-7.87 (m, 1H), 7.74-7.68 (m, 1H), 7.61 (d, J=9.3, 1H), 7.51 (d, J=8.3, 1H), 7.29 (d, J=7.4, 1H), 7.15 (d, J=8.5, 1H), 4.55 (d, J=14.3, 2H), 3.71 (d, J=10.7, 2H), 3.57 (t, J=5.8, 2H), 3.47-3.37 (m, 2H), 3.36-3.17 (m, 4H), 2.84 (t, J=6.1, 2H), 1.97-1.87 (m, 2H), 1.87-1.77 (m, 2H), 1.75-1.65 (m, 2H), 1.31 (s, 6H).

FS303: 3-{4-[2-(5,5,8,8-Tetramethyl-5,6,7,8-tetrahydronaphthalen-2-yl)pyrimidin-4-yl]piperazin-1-yl}propan-1-ol

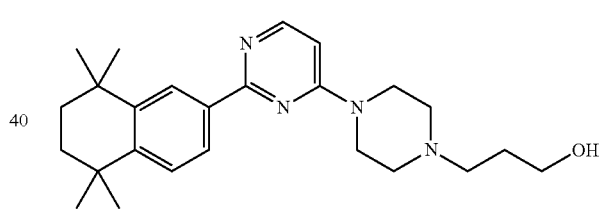

The preparation is carried out analogously to FS301.
Yield: 13 mg, yellow oil. Rt.=2.47 min (method A), LCMS: 409 (M+H).

FS304: 3-{4-[4-(5,5,8,8-Tetramethyl-5,6,7,8-tetrahydronaphthalen-2-yl)pyrimidin-2-yl]-piperazin-1-yl}propan-1-ol

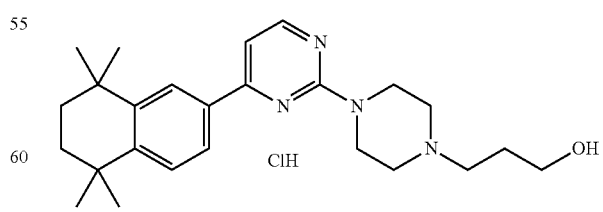

The above compound is prepared analogously to FS301. The product is in the form of the hydrochloride.
Yield: 47 mg, beige solid. Rt.=2.93 min (method A), LCMS: 409 (M+H).

FS305: 2-{4-[2-(5,5,8,8-Tetramethyl-5,6,7,8-tetrahydronaphthalen-2-yl)pyrimidin-4-yl]-piperazin-1-yl}ethanol

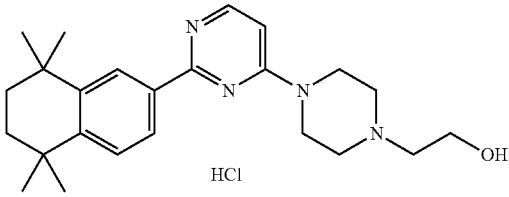 [SMILES: CC1(C)CCC(C)(C)c2cc(-c3nccc(N4CCN(CCO)CC4)n3)ccc21 ; Cl]

The above compound is prepared analogously to FS301. The product is in the form of the hydrochloride.

Yield: 36 mg, beige solid. Rt.=2.41 min (method A), LCMS: 395 (M+H).

FS306: 4-{4-[4-(5,5,8,8-Tetramethyl-5,6,7,8-tetrahydronaphthalen-2-yl)pyrimidin-2-yl]piperazin-1-yl}butan-1-ol

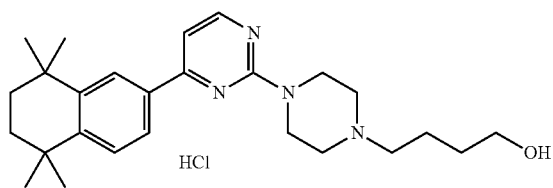 [SMILES: CC1(C)CCC(C)(C)c2cc(-c3ccnc(N4CCN(CCCCO)CC4)n3)ccc21 ; Cl]

The preparation is carried out analogously to FS301. The product is in the form of the hydrochloride.

Yield: 42 mg, beige solid. Rt.=2.96 min (method A), LCMS: 423 (M+H).

$^1$H NMR (500 MHz, DMSO/deuterated TFA) δ 8.49 (d, J=5.7 Hz, 1H), 8.09 (d, J=1.8 Hz, 1H), 7.90 (dd, J=8.3, 1.8 Hz, 1H), 7.47 (d, J=8.3 Hz, 1H), 7.41 (d, J=5.7 Hz, 1H), 4.85 (d, J=14.0 Hz, 2H), 3.66 (d, J=11.7 Hz, 2H), 3.55-3.37 (m, 4H), 3.19 (dd, J=18.2, 10.3 Hz, 4H), 1.78 (dd, J=15.9, 8.1 Hz, 2H), 1.69 (s, 4H), 1.57-1.45 (m, 2H), 1.30 (d, J=20.5 Hz, 12H).

FS307: 7-{4-[6-(5,5,8,8-Tetramethyl-5,6,7,8-tetrahydronaphthalen-2-yl)pyridin-2-yl]-piperazin-1-yl}heptan-1-ol

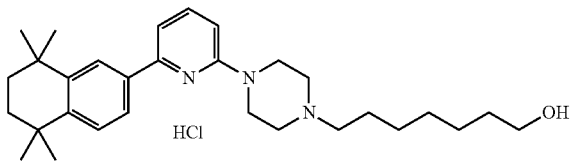 [SMILES: CC1(C)CCC(C)(C)c2cc(-c3cccc(N4CCN(CCCCCCCO)CC4)n3)ccc21 ; Cl]

The preparation is carried out analogously to FS301. The product is in the form of the hydrochloride.

Yield: 25 mg, white solid. Rt.=3.17 min (method A), LCMS: 464 (M+H).

$^1$H NMR (500 MHz, DMSO/deuterated TFA) δ 7.96-7.86 (m, 1H), 7.64-7.56 (m, 1H), 7.47-7.35 (m, 2H), 7.20-7.07 (m, 2H), 4.38 (d, J=12.7 Hz, 2H), 3.66-3.46 (m, 4H), 3.39 (t, J=6.6 Hz, 2H), 3.20-2.99 (m, 4H), 1.72-1.58 (m, 7H), 1.44-1.36 (m, 2H), 1.34-1.15 (m, 18H).

FS308: 6-{4-[6-(5,5,8,8-Tetramethyl-5,6,7,8-tetrahydronaphthalen-2-yl)pyridin-2-yl]-piperazin-1-yl}hexan-1-ol

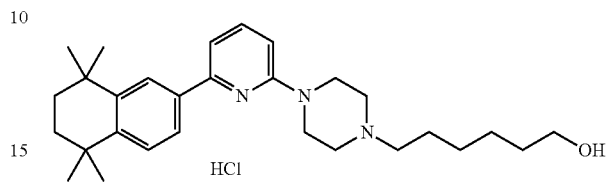

The preparation is carried out analogously to FS301 using (6-bromohexyloxy)-tert-butyldimethylsilane and with subsequent cleaving off of TBDMS analogously to FS520. The product is in the form of the hydrochloride.

Yield: 59 mg, white solid. Rt.=3.09 min (method A), LCMS: 450 (M+H).

$^1$H NMR (400 MHz, DMSO/deuterated TFA) δ 7.92 (d, J=1.8 Hz, 1H), 7.82-7.69 (m, 2H), 7.44 (d, J=8.3 Hz, 1H), 7.30 (d, J=7.5 Hz, 1H), 7.00 (d, J=8.6 Hz, 1H), 4.52 (d, J=14.1 Hz, 2H), 3.65 (d, J=11.9 Hz, 2H), 3.43 (t, J=6.4 Hz, 2H), 3.40-3.27 (m, 2H), 3.18-3.08 (m, 4H), 1.80-1.72 (m, 2H), 1.70 (s, 4H), 1.53-1.42 (m, 2H), 1.42-1.34 (m, 4H), 1.31 (d, J=14.6 Hz, 12H).

FS309: 5-{4-[6-(5,5,8,8-Tetramethyl-5,6,7,8-tetrahydronaphthalen-2-yl)pyridin-2-yl]-piperazin-1-yl}pentanoic acid

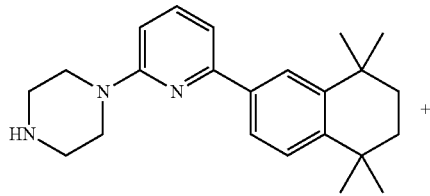

+

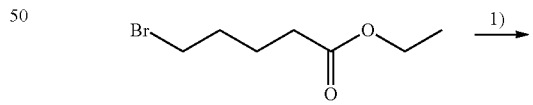

1)

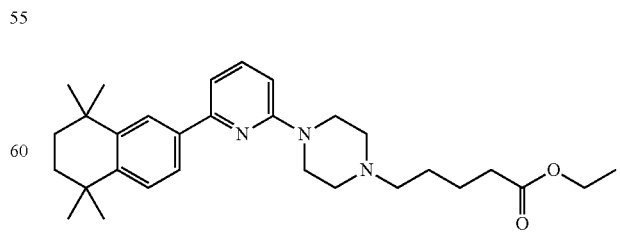

2)

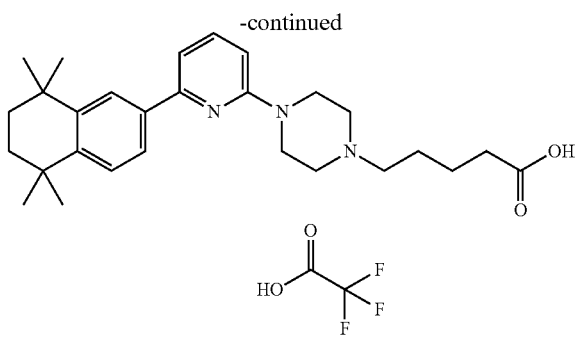

Step 1

100 mg (0.29 mmol) of 1-[6-(5,5,8,8-tetramethyl-5,6,7,8-tetrahydronaphthalen-2-yl)pyridin-2-yl]piperazine, 104 mg (0.572 mmol) of 5-bromovaleric acid ethyl ester, 466 mg (1.43 mmol) of caesium carbonate and 43 mg (0.29 mmol) of sodium iodide are suspended in 2 ml of NMP and stirred at 110° C. for 18 h.

Water is added to the reaction mixture, which is then extracted a number of times with ethyl acetate, dried and evaporated. The product is purified by means of column chromatography on silica gel.

Colourless oil. Rt.=3.25 min (method A), LCMS: 478 (M+H).

Step 2

87 mg (0.175 mmol) of the ester prepared above are suspended in 5 ml of THF and 0.5 ml of water, and 21 mg (0.875 mmol) of lithium hydroxide are added, and the mixture is stirred at room temperature for 3 days. The solution is neutralised, evaporated and purified by means of prep. HPLC. The product is in the form of the trifluoroacetate.

Yield: 35 mg, white solid. Rt.=3.05 min (method A), LCMS: 450 (M+H).

$^1$H NMR (500 MHz, DMSO/deuterated TFA) δ 7.89-7.81 (m, 2H), 7.66 (d, J=8.2 Hz, 1H), 7.45 (d, J=8.3 Hz, 1H), 7.27 (d, J=7.5 Hz, 1H), 7.10 (d, J=8.6 Hz, 1H), 4.51 (d, J=13.9 Hz, 2H), 3.66 (d, J=11.9 Hz, 2H), 3.38 (t, J=12.7 Hz, 2H), 3.25-3.09 (m, 4H), 2.31 (t, J=7.2 Hz, 2H), 1.80-1.70 (m, 2H), 1.69 (s, 4H), 1.63-1.55 (m, 2H), 1.29 (d, J=16.8 Hz, 12H).

FS310: 4-{4-[6-(5,5,8,8-Tetramethyl-5,6,7,8-tetrahydronaphthalen-2-yl)pyridin-2-yl]-piperazin-1-yl}butyric acid

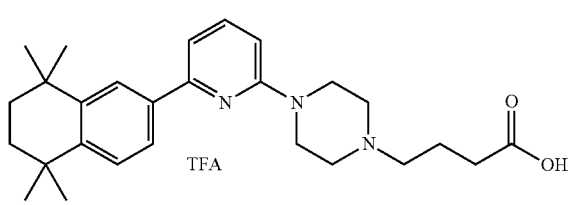 [SMILES: CC1(C)CCC(C)(C)c2cc(-c3cccc(N4CCN(CCCC(=O)O)CC4)n3)ccc21 ; "TFA"]

The preparation is carried out analogously to FS309. The product is in the form of the trifluoroacetate.

Yield: 28 mg, beige solid. Rt.=3.02 min (method A), LCMS: 436 (M+H).

$^1$H NMR (400 MHz, DMSO/deuterated TFA) δ 7.89 (d, J=1.3 Hz, 1H), 7.81 (t, J=8.0 Hz, 1H), 7.71 (dd, J=8.2, 1.4 Hz, 1H), 7.44 (d, J=8.3 Hz, 1H), 7.30 (d, J=7.5 Hz, 1H), 7.05 (d, J=8.5 Hz, 1H), 4.53 (d, J=14.0 Hz, 2H), 3.69 (d, J=11.5 Hz, 2H), 3.33 (t, J=12.5 Hz, 2H), 3.27-3.08 (m, 4H), 2.39 (t, J=7.1 Hz, 2H), 2.05-1.91 (m, 2H), 1.70 (s, 4H), 1.31 (d, J=14.4 Hz, 12H).

FS311: 2-{4-[6-(5,5,8,8-Tetramethyl-5,6,7,8-tetrahydronaphthalen-2-yl)pyridin-2-yl]-piperazin-1-yl}pentane-1,5-diol

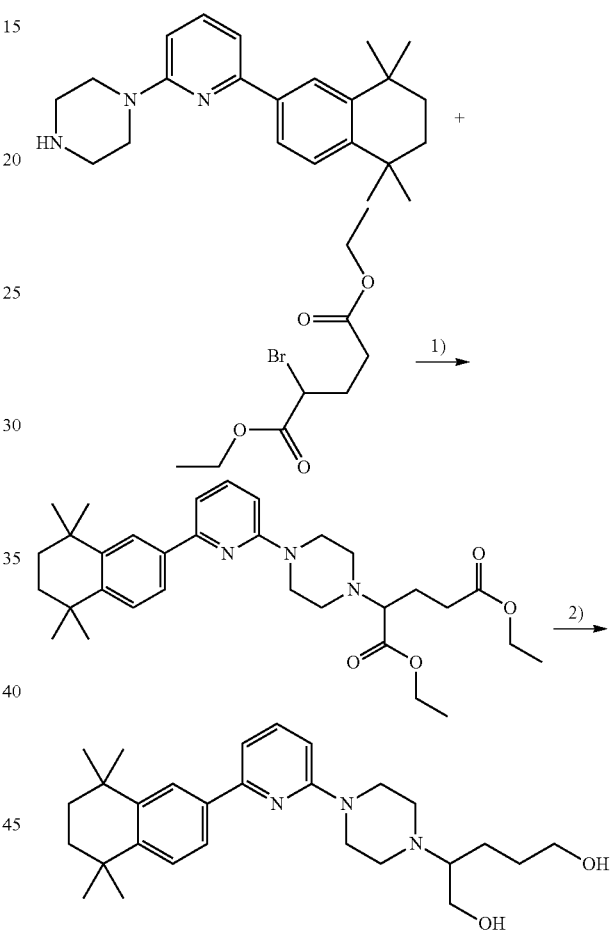

Step 1

The preparation is carried out analogously to FS 301. DMF was used instead of ethanol as solvent, and the reaction mixture was stirred at room temperature for 18 h.

Yield: 576 mg, solid. Rt.=3.40 min (method A), LCMS: 536 (M+H).

Step 2

225 mg (0.32 mmol) of the compound prepared in step 1 are dissolved in 10 ml of THF, and 37 mg (0.97 mmol) of lithium aluminium hydride are added under nitrogen atmosphere. The reaction mixture was stirred at room temperature for 18 h, 3 ml of water were added at 0° C., the mixture was filtered off with suction through Celite and rinsed with ethyl acetate. The filtrate was dried and evaporated to dryness. The crude product was purified by column chromatography on silica gel.

Yield: 61 mg, solid. Rt.=2.95 min (method A), LCMS: 452 (M+H).

¹H NMR (400 MHz, DMSO/deuterated TFA: δ 7.93 (dd, J=8.9, 7.5 Hz, 1H), 7.70 (d, J=1.9 Hz, 1H), 7.53 (dd, J=8.2, 1.9 Hz, 1H), 7.46 (d, J=8.3 Hz, 1H), 7.18 (dd, J=8.2, 2.6 Hz, 2H), 4.51 (b, 2H), 3.87 (dd, J=13.1, 2.9 Hz, 1H), 3.30-3.70 (m, 10H), 1.91-1.69 (m, 2H), 1.68 (s, 4H), 1.64-1.38 (m, 2H), 1.27 (d, J=11.2 Hz, 12H).

FS312: 4-{4-[6-(5,5,8,8-Tetramethyl-5,6,7,8-tetrahydronaphthalen-2-yl)pyridin-2-yl]-piperazin-1-yl}butane-1,3-diol

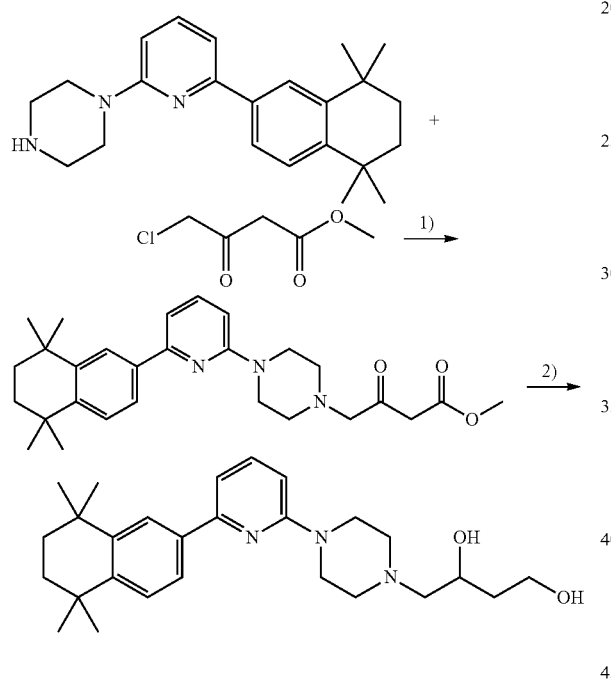

Step 1

The preparation is carried out analogously to FS 301. Dichloromethane was used instead of ethanol as solvent, and the reaction mixture was stirred at room temperature for 18 h.

Yield: 82 mg, solid. Rt.=3.14 min (method A), LCMS: 464 (M+H).

Step 2

The preparation is carried out analogously to FS 311 step 2 using 1.5 eq. of lithium aluminium hydride.

Yield: 13 mg, solid. Rt.=2.94 min (method A), LCMS: 438 (M+H).

¹H NMR (400 MHz, DMSO/deuterated TFA: δ 7.87 (d, J=1.8 Hz, 1H), 7.86-7.79 (m, 1H), 7.70 (dd, J=8.2, 1.9 Hz, 1H), 7.44 (d, J=8.3 Hz, 1H), 7.28 (d, J=7.4 Hz, 1H), 7.06 (d, J=8.6 Hz, 1H), 4.47 (dd, J=28.4, 14.3 Hz, 2H), 4.14 (d, J=7.5 Hz, 1H), 3.75-3.36 (m, 6H), 3.36-3.02 (m, 4H), 1.70 (s, 4H), 1.60 (dd, J=12.4, 6.2 Hz, 2H), 1.30 (d, J=14.1 Hz, 12H).

FS313: 2-(2-{4-[6-(5,5,8,8-Tetramethyl-5,6,7,8-tetrahydronaphthalen-2-yl)pyridin-2-yl]-piperazin-1-yl}ethyl)butane-1,4-diol

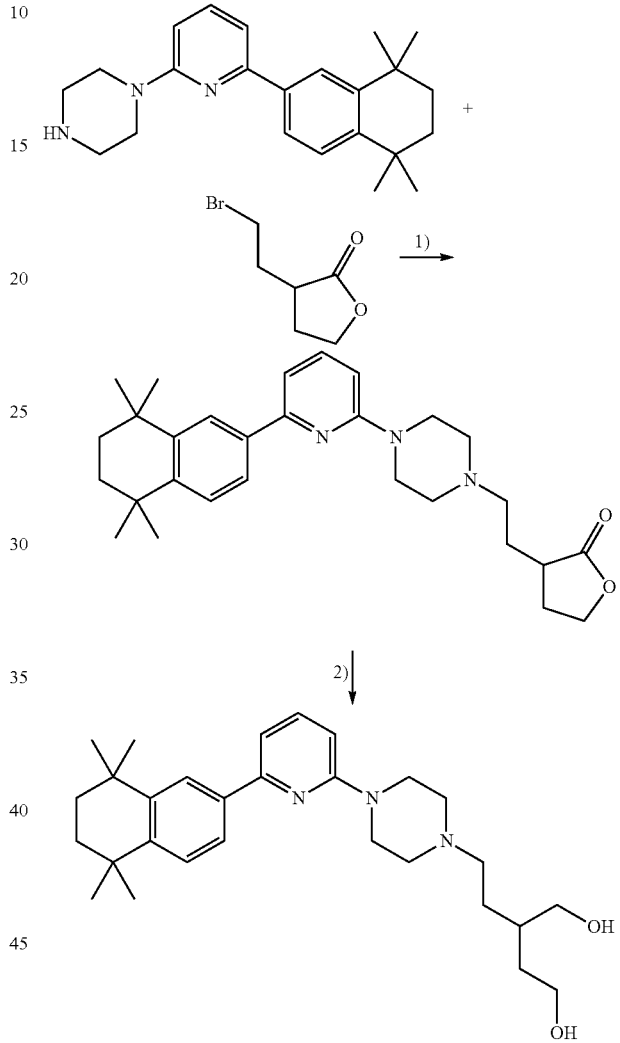

Step 1

The preparation is carried out analogously to FS 301. NMP was used instead of ethanol as solvent, and the reaction mixture was stirred at 70° C. for 12 h.

Yield: 306 mg, solid. Rt.=3.07 min (method A), LCMS: 462 (M+H).

Step 2

The preparation is carried out analogously to FS 312 step 2.

Yield: 144 mg, colourless oil. Rt.=2.94 min (method A), LCMS: 466 (M+H).

¹H NMR (500 MHz, DMSO/deuterated TFA: δ 7.86 (t, J=8.1 Hz, 1H), 7.74 (s, 1H), 7.57 (dd, J=8.2, 1.8 Hz, 1H), 7.42 (d, J=8.3 Hz, 1H), 7.20 (d, J=7.4 Hz, 1H), 7.11 (d, J=8.8 Hz, 1H), 4.45 (d, J=13.7 Hz, 2H), 3.63 (d, J=11.2 Hz, 2H), 3.51-3.08 (m, 10H), 1.82-1.55 (m, 7H), 1.53-1.34 (m, 3H), 1.24 (d, J=15.4 Hz, 12H).

FS314: 4-{(3-Methoxypropyl)-[6'-(5,5,8,8-tetramethyl-5,6,7,8-tetrahydronaphthalen-2-yl)-3,4,5,6-tetrahydro-2H-1,2'-bipyridinyl-4-yl]amino}butan-1-ol

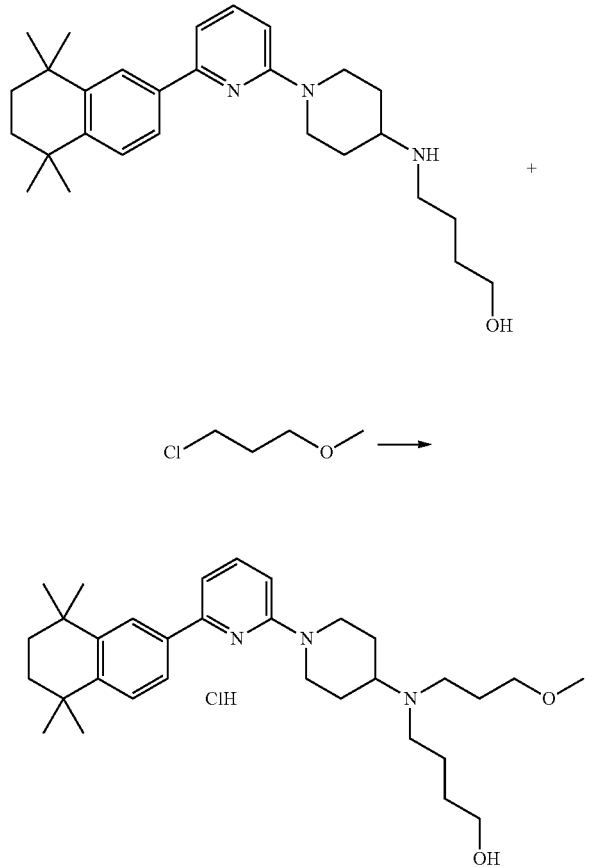

100 mg (0.23 mmol) of 4-[6'-(5,5,8,8-tetramethyl-5,6,7,8-tetrahydronaphthalen-2-yl)-3,4,5,6-tetrahydro-2H-1,2'-bipyridinyl-4-ylamino]butan-1-ol was dissolved in 3 ml of n-butanol with 25 mg (0.23 mmol) of 3-chloropropyl methyl ether, and 38 mg (0.23 mmol) of potassium iodide and 73 mg (0.69 mmol) of sodium carbonate were added, and the mixture was stirred at 120° C. for 48 h. Water was added to the reaction mixture, which was then extracted with ethyl acetate. The org. phase was dried and stripped off to dryness. The residue was purified by column chromatography on silica gel. The product was converted into the hydrochloride using methanolic HCl.

Yield: 27 mg. Rt.=2.85 min (method A), LCMS: 508 (M+H).

$^1$H NMR (500 MHz, DMSO/deuterated TFA: δ 7.96 (dd, J=9.1, 7.4 Hz, 1H), 7.61 (d, J=1.8 Hz, 1H), 7.46 (dt, J=8.3, 5.1 Hz, 2H), 7.28 (d, J=9.1 Hz, 1H), 7.07 (d, J=7.2 Hz, 1H), 4.41 (d, J=13.6 Hz, 2H), 3.78-3.67 (m, 1H), 3.48 (t, J=6.0 Hz, 2H), 3.39 (t, J=5.8 Hz, 2H), 3.34-3.16 (m, 7H), 3.09 (dt, J=15.2, 7.7 Hz, 2H), 2.16 (d, J=10.7 Hz, 2H), 2.02-1.72 (m, 6H), 1.67 (s, 4H), 1.56-1.45 (m, 2H), 1.26 (d, J=9.1 Hz, 12H).

FS315: 4-{(3-Methoxypropyl)-[6'-(5,5,8,8-tetramethyl-5,6,7,8-tetrahydronaphthalen-2-yl)-3,4,5,6-tetrahydro-2H-1,2'-bipyridinyl-4-yl]amino}butan-1-ol

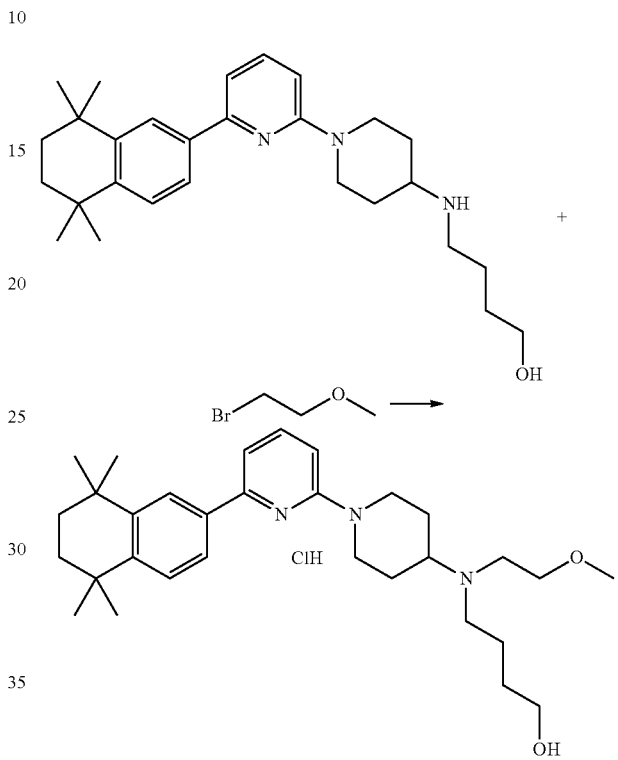

The preparation is carried out analogously to FS314. The product is in the form of the hydrochloride.

Yield: 33 mg. Rt.=2.82 min (method A), LCMS: 494 (M+H).

$^1$H NMR (500 MHz, DMSO/deuterated TFA: δ 7.96 (dd, J=9.1, 7.4 Hz, 1H), 7.62 (d, J=1.7 Hz, 1H), 7.51-7.42 (m, 2H), 7.29 (d, J=9.0 Hz, 1H), 7.07 (d, J=7.2 Hz, 1H), 4.41 (d, J=13.5 Hz, 2H), 3.73 (t, J=12.0 Hz, 1H), 3.64 (d, J=4.2 Hz, 2H), 3.47 (dd, J=13.3, 7.3 Hz, 3H), 3.36-3.04 (m, 8H), 2.15 (d, J=13.6 Hz, 2H), 1.96-1.72 (m, 4H), 1.68 (s, 4H), 1.55-1.40 (m, 2H), 1.27 (d, J=9.1 Hz, 12H).

FS316: [6'-(5,5,8,8-Tetramethyl-5,6,7,8-tetrahydronaphthalen-2-yl)-3,4,5,6-tetrahydro-2H-1,2'-bipyridinyl-4-ylamino]acetic acid

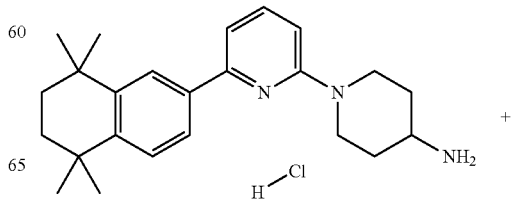

119

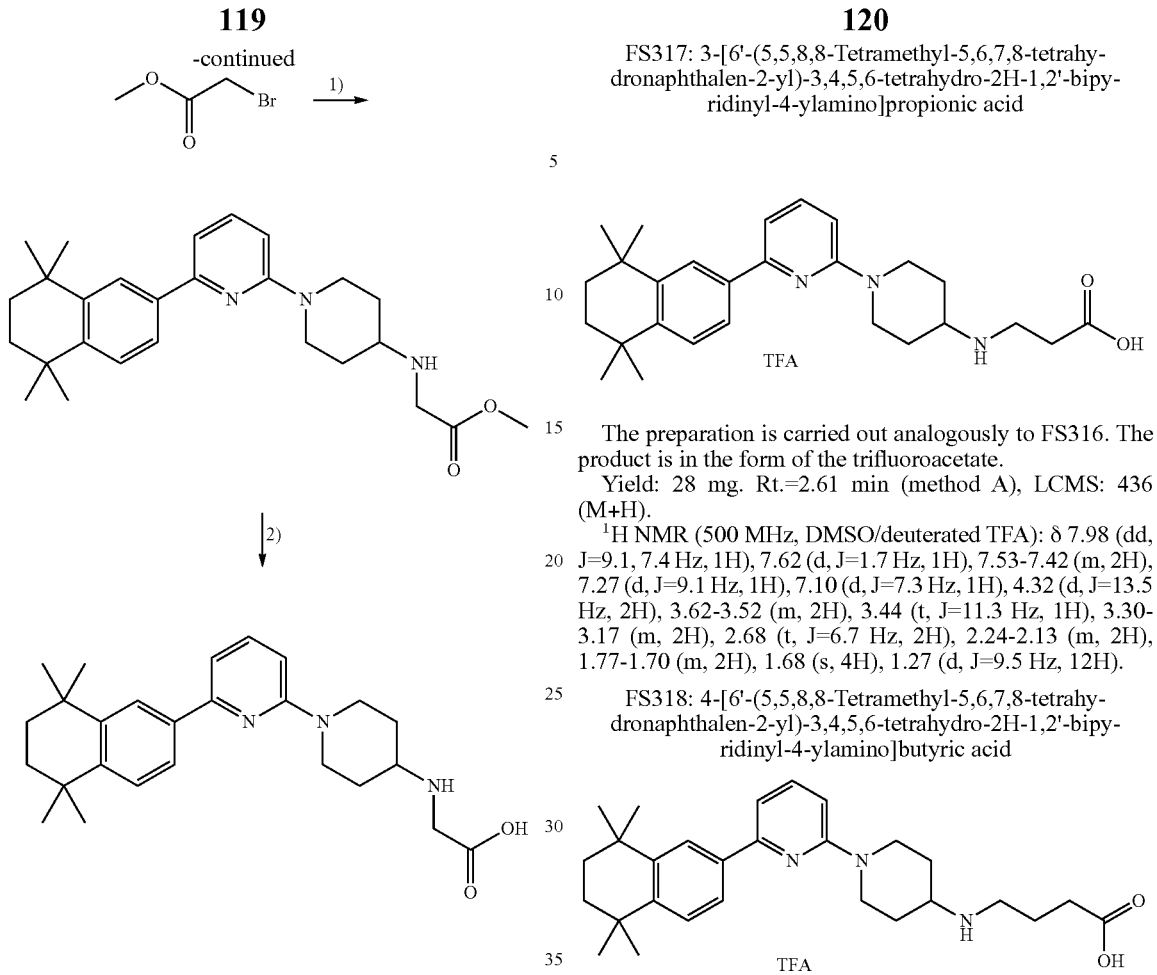

Step 1

150 mg (0.41 mmol) of 6'-(5,5,8,8-tetramethyl-5,6,7,8-tetrahydronaphthalen-2-yl)-3,4,5,6-tetrahydro-2H-1,2'-bipyridinyl-4-ylamine hydrochloride was dissolved in 3 ml of NMP with 75 µl (0.81 mmol) of bromoacetic acid methyl ester, and 661 mg (2.03 mmol) of caesium carbonate and 61 mg (0.41 mmol) of sodium iodide were added. The reaction mixture was stirred at 110° C. for 18 h. 38 µl (0.41 mmol) of bromoacetic acid methyl ester was again added, and the mixture was stirred at 110° C. for a further 24 h. Water was added to the reaction mixture, which was then extracted with ethyl acetate. The org. phase was dried and stripped off to dryness. The residue was purified by column chromatography on silica gel.

Step 2

The product from step 1 was dissolved in 3 ml of THF/water (10:1), and 53 mg of LiOH were added. The reaction mixture was stirred at room temperature for 18 h. The THF was distilled off, slightly acidified using 1 N HCl and purified by means of prep HPLC.

Yield: 3 mg. Rt.=2.81 min (method A), LCMS: 470 (M+H).

$^1$H NMR (400 MHz, DMSO/deuterated TFA: δ 7.98 (dd, J=9.1, 7.4 Hz, 1H), 7.63 (d, J=1.6 Hz, 1H), 7.51-7.43 (m, 2H), 7.27 (d, J=9.2 Hz, 1H), 7.10 (d, J=7.4 Hz, 1H), 4.37-4.26 (m, 2H), 3.94 (s, 2H), 3.23 (t, J=12.4 Hz, 2H), 2.26-2.13 (m, 4H), 1.73 (dd, J=12.9, 9.4 Hz, 2H), 1.68 (s, 4H), 1.34 (s, 12H).

120

FS317: 3-[6'-(5,5,8,8-Tetramethyl-5,6,7,8-tetrahydronaphthalen-2-yl)-3,4,5,6-tetrahydro-2H-1,2'-bipyridinyl-4-ylamino]propionic acid The preparation is carried out analogously to FS316. The product is in the form of the trifluoroacetate.

Yield: 28 mg. Rt.=2.61 min (method A), LCMS: 436 (M+H).

$^1$H NMR (500 MHz, DMSO/deuterated TFA): δ 7.98 (dd, J=9.1, 7.4 Hz, 1H), 7.62 (d, J=1.7 Hz, 1H), 7.53-7.42 (m, 2H), 7.27 (d, J=9.1 Hz, 1H), 7.10 (d, J=7.3 Hz, 1H), 4.32 (d, J=13.5 Hz, 2H), 3.62-3.52 (m, 2H), 3.44 (t, J=11.3 Hz, 1H), 3.30-3.17 (m, 2H), 2.68 (t, J=6.7 Hz, 2H), 2.24-2.13 (m, 2H), 1.77-1.70 (m, 2H), 1.68 (s, 4H), 1.27 (d, J=9.5 Hz, 12H).

FS318: 4-[6'-(5,5,8,8-Tetramethyl-5,6,7,8-tetrahydronaphthalen-2-yl)-3,4,5,6-tetrahydro-2H-1,2'-bipyridinyl-4-ylamino]butyric acid The preparation is carried out analogously to FS316. The product is in the form of the trifluoroacetate.

Yield: 37 mg. Rt.=2.64 min (method A), LCMS: 450 (M+H).

$^1$H NMR (500 MHz, DMSO/deuterated TFA): δ 7.99 (dd, J=9.0, 7.4 Hz, 1H), 7.67 (s, 1H), 7.54-7.48 (m, 2H), 7.30 (d, J=9.1 Hz, 1H), 7.14 (d, J=7.3 Hz, 1H), 4.35 (d, J=13.6 Hz, 2H), 3.61-3.55 (m, 2H), 3.44 (td, J=11.3, 5.7 Hz, 1H), 3.26 (t, J=12.2 Hz, 2H), 3.06-2.98 (m, 2H), 2.38 (t, J=7.1 Hz, 2H), 2.18 (d, J=12.9 Hz, 2H), 1.93-1.83 (m, 2H), 1.77-1.63 (m, 4H), 1.29 (d, J=12.6 Hz, 12H).

FS319: 4-{(4-Hydroxybutyl)-[6'-(5,5,8,8-tetramethyl-5,6,7,8-tetrahydronaphthalen-2-yl)-3,4,5,6-tetrahydro-2H-1,2'-bipyridinyl-4-yl]amino}butyric acid

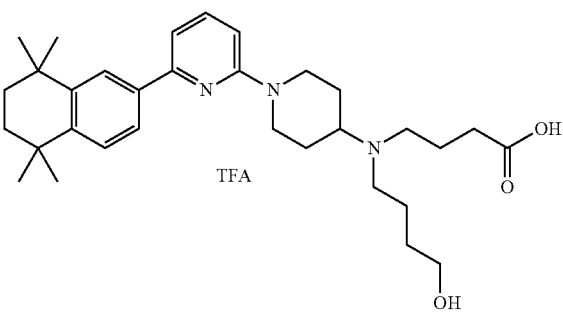 [SMILES: CC1(C)CCC(C)(C)c2cc(-c3cccc(N4CCC(N(CCCCO)CCCC(=O)O)CC4)n3)ccc21 ; "TFA"]

The preparation is carried out analogously to FS316. The product is in the form of the trifluoroacetate.

Yield: 106 mg. Rt.=2.66 min (method A), LCMS: 522 (M+H).

¹H NMR (400 MHz, DMSO/deuterated TFA): δ 7.99 (dd, J=9.0, 7.4 Hz, 1H), 7.70 (d, J=1.6 Hz, 1H), 7.57-7.48 (m, 2H), 7.32 (d, J=9.1 Hz, 1H), 7.14 (d, J=7.3 Hz, 1H), 4.47 (d, J=13.2 Hz, 2H), 3.76 (t, J=11.6 Hz, 1H), 3.60 (ddd, J=6.6, 4.2, 2.6 Hz, 2H), 3.53-3.44 (m, 2H), 3.35-3.18 (m, 4H), 3.17-3.01 (m, 2H), 2.38 (t, J=7.0 Hz, 2H), 2.18 (s, 2H), 2.03-1.63 (m, 8H), 1.57-1.47 (m, 2H), 1.30 (d, J=10.1 Hz, 12H).

FS320: 5-[6'-(5,5,8,8-Tetramethyl-5,6,7,8-tetrahydronaphthalen-2-yl)-3,4,5,6-tetrahydro-2H-1,2'-bipyridinyl-4-ylamino]pentanoic acid

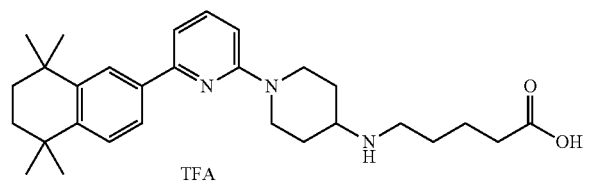 [SMILES: CC1(C)CCC(C)(C)c2cc(-c3cccc(N4CCC(NCCCCC(=O)O)CC4)n3)ccc21 ; "TFA"]

The preparation is carried out analogously to FS316. The product is in the form of the trifluoroacetate.

Yield: 26 mg. Rt.=2.64 min (method A), LCMS: 464 (M+H).

¹H NMR (400 MHz, DMSO/deuterated TFA): δ 8.00 (dd, J=9.0, 7.4 Hz, 1H), 7.70 (d, J=1.7 Hz, 1H), 7.56-7.48 (m, 2H), 7.30 (d, J=9.0 Hz, 1H), 7.15 (d, J=7.3 Hz, 1H), 4.36 (d, J=13.7 Hz, 2H), 3.63-3.55 (m, 2H), 3.42 (dd, J=13.6, 9.5 Hz, 1H), 3.25 (t, J=12.1 Hz, 2H), 3.05-2.94 (m, 2H), 2.29 (t, J=6.9 Hz, 2H), 2.18 (d, J=8.6 Hz, 2H), 1.78-1.56 (m, 8H), 1.30 (d, J=10.3 Hz, 12H).

FS321: 3-{4-[6-(5,5,8,8-Tetramethyl-5,6,7,8-tetrahydronaphthalen-2-yl)pyridin-2-yl]-piperazin-1-yl}propionic acid

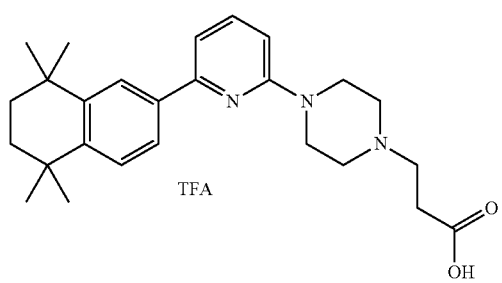 [SMILES: CC1(C)CCC(C)(C)c2cc(-c3cccc(N4CCN(CCC(=O)O)CC4)n3)ccc21]

The preparation is carried out analogously to FS316. The product is in the form of the trifluoroacetate.

Yield: 78 mg. Rt.=2.91 min (method A), LCMS: 422 (M+H).

¹H NMR (400 MHz, DMSO/deuterated TFA): δ 7.87 (dd, J=8.5, 7.7 Hz, 1H), 7.80 (d, J=1.9 Hz, 1H), 7.63 (dd, J=8.2, 1.9 Hz, 1H), 7.45 (t, J=7.1 Hz, 1H), 7.24 (d, J=7.4 Hz, 1H), 7.17-7.09 (m, 1H), 4.65-4.30 (m, 2H), 3.85-3.13 (m, 8H), 2.83 (t, J=7.2 Hz, 2H), 1.69 (s, 4H), 1.28 (d, J=16.3 Hz, 12H).

FS322: {4-[6-(5,5,8,8-Tetramethyl-5,6,7,8-tetrahydronaphthalen-2-yl)pyridin-2-yl]-piperazin-1-yl}acetic acid

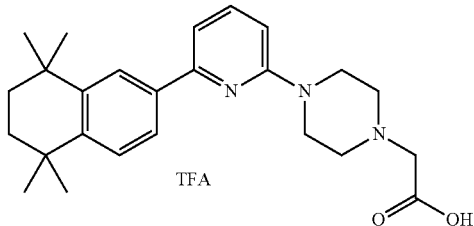 [SMILES: CC1(C)CCC(C)(C)c2cc(-c3cccc(N4CCN(CC(=O)O)CC4)n3)ccc21]

The preparation is carried out analogously to FS316. The product is in the form of the trifluoroacetate.

Yield: 37 mg. Rt.=2.94 min (method A), LCMS: 408 (M+H).

¹H NMR (400 MHz, DMSO/deuterated TFA): δ 7.83 (dd, J=11.4, 5.0 Hz, 2H), 7.67 (dd, J=8.2, 1.9 Hz, 1H), 7.43 (d, J=8.3 Hz, 1H), 7.27 (d, J=7.4 Hz, 1H), 7.05 (d, J=8.7 Hz, 1H), 4.24 (s, 2H), 3.49 (s, 8H), 1.69 (s, 4H), 1.29 (d, J=13.8 Hz, 12H).

FS323: 1-(4-Methoxybutyl)-4-[6-(5,5,8,8-tetramethyl-5,6,7,8-tetrahydronaphthalen-2-yl)pyridin-2-yl]piperazine

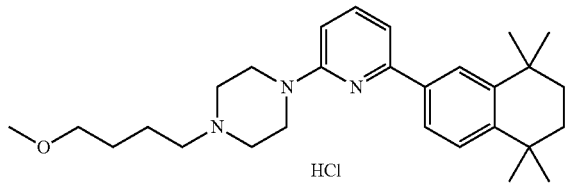 [SMILES: COCCCCN1CCN(c2cccc(-c3ccc4c(c3)C(C)(C)CCC4(C)C)n2)CC1 ; Cl]

The preparation is carried out analogously to FS301. The product is in the form of the hydrochloride.

Yield: 50 mg. Rt.=3.06 min (method A), LCMS: 436 (M+H).

¹H NMR (500 MHz, DMSO/deuterated TFA): δ 7.91 (dd, J=8.7, 7.5 Hz, 1H), 7.74 (d, J=1.8 Hz, 1H), 7.57 (dd, J=8.2, 1.9 Hz, 1H), 7.45 (d, J=8.3 Hz, 1H), 7.21 (d, J=7.4 Hz, 1H), 7.17 (d, J=8.8 Hz, 1H), 4.47 (d, J=13.4 Hz, 2H), 3.64 (d, J=11.6 Hz, 2H), 3.48 (s, 2H), 3.37-3.30 (m, 2H), 3.25-3.11 (m, 7H), 1.82-1.72 (m, 2H), 1.68 (s, 4H), 1.60-1.52 (m, 2H), 1.27 (d, J=14.4 Hz, 12H).

FS324: 2-(3-{4-[6-(5,5,8,8-Tetramethyl-5,6,7,8-tetrahydronaphthalen-2-yl)pyridin-2-yl]-piperazin-1-yl}propyl)propane-1,3-diol

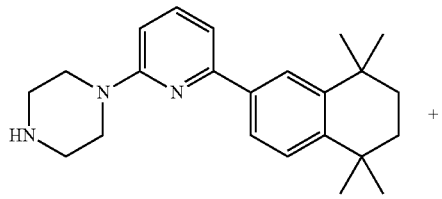

123
-continued

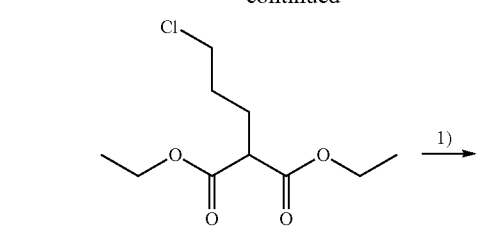

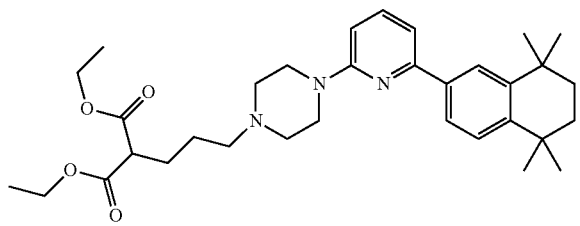

↓ 2)

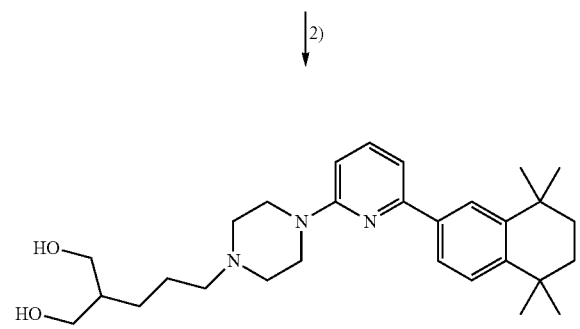

The preparation is carried out analogously to FS311.

Yield: 20 mg. Rt.=2.84 min (method A), LCMS: 466 (M+H).

$^1$H NMR (500 MHz, DMSO/deuterated TFA): δ 7.92-7.76 (m, 2H), 7.65 (dd, J=8.2, 1.9 Hz, 1H), 7.45 (d, J=8.3 Hz, 1H), 7.26 (d, J=7.4 Hz, 1H), 7.10 (d, J=8.7 Hz, 1H), 4.46 (dd, J=48.1, 9.9 Hz, 2H), 3.66 (d, J=11.7 Hz, 2H), 3.52-3.34 (m, 6H), 3.24-3.07 (m, 4H), 1.86-1.73 (m, 2H), 1.69 (s, 4H), 1.60-1.50 (m, 1H), 1.38-1.22 (m, 14H).

FS325: 3,3-Dimethyl-5-{4-[6-(5,5,8,8-tetramethyl-5,6,7,8-tetrahydronaphthalen-2-yl)-pyridin-2-yl]piperazin-1-yl}pentane-1,4-diol

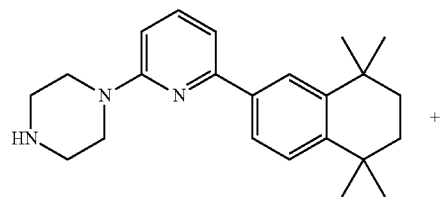

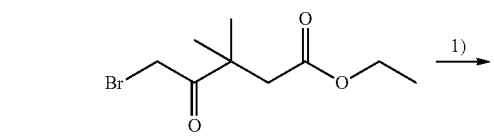

124
-continued

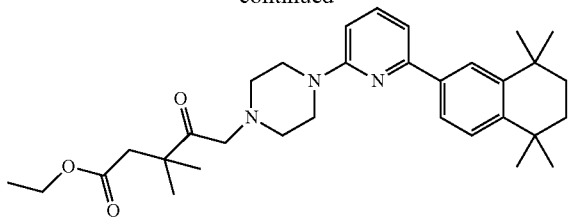

↓ 2)

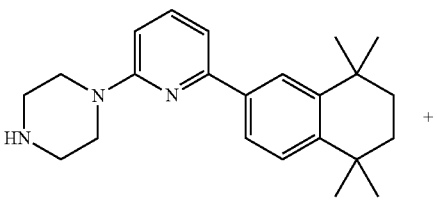

The preparation is carried out analogously to FS324.

Yield: 31 mg. Rt.=2.99 min (method A), LCMS: 480 (M+H).

$^1$H NMR (500 MHz, DMSO/deuterated TFA): δ 7.93-7.86 (m, 1H), 7.78 (d, J=1.4 Hz, 1H), 7.61 (dd, J=8.2, 1.7 Hz, 1H), 7.45 (d, J=8.3 Hz, 1H), 7.23 (d, J=7.4 Hz, 1H), 7.15 (d, J=8.8 Hz, 1H), 4.44 (dd, J=35.2, 13.7 Hz, 2H), 3.78-3.43 (m, 6H), 3.34-3.10 (m, 5H), 1.69 (s, 4H), 1.54 (dt, J=13.4, 6.5 Hz, 1H), 1.47-1.36 (m, 1H), 1.28 (d, J=15.6 Hz, 12H), 0.89 (d, J=6.9 Hz, 6H).

FS326: 2-{4-[4-(5,5,8,8-Tetramethyl-5,6,7,8-tetrahydronaphthalen-2-yl)-1,3,5-triazin-2-yl]piperazin-1-yl}pentane-1,5-diol

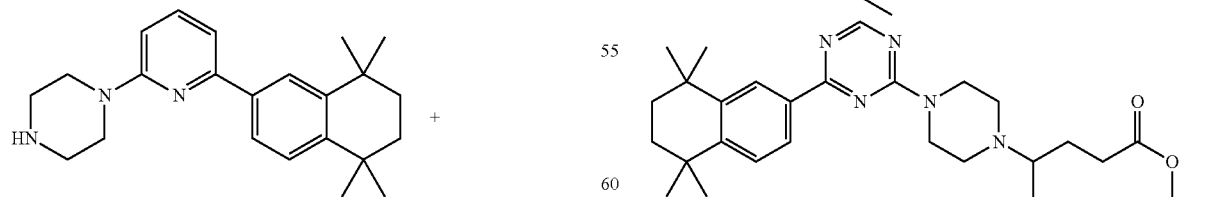

↓ 2)

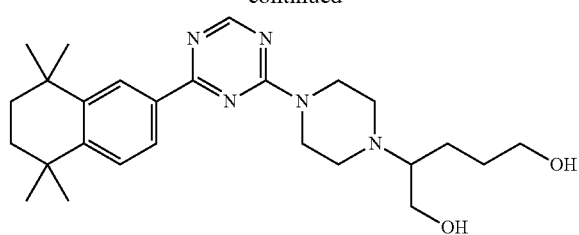

The preparation is carried out analogously to FS324.

Yield: 8 mg. Rt.=2.65 min (method A), LCMS: 454 (M+H).

¹H NMR (500 MHz, DMSO/deuterated TFA): δ 8.92 (d, J=1.0 Hz, 1H), 8.32 (d, J=1.5 Hz, 1H), 8.11 (dd, J=8.4, 1.7 Hz, 1H), 7.59-7.49 (m, 1H), 4.95 (t, J=64.3 Hz, 2H), 3.88 (dd, J=13.0, 2.8 Hz, 1H), 3.79-3.23 (m, 10H), 1.89-1.78 (m, 1H), 1.80-1.65 (m, 5H), 1.65-1.41 (m, 2H), 1.30 (d, J=16.3 Hz, 12H).

FS327: 2-[6'-(5,5,8,8-Tetramethyl-5,6,7,8-tetrahydronaphthalen-2-yl)-3,4,5,6-tetrahydro-2H-1,2'-bipyridinyl-4-ylamino]pentane-1,5-diol

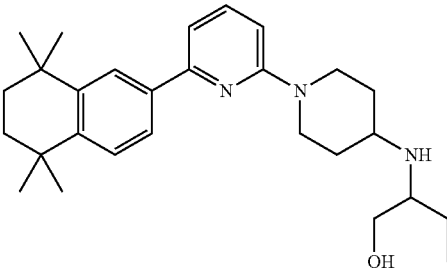

The preparation is carried out analogously to FS324.

Yield: 11 mg. Rt.=2.57 min (method A), LCMS: 466 (M+H).

¹H NMR (500 MHz, DMSO/deuterated TFA): δ 8.00 (dd, J=9.0, 7.4 Hz, 1H), 7.71 (d, J=1.8 Hz, 1H), 7.54 (dt, J=18.3, 5.1 Hz, 2H), 7.32 (d, J=9.1 Hz, 1H), 7.16 (d, J=7.3 Hz, 1H), 4.38 (d, J=13.8 Hz, 2H), 3.77 (dd, J=12.2, 3.1 Hz, 1H), 3.66-3.55 (m, 2H), 3.52-3.42 (m, 2H), 3.33-3.21 (m, 3H), 2.25-2.14 (m, 2H), 1.81-1.66 (m, 8H), 1.65-1.45 (m, 2H), 1.30 (d, J=13.3 Hz, 12H).

FS328 3-(2-{4-[6-(5,5,8,8-Tetramethyl-5,6,7,8-tetrahydronaphthalen-2-yl)pyridin-2-yl]-piperazin-1-yl}ethyl)oxazolidin-2-one

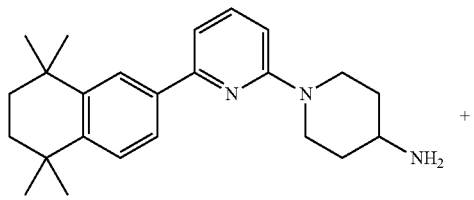

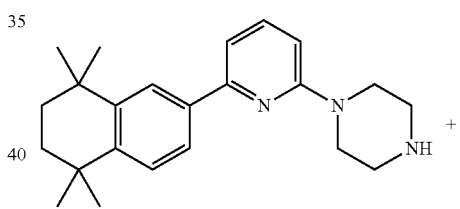

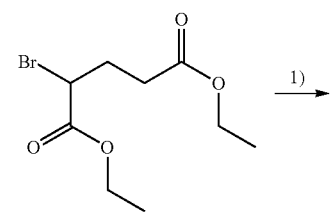

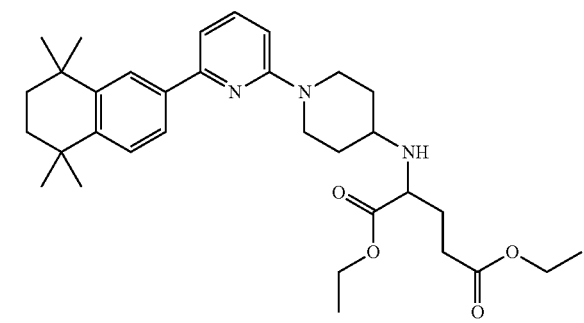

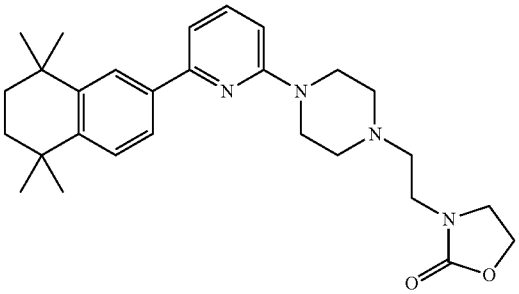

The preparation is carried out analogously to FS301.

Yield: 75 mg. Rt.=2.93 min (method A), LCMS: 463 (M+H).

¹H NMR (500 MHz, DMSO/deuterated TFA): δ 7.91 (dd, J=8.7, 7.6 Hz, 1H), 7.74 (d, J=1.9 Hz, 1H), 7.58 (dd, J=8.2, 1.9 Hz, 1H), 7.45 (d, J=8.3 Hz, 1H), 7.22 (d, J=7.4 Hz, 1H), 7.17 (d, J=8.8 Hz, 1H), 4.34-4.26 (m, 2H), 3.61 (dd, J=10.8, 4.9 Hz, 4H), 3.43 (t, J=5.8 Hz, 2H), 4.60-3.10 (b, 8H), 1.68 (s, 4H), 1.27 (d, J=15.6 Hz, 12H).

FS329 2-(2-{4-[6-(5,5,8,8-Tetramethyl-5,6,7,8-tetrahydronaphthalen-2-yl)pyridin-2-yl]-piperazin-1-yl}ethoxy)ethanol

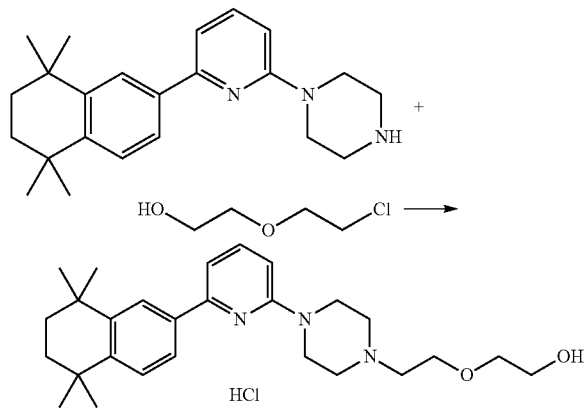

The preparation is carried out analogously to FS301.
Yield: 51 mg. Rt.=2.88 min (method A), LCMS: 438 (M+H).
$^1$H NMR (500 MHz, DMSO/deuterated TFA): δ 7.90 (dd, J=8.6, 7.6 Hz, 1H), 7.78 (d, J=1.9 Hz, 1H), 7.61 (dd, J=8.2, 1.9 Hz, 1H), 7.48-7.44 (m, 1H), 7.23 (d, J=7.4 Hz, 1H), 7.15 (d, J=8.8 Hz, 1H), 4.46 (b, 2H), 3.83-3.79 (m, 2H), 3.76-3.45 (m, 8H), 3.45-3.38 (m, 2H), 3.27 (b, 2H), 1.68 (s, 4H), 1.28 (d, J=15.9 Hz, 12H).

FS401: Acetic acid 4-{4-[6-(5,5,8,8-tetramethyl-5,6,7,8-tetrahydronaphthalen-2-yl)-pyridin-2-yl]piperazin-1-yl}butyl ester

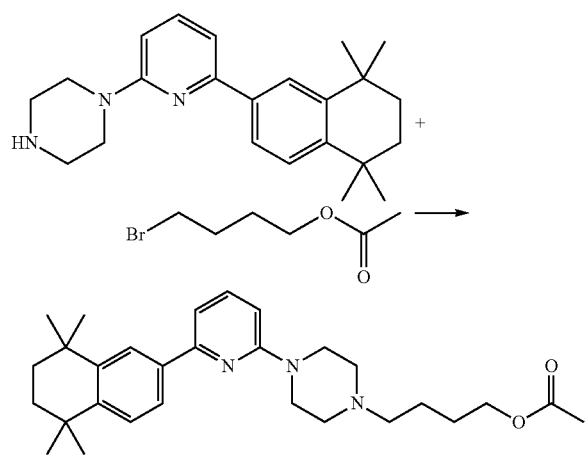

100 mg (0.29 mmol) of 1-[6-(5,5,8,8-tetramethyl-5,6,7,8-tetrahydronaphthalen-2-yl)pyridin-2-yl]piperazine are dissolved in 2 ml of DMF, and 47 mg (0.29 mmol) of potassium carbonate are added. 42 µl (0.29 mmol) of 4-bromobutyl acetate are subsequently added, and the mixture is stirred at 50° C. for 24 h. A further 11 µl (0.07 mmol) of 4-bromobutyl acetate are subsequently added, and the mixture is stirred at 50° C. for a further 48 h. The reaction mixture is evaporated, water is added to the residue, the mixture is rendered basic using 1 N NaOH and extracted three times with ethyl acetate. The organic phase is dried over Na$_2$SO$_4$ and evaporated. The crude product is purified by means of column chromatography on silica gel.

133 mg, oil. Rt.=2.88 min (method B), LCMS: 464 (M+H).

FS402: 4-{4-[6-(5,5,8,8-Tetramethyl-5,6,7,8-tetrahydronaphthalen-2-yl)pyridin-2-yl]-piperazin-1-yl}butan-1-ol

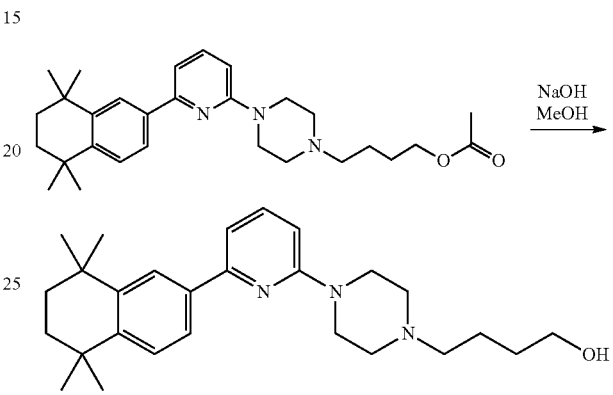

133 mg (0.29 mmol) of acetic acid 3-{4-[6-(5,5,8,8-tetramethyl-5,6,7,8-tetrahydronaphthalen-2-yl)pyridin-2-yl]piperazin-1-yl}propyl ester are dissolved in 4 ml of methanol, and 430 µl (0.43 mmol) of 1N NaOH are added. The reaction mixture is stirred at RT overnight. The mixture is subsequently neutralised using 430 µl of 1N HCl, the solvent is distilled off, and the residue is purified by means of column chromatography on RP silica gel.

78 mg, white solid. Rt.=2.69 min (method B), LCMS: 422 (M+H).

$^1$H NMR (500 MHz, DMSO/deuterated TFA) δ 7.91 (d, J=1.3, 1H), 7.80-7.70 (m, 2H), 7.43 (d, J=8.3, 1H), 7.30 (d, J=7.5, 1H), 6.99 (d, J=8.5, 1H), 4.52 (d, J=14.1, 2H), 3.65 (d, J=11.7, 2H), 3.47 (t, J=6.2, 2H), 3.30 (t, J=12.5, 2H), 3.23-3.09 (m, 4H), 1.82-1.73 (m, 2H), 1.70 (s, 4H), 1.55-1.46 (m, 2H), 1.30 (d, J=18.4, 12H).

FS403: Acetic acid 4-{4-[6-(5,5-dimethyl-5,6,7,8-tetrahydronaphthalen-2-yl)pyridin-2-yl]piperazin-1-yl}butyl ester

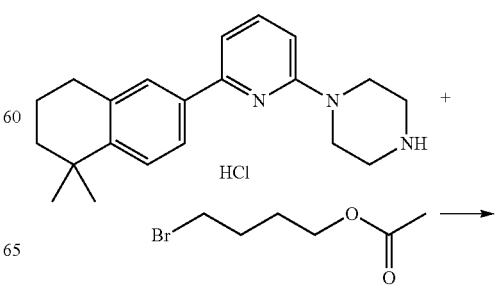

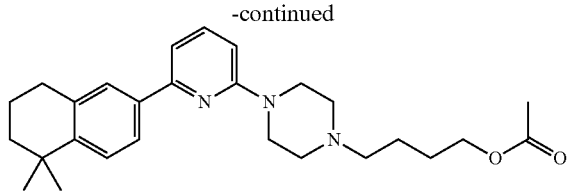

The preparation is carried out analogously to FS401 using 2 equiv. of potassium carbonate.

Yield: 89 mg, yellow oil. Rt.=2.83 min (method B), LCMS: 436 (M+H).

FS404: 4-{4-[6-(5,5-Dimethyl-5,6,7,8-tetrahydronaphthalen-2-yl)pyridin-2-yl]-piperazin-1-yl}butan-1-ol

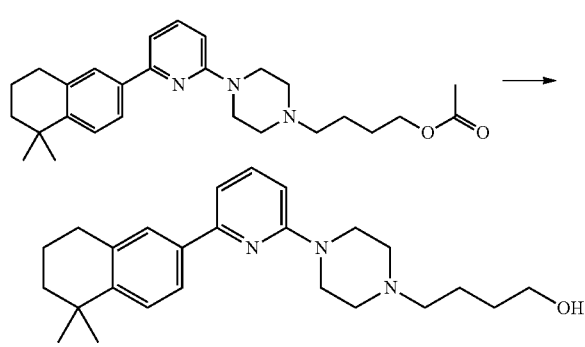

The preparation is carried out analogously to FS402.

Yield: 48 mg, white solid. Rt.=2.64 min (method B), LCMS: 394 (M+H).

$^1$H NMR (500 MHz, DMSO/deuterated TFA) δ 7.80 (t, J=8.0, 1H), 7.74 (d, J=8.2, 1H), 7.64 (s, 1H), 7.47 (d, J=8.3, 1H), 7.28 (d, J=7.5, 1H), 7.02 (d, J=8.6, 1H), 4.54 (d, J=14.0, 2H), 3.65 (d, J=11.5, 2H), 3.49 (t, J=6.1, 2H), 3.32 (t, J=12.3, 2H), 3.25-3.11 (m, 4H), 2.82 (t, J=6.3, 2H), 1.84-1.75 (m, 4H), 1.72-1.65 (m, 2H), 1.56-1.48 (m, 2H), 1.29 (s, 6H).

FS405: Acetic acid 4-{4-[6-(8,8-dimethyl-5,6,7,8-tetrahydronaphthalen-2-yl)-pyridin-2-yl]piperazin-1-yl}butyl ester

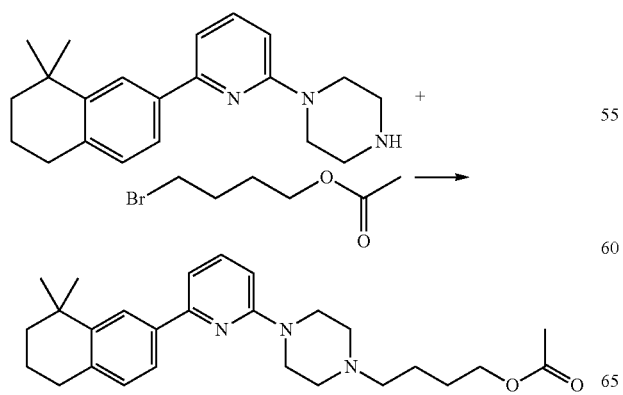

The preparation is carried out analogously to FS401.

Yield: 81 mg, colourless oil. Rt.=2.70 min (method B), LCMS: 436 (M+H).

FS406: 4-{4-[6-(8,8-Dimethyl-5,6,7,8-tetrahydronaphthalen-2-yl)pyridin-2-yl]-piperazin-1-yl}butan-1-ol

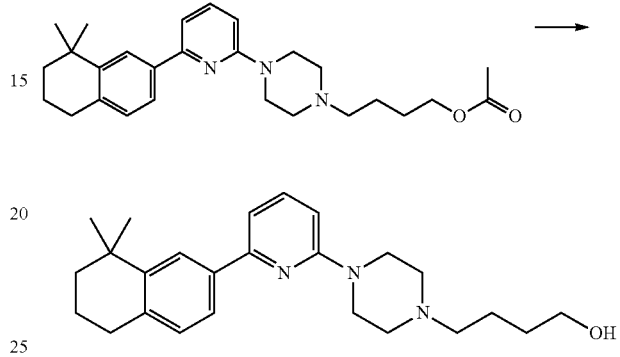

The preparation is carried out analogously to FS402.

Yield: 49 mg, viscous oil. Rt.=2.63 min (method B), LCMS: 394 (M+H).

$^1$H NMR (500 MHz, DMSO/deuterated TFA) δ 7.96 (d, J=1.5, 1H), 7.76 (t, J=8.0, 1H), 7.70 (dd, J=7.9, 1.7, 1H), 7.31 (d, J=7.5, 1H), 7.14 (d, J=8.0, 1H), 6.99 (d, J=8.5, 1H), 4.53 (d, J=13.9, 2H), 3.65 (d, J=11.8, 2H), 3.48 (t, J=6.1, 2H), 3.30 (t, J=12.7, 2H), 3.25-3.09 (m, 4H), 2.78 (t, J=6.3, 2H), 1.83-1.74 (m, 4H), 1.70-1.65 (m, 2H), 1.55-1.48 (m, 2H), 1.33 (s, 6H).

FS407: Acetic acid 4-{4-[6-(1,1,3,3-tetramethylindan-5-yl)pyridin-2-yl]piperazin-1-yl}butyl ester

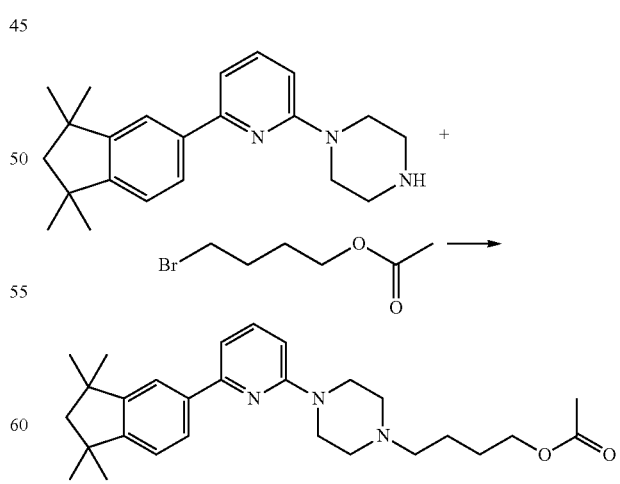

The preparation is carried out analogously to FS401.

Yield: 50 mg, colourless oil. Rt.=2.93 min (method B), LCMS: 450 (M+H).

FS408: 4-{4-[6-(1,1,3,3-Tetramethylindan-5-yl)pyridin-2-yl]piperazin-1-yl}butan-1-ol

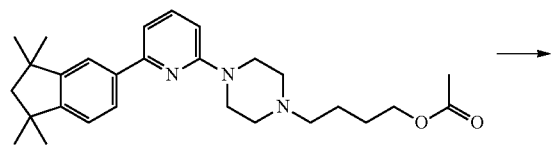

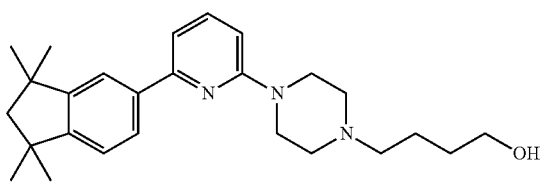

The preparation is carried out analogously to FS402.

Yield: 44 mg, viscous oil. Rt.=2.71 min (method B), LCMS: 408 (M+H).

¹H NMR (400 MHz, DMSO/deuterated TFA) δ 7.97-7.88 (m, 1H), 7.75 (dd, J=7.9, 1.5, 1H), 7.66 (d, J=1.2, 1H), 7.30 (t, J=7.2, 2H), 7.18 (d, J=8.8, 1H), 4.53 (d, J=13.9, 2H), 3.68 (d, J=11.8, 2H), 3.53-3.39 (m, 4H), 3.26-3.13 (m, 4H), 1.95 (s, 2H), 1.88-1.74 (m, 2H), 1.58-1.48 (m, 2H), 1.33 (d, J=10.0, 12H).

FS409: Acetic acid 4-[6'-(5,5,8,8-tetramethyl-5,6,7,8-tetrahydronaphthalen-2-yl)-3,4,5,6-tetrahydro-2H-1,2'-bipyridinyl-4-ylamino]butyl ester

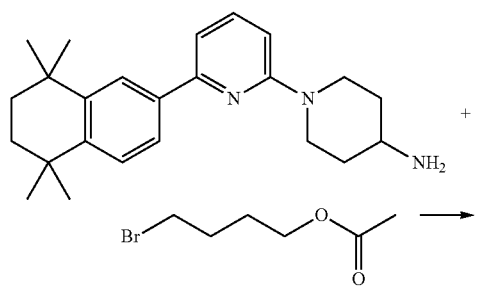

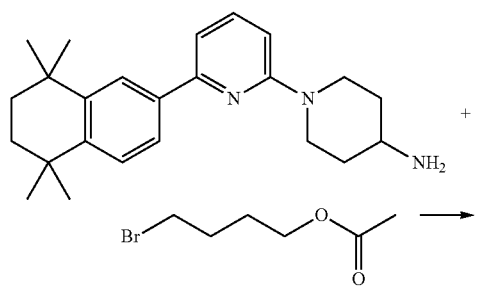

The preparation is carried out analogously to FS401.

Yield: 60 mg, yellow oil. Rt.=2.90 min (method A), LCMS: 478 (M+H).

FS410: 4-[6'-(5,5,8,8-Tetramethyl-5,6,7,8-tetrahydronaphthalen-2-yl)-3,4,5,6-tetrahydro-2H-1,2'-bipyridinyl-4-ylamino]butan-1-ol

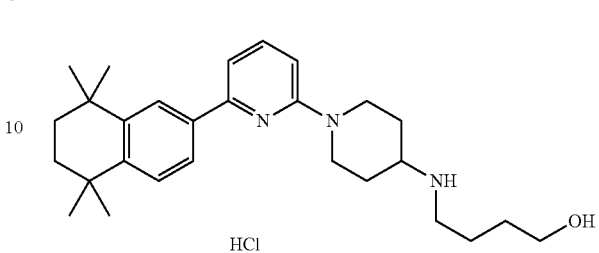

The preparation is carried out analogously to FS402. The product is in the form of the hydrochloride.

Yield: 25 mg, Beige solid. Rt.=2.76 min (method B), LCMS: 436 (M+H).

¹H NMR (500 MHz, DMSO/deuterated TFA) δ 8.04 (dd, J=8.9, 7.5, 1H), 7.73 (d, J=1.7, 1H), 7.56 (dt, J=14.4, 5.0, 2H), 7.34 (d, J=9.0, 1H), 7.19 (d, J=7.4, 1H), 4.40 (d, J=13.7, 2H), 3.54-3.42 (m, 3H), 3.33-3.25 (m, 2H), 3.07-3.00 (m, 2H), 2.22 (d, J=10.3, 2H), 1.75 (d, J=20.1, 8H), 1.60-1.53 (m, 2H), 1.33 (d, J=12.9, 12H).

FS411: Acetic acid 4-{4-[4-(5,5,8,8-tetramethyl-5,6,7,8-tetrahydronaphthalen-2-yl)-1,3,5-triazin-2-yl]piperazin-1-yl}butyl ester

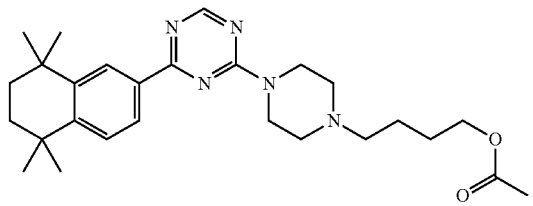 [SMILES: CC(=O)OCCCCN1CCN(c2ncnc(-c3ccc4c(c3)C(C)(C)CCC4(C)C)n2)CC1]

The preparation is carried out analogously to FS401.

Yield: 65 mg, Oily residue. Rt.=2.97 min (method A), LCMS: 466 (M+H).

FS412: 4-{4-[4-(5,5,8,8-Tetramethyl-5,6,7,8-tetrahydronaphthalen-2-yl)-1,3,5-triazin-2-yl]piperazin-1-yl}butan-1-ol

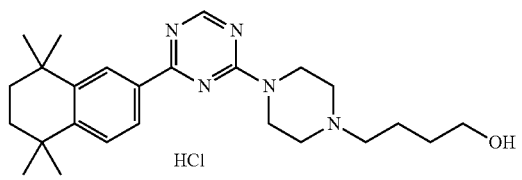 [SMILES: CC1(C)CCC(C)(C)c2cc(-c3ncnc(N4CCN(CCCCO)CC4)n3)ccc21 ; Cl]

The preparation is carried out analogously to FS402. The product is in the form of the hydrochloride.

Yield: 30 mg, Beige solid. Rt.=2.83 min (method A), LCMS: 424 (M+H).

¹H NMR (500 MHz, DMSO/deuterated TFA) δ 8.86 (s, 1H), 8.32 (d, J=1.9, 1H), 8.11 (dd, J=8.3, 1.9, 1H), 7.51 (d, J=8.4, 1H), 4.91 (d, J=67.8, 2H), 3.65 (s, 2H), 3.51 (s, 2H), 3.45 (t, J=6.1, 2H), 3.25-3.07 (m, 4H), 1.84-1.72 (m, 2H), 1.68 (s, 4H), 1.55-1.44 (m, 2H), 1.28 (d, J=14.4, 12H).

FS413: Acetic acid 4-{4-[2-(5,5,8,8-tetramethyl-5,6,7,8-tetrahydronaphthalen-2-yl)pyridin-4-yl]piperazin-1-yl}butyl ester

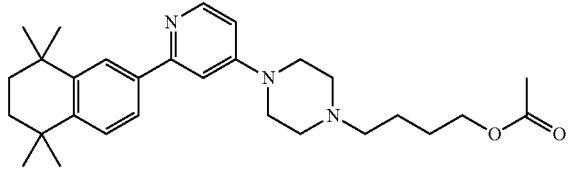 [SMILES: CC(=O)OCCCCN1CCN(c2ccnc(-c3ccc4c(c3)C(C)(C)CCC4(C)C)c2)CC1]

The preparation is carried out analogously to FS401.
Yield: 56 mg, Oily residue. Rt.=2.31 min (method B), LCMS: 464 (M+H).

FS414: 4-{4-[2-(5,5,8,8-Tetramethyl-5,6,7,8-tetrahydronaphthalen-2-yl)pyridin-4-yl]-piperazin-1-yl}butan-1-ol

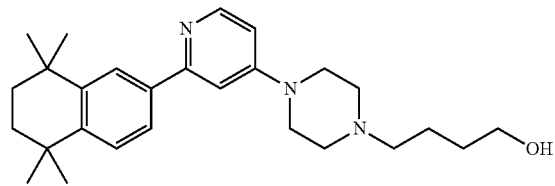 [SMILES: CC1(C)CCC(C)(C)c2cc(-c3cc(N4CCN(CCCCO)CC4)ccn3)ccc21]

The preparation is carried out analogously to FS402.
Yield: 50 mg, colourless oil. Rt.=1.97 min (method B), LCMS: 422 (M+H).
¹H NMR (400 MHz, DMSO/deuterated TFA) δ 8.32 (d, J=7.3, 1H), 7.74 (d, J=2.0, 1H), 7.62 (dd, J=8.3, 2.0, 1H), 7.54 (d, J=8.3, 1H), 7.44 (d, J=2.6, 1H), 7.25 (dd, J=7.4, 2.7, 1H), 4.64-4.47 (m, 2H), 3.72-3.48 (m, 4H), 3.45 (t, J=6.1, 2H), 3.23-3.16 (m, 4H), 1.81-1.64 (m, 6H), 1.55-1.42 (m, 2H), 1.26 (t, J=15.2, 12H).

FS415: Acetic acid 4-{4-[4-(5,5,8,8-tetramethyl-5,6,7,8-tetrahydronaphthalen-2-yl)pyridin-2-yl]piperazin-1-yl}butyl ester

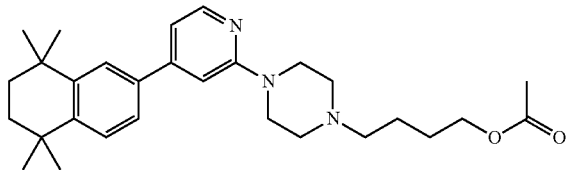 [SMILES: CC(=O)OCCCCN1CCN(c2cc(-c3ccc4c(c3)C(C)(C)CCC4(C)C)ccn2)CC1]

The preparation is carried out analogously to FS401.
Yield: 108 mg, Oily residue. Rt.=2.53 min (method B), LCMS: 464 (M+H).

FS416: 4-{4-[4-(5,5,8,8-Tetramethyl-5,6,7,8-tetrahydronaphthalen-2-yl)pyridin-2-yl]-piperazin-1-yl}butan-1-ol

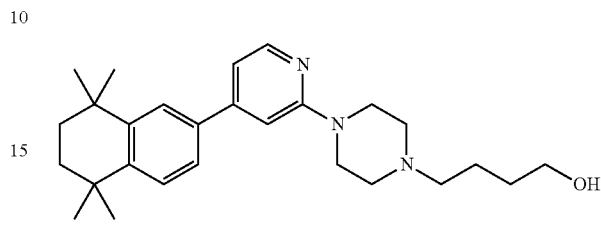

The preparation is carried out analogously to FS402.
Yield: 82 mg, white solid. Rt.=2.43 min (method B), LCMS: 422 (M+H).
¹H NMR (400 MHz, DMSO/deuterated TFA) δ 8.20 (d, J=6.6, 1H), 7.78 (d, J=2.0, 1H), 7.68 (dd, J=8.3, 2.0, 1H), 7.60 (s, 1H), 7.54 (d, J=8.3, 1H), 7.45 (dd, J=6.6, 1.4, 1H), 4.50 (s, 2H), 3.65 (d, J=50.2, 4H), 3.48 (t, J=6.1, 2H), 3.22 (d, J=8.0, 3H), 1.85-1.73 (m, 2H), 1.71 (s, 4H), 1.50 (td, J=13.7, 6.7, 2H), 1.32 (d, J=19.5, 12H).

FS417: Acetic acid 4-{4-[6-(1,1-dimethylindan-5-yl)pyridin-2-yl]piperazin-1-yl}butyl ester

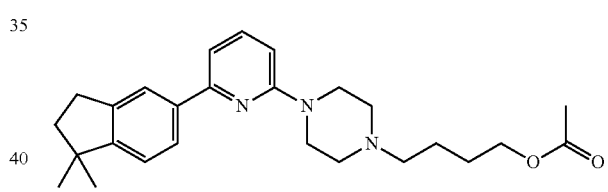

The preparation is carried out analogously to FS401.
Yield: 77 mg, yellow oil. Rt.=1.85 min (method B), LCMS: 422 (M+H).

FS418: 4-{4-[6-(1,1-Dimethylindan-5-yl)pyridin-2-yl]piperazin-1-yl}butan-1-ol

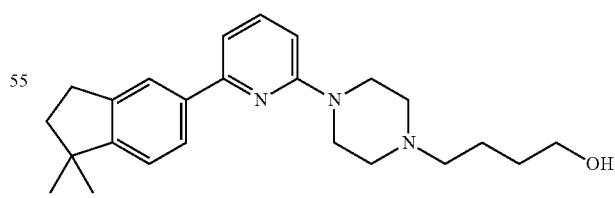

The preparation is carried out analogously to FS402.
Yield: 69 mg, colourless oil. Rt.=1.66 min (method B), LCMS: 380 (M+H).
¹H NMR (500 MHz, DMSO/deuterated TFA) δ 7.85-7.74 (m, 3H), 7.28 (dd, J=7.6, 5.0, 2H), 7.00 (d, J=8.5, 1H), 4.54 (d, J=13.9, 2H), 3.65 (d, J=12.5, 2H), 3.48 (t, J=6.1, 2H), 3.30 (t, J=13.0, 2H), 3.24-3.09 (m, 4H), 2.94 (t, J=7.2, 2H), 1.94 (dd, J=11.9, 4.6, 2H), 1.84-1.72 (m, 2H), 1.56-1.47 (m, 2H), 1.27 (s, 7H).

FS419: Acetic acid 4-{4-[3-(5,5,8,8-tetramethyl-5,6,7,8-tetrahydronaphthalen-2-yl)-phenyl]piperazin-1-yl}butyl ester

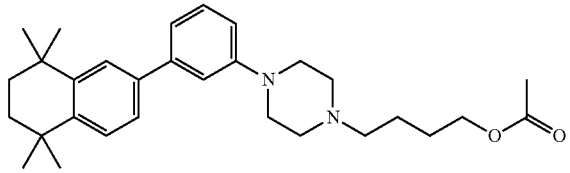 [SMILES: CC(=O)OCCCCN1CCN(c2cccc(-c3ccc4c(c3)C(C)(C)CCC4(C)C)c2)CC1]

The preparation is carried out analogously to FS401.
Yield: 108 mg, colourless oil. Rt.=3.03 min (method B), LCMS: 463 (M+H).
$^1$H NMR (400 MHz, DMSO/deuterated TFA) 7.47 (s, 1H), 7.37-7.25 (m, 3H), 7.15 (s, 1H), 7.08 (d, J=7.8, 1H), 6.95 (dd, J=8.2, 1.9, 1H), 4.02 (t, J=6.3, 2H), 3.90 (d, J=12.5, 2H), 3.58 (d, J=10.7, 2H), 3.24-2.99 (m, 4H), 1.96 (s, 3H), 1.82-1.69 (m, 2H), 1.68-1.56 (m, 6H), 1.23 (t, J=12.9, 12H).

FS420: 4-{4-[3-(5,5,8,8-Tetramethyl-5,6,7,8-tetrahydronaphthalen-2-yl)phenyl]-piperazin-1-yl}butan-1-ol

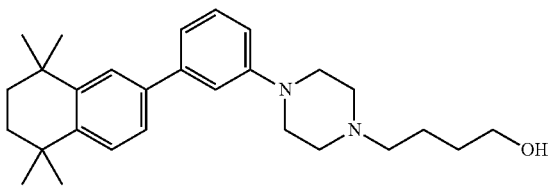 [SMILES: CC1(C)CCC(C)(C)c2cc(-c3cccc(N4CCN(CCCCO)CC4)c3)ccc21]

The preparation is carried out analogously to FS402.
Yield: 79 mg, colourless oil. Rt.=2.91 min (method B), LCMS: 421 (M+H).
$^1$H NMR (400 MHz, DMSO/deuterated TFA) δ 7.48 (s, 1H), 7.33 (s, 2H), 7.29 (t, J=7.9, 1H), 7.15 (b, 1H), 7.08 (d, J=7.7, 1H), 6.95 (dd, J=8.1, 2.0, 1H), 3.91 (d, J=13.1, 2H), 3.58 (d, J=11.7, 2H), 3.45 (t, J=6.1, 2H), 3.20-3.12 (m, 4H), 3.07 (t, J=11.9, 2H), 1.74 (dt, J=15.5, 7.7, 2H), 1.64 (s, 4H), 1.52-1.43 (m, 2H), 1.25 (d, J=15.2, 12H).

FS421: Acetic acid 4-{4-[4-(5,5,8,8-tetramethyl-5,6,7,8-tetrahydronaphthalen-2-yl)-1,3,5-triazin-2-yl]piperazin-1-yl}butyl ester

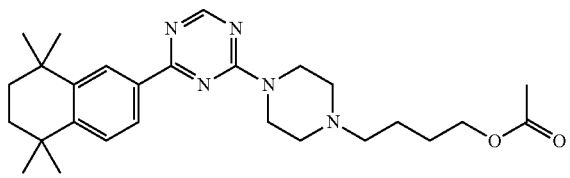 [SMILES: CC(=O)OCCCCN1CCN(c2ncnc(-c3ccc4c(c3)C(C)(C)CCC4(C)C)n2)CC1]

The preparation is carried out analogously to FS401.
Yield: 65 mg, oil. Rt.=2.97 min (method A), LCMS: 466 (M+H).

FS422: 4-{4-[4-(5,5,8,8-Tetramethyl-5,6,7,8-tetrahydronaphthalen-2-yl)-1,3,5-triazin-2-yl]piperazin-1-yl}butan-1-ol

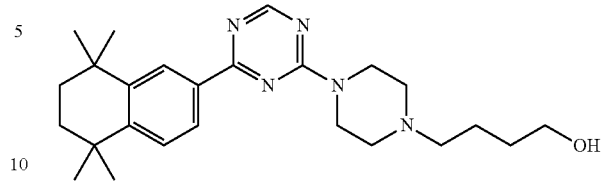

The preparation is carried out analogously to FS402. The product is in the form of the hydrochloride.
Yield: 30 mg, yellow solid. Rt.=2.83 min (method A), LCMS: 424 (M+H).
$^1$H NMR (500 MHz, DMSO/deuterated TFA) δ 8.86 (s, 1H), 8.32 (d, J=1.9, 1H), 8.11 (dd, J=8.3, 1.9, 1H), 7.51 (d, J=8.4, 1H), 4.91 (d, J=67.8, 2H), 3.58 (d, J=71.3, 4H), 3.45 (t, J=6.1, 2H), 3.22-3.09 (m, 4H), 1.82-1.71 (m, 2H), 1.68 (s, 4H), 1.52-1.45 (m, 2H), 1.28 (d, J=14.4, 12H).

FS423: Acetic acid 4-{1-[4-(5,5,8,8-tetramethyl-5,6,7,8-tetrahydronaphthalen-2-yl)-1,3,5-triazin-2-yl]piperidin-4-ylamino}butyl ester

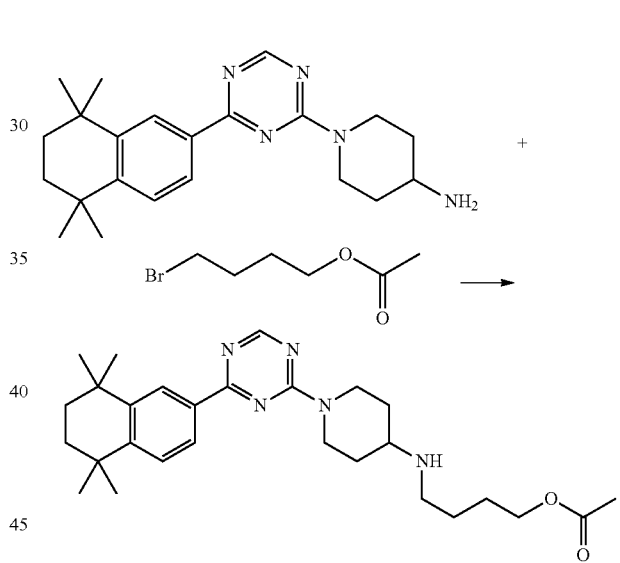

The preparation is carried out analogously to FS401.
Yield: 16 mg, colourless oil., Rt.=2.69 min (method B), LCMS: 480 (M+H).

FS424: 4-{1-[4-(5,5,8,8-Tetramethyl-5,6,7,8-tetrahydronaphthalen-2-yl)-1,3,5-triazin-2-yl]piperidin-4-ylamino}butan-1-ol

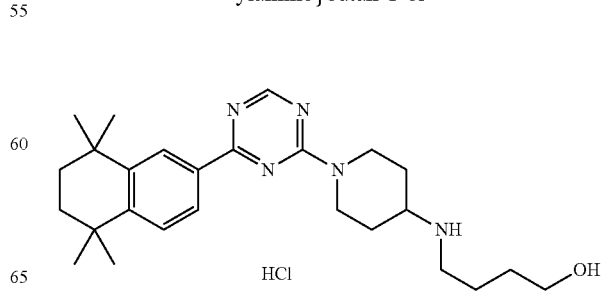

The preparation is carried out analogously to FS402. The product is in the form of the hydrochloride.

Yield: 22 mg, Beige solid. Rt.=2.49 min (method B), LCMS: 438 (M+H).

¹H NMR (500 MHz, DMSO/deuterated TFA) δ 8.89 (s, 1H), 8.20 (d, J=2.0, 1H), 8.01 (dd, J=8.4, 2.0, 1H), 7.52 (d, J=8.5, 1H), 5.02 (d, J=14.0, 1H), 4.89 (d, J=14.3, 1H), 3.45 (t, J=6.0, 2H), 3.28 (q, J=13.1, 2H), 2.99-2.93 (m, 2H), 2.27-2.18 (m, 2H), 1.75-1.59 (m, 8H), 1.54-1.46 (m, 2H), 1.26 (d, J=18.6, 12H).

FS425: Acetic acid 4-{4-[2-(5,5,8,8-tetramethyl-5,6,7,8-tetrahydronaphthalen-2-yl)-pyrimidin-4-yl]piperazin-1-yl}butyl ester

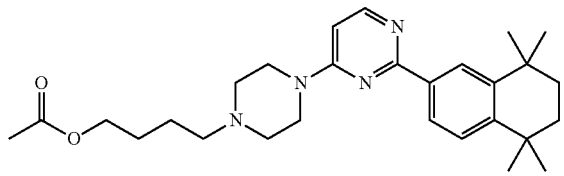 [SMILES: CC(=O)OCCCCN1CCN(c2ccnc(-c3ccc4c(c3)C(C)(C)CCC4(C)C)n2)CC1]

The preparation is carried out analogously to FS401. The product was reacted further directly.

Rt.=2.54 min (method A), LCMS: 465 (M+H).

FS426: 4-{4-[2-(5,5,8,8-Tetramethyl-5,6,7,8-tetrahydronaphthalen-2-yl)pyrimidin-4-yl]-piperazin-1-yl}butan-1-ol

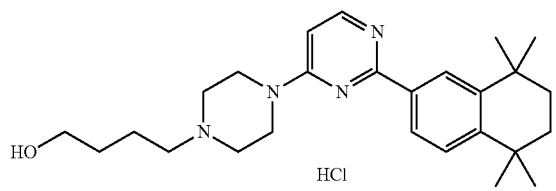 [SMILES: CC1(C)CCC(C)(C)c2cc(-c3nccc(N4CCN(CCCCO)CC4)n3)ccc21 ; Cl]

The preparation is carried out analogously to FS402. The product is in the form of the hydrochloride.

Yield: 34 mg, beige solid. Rt.=2.41 min (method A), LCMS: 423 (M+H).

¹H NMR (500 MHz, DMSO/deuterated TFA) δ 8.50 (d, J=7.5 Hz, 1H), 8.21 (d, J=2.0 Hz, 1H), 8.03 (dd, J=8.4, 2.0 Hz, 1H), 7.60 (d, J=8.4 Hz, 1H), 7.29 (d, J=7.5 Hz, 1H), 5.29 (b, 1H), 4.59 (b, 1H), 3.55-3.85 (m, 4H), 3.54 (t, J=6.0 Hz, 2H), 3.35-3.18 (m, 4H), 1.93-1.80 (m, 2H), 1.75 (s, 4H), 1.61-1.52 (m, 2H), 1.35 (d, J=23.2 Hz, 12H).

FS427: Acetic acid 4-{1-[2-(5,5,8,8-tetramethyl-5,6,7,8-tetrahydronaphthalen-2-yl)-pyrimidin-4-yl]piperidin-4-ylamino}butyl ester

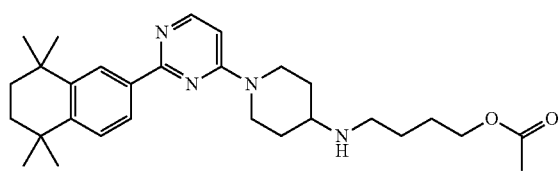 [SMILES: CC(=O)OCCCCNC1CCN(c2ccnc(-c3ccc4c(c3)C(C)(C)CCC4(C)C)n2)CC1]

The preparation is carried out analogously to FS401.

Yield: 38 mg, Rt.=2.56 min (method A), LCMS: 479 (M+H).

FS428: 4-{1-[2-(5,5,8,8-Tetramethyl-5,6,7,8-tetrahydronaphthalen-2-yl)pyrimidin-4-yl]-piperidin-4-ylamino}butan-1-ol

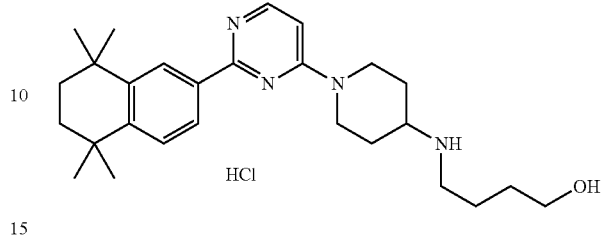

The preparation is carried out analogously to FS402. The product is in the form of the hydrochloride.

Yield: 12 mg, beige solid. Rt.=2.46 min (method A), LCMS: 437 (M+H).

¹H NMR (500 MHz, DMSO/deuterated TFA) δ 8.27 (d, J=7.5 Hz, 1H), 8.12 (s, 1H), 7.93 (d, J=8.3 Hz, 1H), 7.51 (d, J=8.4 Hz, 1H), 7.11 (d, J=7.6 Hz, 1H), 5.21 (d, J=12.3 Hz, 1H), 4.36 (d, J=14.3 Hz, 1H), 3.53-3.42 (m, 3H), 3.35 (t, J=13.0 Hz, 1H), 3.18 (t, J=12.9 Hz, 1H), 3.01-2.92 (m, 2H), 2.24 (d, J=12.6 Hz, 2H), 1.77-1.57 (m, 8H), 1.55-1.47 (m, 2H), 1.27 (d, J=21.5 Hz, 12H).

FS429: Acetic acid 4-{1-[2-(5,5,8,8-tetramethyl-5,6,7,8-tetrahydronaphthalen-2-yl)-pyrimidin-4-yl]piperidin-4-ylamino}butyl ester

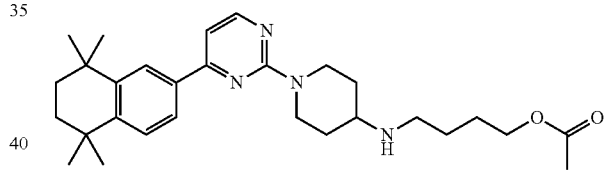

The preparation is carried out analogously to FS401.

Yield: 37 mg, Rt.=2.89 min (method A), LCMS: 479 (M+H).

FS430: 4-{1-[2-(5,5,8,8-Tetramethyl-5,6,7,8-tetrahydronaphthalen-2-yl)pyrimidin-4-yl]-piperidin-4-ylamino}butan-1-ol

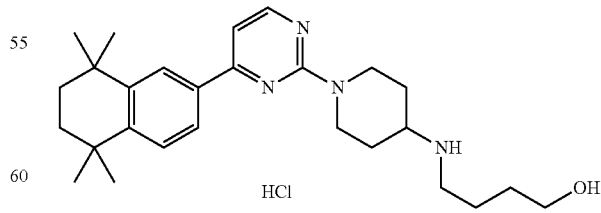

The preparation is carried out analogously to FS402. The product is in the form of the hydrochloride.

Yield: 8 mg, beige solid. Rt.=2.76 min (method A), LCMS: 437 (M+H).

¹H NMR (500 MHz, DMSO/deuterated TFA) δ 8.41 (d, J=6.5 Hz, 1H), 8.13 (d, J=1.9 Hz, 1H), 7.95 (dd, J=8.4, 1.9 Hz, 1H), 7.55 (d, J=6.6 Hz, 1H), 7.49 (d, J=8.4 Hz, 1H), 4.72 (b, 2H), 3.52-3.41 (m, 3H), 3.27 (t, J=12.1 Hz, 2H), 3.03-2.94 (m, 2H), 2.23 (d, J=10.2 Hz, 2H), 1.76-1.64 (m, 8H), 1.56-1.48 (m, 2H), 1.28 (d, J=19.3 Hz, 12H).

FS431: Acetic acid 4-{4-[4-(5,5,8,8-tetramethyl-5,6,7,8-tetrahydronaphthalen-2-yl)-pyrimidin-2-yl]piperazin-1-yl}butyl ester

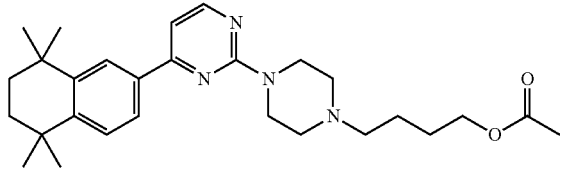 [SMILES: CC(=O)OCCCCN1CCN(c2nccc(-c3ccc4c(c3)C(C)(C)CCC4(C)C)n2)CC1]

The preparation is carried out analogously to FS401. The crude product is employed directly in the cleaving-off of actyl.
Rt.=3.10 min (method A), LCMS: 465 (M+H).

FS432: 4-{4-[4-(5,5,8,8-Tetramethyl-5,6,7,8-tetrahydronaphthalen-2-yl)pyrimidin-2-yl]-piperazin-1-yl}butan-1-ol

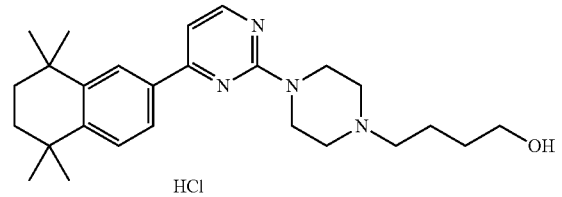 [SMILES: CC1(C)CCC(C)(C)c2cc(-c3ccnc(N4CCN(CCCCO)CC4)n3)ccc21 ; Cl]

The preparation is carried out analogously to FS402. The product is in the form of the hydrochloride.
Yield: 42 mg, beige solid. Rt.=2.96 min (method A), LCMS: 423 (M+H).
¹H NMR (500 MHz, DMSO/deuterated TFA) δ 8.49 (d, J=5.7 Hz, 1H), 8.08 (d, J=1.8 Hz, 1H), 7.90 (dd, J=8.3, 1.8 Hz, 1H), 7.46 (d, J=8.3 Hz, 1H), 7.41 (d, J=5.7 Hz, 1H), 4.85 (d, J=14.0 Hz, 2H), 3.66 (d, J=11.7 Hz, 2H), 3.55-3.38 (m, 4H), 3.26-3.06 (m, 4H), 1.86-1.76 (m, 2H), 1.69 (s, 4H), 1.58-1.45 (m, 2H), 1.29 (d, J=20.5 Hz, 12H).

FS433: Acetic acid 4-{4-[4-(5,5,8,8-tetramethyl-5,6,7,8-tetrahydronaphthalen-2-yl)-pyrimidin-2-yl]piperazin-1-yl}butyl ester

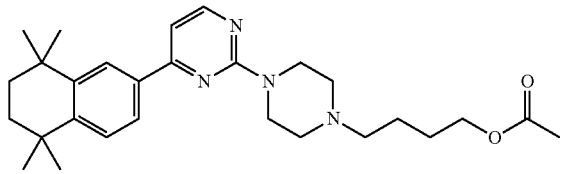 [SMILES: CC(=O)OCCCCN1CCN(c2nccc(-c3ccc4c(c3)C(C)(C)CCC4(C)C)n2)CC1]

The preparation is carried out analogously to FS401. The crude product is employed directly in the cleaving-off of actyl.
Rt.=3.15 min (method A), LCMS: 494 (M+H).

FS434: 4-{4-[5-Methoxy-6-(5,5,8,8-tetramethyl-5,6,7,8-tetrahydronaphthalen-2-yl)pyridin-2-yl]piperazin-1-yl}butan-1-ol acid

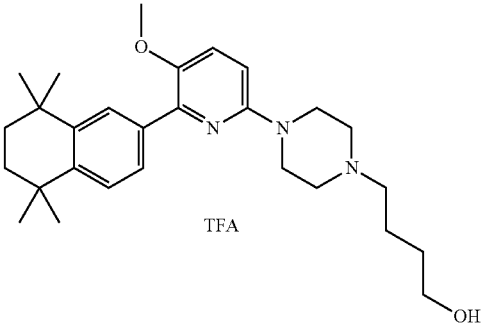 [SMILES: COc1ccc(N2CCN(CCCCO)CC2)nc1-c1ccc2c(c1)C(C)(C)CCC2(C)C ; "TFA"]

The preparation is carried out analogously to FS402. The product is in the form of the trifluoroacetate.
Yield: 14 mg, colourless oil. Rt.=2.98 min (method A), LCMS: 452 (M+H).
¹H NMR (500 MHz, DMSO/deuterated TFA) δ 7.82 (d, J=9.4 Hz, 1H), 7.72 (s, 1H), 7.49 (dd, J=8.2, 1.8 Hz, 1H), 7.40 (d, J=8.3 Hz, 1H), 7.15 (d, J=9.4 Hz, 1H), 4.27 (d, J=13.2 Hz, 2H), 3.80 (s, 3H), 3.67-3.56 (m, 2H), 3.48 (t, J=6.0 Hz, 2H), 3.40-3.30 (m, 2H), 3.20-3.08 (m, 4H), 1.81-1.73 (m, 2H), 1.67 (s, 4H), 1.54-1.46 (m, 2H), 1.26 (s, 12H).

FS501: Preparation of 5-{4-[6-(5,5,8,8-tetramethyl-5,6,7,8-tetrahydronaphthalen-2-yl)pyridin-2-yl]piperazin-1-yl}pentan-1-ol

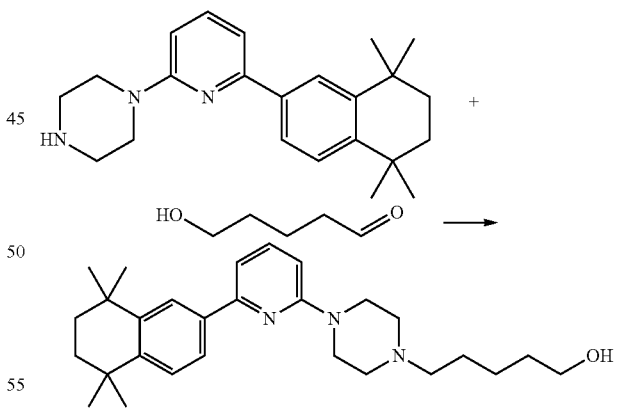

5 ml of THF and 200 μl of glacial acetic acid are added to 100 mg (0.29 mmol) of 1-[6-(5,5,8,8-tetramethyl-5,6,7,8-tetrahydronaphthalen-2-yl)pyridin-2-yl]piperazine, and 58 mg (0.57 mmol) of 5-hydroxypentanal were added. The reaction mixture is stirred for 15 min. 128 mg (0.57 mmol) of sodium trisacetoxyborohydride are subsequently added, and the reaction mixture is stirred at room temperature for 18 h and subsequently filtered. The mother liquor is evaporated, and the residue is purified by means of reversed phase chromatography.

Yield: 64 mg, white solid. Rt.=2.69 min (method B), LCMS: 436 (M+H).

¹H NMR (400 MHz, DMSO/deuterated TFA) δ 7.90-7.84 (m, 2H), 7.69 (dd, J=8.2, 1.9, 1H), 7.47 (d, J=8.3, 1H), 7.29 (d, J=7.4, 1H), 7.11 (d, J=8.7, 1H), 4.54 (d, J=13.9, 2H), 3.68 (d, J=11.6, 2H), 3.47 (t, J=6.3, 2H), 3.40 (t, J=12.4, 2H), 3.24-3.14 (m, 4H), 1.79-1.72 (m, 2H), 1.72 (s, 4H), 1.58-1.47 (m, 2H), 1.47-1.37 (m, 2H), 1.32 (d, J=13.5, 12H).

The following compounds were prepared analogously to FS501. If the hydrochloride was employed as starting material, the starting material was suspended in THF with 2 euiv. of DIPEA, stirred for 30 min, and glacial acetic acid, aldehyde and reducing agent were subsequently added.

FS502: 5-{4-[6-(5,5-Dimethyl-5,6,7,8-tetrahydronaphthalen-2-yl)pyridin-2-yl]-piperazin-1-yl}pentan-1-ol

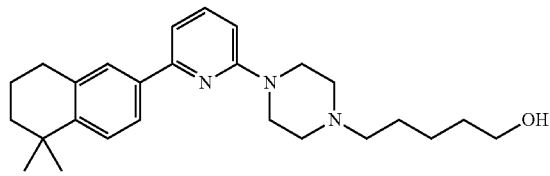 [SMILES: CC1(C)CCCc2cc(-c3cccc(N4CCN(CCCCCO)CC4)n3)ccc21]

The preparation is carried out analogously to F501.

Yield: 92 mg, beige solid. Rt.=2.65 min (method B), LCMS: 408 (M+H).

¹H NMR (400 MHz, DMSO/deuterated TFA) δ 7.97-7.90 (m, 1H), 7.68 (d, J=8.3, 1H), 7.59 (d, J=8.3, 1H), 7.53 (d, J=8.3, 1H), 7.29 (d, J=7.4, 1H), 7.19 (d, J=8.8, 1H), 4.55 (d, J=13.7, 2H), 3.69 (d, J=11.3, 2H), 3.49 (t, J=6.2, 3H), 3.38-3.31 (m, 1H), 3.29-3.15 (m, 4H), 2.85 (t, J=6.3, 2H), 1.87-1.67 (m, 6H), 1.59-1.49 (m, 2H), 1.43 (dd, J=14.8, 7.9, 2H), 1.31 (s, 6H).

FS503: 5-{4-[6-(8,8-Dimethyl-5,6,7,8-tetrahydronaphthalen-2-yl)pyridin-2-yl]-piperazin-1-yl}pentan-1-ol

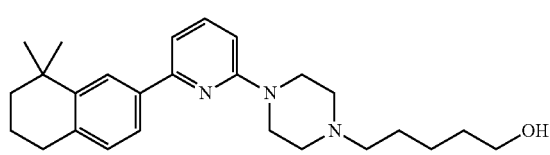 [SMILES: CC1(C)CCCc2ccc(-c3cccc(N4CCN(CCCCCO)CC4)n3)cc21]

The preparation is carried out analogously to F501.

Yield: 99 mg, yellow oil., Rt.=2.59 min (method B), LCMS: 408 (M+H).

¹H NMR (500 MHz, DMSO/deuterated TFA) δ 7.96 (s, 1H), 7.79-7.73 (m, 1H), 7.73-7.66 (m, 1H), 7.31 (d, J=7.4, 1H), 7.14 (d, J=8.0, 1H), 6.98 (d, J=8.0, 1H), 4.52 (d, J=14.1, 2H), 3.65 (d, J=12.0, 2H), 3.45 (t, J=6.3, 2H), 3.34-3.24 (m, 2H), 3.21-3.10 (m, 4H), 2.78 (t, J=6.2, 2H), 1.83-1.64 (m, 6H), 1.53-1.46 (m, 2H), 1.39 (dd, J=15.1, 7.9, 2H), 1.32 (s, 6H).

FS504: 5-[6'-(5,5,8,8-Tetramethyl-5,6,7,8-tetrahydronaphthalen-2-yl)-3,4,5,6-tetrahydro-2H-1,2'-bipyridinyl-4-ylamino]pentan-1-ol

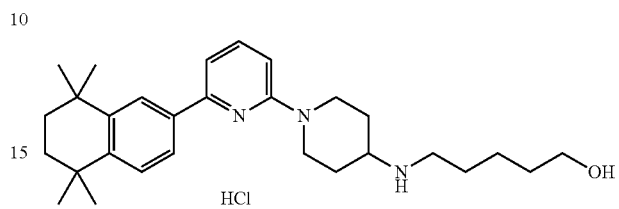

The preparation is carried out analogously to F501.

Yield: 24 mg, pale-yellow solid. Rt.=2.77 min (method A), LCMS: 450 (M+H).

¹H NMR (500 MHz, DMSO/deuterated TFA) δ 8.03 (dd, J=9.0, 7.5, 1H), 7.74 (d, J=1.8, 1H), 7.60-7.52 (m, 2H), 7.33 (d, J=9.0, 1H), 7.20 (d, J=7.3, 1H), 4.40 (d, J=13.4, 2H), 3.51-3.42 (m, 3H), 3.27 (t, J=12.1, 2H), 3.03-2.98 (m, 2H), 2.21 (d, J=10.3, 2H), 1.78-1.63 (m, 8H), 1.55-1.39 (m, 4H), 1.33 (d, J=13.0, 12H).

FS505: 5-{4-[6-(1,1,3,3-Tetramethylindan-5-yl)pyridin-2-yl]piperazin-1-yl}pentan-1-ol

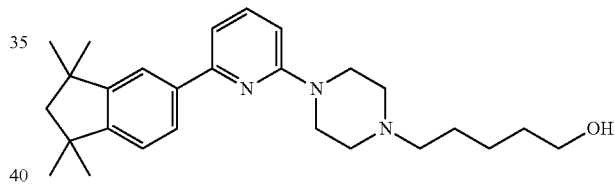

The preparation is carried out analogously to F501.

Yield: 98 mg, oil. Rt.=2.72 min (method B), LCMS: 422 (M+H).

¹H NMR (400 MHz, DMSO/deuterated TFA) δ 7.88-7.79 (m, 2H), 7.72 (d, J=1.4, 1H), 7.30 (dd, J=10.4, 7.7, 2H), 7.08 (d, J=8.6, 1H), 4.54 (d, J=13.9, 2H), 3.67 (d, J=12.5, 2H), 3.46 (t, J=6.3, 2H), 3.36 (t, J=12.5, 2H), 3.25-3.12 (m, 4H), 1.96 (s, 2H), 1.74 (dt, J=15.5, 7.9, 2H), 1.52 (dt, J=13.9, 6.8, 2H), 1.46-1.28 (m, 14H).

FS506: 5-{4-[6-(1,1-Dimethylindan-5-yl)pyridin-2-yl]piperazin-1-yl}pentan-1-ol

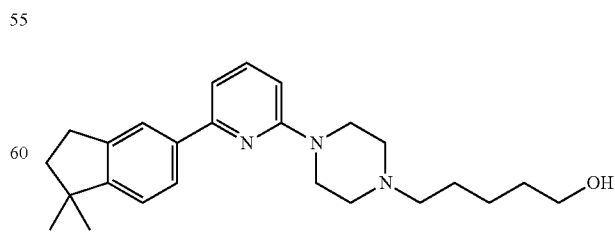

The preparation is carried out analogously to F501.

Yield: 105 mg, viscous oil. Rt.=1.71 min (method C), LCMS: 394 (M+H).

¹H NMR (400 MHz, DMSO/deuterated TFA) δ 7.90 (t, J=8.1, 1H), 7.81-7.72 (m, 2H), 7.31 (dd, J=10.1, 7.7, 2H), 7.14 (d, J=8.7, 1H), 4.55 (d, J=14.4, 2H), 3.68 (d, J=12.0, 2H), 3.48 (t, J=6.3, 2H), 3.46-3.35 (m, 2H), 3.29-3.09 (m, 4H), 2.97 (t, J=7.2, 2H), 1.97 (t, J=7.2, 2H), 1.76 (dt, J=15.5, 7.8, 2H), 1.58-1.37 (m, 4H), 1.28 (s, 6H).

FS507: (R)-2-Amino-3-{4-[6-(5,5,8,8-tetramethyl-5,6,7,8-tetrahydronaphthalen-2-yl)-pyridin-2-yl]piperazin-1-yl}propan-1-ol

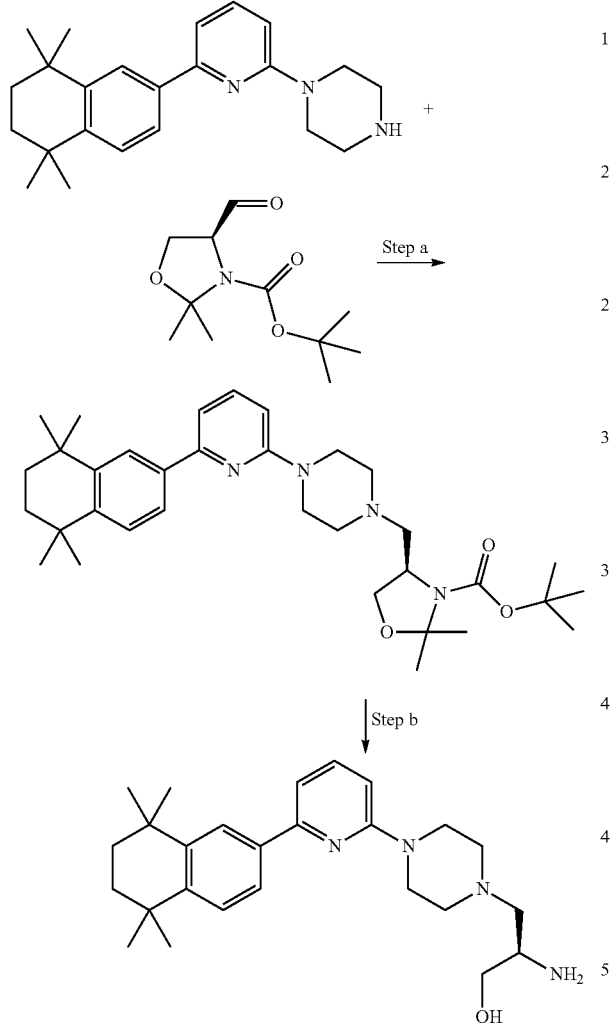

Step a

The reaction is carried out analogously to F501.
Yield: 220 mg, oil. Rt.=3.59 min (method A), LCMS: 563 (M+H).

Step b

The protecting group is cleaved off analogously to FS 201:
Yield: 51 mg, yellow solid. Rt.=2.78 min (method A), LCMS: 423 (M+H).
¹H NMR (500 MHz, DMSO/deuterated TFA) δ 7.91-7.84 (m, 2H), 7.71 (dd, J=8.3, 1.9, 1H), 7.47 (d, J=8.3, 1H), 7.31 (d, J=7.5, 1H), 7.12 (d, J=8.7, 1H), 4.02 (b, 3H), 3.90-3.81 (m, 1H), 3.73 (ddd, J=16.9, 11.6, 4.9, 2H), 3.55 (dd, J=14.1, 4.6, 6H), 3.40 (dd, J=14.2, 6.6, 1H), 1.72 (s, 4H), 1.32 (d, J=17.6, 12H).

FS508: 5-{4-[3-(5,5,8,8-Tetramethyl-5,6,7,8-tetrahydronaphthalen-2-yl)phenyl]-piperazin-1-yl}pentan-1-ol

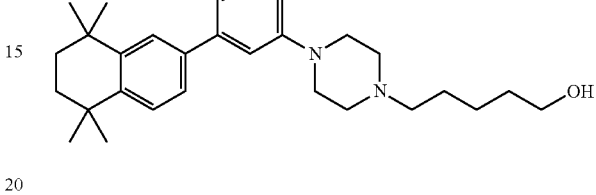

The preparation is carried out analogously to F501.
Yield: 165 mg, yellow oil. Rt.=2.88 min (method B), LCMS: 435 (M+H).
¹H NMR (400 MHz, DMSO/deuterated TFA) δ 7.54 (s, 1H), 7.43-7.32 (m, 3H), 7.21 (s, 1H), 7.15 (d, J=7.9, 1H), 7.01 (dd, J=8.1, 1.9, 1H), 3.97 (d, J=12.8, 2H), 3.64 (d, J=11.5, 2H), 3.48 (t, J=6.2, 2H), 3.29-3.07 (m, 6H), 1.84-1.68 (m, 6H), 1.59-1.38 (m, 4H), 1.31 (d, J=15.1, 12H).

FS509: 5-{4-[3-(2-Methoxyethoxy)-6-(5,5,8,8-tetramethyl-5,6,7,8-tetrahydronaphthalen-2-yl)pyridin-2-yl]piperazin-1-yl}pentan-1-ol

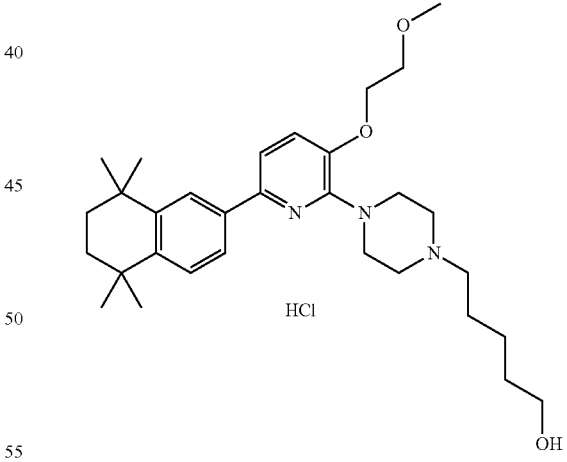

The preparation is carried out analogously to F501. The product is in the form of the hydrochloride.
Yield: 36 mg, yellow oil. Rt.=3.15 min (method A), LCMS: 510 (M+H).
¹H NMR (400 MHz, DMSO/deuterated TFA) δ 7.90 (d, J=1.8, 1H), 7.69 (dd, J=8.2, 1.7, 1H), 7.42 (dt, J=14.7, 8.3, 3H), 4.33 (d, J=13.5, 2H), 4.25-4.20 (m, 2H), 3.78-3.72 (m, 2H), 3.63 (d, J=11.6, 2H), 3.47 (t, J=6.3, 2H), 3.38 (s, 3H), 3.36-3.15 (m, 6H), 1.73 (d, J=24.6, 6H), 1.57-1.47 (m, 2H), 1.41 (d, J=7.3, 2H), 1.31 (d, J=21.0, 12H).

FS510: 5-{4-[2-(5,5,8,8-Tetramethyl-5,6,7,8-tetrahydronaphthalen-2-yl)pyrimidin-4-yl]-piperazin-1-yl}pentan-1-ol

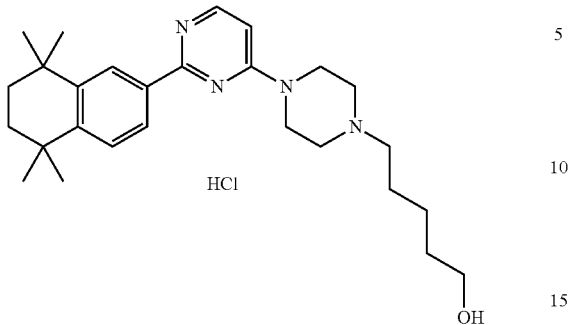

The preparation is carried out analogously to FS501. The product is in the form of the hydrochloride.

Yield: 77 mg, beige solid. Rt.=2.43 min (method A), LCMS: 437 (M+H).

$^1$H NMR (500 MHz, DMSO) δ 11.03 (s, 1H), 8.46 (d, J=7.1 Hz, 1H), 8.29 (d, J=1.8 Hz, 1H), 8.06 (dd, J=8.4, 1.9 Hz, 1H), 7.55 (d, J=8.4 Hz, 1H), 7.17 (d, J=6.1 Hz, 1H), 4.77 (b, 1H), 3.6-4.1 (superimposed, 6H), 3.42 (t, J=6.3 Hz, 2H), 3.25-3.05 (m, 4H), 1.84-1.61 (m, 6H), 1.53-1.41 (m, 2H), 1.41-1.19 (m, 14H).

FS511: 5-{1-[4-(5,5,8,8-Tetramethyl-5,6,7,8-tetrahydronaphthalen-2-yl)pyrimidin-2-yl]-piperidin-4-ylamino}pentan-1-ol

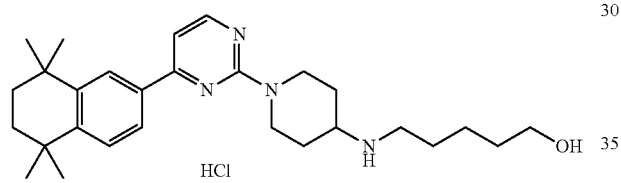

The preparation is carried out analogously to FS501 using 1 eq. of 5-hydroxypentanal. The product is in the form of the hydrochloride.

Yield: 23 mg, beige solid. Rt.=2.80 min (method A), LCMS: 451 (M+H).

1H NMR (400 MHz, DMSO/deuterated TFA) δ 8.51 (d, J=6.3 Hz, 1H), 8.17 (d, J=1.9 Hz, 1H), 8.00 (dd, J=8.4, 1.9 Hz, 1H), 7.57 (dd, J=20.1, 7.4 Hz, 2H), 4.77 (b, 2H), 3.54-3.42 (m, 3H), 3.26 (t, J=12.1 Hz, 2H), 3.04-2.95 (m, 2H), 2.24 (d, J=10.3 Hz, 2H), 1.78-1.61 (m, 8H), 1.55-1.39 (m, 4H), 1.33 (d, J=16.5 Hz, 12H).

FS512: 5-{1-[2-(5,5,8,8-Tetramethyl-5,6,7,8-tetrahydronaphthalen-2-yl)pyrimidin-4-yl]piperidin-4-ylamino}pentan-1-ol

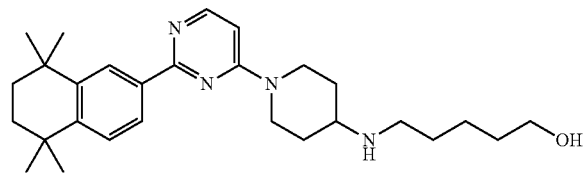 [SMILES: CC1(C)CCC(C)(C)c2cc(-c3cccc(N4CCC(NCCCCCO)CC4)n3)ccc21 ; Cl]

The preparation is carried out analogously to FS511. The product is in the form of the hydrochloride.

Yield: 30 mg, beige solid. Rt.=2.49 min (method A), LCMS: 451 (M+H).

1H NMR (500 MHz, DMSO/deuterated TFA) δ 8.39 (d, J=7.5 Hz, 1H), 8.20 (d, J=2.0 Hz, 1H), 8.01 (dd, J=8.4, 2.0 Hz, 1H), 7.59 (d, J=8.4 Hz, 1H), 7.22 (d, J=7.6 Hz, 1H), 5.26 (d, J=13.3 Hz, 1H), 4.45 (d, J=13.6 Hz, 1H), 3.55 (dd, J=13.3, 9.2 Hz, 1H), 3.49 (t, J=6.2 Hz, 2H), 3.42 (t, J=12.7 Hz, 1H), 3.30-3.21 (m, 2H), 3.06-2.97 (m, 2H), 2.29 (s, 2H), 1.80-1.63 (m, 8H), 1.57-1.49 (m, 2H), 1.49-1.40 (m, 2H), 1.34 (d, J=22.5 Hz, 12H).

FS 513: 5-{4-[5-(2-Hydroxyethoxy)-6-(5,5,8,8-tetramethyl-5,6,7,8-tetrahydronaphthalen-2-yl)pyridin-2-yl]piperazin-1-yl}pentan-1-ol

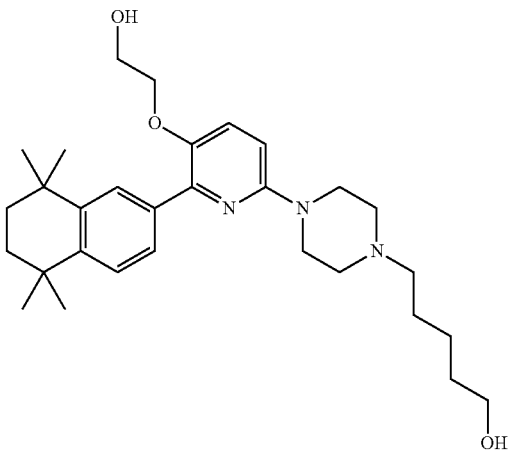 [SMILES: CC1(C)CCC(C)(C)c2cc(-c3nc(N4CCN(CCCCCO)CC4)ccc3OCCO)ccc21]

The preparation is carried out analogously to FS501.

Yield: 63 mg, beige solid. Rt.=2.75 min (method A), LCMS: 496 (M+H).

$^1$H NMR (500 MHz, DMSO/deuterated TFA) δ 8.01 (s, 1H), 7.72 (d, J=8.3 Hz, 1H), 7.61 (dd, J=9.1, 2.7 Hz, 1H), 7.37 (d, J=8.3 Hz, 1H), 6.97 (dd, J=9.1, 1.7 Hz, 1H), 4.32 (d, J=13.4 Hz, 2H), 4.04 (t, J=5.0 Hz, 2H), 3.73 (t, J=5.0 Hz, 2H), 3.61 (d, J=11.7 Hz, 2H), 3.43 (t, J=6.3 Hz, 2H), 3.26-3.07 (m, 6H), 1.78-1.63 (m, 6H), 1.53-1.44 (m, 2H), 1.40-1.34 (m, 2H), 1.29 (d, J=6.5 Hz, 12H).

FS514: 2-{2-[6-[4-(5-Hydroxypentyl)piperazin-1-yl]-2-(5,5,8,8-tetramethyl-5,6,7,8-tetrahydronaphthalen-2-yl)pyridin-3-yloxy]ethyl}isoindole-1,3-dione

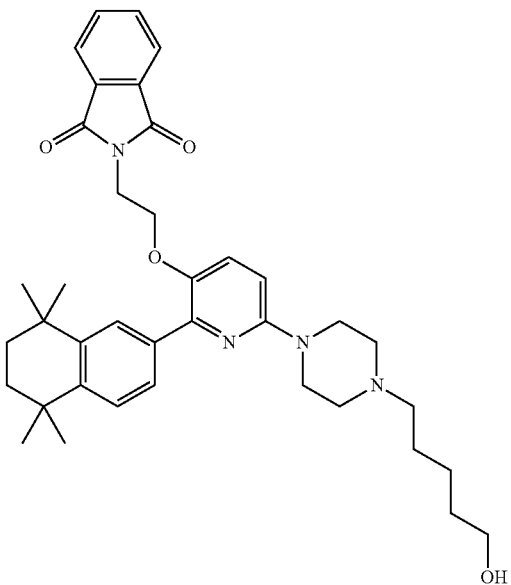 [SMILES: CC1(C)CCC(C)(C)c2cc(-c3nc(N4CCN(CCCCCO)CC4)ccc3OCCN3C(=O)c4ccccc4C3=O)ccc21]

The preparation is carried out analogously to FS501.

Yield: 74 mg. Rt.=3.14 min (method A), LCMS: 625 (M+H).

FS515: 5-{4-[5-(5,5,8,8-Tetramethyl-5,6,7,8-tetrahydronaphthalen-2-yl)pyridin-3-yl]-piperazin-1-yl}pentan-1-ol

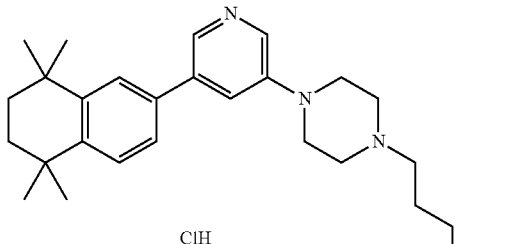

The preparation is carried out analogously to FS501. The product is in the form of the hydrochloride.

Yield: 29 mg, beige solid. Rt.=2.51 min (method A), LCMS: 436 (M+H).

$^1$H NMR (500 MHz, DMSO/deuterated TFA) δ 8.58 (d, J=1.0 Hz, 1H), 8.52 (d, J=2.4 Hz, 1H), 8.29 (s, 1H), 7.71 (s, 1H), 7.62-7.47 (m, 2H), 4.31 (d, J=14.0 Hz, 2H), 3.71 (d, J=12.1 Hz, 2H), 3.55 (t, J=6.2 Hz, 2H), 3.46 (t, J=12.3 Hz, 2H), 3.23 (dd, J=21.1, 12.8 Hz, 4H), 1.81 (dt, J=16.1, 8.0 Hz, 2H), 1.75 (s, 4H), 1.64-1.53 (m, 2H), 1.53-1.41 (m, 2H), 1.34 (d, J=17.0 Hz, 12H).

FS516: 5-{4-[5-Methoxy-6-(5,5,8,8-tetramethyl-5,6,7,8-tetrahydronaphthalen-2-yl)pyridin-2-yl]piperazin-1-yl}pentan-1-ol

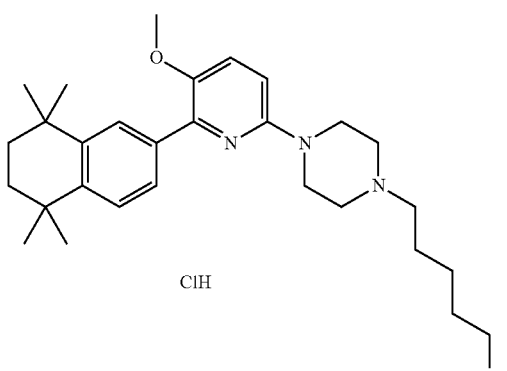

The preparation is carried out analogously to FS501. The product is in the form of the hydrochloride.

Yield: 70 mg, viscous oil. Rt.=3.05 min (method A), LCMS: 466 (M+H).

FS517: (S)-3-{1-[4-(5,5,8,8-Tetramethyl-5,6,7,8-tetrahydronaphthalen-2-yl)pyrimidin-2-yl]piperidin-4-ylamino}propane-1,2-diol

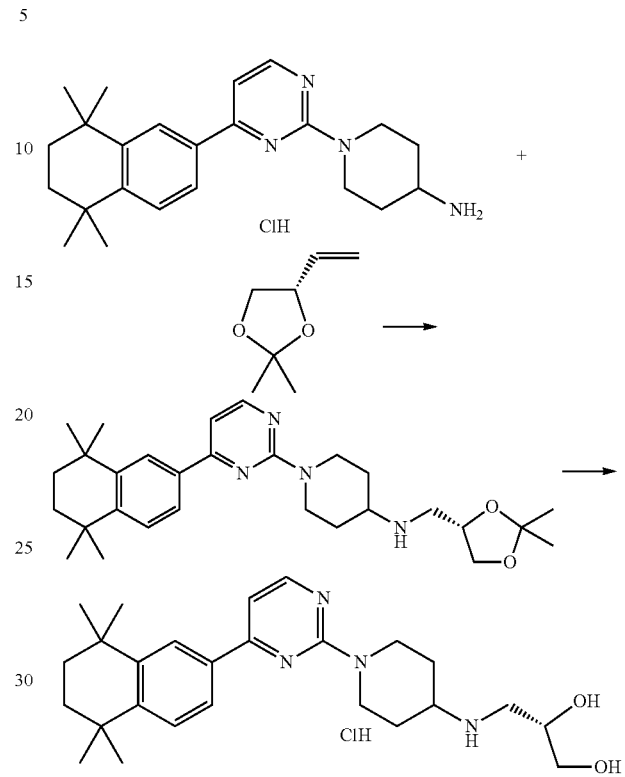

The preparation is carried out analogously to FS511. The intermediate is dissolved in methanol for the acetal cleavage, and methanolic HCl is added, and the mixture is stirred at room temperature for 1 h. The crude product was purified by means of preparative HPLC and converted into the hydrochloride using methanolic HCl.

Yield: 16 mg, viscous oil. Rt.=2.70 min (method A), LCMS: 439 (M+H).

$^1$H NMR (500 MHz, DMSO/deuterated TFA) δ 8.49 (d, 1H), 8.19 (d, J=1.8 Hz, 1H), 8.01 (dd, J=8.4, 1.8 Hz, 1H), 7.61 (d, J=6.5 Hz, 1H), 7.55 (d, J=8.4 Hz, 1H), 4.78 (b, 2H), 3.92-3.83 (m, 1H), 3.59-3.49 (m, 2H), 3.46-3.39 (m, 1H), 3.28 (t, J=12.4 Hz, 2H), 3.19 (dd, J=12.6, 2.8 Hz, 1H), 2.96 (dd, J=12.6, 9.5 Hz, 1H), 2.35-2.23 (m, 2H), 1.85-1.69 (m, 6H), 1.34 (d, J=20.5 Hz, 12H).

FS518: (S)-3-{1-[2-(5,5,8,8-Tetramethyl-5,6,7,8-tetrahydronaphthalen-2-yl)pyrimidin-4-yl]piperidin-4-ylamino}propane-1,2-diol

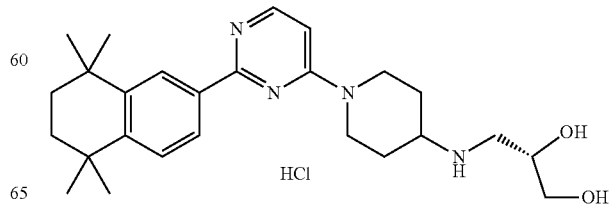

The preparation is carried out analogously to FS517. The product is in the form of the hydrochloride.

Yield: 22 mg, solid. Rt.=2.42 min (method A), LCMS: 439 (M+H).

$^1$H NMR (500 MHz, DMSO/deuterated TFA) δ 8.36 (d, J=7.5 Hz, 1H), 8.20 (d, J=2.0 Hz, 1H), 8.01 (dd, J=8.4, 2.0 Hz, 1H), 7.59 (d, J=8.4 Hz, 1H), 7.19 (d, J=7.5 Hz, 1H), 5.30 (d, J=12.8 Hz, 1H), 4.45 (d, J=12.5 Hz, 1H), 3.96-3.85 (m, 1H), 3.64-3.50 (m, 2H), 3.50-3.33 (m, 2H), 3.27-3.16 (m, 2H), 2.98 (dd, J=12.6, 9.5 Hz, 1H), 2.41-2.25 (m, 2H), 1.86-1.67 (m, 6H), 1.43-1.28 (m, 12H).

FS519: 5-{4-[4-(5,5,8,8-Tetramethyl-5,6,7,8-tetrahydronaphthalen-2-yl)pyrimidin-2-yl]-piperazin-1-yl}pentan-1-ol

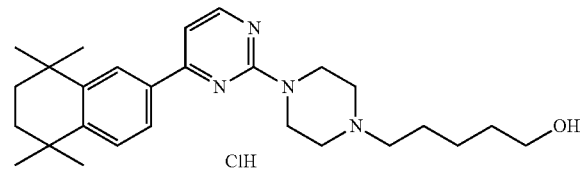 [SMILES: CC1(C)CCC(C)(C)c2cc(-c3ccnc(N4CCN(CCCCCO)CC4)n3)ccc21 ; Cl]

The preparation is carried out analogously to FS501. The product is in the form of the hydrochloride.

Yield: 58 mg, beige solid. Rt.=2.98 min (method A), LCMS: 437 (M+H).

$^1$H NMR (400 MHz, DMSO/deuterated TFA) δ 8.47 (d, J=5.6 Hz, 1H), 8.05 (d, J=1.9 Hz, 1H), 7.87 (dd, J=8.3, 1.9 Hz, 1H), 7.44 (d, J=8.4 Hz, 1H), 7.38 (d, J=5.6 Hz, 1H), 4.82 (d, J=14.6 Hz, 2H), 3.62 (d, J=11.7 Hz, 2H), 3.48-3.34 (m, 4H), 3.14-3.03 (m, 4H), 1.68 (d, J=15.8 Hz, 6H), 1.51-1.41 (m, 2H), 1.35 (dd, J=15.1, 7.9 Hz, 2H), 1.26 (d, J=16.5 Hz, 12H).

FS520: 3-{1-[2-(5,5,8,8-Tetramethyl-5,6,7,8-tetrahydronaphthalen-2-yl)pyrimidin-4-yl]-piperidin-4-ylamino}propan-1-ol

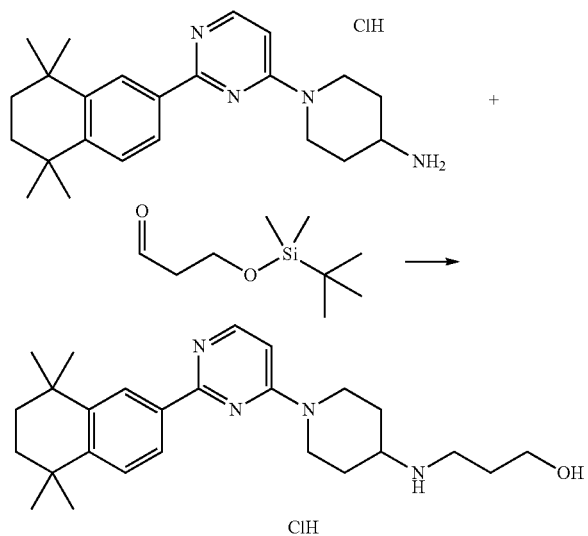

The preparation is carried out analogously to FS511. The protecting group was cleaved off by treatment with TMAF in THF at room temperature. The product is in the form of the hydrochloride.

Yield: 18 mg, beige solid. Rt.=2.46 min (method A), LCMS: 423 (M+H).

$^1$H NMR (400 MHz, DMSO/deuterated TFA) δ 8.31 (d, J=7.5 Hz, 1H), 8.14 (d, J=2.0 Hz, 1H), 7.95 (dd, J=8.4, 1.9 Hz, 1H), 7.53 (d, J=8.4 Hz, 1H), 7.14 (d, J=7.6 Hz, 1H), 5.22 (d, J=13.3 Hz, 1H), 4.38 (d, J=13.4 Hz, 1H), 3.58-3.46 (m, 3H), 3.36 (t, J=12.6 Hz, 1H), 3.26-3.12 (m, 1H), 3.07 (t, J=7.5 Hz, 2H), 2.25 (d, J=12.0 Hz, 2H), 1.86-1.75 (m, 2H), 1.75-1.57 (m, 6H), 1.30 (d, J=16.4, 12H).

FS521: (S)-3-{1-[2-(5,5,8,8-Tetramethyl-5,6,7,8-tetrahydronaphthalen-2-yl)pyrimidin-4-yl]piperidin-4-ylamino}propane-1,2-diol

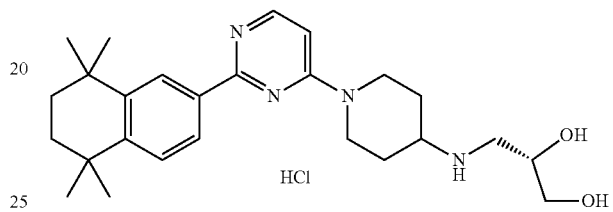

The preparation is carried out analogously to FS517. The product is in the form of the hydrochloride.

Yield: 17 mg, solid. Rt.=2.68 min (method A), LCMS: 438 (M+H).

$^1$H NMR (400 MHz, DMSO/deuterated TFA) δ 7.98 (dd, J=9.1, 7.4 Hz, 1H), 7.63 (d, J=1.3 Hz, 1H), 7.52-7.41 (m, 2H), 7.28 (d, J=9.1 Hz, 1H), 7.10 (d, J=7.3 Hz, 1H), 4.33 (d, J=13.7 Hz, 2H), 3.83 (q, J=9.0 Hz, 1H), 3.53-3.33 (m, 3H), 3.24 (t, J=12.1 Hz, 2H), 3.12 (dd, J=12.6, 2.9 Hz, 1H), 2.91 (dd, J=12.6, 9.5 Hz, 1H), 2.21 (t, J=13.1 Hz, 2H), 1.89-1.70 (m, 2H), 1.67 (s, 4H), 1.27 (d, J=9.9 Hz, 12H).

FS522: 5-{4-[2-Methoxy-5-(5,5,8,8-tetramethyl-5,6,7,8-tetrahydronaphthalen-2-yl)-phenyl]piperazin-1-yl}pentan-1-ol

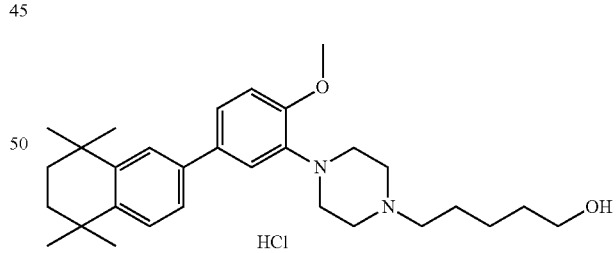

The preparation is carried out analogously to FS501. The product is in the form of the hydrochloride.

Yield: 13 mg, white solid. Rt.=3.13 min (method A), LCMS: 465 (M+H).

$^1$H NMR (500 MHz, DMSO/deuterated TFA) δ 7.47 (d, J=1.5 Hz, 1H), 7.38-7.30 (m, 2H), 7.27 (dd, J=8.4, 2.0 Hz, 1H), 7.13 (d, J=1.9 Hz, 1H), 7.05 (d, J=8.5 Hz, 1H), 3.85 (s, 3H), 3.64 (dd, J=34.9, 11.7 Hz, 4H), 3.45 (t, J=6.3 Hz, 2H), 3.31-3.21 (m, 2H), 3.21-3.14 (m, 2H), 3.14-3.03 (m, 2H), 1.77-1.69 (m, 2H), 1.68 (s, 4H), 1.54-1.46 (m, 2H), 1.44-1.34 (m, 2H), 1.28 (d, J=19.2 Hz, 12H).

FS523: 2-{4-[6-(5,5,8,8-Tetramethyl-5,6,7,8-tetrahydronaphthalen-2-yl)pyridin-2-yl]-piperazin-1-ylmethyl}cyclopropanecarboxylic acid ethyl ester

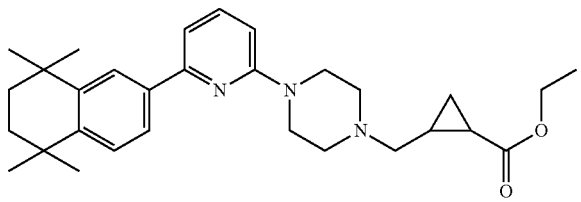 [SMILES: CCOC(=O)C1CC1CN1CCN(c2cccc(-c3ccc4c(c3)C(C)(C)CCC4(C)C)n2)CC1]

The preparation is carried out analogously to FS501.
Yield: 107 mg, white solid. Rt.=3.25 min (method A), LCMS: 467 (M+H).

FS524: 2-{2-[6-[4-(5-Hydroxypentyl)piperazin-1-yl]-2-(5,5,8,8-tetramethyl-5,6,7,8-tetrahydronaphthalen-2-yl)pyridin-3-yloxy]ethyl}isoindole-1,3-dione

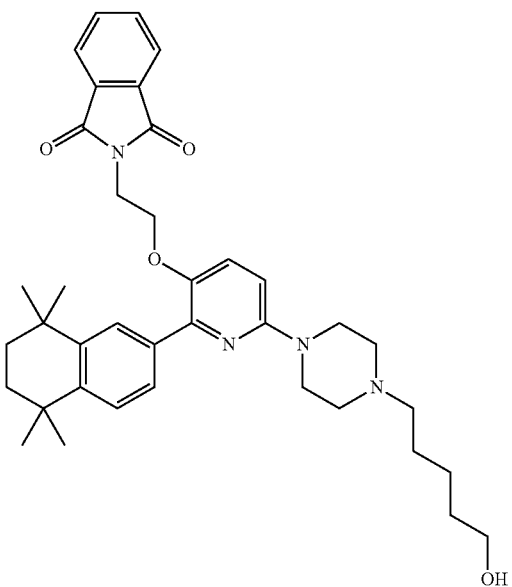 [SMILES: CC1(C)CCC(C)(C)c2cc(-c3nc(N4CCN(CCCCCO)CC4)ccc3OCCN3C(=O)c4ccccc4C3=O)ccc21]

The preparation is carried out analogously to FS501.
Yield: 74 mg, beige solid. Rt.=3.14 min (method A), LCMS: 625 (M+H).

FS525: 2-[6'-(5,5,8,8-Tetramethyl-5,6,7,8-tetrahydronaphthalen-2-yl)-3,4,5,6-tetrahydro-2H-1,2'-bipyridinyl-4-ylamino]ethanol

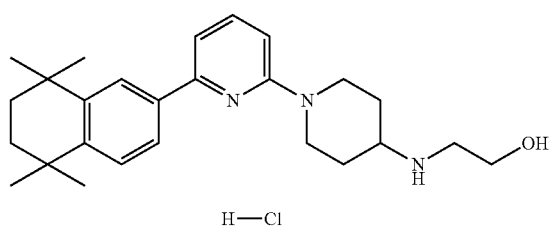 [SMILES: CC1(C)CCC(C)(C)c2cc(-c3cccc(N4CCC(NCCO)CC4)n3)ccc21 ; Cl]

The preparation is carried out analogously to FS520. The product is in the form of the hydrochloride.
Yield: 13 mg, beige solid. Rt.=2.70 min (method A), LCMS: 408 (M+H).
$^1$H NMR (500 MHz, DMSO/deuterated TFA) δ 8.00 (dd, J=8.9, 7.5 Hz, 1H), 7.72 (d, J=1.8 Hz, 1H), 7.56 (dd, J=8.2, 1.9 Hz, 1H), 7.51 (d, J=8.3 Hz, 1H), 7.31 (d, J=9.0 Hz, 1H), 7.17 (d, J=7.3 Hz, 1H), 4.38 (d, J=13.8 Hz, 2H), 3.74-3.69 (m, 2H), 3.46 (dd, J=13.6, 9.2 Hz, 1H), 3.23 (t, J=12.2 Hz, 2H), 3.12-3.06 (m, 2H), 2.21 (d, J=10.4 Hz, 2H), 1.79-1.66 (m, 6H), 1.30 (d, J=13.4 Hz, 12H).

FS526: 3-[6'-(5,5,8,8-Tetramethyl-5,6,7,8-tetrahydronaphthalen-2-yl)-3,4,5,6-tetrahydro-2H-1,2'-bipyridinyl-4-ylamino]propan-1-ol

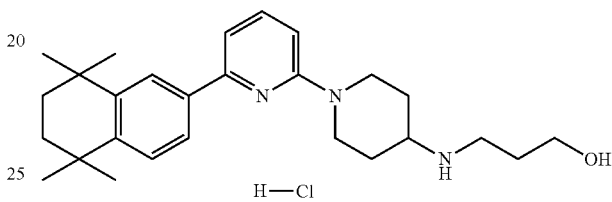

The preparation is carried out analogously to FS520. The product is in the form of the hydrochloride.
Yield: 6 mg, beige solid. Rt.=2.72 min (method A), LCMS: 422 (M+H).
$^1$H NMR (500 MHz, DMSO/deuterated TFA) δ 7.84 (s, 2H), 7.67 (d, J=8.0 Hz, 1H), 7.49 (d, J=8.3 Hz, 1H), 7.19 (t, J=14.2 Hz, 2H), 4.45 (d, J=13.8 Hz, 2H), 3.53 (t, J=5.9 Hz, 2H), 3.44 (s, 1H), 3.18-3.02 (m, 4H), 2.15 (d, J=11.0 Hz, 2H), 1.85-1.76 (m, 2H), 1.72 (s, 4H), 1.65 (d, J=10.2 Hz, 2H), 1.34 (t, J=13.7 Hz, 12H).

FS527: (R)-2-Amino-3-[6'-(5,5,8,8-tetramethyl-5,6,7,8-tetrahydronaphthalen-2-yl)-3,4,5,6-tetrahydro-2H-1,2'-bipyridinyl-4-ylamino]propan-1-ol

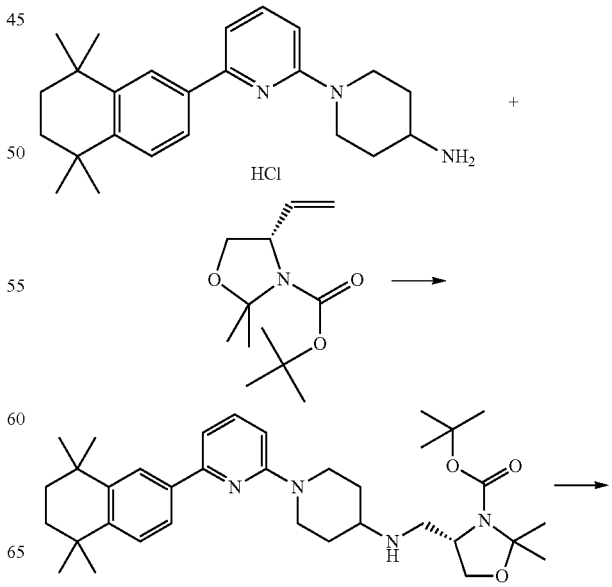

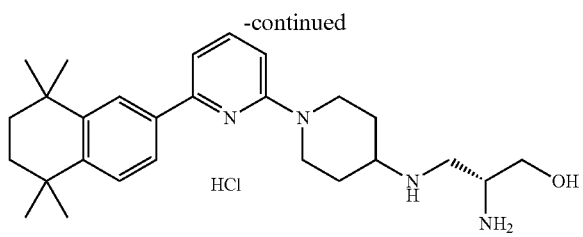

The preparation is carried out analogously to FS517. The product is in the form of the hydrochloride.

Yield: 9 mg, solid. Rt.=2.59 min (method A), LCMS: 437 (M+H).

$^1$H NMR (500 MHz, DMSO/deuterated TFA) δ 7.99 (dd, J=9.0, 7.5 Hz, 1H), 7.68-7.62 (m, 1H), 7.50-7.47 (m, 2H), 7.30 (d, J=9.1 Hz, 1H), 7.12 (d, J=7.4 Hz, 1H), 4.35 (d, J=13.3 Hz, 2H), 3.75-3.64 (m, 2H), 3.62-3.48 (m, 2H), 3.36-3.19 (m, 4H), 2.26-2.16 (m, 2H), 1.84-1.73 (m, 2H), 1.68 (s, 4H), 1.27 (d, J=12.5 Hz, 12H).

FS528: (S)-2-Amino-3-[6'-(5,5,8,8-tetramethyl-5,6,7,8-tetrahydronaphthalen-2-yl)-3,4,5,6-tetrahydro-2H-1,2'-bipyridinyl-4-ylamino]propan-1-ol

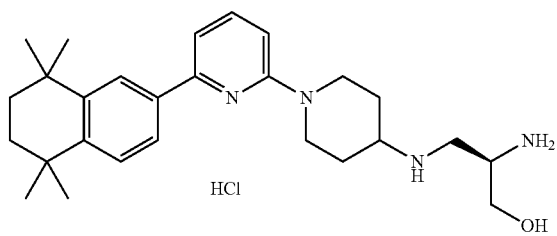 [SMILES: CC1(C)CCC(C)(C)c2cc(-c3cccc(N4CCC(NC[C@@H](N)CO)CC4)n3)ccc21 ; Cl]

The preparation is carried out analogously to FS527. The product is in the form of the hydrochloride.

Yield: 8 mg, solid. Rt.=2.59 min (method A), LCMS: 437 (M+H).

$^1$H NMR (500 MHz, DMSO/deuterated TFA) δ 7.99 (dd, J=9.0, 7.5 Hz, 1H), 7.64 (d, J=1.1 Hz, 1H), 7.52-7.45 (m, 2H), 7.29 (d, J=9.1 Hz, 1H), 7.11 (d, J=7.4 Hz, 1H), 4.35 (d, J=13.5 Hz, 2H), 3.74-3.61 (m, 2H), 3.61-3.47 (m, 2H), 3.36-3.19 (m, 4H), 2.26-2.17 (m, 2H), 1.86-1.73 (m, 2H), 1.68 (s, 4H), 1.27 (d, J=12.5 Hz, 12H).

FS529: (S)-2-Amino-3-{4-[6-(5,5,8,8-tetramethyl-5,6,7,8-tetrahydronaphthalen-2-yl)-pyridin-2-yl]piperazin-1-yl}propan-1-ol

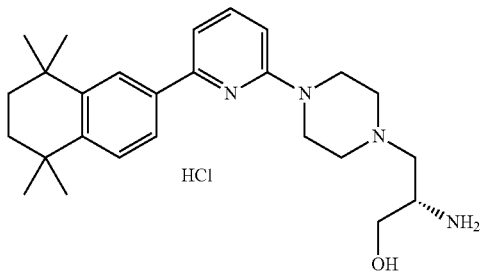 [SMILES: CC1(C)CCC(C)(C)c2cc(-c3cccc(N4CCN(C[C@H](N)CO)CC4)n3)ccc21 ; Cl]

The preparation is carried out analogously to FS527. The product is in the form of the hydrochloride.

Yield: 86 mg, solid. Rt.=2.75 min (method A), LCMS: 423 (M+H).

$^1$H NMR (500 MHz, DMSO/deuterated TFA) δ 7.88-7.80 (m, 2H), 7.68 (dd, J=8.3, 1.9 Hz, 1H), 7.44 (d, J=8.3 Hz, 1H), 7.28 (d, J=7.5 Hz, 1H), 7.09 (d, J=8.6 Hz, 1H), 4.22-3.81 (m, 4H), 3.69 (dd, J=8.0, 3.0 Hz, 2H), 3.66-3.46 (m, 6H), 3.44-3.33 (m, 1H), 1.69 (s, 4H), 1.29 (d, J=14.4 Hz, 12H).

FS530: (R)-2-Amino-3-{4-[6-(5,5,8,8-tetramethyl-5,6,7,8-tetrahydronaphthalen-2-yl)-pyridin-2-yl]piperazin-1-yl}propan-1-ol

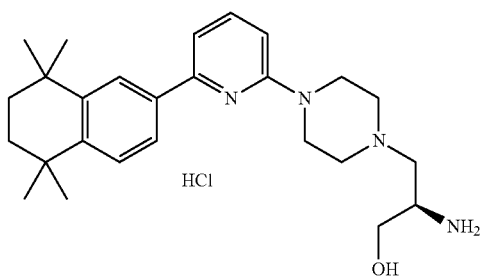 [SMILES: CC1(C)CCC(C)(C)c2cc(-c3cccc(N4CCN(C[C@@H](N)CO)CC4)n3)ccc21 ; Cl]

The preparation is carried out analogously to FS527. The product is in the form of the hydrochloride.

Yield: 52 mg, solid. Rt.=2.77 min (method A), LCMS: 423 (M+H).

$^1$H NMR (500 MHz, DMSO/deuterated TFA) δ 7.89 (s, 1H), 7.83 (t, J=8.0 Hz, 1H), 7.71 (d, J=8.2 Hz, 1H), 7.44 (d, J=8.3 Hz, 1H), 7.30 (d, J=7.5 Hz, 1H), 7.09 (d, J=8.6 Hz, 1H), 3.90 (dd, J=26.4, 19.6 Hz, 2H), 3.75-3.42 (m, 10H), 3.39 (dd, J=14.2, 7.2 Hz, 1H), 1.69 (s, 4H), 1.30 (d, J=18.6 Hz, 12H).

FS531: (S)-3-{4-[6-(5,5,8,8-Tetramethyl-5,6,7,8-tetrahydronaphthalen-2-yl)pyridin-2-yl]piperazin-1-yl}propane-1,2-diol

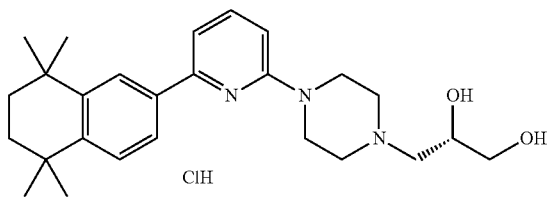 [SMILES: CC1(C)CCC(C)(C)c2cc(-c3cccc(N4CCN(C[C@H](O)CO)CC4)n3)ccc21 ; Cl]

The preparation is carried out analogously to FS517. The product is in the form of the hydrochloride.

Yield: 37 mg, white solid. Rt.=2.89 min (method A), LCMS: 424 (M+H).

$^1$H NMR (500 MHz, DMSO/deuterated TFA) δ 7.88 (dd, J=8.6, 7.6 Hz, 1H), 7.81 (d, J=1.9 Hz, 1H), 7.64 (dd, J=8.2, 1.9 Hz, 1H), 7.45 (d, J=8.3 Hz, 1H), 7.25 (d, J=7.4 Hz, 1H), 7.13 (d, J=8.7 Hz, 1H), 4.55-4.36 (m, 2H), 4.06-3.96 (m, 1H), 3.78-3.10 (m, 10H), 1.69 (s, 4H), 1.29 (d, J=13.4 Hz, 12H).

FS532: 2-{4-[6'-(5,5,8,8-Tetramethyl-5,6,7,8-tetrahydronaphthalen-2-yl)-3,4,5,6-tetrahydro-2H-1,2'-bipyridinyl-4-yl]piperazin-1-yl}ethanol

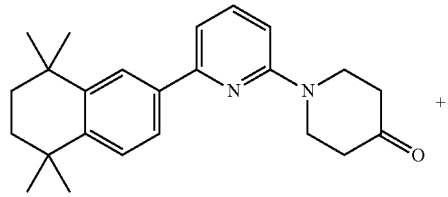

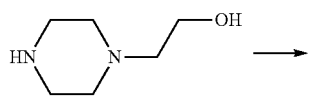

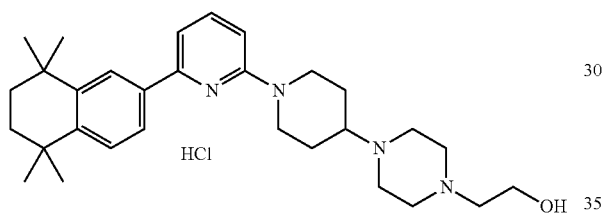

The preparation is carried out analogously to FS502. The product is in the form of the hydrochloride.

Yield: 15 mg, white solid. Rt.=2.65 min (method A), LCMS: 477 (M+H).

¹H NMR (500 MHz, DMSO/deuterated TFA) δ 7.90 (dd, J=9.1, 7.4 Hz, 1H), 7.57 (s, 1H), 7.41 (s, 2H), 7.22 (d, J=9.1 Hz, 1H), 7.04 (d, J=7.0 Hz, 1H), 4.37 (d, J=13.0 Hz, 2H), 3.80-3.35 (m, 11H), 3.30-3.22 (m, 2H), 3.15 (t, J=13.3 Hz, 2H), 2.22-2.13 (m, 2H), 1.83-1.69 (m, 2H), 1.60 (s, 4H), 1.19 (d, J=9.7 Hz, 12H).

FS533: 5-{4-[5-Methoxy-6-(5,5,8,8-tetramethyl-5,6,7,8-tetrahydronaphthalen-2-yl)pyridin-2-yl]piperazin-1-yl}pentan-1-ol

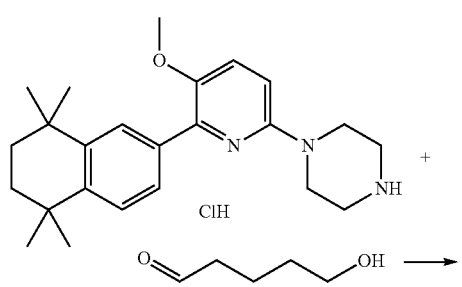

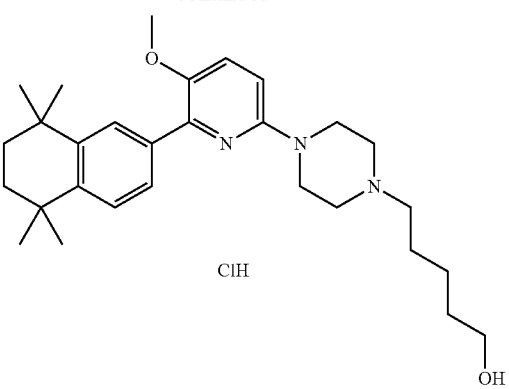

The preparation is carried out analogously to FS501. The product is in the form of the hydrochloride.

Yield: 70 mg. Rt.=3.05 min (method A), LCMS: 466 (M+H).

¹H NMR (500 MHz, DMSO) δ 7.85 (dd, J=4.9, 1.8 Hz, 1H), 7.65-7.60 (m, 1H), 7.52 (dt, J=10.6, 5.3 Hz, 1H), 7.33 (t, J=7.8 Hz, 1H), 6.96-6.89 (m, 1H), 4.28 (d, J=13.9 Hz, 1H), 3.80-3.73 (m, 5H), 3.69-3.35 (m, 6H), 3.27-2.96 (m, 4H), 1.86-1.54 (m, 8H), 1.50-1.31 (m, 2H), 1.31-1.22 (m, 12H).

FS534: (2-{[6'-(5,5,8,8-Tetramethyl-5,6,7,8-tetrahydronaphthalen-2-yl)-3,4,5,6-tetrahydro-2H-1,2'-bipyridinyl-4-ylamino]methyl}cyclopropyl)methanol

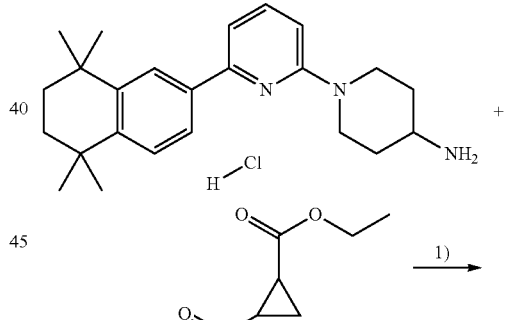

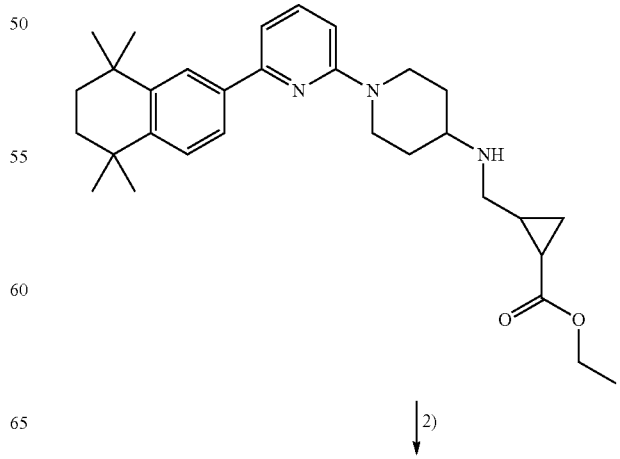

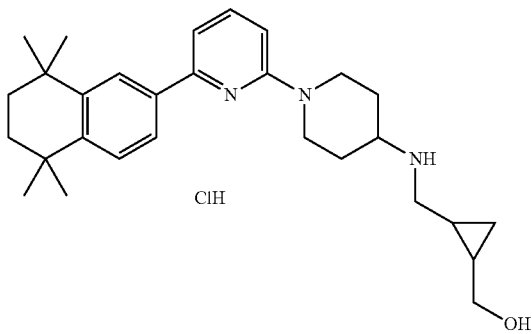

Step 1

The preparation is carried out analogously to FS501.

Yield: 151 mg. Rt.=2.95 min (method A), LCMS: 490 (M+H).

Step 2

The reduction is carried out in THF with addition of 5 eq. of DIBAH. The mixture was stirred at 60° C. for 18 h. The work-up is carried out analogously to FS 311 step 2.

Yield: 23 mg. Rt.=2.71 min (method A), LCMS: 448 (M+H).

$^1$H NMR (500 MHz, DMSO) δ 8.02-7.95 (m, 1H), 7.65 (s, 1H), 7.49 (s, 2H), 7.30-7.26 (m, 1H), 7.11 (dd, J=11.6, 7.3 Hz, 1H), 4.49-4.30 (m, 2H), 3.67-3.40 (m, 2H), 3.35-3.18 (m, 3H), 3.15-2.80 (m, 2H), 2.18 (d, J=11.2 Hz, 2H), 1.98-1.77 (m, 1H), 1.76-1.63 (m, 5H), 1.26 (t, J=18.1 Hz, 12H), 1.19-0.72 (m, 3H), 0.66-0.46 (m, 2H).

FS535: 4-{(2-Aminoethyl)-[6'-(5,5,8,8-tetramethyl-5,6,7,8-tetrahydronaphthalen-2-yl)-3,4,5,6-tetrahydro-2H-1,2'-bipyridinyl-4-yl]amino}butan-1-ol

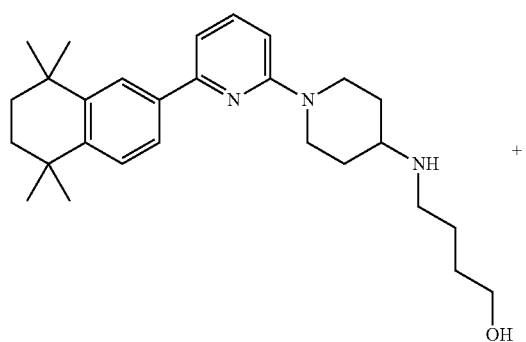

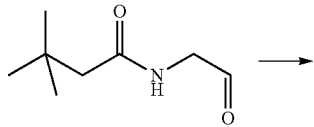

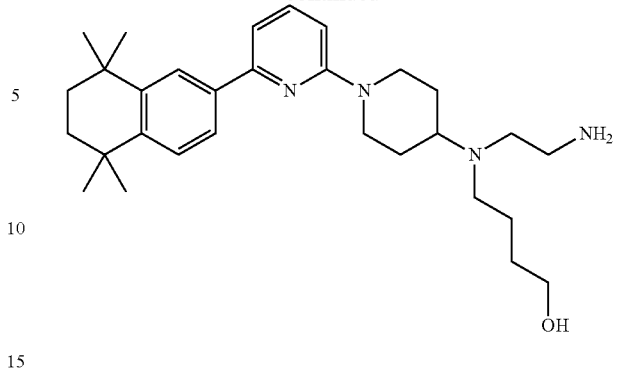

The preparation is carried out similarly to FS501. The Boc protecting group was cleaved off using HCl in dioxane. The product is in the form of the hydrochloride.

Yield: 14 mg. Rt.=2.58 min (method A), LCMS: 479 (M+H).

$^1$H NMR (500 MHz, DMSO/deuterated TFA): δ 7.98 (dd, J=9.0, 7.4 Hz, 1H), 7.67 (s, 1H), 7.54-7.47 (m, 2H), 7.31 (t, J=8.8 Hz, 1H), 7.12 (d, J=7.3 Hz, 1H), 4.46 (d, J=13.6 Hz, 2H), 3.82 (dd, J=23.3, 11.4 Hz, 1H), 3.54-3.04 (m, 10H), 2.23 (d, J=10.7 Hz, 2H), 1.97-1.75 (m, 4H), 1.69 (s, 4H), 1.58-1.48 (m, 2H), 1.28 (d, J=12.7 Hz, 12H).

FS536: (S)-3-{(R)-1-[2-(5,5,8,8-Tetramethyl-5,6,7,8-tetrahydronaphthalen-2-yl)-pyrimidin-4-yl]pyrrolidin-3-ylamino}propane-1,2-diol

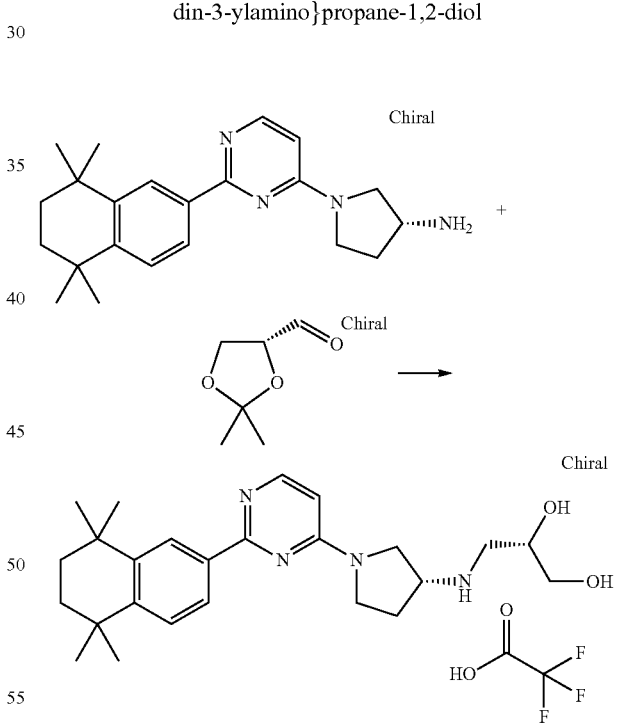

The preparation is carried out similarly to FS501. The acetal was cleaved off using methanolic HCl. The product is in the form of the trifluoroacetate.

Yield: 44 mg. Rt.=2.40 min (method A), LCMS: 425 (M+H).

$^1$H NMR (500 MHz, DMSO/deuterated TFA): δ 8.25 (t, J=8.3 Hz, 1H), 8.19-8.12 (m, 1H), 7.99-7.92 (m, 1H), 7.52 (dd, J=8.4, 1.9 Hz, 1H), 6.83-6.75 (m, 1H), 4.22-3.95 (m, 3H), 3.88-3.78 (m, 2H), 3.55-3.34 (m, 2H), 3.25-3.14 (m, 2H), 3.02-2.94 (m, 1H), 2.50-2.24 (m, 2H), 1.67 (s, 4H), 1.35-1.21 (m, 12H).

FS537: (S)-3-{(R)-1-[4-(5,5,8,8-Tetramethyl-5,6,7,8-tetrahydronaphthalen-2-yl)-pyrimidin-2-yl]pyrrolidin-3-ylamino}propane-1,2-diol

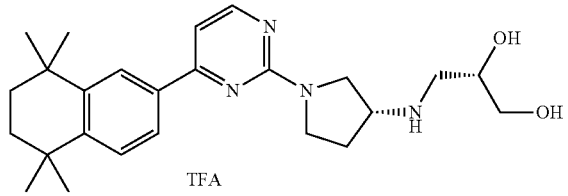

The preparation is carried out analogously to FS536. The product is in the form of the trifluoroacetate.

Yield: 35 mg. Rt.=2.57 min (method A), LCMS: 425 (M+H).

$^1$H NMR (500 MHz, DMSO/deuterated TFA): δ 8.45 (d, J=6.7 Hz, 1H), 8.21 (s, 1H), 7.99 (d, J=7.9 Hz, 1H), 7.63 (d, J=6.6 Hz, 1H), 7.51 (d, J=8.4 Hz, 1H), 3.93 (dd, J=163.8, 54.5 Hz, 6H), 3.49 (dd, J=10.8, 4.7 Hz, 1H), 3.44-3.34 (m, 1H), 3.29-3.13 (m, 1H), 3.06-2.88 (m, 1H), 2.52-2.28 (m, 2H), 1.68 (s, 4H), 1.28 (d, J=20.5 Hz, 12H).

FS538: (S)-3-{(S)-1-[2-(5,5,8,8-Tetramethyl-5,6,7,8-tetrahydronaphthalen-2-yl)-pyrimidin-4-yl]pyrrolidin-3-ylamino}propane-1,2-diol

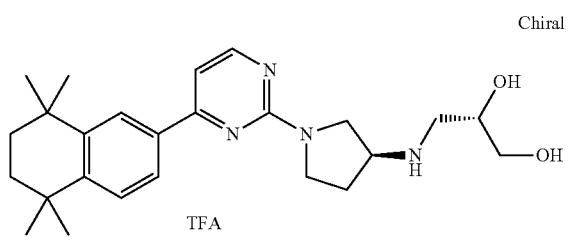 [SMILES: CC1(C)CCC(C)(C)c2cc(-c3ccnc(N4CC[C@H](NC[C@H](O)CO)C4)n3)ccc21]

The preparation is carried out analogously to FS536. The product is in the form of the trifluoroacetate.

Yield: 15 mg. Rt.=2.38 min (method A), LCMS: 425 (M+H).

$^1$H NMR (400 MHz, DMSO/deuterated TFA): δ 8.37 (d, J=7.4 Hz, 1H), 8.20 (dd, J=4.4, 2.1 Hz, 1H), 8.03-7.96 (m, 1H), 7.57 (dd, J=8.4, 3.1 Hz, 1H), 6.92-6.84 (m, 1H), 4.26-3.98 (m, 3H), 3.95-3.62 (m, 3H), 3.57-3.34 (m, 2H), 3.30-3.15 (m, 1H), 3.07-2.91 (m, 1H), 2.51-2.22 (m, 2H), 1.70 (s, 4H), 1.32 (dd, J=11.7, 9.3 Hz, 12H).

FS539: (S)-3-{(S)-1-[4-(5,5,8,8-Tetramethyl-5,6,7,8-tetrahydronaphthalen-2-yl)-pyrimidin-2-yl]pyrrolidin-3-ylamino}propane-1,2-diol The preparation is carried out analogously to FS536. The product is in the form of the trifluoroacetate.

Yield: 38 mg. Rt.=2.57 min (method A), LCMS: 425 (M+H).

$^1$H NMR (500 MHz, DMSO/deuterated TFA): δ 8.39 (d, J=6.7 Hz, 1H), 8.18 (s, 1H), 7.95 (d, J=8.0 Hz, 1H), 7.57 (d, J=6.6 Hz, 1H), 7.49 (d, J=8.4 Hz, 1H), 4.25-3.93 (m, 3H), 3.84 (b, 2H), 3.68 (b, 1H), 3.56-3.33 (m, 2H), 3.23 (dd, J=12.5, 2.7 Hz, 1H), 3.05-2.88 (m, 1H), 2.52-2.28 (m, 2H), 1.67 (s, 4H), 1.26 (d, J=19.6 Hz, 12H).

FS540: (R)-3-{4-[6-(5,5,8,8-Tetramethyl-5,6,7,8-tetrahydronaphthalen-2-yl)pyridin-2-yl]piperazin-1-yl}propane-1,2-diol

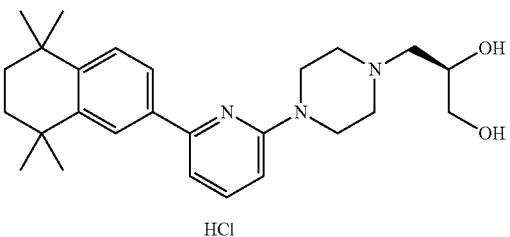 [SMILES: CC1(C)CCC(C)(C)c2cc(-c3cccc(N4CCN(C[C@@H](O)CO)CC4)n3)ccc21 ; Cl]

The preparation is carried out analogously to FS536. The product is in the form of the hydrochloride.

Yield: 58 mg. Rt.=2.82 min (method A), LCMS: 424 (M+H).

$^1$H NMR (500 MHz, DMSO/deuterated TFA): δ 7.94 (dd, J=8.8, 7.5 Hz, 1H), 7.69 (d, J=1.9 Hz, 1H), 7.52 (dd, J=8.2, 1.9 Hz, 1H), 7.46 (d, J=8.3 Hz, 1H), 7.24-7.15 (m, 2H), 4.52-4.27 (m, 2H), 4.03-3.95 (m, 1H), 3.76-3.52 (m, 4H), 3.52-3.35 (m, 2H), 3.35-3.20 (m, 3H), 3.20-3.09 (m, 1H), 1.67 (s, 4H), 1.26 (d, J=13.6 Hz, 12H).

FS541: (R)-3-[6'-(5,5,8,8-Tetramethyl-5,6,7,8-tetrahydronaphthalen-2-yl)-3,4,5,6-tetrahydro-2H-1,2'-bipyridinyl-4-ylamino]propane-1,2-diol

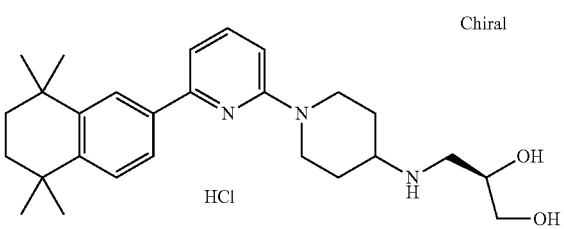 [SMILES: CC1(C)CCC(C)(C)c2cc(-c3cccc(N4CCC(NC[C@@H](O)CO)CC4)n3)ccc21 ; Cl]

The preparation is carried out analogously to FS536. The product is in the form of the hydrochloride.

Yield: 36 mg. Rt.=2.55 min (method A), LCMS: 438 (M+H).

$^1$H NMR (500 MHz, DMSO/deuterated TFA): δ 7.97 (dd, J=9.1, 7.4 Hz, 1H), 7.61 (d, J=1.8 Hz, 1H), 7.46 (dt, J=8.2, 5.1 Hz, 2H), 7.26 (d, J=9.1 Hz, 1H), 7.08 (d, J=7.3 Hz, 1H), 4.32 (d, J=13.4 Hz, 2H), 3.83 (td, J=9.0, 5.7 Hz, 1H), 3.51-3.37 (m, 3H), 3.23 (t, J=12.1 Hz, 2H), 3.11 (dd, J=12.6, 2.9 Hz, 1H), 2.91 (dd, J=12.6, 9.4 Hz, 1H), 2.19 (dd, J=30.6, 15.2 Hz, 2H), 1.86-1.69 (m, 2H), 1.67 (s, 4H), 1.26 (d, J=11.7 Hz, 12H).

FS542: (R)-3-{1-[2-(5,5,8,8-Tetramethyl-5,6,7,8-tetrahydronaphthalen-2-yl)pyrimidin-4-yl]piperidin-4-ylamino}propane-1,2-diol

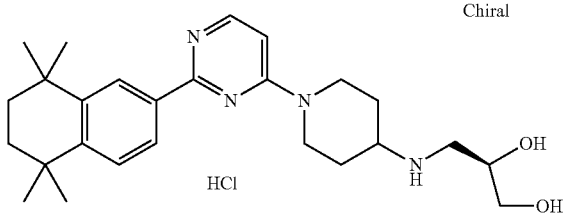 [SMILES: CC1(C)CCC(C)(C)c2cc(-c3nccc(N4CCC(NC[C@@H](O)CO)CC4)n3)ccc21 ; Cl]

The preparation is carried out analogously to FS536. The product is in the form of the hydrochloride.

Yield: 26 mg. Rt.=2.32 min (method A), LCMS: 439 (M+H).

¹H NMR (400 MHz, DMSO/deuterated TFA): δ 8.37 (d, J=7.5 Hz, 1H), 8.16 (d, J=2.0 Hz, 1H), 7.98 (dd, J=8.4, 2.0 Hz, 1H), 7.56 (d, J=8.4 Hz, 1H), 7.20 (d, J=7.5 Hz, 1H), 5.23 (d, J=13.3 Hz, 1H), 4.42 (d, J=13.2 Hz, 1H), 3.91-3.78 (m, 1H), 3.62-3.45 (m, 2H), 3.45-3.28 (m, 2H), 3.27-3.10 (m, 2H), 2.93 (dd, J=12.6, 9.5 Hz, 1H), 2.36-2.20 (m, 2H), 1.83-1.59 (m, 6H), 1.31 (d, J=17.7 Hz, 12H).

FS543: (R)-3-{1-[4-(5,5,8,8-Tetramethyl-5,6,7,8-tetrahydronaphthalen-2-yl)pyrimidin-2-yl]piperidin-4-ylamino}propane-1,2-diol

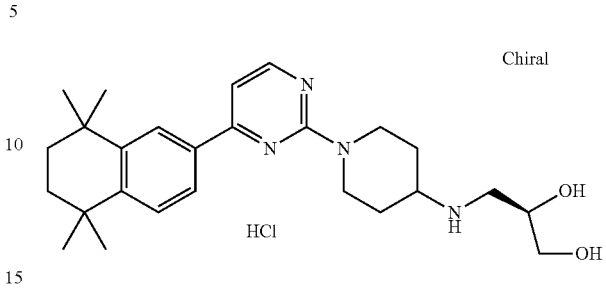

The preparation is carried out analogously to FS536. The product is in the form of the hydrochloride.

Yield: 41 mg. Rt.=2.59 min (method A), LCMS: 439 (M+H).

¹H NMR (400 MHz, DMSO/deuterated TFA): δ 8.45 (d, J=6.4 Hz, 1H), 8.14 (d, J=1.9 Hz, 1H), 7.97 (dd, J=8.4, 1.9 Hz, 1H), 7.57 (d, J=6.4 Hz, 1H), 7.51 (d, J=8.4 Hz, 1H), 4.75 (b, 2H), 3.84 (q, J=9.2 Hz, 1H), 3.55-3.43 (m, 2H), 3.38 (dd, J=11.1, 6.2 Hz, 1H), 3.30-3.11 (m, 3H), 2.92 (dd, J=12.6, 9.5 Hz, 1H), 2.25 (t, J=13.6 Hz, 2H), 1.82-1.62 (m, 6H), 1.30 (d, J=16.5 Hz, 12H).

FS601: Preparation of 6-(5,5,8,8-tetramethyl-5,6,7,8-tetrahydronaphthalen-2-yl)-1',2',3',4',5',6'-hexahydro-2,4'-bipyridinyl and 6-(5,5,8,8-tetramethyl-5,6,7,8-tetrahydronaphthalen-2-yl)-1',2',3',6'-tetrahydro-2,4'-bipyridinyl

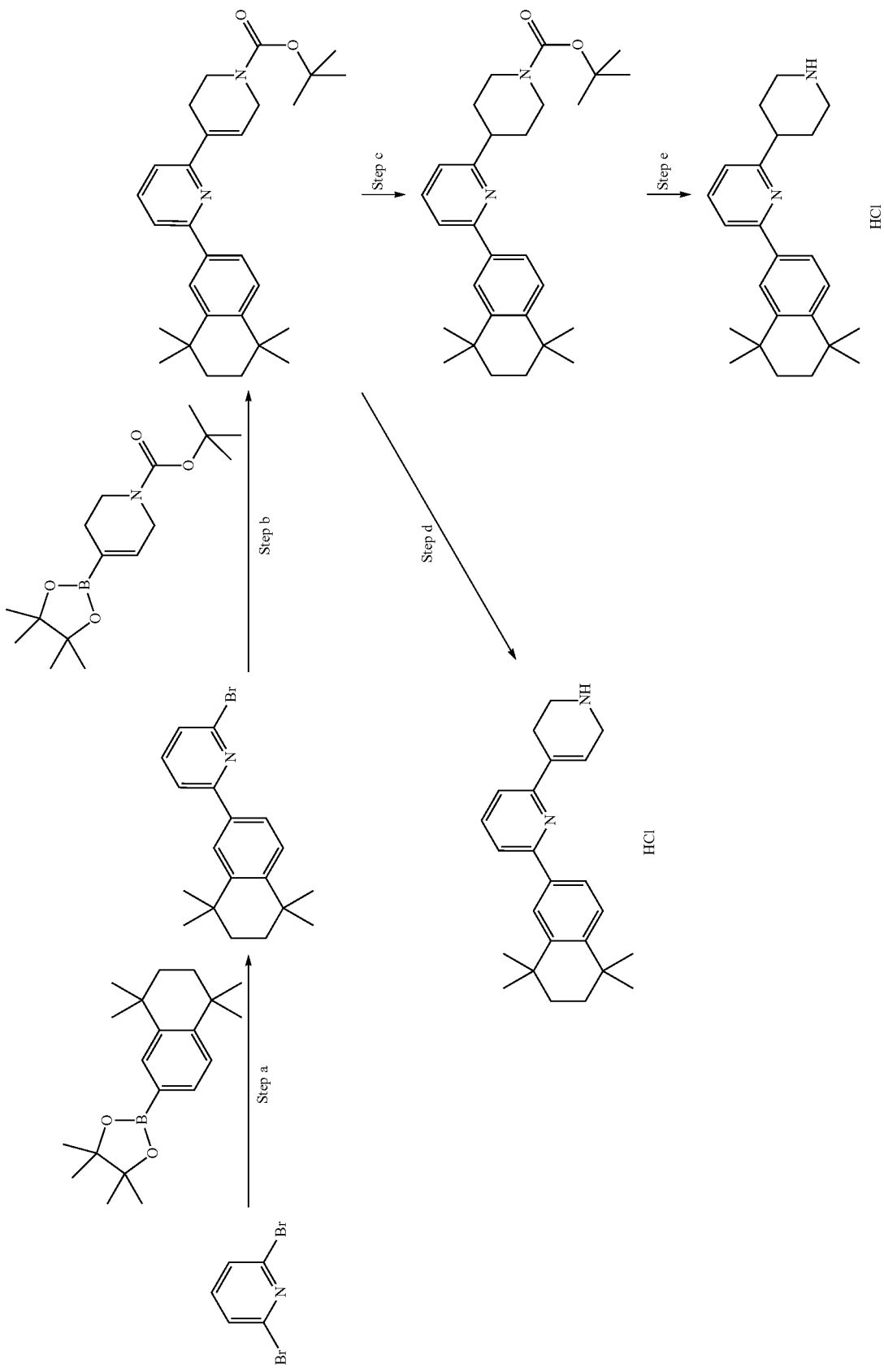

Step a

2-Bromo-6-(5,5,8,8-tetramethyl-5,6,7,8-tetrahydronaphthalen-2-yl)pyridine

200 mg (0.84 mmol) of 2,6-dibromopyridine and 265 mg (0.84 mmol) of 4,4,5,5-tetramethyl-2-(5,5,8,8-tetramethyl-5,6,7,8-tetrahydronaphthalen-2-yl)-1,3,2-dioxaborolane are dissolved in 6 ml of 2M sodium carbonate solution and in 2.5 ml of dimethoxyethane. The reaction mixture is degassed a number of times, and 49 mg (0.04 mmol) of tetrakis(triphenylphosphine)palladium are added under nitrogen atmosphere, the mixture is stirred at 80° C. for 16 h and subsequently irradiated in the microwave for 30 min. The reaction mixture is evaporated, and saturated sodium hydrogencarbonate solution is added. This mixture is extracted three times with ethyl acetate and three times with dichloromethane, the combined organic phases are dried over $Na_2SO_4$ and evaporated. The crude product is reacted further without further purification.

210 mg oil, Rt.=4.25 min (method A), LCMS: 345 (M+H).

Step b

6-(5,5,8,8-Tetramethyl-5,6,7,8-tetrahydronaphthalen-2-yl)-3',6'-dihydro-2'H-2,4'-bipyridinyl-1'-carboxylic acid tert-butyl ester

100 mg (0.29 mmol) of 2-bromo-6-(5,5,8,8-tetramethyl-5,6,7,8-tetrahydronaphthalen-2-yl)pyridine and 135 mg (0.44 mmol) of 4-(4,4,5,5-tetramethyl-1,3,2-dioxaborolan-2-yl)-3,6-dihydro-2H-pyridine-1-carboxylic acid tert-butyl ester are dissolved in 2 ml of 2M sodium carbonate solution and in 2 ml of dimethoxyethane. The reaction mixture is degassed a number of times, 34 mg (0.03 mmol) of tetrakis(triphenylphosphine)palladium are added under nitrogen atmosphere, and the mixture is irradiated in the microwave for 30 min, subsequently evaporated, and saturated sodium hydrogencarbonate solution is added. This mixture is extracted three times with ethyl acetate, the combined organic phases are dried over $Na_2SO_4$ and evaporated. The crude product is purified by column chromatography on silica gel.

67 mg oil, Rt.=4.14 min (method A), LCMS: 447 (M+H).

Step c

6-(5,5,8,8-Tetramethyl-5,6,7,8-tetrahydronaphthalen-2-yl)-3',4',5',6'-tetrahydro-2'H-2,4'-bipyridinyl-1'-carboxylic acid tert-butyl ester

52 mg (0.11 mmol) of 6-(5,5,8,8-tetramethyl-5,6,7,8-tetrahydronaphthalen-2-yl)-3',6'-dihydro-2'H-2,4'-bipyridinyl-1'-carboxylic acid tert-butyl ester are dissolved in 20 ml of ethanol and hydrogenated using a Pd/C cartridge (10%, 30×4 mm) in an H Cube (Thales Nanotechnology). The solvent is subsequently distilled off.

42 mg white solid, Rt.=4.17 min (method A), LCMS: 449 (M+H).

Step d

6-(5,5,8,8-Tetramethyl-5,6,7,8-tetrahydronaphthalen-2-yl)-1',2',3',6'-tetrahydro-2,4'-bipyridinyl

The protecting group is cleaved off in a corresponding manner to Example FS201. The product is in the form of the hydrochloride. 8 mg, beige solid. Rt.=3.01 min (method A), LCMS: 347 (M+H).

$^1$H NMR (500 MHz, DMSO/deuterated TFA) δ 8.05 (d, J=1.9, 1H), 7.95 (t, J=7.8, 1H), 7.89 (d, J=7.6, 1H), 7.83 (dd, J=8.2, 1.9, 1H), 7.61 (d, J=7.6, 1H), 7.46 (d, J=8.3, 1H), 6.83 (s, 1H), 3.91 (s, 2H), 3.43 (t, J=6.0, 2H), 2.92 (s, 2H), 1.71 (s, 4H), 1.32 (d, J=21.1, 12H).

Step e

6-(5,5,8,8-Tetramethyl-5,6,7,8-tetrahydronaphthalen-2-yl)-1',2',3',4',5',6'-hexahydro-2,4'-bipyridinyl

The protecting group is cleaved off in a corresponding manner to Example FS201. The product is in the form of the hydrochloride.

14 mg, beige solid. Rt.=2.66 min (method A), LCMS: 349 (M+H).

$^1$H NMR (500 MHz, DMSO/deuterated TFA) δ 8.44 (t, J=8.0, 1H), 8.12 (d, J=7.9, 1H), 7.88 (d, J=1.9, 1H), 7.75 (d, J=7.9, 1H), 7.71 (dd, J=8.2, 1.9, 1H), 7.60 (d, J=8.3, 1H), 3.52 (d, J=12.9, 2H), 3.44 (dd, J=13.3, 10.6, 1H), 3.10 (dd, J=12.9, 10.3, 2H), 2.22 (d, J=13.5, 2H), 2.04 (qd, J=13.4, 3.8, 2H), 1.74 (s, 4H), 1.34 (d, J=16.2, 12H).

FS602: 1-[4-(5,5,8,8-Tetramethyl-5,6,7,8-tetrahydronaphthalen-2-yl)pyridin-2-yl]-piperazine

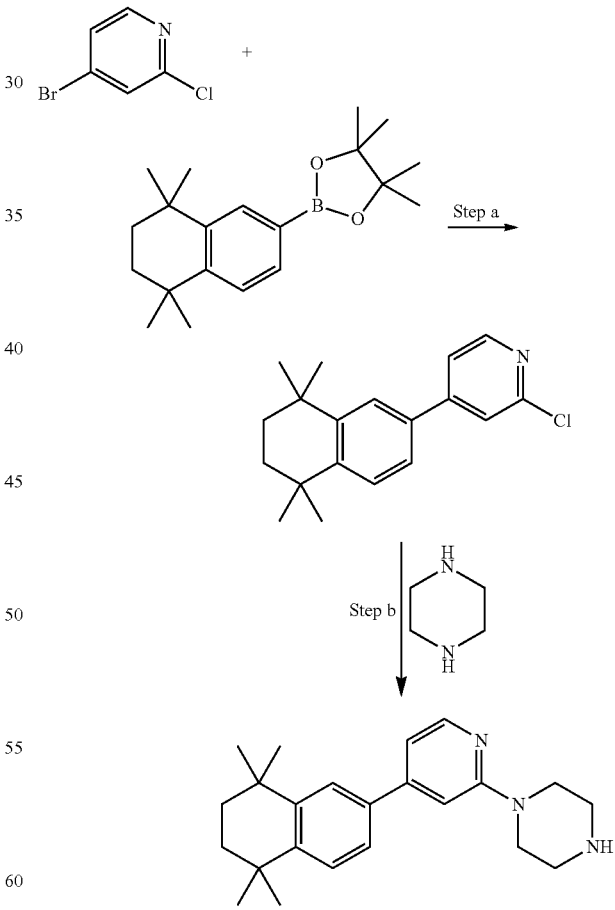

Step a

173 μl (1.56 mmol) of 4-bromo-2-chloropyridine, 735 mg (2.34 mmol) of 4,4,5,5-tetramethyl-2-(5,5,8,8-tetramethyl-5, 6,7,8-tetrahydronaphthalen-2-yl)-1,3,2-dioxaborolane, 18 mg (0.03 mmol) of xantphos, 687 mg (3.24 mmol) of tripotassium phosphate trihydrate and 11 mg (0.05 mmol of palladium(II) acetate are suspended in 5 ml of toluene and 500 µl of water. The reaction mixture is degassed a number of times, irradiated in the microwave at 100° C. under nitrogen atmosphere for 90 min, diluted with 30 ml of water and extracted three times with ethyl acetate. The combined organic phases are dried over Na₂SO₄ and evaporated. The crude product is purified by column chromatography on silica gel.

417 mg, viscous oil, Rt.=3.95 min (method B), LCMS: 300 (M+H).

¹H NMR (400 MHz, DMSO/deuterated TFA) δ 8.41 (d, J=5.2, 1H), 7.80 (d, J=0.6, 1H), 7.72 (d, J=2.0, 1H), 7.70 (dd, J=5.3, 1.1, 1H), 7.54 (dd, J=8.3, 1.9, 1H), 7.45 (d, J=8.3, 1H), 1.66 (s, 4H), 1.28 (d, J=19.4, 12H).

Step b 2 ml of toluene are added to 145 mg (0.48 mmol) of 2-chloro-4-(5,5,8,8-tetramethyl-5,6,7,8-tetrahydronaphthalen-2-yl)pyridine and 333 mg (3.87 mmol) of piperazine, and the mixture is irradiated in the microwave at 180° C. for 8 h. Water is added to the residue, the mixture is rendered slightly basic using NaOH and subsequently extracted three times with ethyl acetate. The combined organic phases are dried over Na₂SO₄ and evaporated. The crude product is purified by column chromatography on RP silica gel.

125 mg, viscous oil, Rt.=2.33 min (method B), LCMS: 350 (M+H).

¹H NMR (400 MHz, DMSO/deuterated TFA) ¹H NMR (400 MHz, DMSO) δ 8.17 (d, J=6.6, 1H), 7.78 (d, J=2.0, 1H), 7.67 (dd, J=8.3, 2.0, 1H), 7.61 (s, 1H), 7.54 (d, J=8.3, 1H), 7.43 (dd, J=6.7, 1.4, 1H), 4.09-3.98 (m, 4H), 3.45-3.36 (m, 4H), 1.72 (s, 4H), 1.33 (d, J=19.3, 12H).

FS603: 1'-(4-Chloro-1,3,5-triazin-2-yl)-1,4'-bipiperidinyl-3-ol

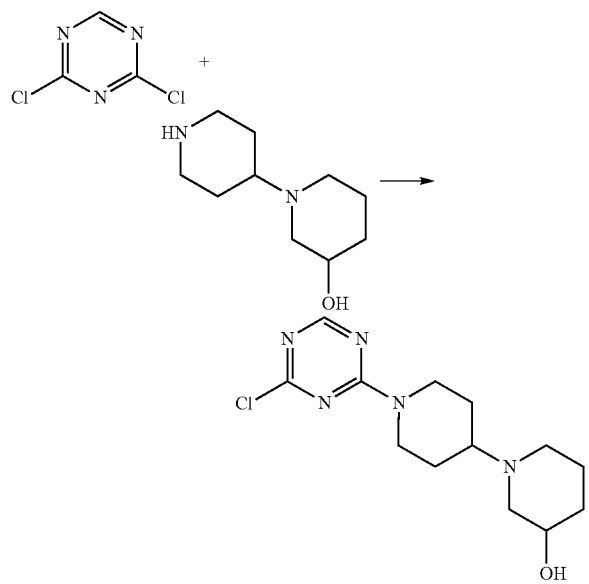

200 mg (1.27 mmol) of 2,4-dichloro-1,3,5-triazine are dissolved in 2 ml of acetonitrile, cooled to 0° C., 176 µl of triethylamine and 223 mg (1.27 mmol) of 1,4'-bipiperidinyl-3-ol are added. The reaction mixture is stirred at 0° C. for 2 h and subsequently at room temperature for 48 h. Sat. NaCl solution is subsequently added, and the mixture is extracted three times with ethyl acetate. The combined organic phases are washed with 1N NaOH and water, dried over Na₂SO₄ and evaporated.

245 mg, viscous oil, Rt.=2.27 min (method B), LCMS: 298 (M+H).

FS604: 1'-[4-(5,5,8,8-Tetramethyl-5,6,7,8-tetrahydronaphthalen-2-yl)-1,3,5-triazin-2-yl]-1,4'-bipiperidinyl-3-ol

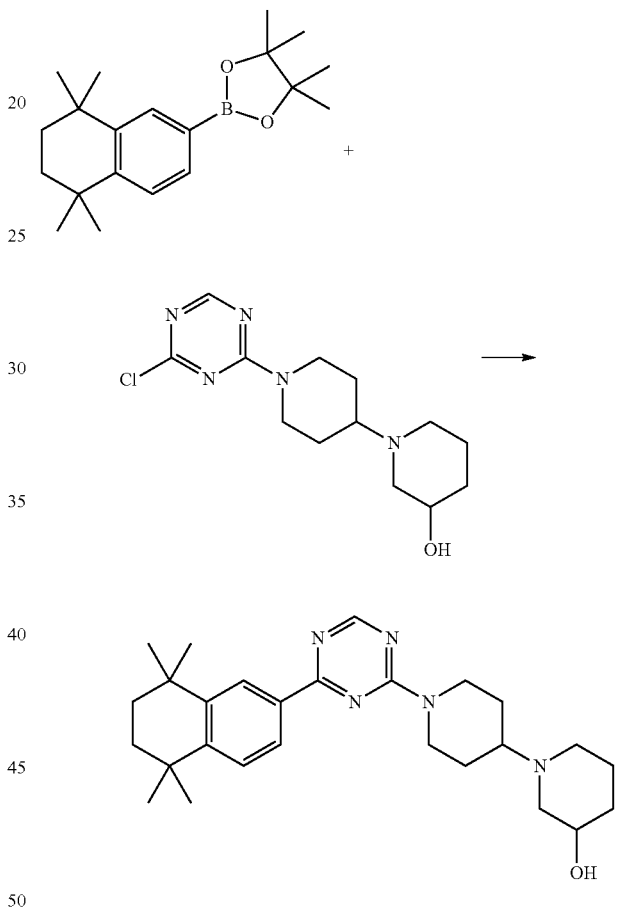

45 mg (0.42 mmol) of sodium carbonate are added to 50 mg (0.17 mmol) of 1'-(4-chloro-1,3,5-triazin-2-yl)-1,4'-bipiperidinyl-3-ol and 139 mg (0.42 mmol) of 4,4,5,5-tetramethyl-2-(5,5,8,8-tetramethyl-5,6,7,8-tetrahydronaphthalen-2-yl)-1,3,2-dioxaborolane in 3.2 ml of toluene/ethanol/water (3.2/3.2/1). The reaction mixture is degassed a number of times, and 19 mg (0.017 mmol) of tetrakis-(triphenylphosphine)palladium(0) are added under nitrogen atmosphere, the mixture is treated in an ultrasound bath for 10 min and subsequently heated at 90° C. for 5 h. Water is added to the reaction mixture, which is then extracted three times with ethyl acetate/ether. The combined organic phases are dried over Na₂SO₄ and evaporated. The crude product is purified by means of preparative HPLC.

14 mg, white solid, Rt.=2.61 min (method B), LCMS: 450 (M+H).

FS605: {1-[1-(4-Chloro-1,3,5-triazin-2-yl)piperidin-4-yl]pyrrolidin-3-yl}carbamic acid tert-butyl ester

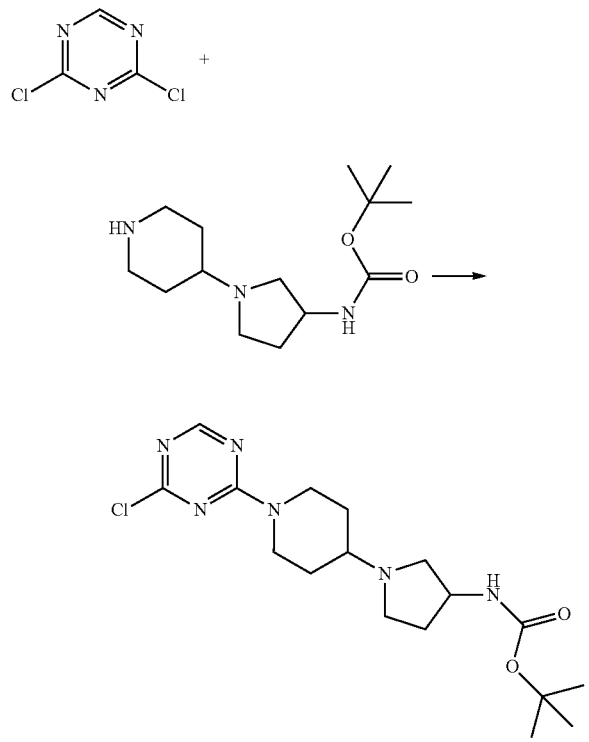

The preparation is carried out analogously to FS603.

650 mg, yellow oil, Rt.=2.71 min (method B), LCMS: 383 (M+H).

FS606: (1-{1-[4-(5,5,8,8-Tetramethyl-5,6,7,8-tetrahydronaphthalen-2-yl)-1,3,5-triazin-2-yl]piperidin-4-yl}pyrrolidin-3-yl)carbamic acid tert-butyl ester

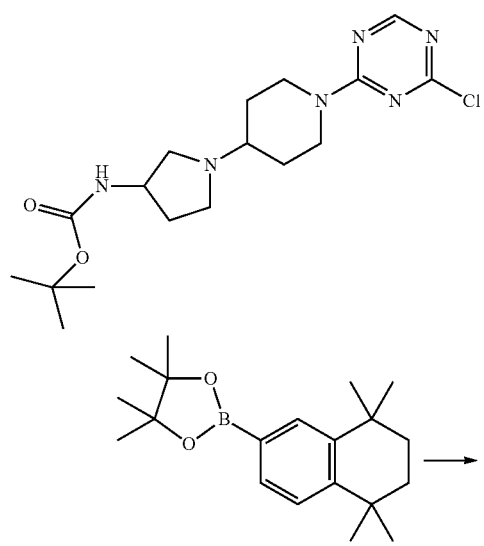

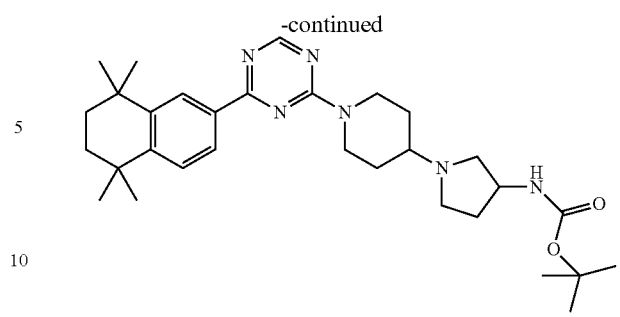

23 mg (0.22 mmol) of sodium carbonate are added to 50 mg (0.11 mmol) of {1-[1-(4-chloro-1,3,5-triazin-2-yl)piperidin-4-yl]pyrrolidin-3-yl}carbamic acid tert-butyl ester and 45 mg (0.12 mmol) of 4,4,5,5-tetramethyl-2-(5,5,8,8-tetramethyl-5,6,7,8-tetrahydronaphthalen-2-yl)-1,3,2-dioxaborolane in 1.5 ml of DMF/DME/methanol/water (1/1/0.9/0.3). The reaction mixture is degassed a number of times, 8 mg (0.017 mmol) of bis(triphenylphosphine)palladium(II) dichloride are added under nitrogen atmosphere, the mixture is treated in an ultrasound bath for 10 min and subsequently irradiated in the microwave at 100° C. for 20 min. The reaction mixture is diluted with methanol, filtered, and the crude product is purified by means of preparative HPLC.

24 mg, white solid, Rt.=2.95 min (method B), LCMS: 535 (M+H).

FS607: (2-{-4-[6-(5,5,8,8-Tetramethyl-5,6,7,8-tetrahydronaphthalen-2-yl)pyridin-2-yl]-piperazin-1-ylmethyl}cyclopropyl)methanol

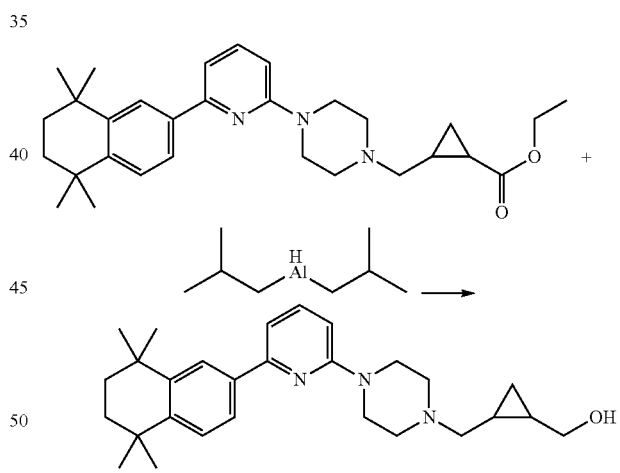

100 mg (0.21 mmol) of 2-{4-[6-(5,5,8,8-tetramethyl-5,6,7,8-tetrahydronaphthalen-2-yl)pyridin-2-yl]piperazin-1-ylmethyl}cyclopropanecarboxylic acid ethyl ester is dissolved in 4 ml of THF, and 1.05 ml (1.05 mmol) of diisobutylaluminium hydride (1.0 M in THF) are added. The reaction mixture is stirred at room temperature under nitrogen atmosphere for 18 h. Water is added to the reaction mixture, which is then briefly stirred, ethyl acetate is added, and the mixture is filtered through Celite. The filter cake is washed with ethyl acetate and methanol, and the mother liquor is evaporated. The residue is purified by column chromatography on silica gel.

Yield: 50 mg, yellow oil. Rt.=3.07 min (method A), LCMS: 434 (M+H).

¹H NMR (500 MHz, DMSO/deuterated TFA) δ 7.90 (d, J=1.6 Hz, 1H), 7.81 (t, J=8.1 Hz, 1H), 7.72 (d, J=8.1 Hz, 1H), 7.44 (d, J=8.3 Hz, 1H), 7.30 (d, J=7.4 Hz, 1H), 7.04 (d, J=8.5 Hz, 1H), 4.55 (d, J=13.2 Hz, 2H), 3.84-3.64 (m, 2H), 3.57 (dd, J=11.2, 5.4 Hz, 1H), 3.43-3.16 (m, 6H), 3.07-2.98 (m, 1H), 1.70 (s, 4H), 1.31 (d, J=14.7 Hz, 12H), 1.16-1.07 (m, 1H), 1.07-0.94 (m, 1H), 0.67-0.60 (m, 1H), 0.60-0.53 (m, 1H).

FS608: 4-{(4-Hydroxybutyl)-[6'-(5,5,8,8-tetramethyl-5,6,7,8-tetrahydronaphthalen-2-yl)-3,4,5,6-tetrahydro-2H-1,2'-bipyridinyl-4-yl]amino}butan-1-ol

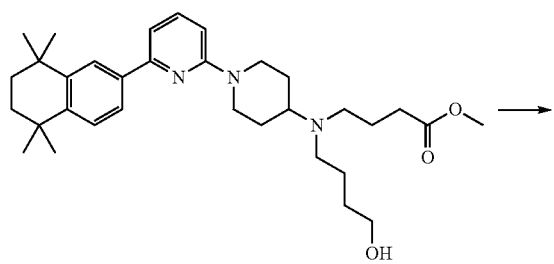

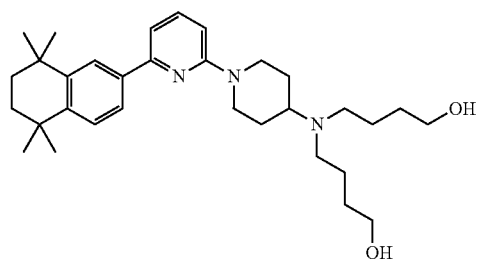

The preparation is carried out similarly to FS311 step 2.

Yield: 27 mg. Rt.=2.66 min (method A), LCMS: 508 (M+H).

¹H NMR (500 MHz, DMSO/deuterated TFA): δ 7.99 (dd, J=8.9, 7.5 Hz, 1H), 7.71 (d, J=1.5 Hz, 1H), 7.58-7.49 (m, 2H), 7.31 (d, J=9.0 Hz, 1H), 7.15 (d, J=7.4 Hz, 1H), 4.47 (d, J=13.6 Hz, 2H), 3.74 (s, 1H), 3.55-3.43 (m, 4H), 3.34-3.16 (m, 4H), 3.15-3.00 (m, 2H), 2.16 (d, J=10.4 Hz, 2H), 1.94-1.73 (m, 6H), 1.70 (s, 4H), 1.59-1.43 (m, 4H), 1.37-1.24 (m, 12H).

FS609: (2R,3S)-2-{[6'-(5,5,8,8-Tetramethyl-5,6,7,8-tetrahydronaphthalen-2-yl)-3,4,5,6-tetrahydro-2H-1,2'-bipyridinyl-4-ylamino]methyl}pyrrolidin-3-ol

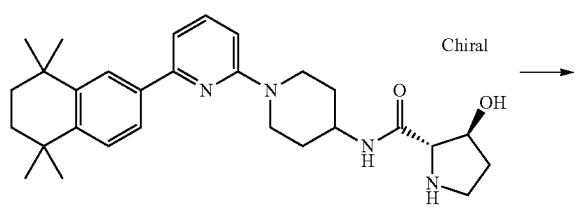

-continued

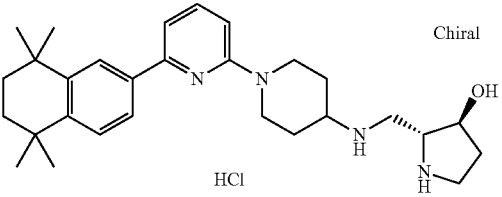

184 mg (0.39 mmol) of (2S,3S)-3-hydroxypyrrolidine-2-carboxylic acid [6'-(5,5,8,8-tetramethyl-5,6,7,8-tetrahydronaphthalen-2-yl)-3,4,5,6-tetrahydro-2H-1,2'-bipyridinyl-4-yl]amide was dissolved in 5 ml of THF, and 579 µl of 2M borane dimethyl sulfide solution in THF were added at 70° C. under nitrogen atmosphere, and the mixture was subsequently stirred at 70° C. for 2 hours. 579 µl of borane/dimethyl sulfide solution was again added, and the mixture was heated in a heating block at 70° C. for a further 4 hours. In order to decompose the excess borane, 1 ml of MeOH was added dropwise. The reaction mixture was evaporated, and 1 ml of water and 1 ml of conc HCl were added to the oily residue. The mixture was stirred at room temperature for 2 h, rendered alkaline using 2 molar NaOH and extracted with ethyl acetate. The organic phase was dried and purified by column chromatography on silica gel.

Yield: 51 mg, beige solid. Rt.=2.51 min (method A), LCMS: 463 (M+H).

¹H NMR (500 MHz, DMSO/deuterated TFA) δ 7.94 (dd, J=9.0, 7.4 Hz, 1H), 7.56 (d, J=1.9 Hz, 1H), 7.46 (d, J=8.3 Hz, 1H), 7.40 (dd, J=8.2, 1.9 Hz, 1H), 7.20 (d, J=9.1 Hz, 1H), 7.05 (d, J=7.3 Hz, 1H), 4.35-4.17 (m, 3H), 3.67 (dt, J=8.7, 4.5 Hz, 1H), 3.47 (t, J=11.1 Hz, 1H), 3.42-3.16 (m, 6H), 2.14 (ddd, J=21.5, 18.1, 9.9 Hz, 3H), 1.87 (ddd, J=30.3, 19.0, 8.5 Hz, 3H), 1.66 (s, 4H), 1.24 (d, J=8.7 Hz, 12H).

FS610: (2R,3S)-2-{4-[6-(5,5,8,8-Tetramethyl-5,6,7,8-tetrahydronaphthalen-2-yl)pyridin-2-yl]piperazin-1-ylmethyl}pyrrolidin-3-ol

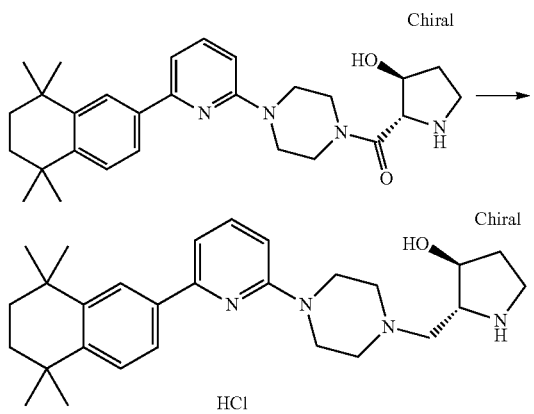

The preparation is carried out analogously to FS609.

Yield: 79 mg. Rt.=2.67 min (method A), LCMS: 449 (M+H).

¹H NMR (500 MHz, DMSO/deuterated TEAS 7.85 (dd, J=12.6, 5.0 Hz, 2H), 7.68 (dd, J=8.2, 1.9 Hz, 1H), 7.44 (d, J=8.3 Hz, 1H), 7.28 (d, J=7.5 Hz, 1H), 7.10 (d, J=8.6 Hz, 1H), 3.99 (d, J=39.3 Hz, 6H), 3.65-3.33 (m, 8H), 2.17 (td, J=13.6, 7.8 Hz, 1H), 1.90 (dq, J=8.1, 6.2 Hz, 1H), 1.69 (s, 4H), 1.29 (d, J=18.4 Hz, 12H).

FS611: (2R,3R)-3-Amino-4-{4-[6-(5,5,8,8-tetramethyl-5,6,7,8-tetrahydronaphthalen-2-yl)pyridin-2-yl]piperazin-1-yl}butan-2-ol

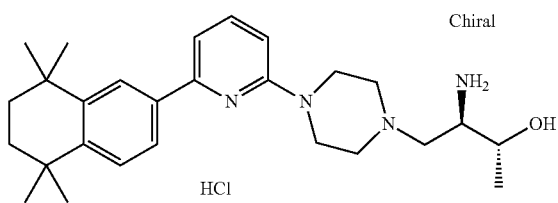 [SMILES: C[C@@H](O)[C@H](N)CN1CCN(c2cccc(-c3ccc4c(c3)C(C)(C)CCC4(C)C)n2)CC1 ; Cl]

The preparation is carried out analogously to FS609.
Yield: 37 mg. Rt.=2.67 min (method A), LCMS: 437 (M+H).
¹H NMR (400 MHz, DMSO/deuterated TFA): δ 7.89-7.80 (m, 2H), 7.65 (dd, J=8.2, 1.9 Hz, 1H), 7.44 (d, J=8.3 Hz, 1H), 7.26 (d, J=7.4 Hz, 1H), 7.12 (d, J=8.7 Hz, 1H), 4.27-3.33 (m, 12H), 1.69 (s, 4H), 1.29 (d, J=14.0 Hz, 12H), 1.23 (d, J=6.4 Hz, 3H).

FS612: (2R,3R)-3-Amino-4-[6'-(5,5,8,8-tetramethyl-5,6,7,8-tetrahydronaphthalen-2-yl)-3,4,5,6-tetrahydro-2H-1,2'-bipyridinyl-4-ylamino]butan-2-ol

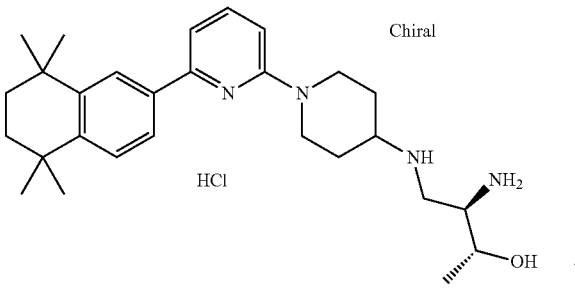

The preparation is carried out analogously to FS609.
Yield: 30 mg. Rt.=2.50 min (method A), LCMS: 451 (M+H).
¹H NMR (400 MHz, DMSO/deuterated TFA δ 8.00 (dd, J=9.0, 7.4 Hz, 1H), 7.73 (d, J=1.9 Hz, 1H), 7.54 (dt, J=21.8, 5.1 Hz, 2H), 7.30 (d, J=9.1 Hz, 1H), 7.18 (d, J=7.3 Hz, 1H), 4.40 (d, J=13.2 Hz, 2H), 3.98-3.90 (m, 1H), 3.59-3.49 (m, 1H), 3.45-3.15 (m, 5H), 2.22 (s, 2H), 1.78 (d, J=12.1 Hz, 2H), 1.70 (s, 4H), 1.32 (t, J=11.5 Hz, 12H), 1.23 (t, J=5.3 Hz, 3H).

FS701: 6'-(5,5,8,8-Tetramethyl-5,6,7,8-tetrahydronaphthalen-2-yl)-3,4,5,6-tetrahydro-2H-1,2'-bipyridinyl-4-ylamine

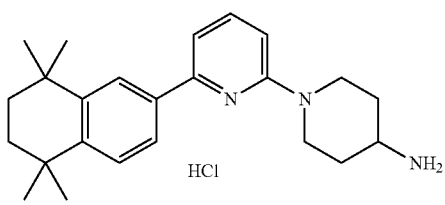 [SMILES: CC1(C)CCC(C)(C)c2cc(-c3cccc(N4CCC(N)CC4)n3)ccc21 ; Cl]

The preparation is carried out analogously to FS 102 starting from (6'-bromo-3,4,5,6-tetrahydro-2H-1,2'-bipyridinyl-4-yl)carbamic acid tert-butyl ester (preparation analogous to WO2005/26149) and 5,5,8,8-tetramethyl-5,6,7,8-tetrahydronaphthalen-2-ylboronic acid. The protecting group is subsequently cleaved off in a corresponding manner to FS201. The product is in the form of the hydrochloride.
55 mg, yellow oil, Rt.=2.68 min (method A), LCMS: 364 (M+H).
¹H NMR (500 MHz, DMSO/deuterated TFA) δ 7.96 (dd, J=8.5, 7.8, 1H), 7.78 (d, J=1.7, 1H), 7.61 (dd, J=8.2, 1.8, 1H), 7.51 (d, J=8.3, 1H), 7.24 (d, J=8.9, 1H), 7.19 (d, J=7.4, 1H), 4.36 (d, J=13.6, 2H), 3.46-3.38 (m, 1H), 3.24 (t, J=12.1, 2H), 2.10-2.02 (m, 2H), 1.71 (s, 4H), 1.65 (ddd, J=15.7, 12.4, 3.9, 2H), 1.32 (d, J=13.7, 12H).

FS702: (S)-2-Amino-3-hydroxy-1-{4-[6-(5,5,8,8-tetramethyl-5,6,7,8-tetrahydronaphthalen-2-yl)pyridin-2-yl]piperazin-1-yl}butan-1-one

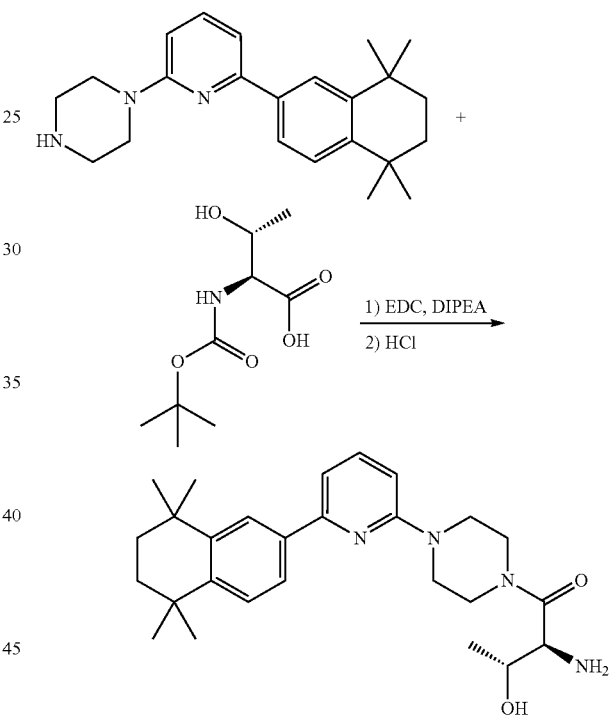

200 mg (0.57 mmol) of 1-[6-(5,5,8,8-tetramethyl-5,6,7,8-tetrahydronaphthalen-2-yl)-pyridin-2-yl]piperazine, 138 mg (0.629 mmol) of N-(tert-butoxycarbonyl)-L-threonine, 105 mg (0.69 mmol) of HOBt, 132 mg (0.69 mmol) of N-(3-dimethylaminopropyl)-N'-ethylcarbodiimide hydrochloride and 291 μl (1.72 mmol) of DIPEA are dissolved in 5 ml of THF and stirred at room temperature for 18 h. The crude product was purified by column chromatography and silica gel, dissolved in dioxane, and an excess of 4N HCl in dioxane was added. The reaction mixture is stirred at room temperature for 12 h, evaporated and purified by means of preparative HPLC. The product is converted into the hydrochloride using methanolic HCl.
Yield: 95 mg, beige solid. Rt.=2.75 min (method A), LCMS: 451 (M+H).
¹H NMR (500 MHz, DMSO/deuterated TFA) δ 7.96 (dd, J=8.8, 7.6 Hz, 1H), 7.59 (s, 1H), 7.48 (d, J=8.2 Hz, 1H), 7.43 (d, J=8.2 Hz, 1H), 7.21 (d, J=9.1 Hz, 1H), 7.08 (d, J=7.4 Hz, 1H), 4.32 (d, J=4.9 Hz, 1H), 4.04-3.96 (m, 1H), 3.89-3.64 (m, 8H), 1.67 (s, 4H), 1.32-1.21 (m, 12H), 1.18 (d, J=6.5 Hz, 3H).

FS703: (S)-2-Amino-3-hydroxy-1-{4-[6-(5,5,8,8-tetramethyl-5,6,7,8-tetrahydronaphthalen-2-yl)pyridin-2-yl]piperazin-1-yl}propan-1-one

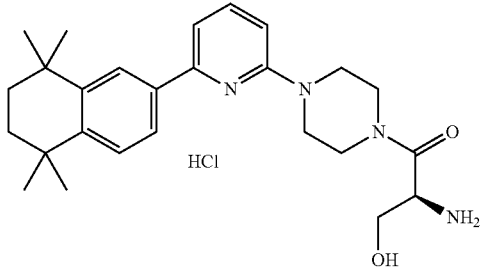 [SMILES: CC1(C)CCC(C)(C)c2cc(-c3cccc(N4CCN(C(=O)[C@@H](N)CO)CC4)n3)ccc21 ; Cl]

The preparation is carried out analogously to FS702. The product is in the form of the hydrochloride.

Yield: 105 mg, beige solid. Rt.=2.70 min (method A), LCMS: 437 (M+H).

$^1$H NMR (500 MHz, DMSO/deuterated TFA): δ 8.00 (dd, J=9.0, 7.5 Hz, 1H), 7.67 (b, 1H), 7.50 (b, 2H), 7.27 (d, J=9.1 Hz, 1H), 7.14 (d, J=7.4 Hz, 1H), 4.49 (t, J=5.3 Hz, 1H), 3.91-3.65 (m, 10H), 1.69 (s, 4H), 1.28 (d, J=13.4 Hz, 12H).

FS704: Morpholine-2-carboxylic acid [6-(5,5,8,8-tetramethyl-5,6,7,8-tetrahydronaphthalen-2-yl)pyridin-2-yl]amide

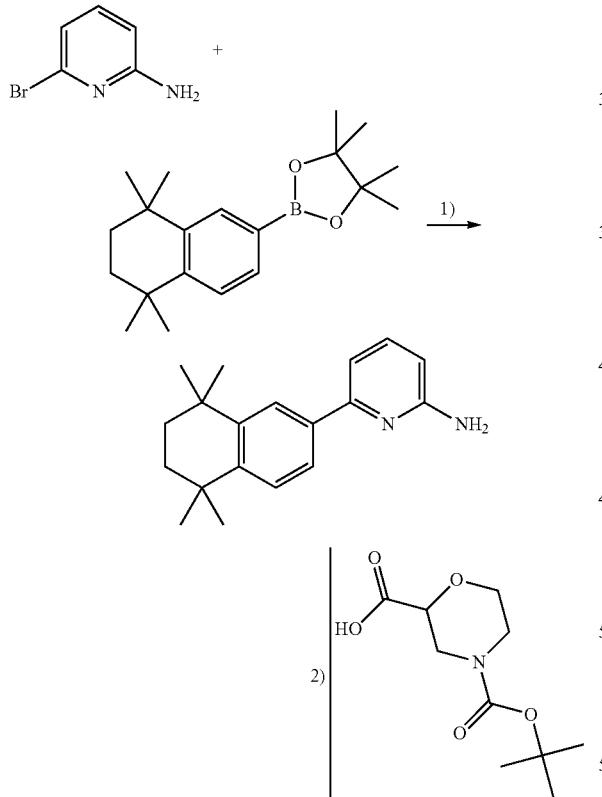

Step 1

The Suzuki reaction was carried out with tetrakis(triphenylphosphine)palladium-(0) and 2M sodium carbonate solution in dioxane. The reaction mixture was refluxed for 18 h. Work-up as described in the case of the other Suzuki reactions.

Yield: 4.4 g, beige solid. Rt.=2.39 min (method B), LCMS: 281 (M+H).

Step 2

The preparation is carried out analogously to FS702. The product is in the form of the trifluoroacetate.

Yield: 23 mg, beige solid. Rt.=2.63 min (method B), LCMS: 394 (M+H).

FS705: Morpholine-2-carboxylic acid [6'-(5,5,8,8-tetramethyl-5,6,7,8-tetrahydronaphthalen-2-yl)-3,4,5,6-tetrahydro-2H-1,2'-bipyridinyl-4-yl]amide

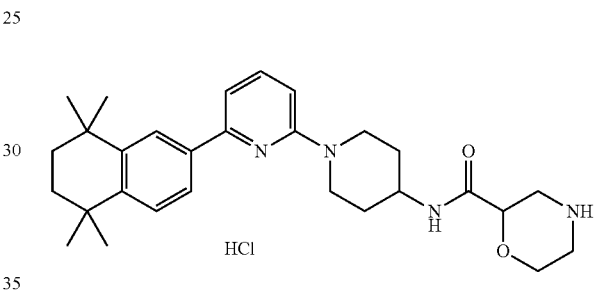

The preparation is carried out analogously to FS702. The product is in the form of the hydrochloride.

Yield: 244 mg, beige solid. Rt.=2.58 min (method A), LCMS: 477 (M+H).

$^1$H NMR (500 MHz, DMSO/deuterated TFA) δ 7.98 (dd, J=9.1, 7.4 Hz, 1H), 7.62 (d, J=1.6 Hz, 1H), 7.48 (dt, J=8.2, 5.0 Hz, 2H), 7.30 (d, J=9.2 Hz, 1H), 7.08 (d, J=7.3 Hz, 1H), 4.29-4.18 (m, 3H), 4.07-3.97 (m, 2H), 3.81 (dt, J=18.2, 3.8 Hz, 1H), 3.47 (dd, J=12.9, 2.0 Hz, 1H), 3.35 (t, J=11.7 Hz, 2H), 3.22 (d, J=12.9 Hz, 1H), 3.15-2.95 (m, 2H), 1.95-1.85 (m, 2H), 1.75-1.63 (m, 6H), 1.28 (d, J=11.5 Hz, 12H).

FS706: (2S,3S)-3-Hydroxypyrrolidine-2-carboxylic acid [6'-(5,5,8,8-tetramethyl-5,6,7,8-tetrahydronaphthalen-2-yl)-3,4,5,6-tetrahydro-2H-1,2'-bipyridinyl-4-yl]amide

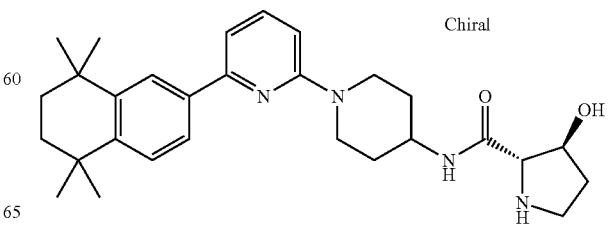

The preparation is carried out analogously to FS702.

Yield: 184 mg, beige solid. Rt.=2.54 min (method A), LCMS: 477 (M+H).

¹H NMR (500 MHz, DMSO/deuterated TFA) δ 7.99 (dd, J=9.1, 7.4 Hz, 1H), 7.64 (d, J=1.6 Hz, 1H), 7.49 (dt, J=8.3, 5.0 Hz, 2H), 7.31 (d, J=9.2 Hz, 1H), 7.09 (d, J=7.3 Hz, 1H), 4.40 (dd, J=5.5, 3.4 Hz, 1H), 4.21-4.11 (m, 2H), 4.07 (d, J=1.9 Hz, 1H), 4.05-3.95 (m, 1H), 3.51-3.29 (m, 4H), 2.05-1.88 (m, 4H), 1.76-1.56 (m, 6H), 1.28 (d, J=11.4 Hz, 12H).

FS707: ((2S,3S)-3-Hydroxypyrrolidin-2-yl)-{4-[6-(5,5,8,8-tetramethyl-5,6,7,8-tetrahydronaphthalen-2-yl)pyridin-2-yl]piperazin-1-yl}methanone

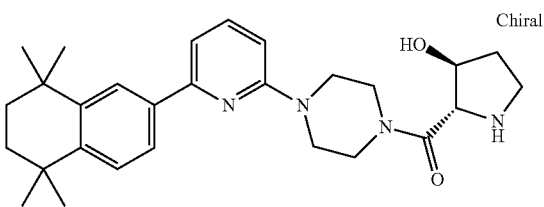 [SMILES: CC1(C)CCC(C)(C)c2cc(-c3cccc(N4CCN(C(=O)[C@H]5NCC[C@@H]5O)CC4)n3)ccc21]

The preparation is carried out analogously to FS702.

Yield: 155 mg, crystalline solid. Rt.=2.72 min (method A), LCMS: 463 (M+H).

¹H NMR (500 MHz, DMSO/deuterated TFA): δ 8.04 (dd, J=8.8, 7.6 Hz, 1H), 7.77 (d, J=2.0 Hz, 1H), 7.63-7.52 (m, 2H), 7.32 (d, J=9.0 Hz, 1H), 7.22 (dd, J=7.3, 1.9 Hz, 1H), 4.63 (s, 1H), 4.54-4.45 (m, 1H), 3.98-3.71 (m, 8H), 3.57-3.47 (m, 1H), 3.47-3.36 (m, 1H), 2.04-1.89 (m, 2H), 1.74 (s, 4H), 1.34 (d, J=15.1 Hz, 12H).

FS708: (S)-2-Amino-3-hydroxy-N-[6'-(5,5,8,8-tetramethyl-5,6,7,8-tetrahydronaphthalen-2-yl)-3,4,5,6-tetrahydro-2H-1,2'-bipyridinyl-4-yl]propionamide

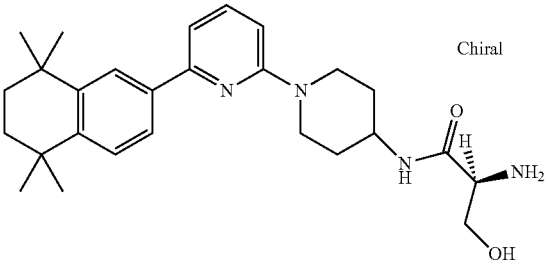 [SMILES: CC1(C)CCC(C)(C)c2cc(-c3cccc(N4CCC(NC(=O)[C@@H](N)CO)CC4)n3)ccc21]

The preparation is carried out analogously to FS702.

Yield: 187 mg, colourless oil. Rt.=2.50 min (method A), LCMS: 451 (M+H).

¹H NMR (500 MHz, DMSO/deuterated TFA) δ 8.01 (dd, J=9.1, 7.4 Hz, 1H), 7.67 (s, 1H), 7.55-7.48 (m, 2H), 7.34 (d, J=9.1 Hz, 1H), 7.12 (d, J=7.3 Hz, 1H), 4.21-4.10 (m, 2H), 4.07-3.98 (m, 1H), 3.85-3.76 (m, 2H), 3.76-3.69 (m, 1H), 3.52-3.38 (m, 2H), 2.02-1.93 (m, 2H), 1.70 (s, 4H), 1.67-1.56 (m, 2H), 1.30 (d, J=11.8 Hz, 12H).

FS709: (2S,3R)-2-Amino-3-hydroxy-N-[6'-(5,5,8,8-tetramethyl-5,6,7,8-tetrahydronaphthalen-2-yl)-3,4,5,6-tetrahydro-2H-1,2'-bipyridinyl-4-yl]butyramide

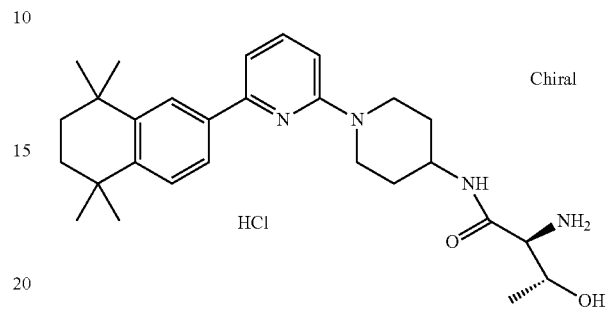

The preparation is carried out analogously to FS702.

Yield: 274 mg, colourless oil. Rt.=2.54 min (method A), LCMS: 465 (M+H).

¹H NMR (500 MHz, DMSO/deuterated TFA): δ 8.04 (dd, J=9.1, 7.4 Hz, 1H), 7.70 (d, J=1.6 Hz, 1H), 7.58-7.49 (m, 2H), 7.37 (d, J=9.1 Hz, 1H), 7.15 (d, J=7.3 Hz, 1H), 4.21 (t, J=13.1 Hz, 2H), 4.08 (ddd, J=14.2, 9.7, 4.3 Hz, 1H), 3.95 (p, J=6.4 Hz, 1H), 3.56 (d, J=6.9 Hz, 1H), 3.55-3.43 (m, 2H), 2.08-1.98 (m, 2H), 1.74 (s, 4H), 1.72-1.58 (m, 2H), 1.33 (d, J=11.5 Hz, 12H), 1.22 (d, J=6.3 Hz, 3H).

FS710: 2-{Methyl-[6'-(5,5,8,8-tetramethyl-5,6,7,8-tetrahydronaphthalen-2-yl)-3,4,5,6-tetrahydro-2H-1,2'-bipyridinyl-4-ylmethyl]amino}ethanol

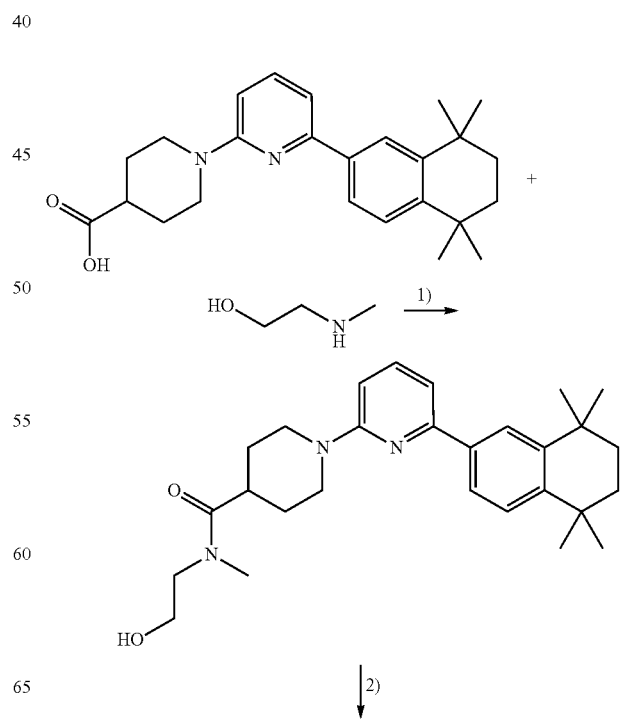

-continued

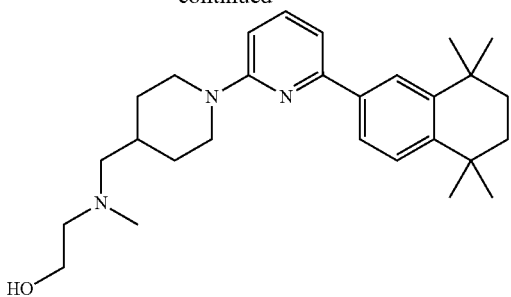

Step 1

The preparation is carried out analogously to FS702.

Yield: 110 mg, colourless oil. Rt.=2.80 min (method A), LCMS: 450 (M+H).

Step 2

The preparation is carried out analogously to FS311.

Yield: 6 mg, colourless oil. Rt.=2.56 min (method A), LCMS: 436 (M+H).

$^1$H NMR (500 MHz, DMSO/deuterated TFA): δ 8.06-8.00 (m, 1H), 7.69 (s, 1H), 7.54 (q, J=8.2 Hz, 2H), 7.37 (d, J=9.0 Hz, 1H), 7.13 (d, J=7.3 Hz, 1H), 4.34 (d, J=13.4 Hz, 2H), 3.86-3.80 (m, 2H), 3.33 (dt, J=27.7, 9.1 Hz, 3H), 3.21 (dd, J=17.9, 10.6 Hz, 2H), 3.05 (dd, J=13.1, 6.3 Hz, 1H), 2.91 (s, 3H), 2.35-2.21 (m, 1H), 1.99 (dd, J=39.5, 12.9 Hz, 2H), 1.74 (s, 4H), 1.50-1.37 (m, 2H), 1.33 (d, J=11.3 Hz, 12H).

FS711: 2-{[6'-(5,5,8,8-Tetramethyl-5,6,7,8-tetrahydronaphthalen-2-yl)-3,4,5,6-tetrahydro-2H-1,2'-bipyridinyl-4-ylmethyl]amino}ethanol

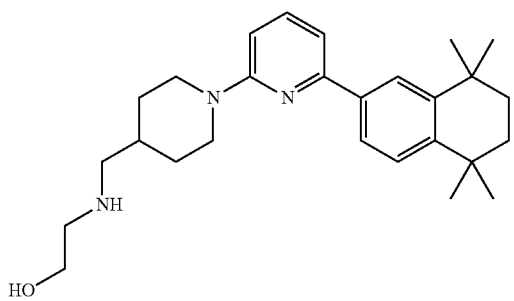 [SMILES: CC1(C)CCC(C)(C)c2cc(-c3cccc(N4CCC(CNCCO)CC4)n3)ccc21]

The preparation is carried out analogously to FS702.

Yield: 27 mg, colourless oil. Rt.=2.52 min (method A), LCMS: 422 (M+H).

$^1$H NMR (500 MHz, DMSO/deuterated TFA): δ 7.95 (dd, J=9.2, 7.4 Hz, 1H), 7.59 (d, J=1.9 Hz, 1H), 7.49 (d, J=8.2 Hz, 1H), 7.43 (dd, J=8.2, 1.9 Hz, 1H), 7.27 (d, J=9.1 Hz, 1H), 7.04 (d, J=7.2 Hz, 1H), 4.26 (d, J=13.5 Hz, 2H), 3.73-3.66 (m, 2H), 3.23 (t, J=11.8 Hz, 2H), 3.07-3.00 (m, 2H), 2.89 (d, J=6.9 Hz, 2H), 2.12 (s, 1H), 1.94 (d, J=11.0 Hz, 2H), 1.68 (s, 4H), 1.45-1.16 (m, 14H).

FS 801: 2-(5,5-Dimethyl-5,6,7,8-tetrahydronaphthalen-2-yl)-4,4,5,5-tetramethyl-1,3,2-dioxaborolane

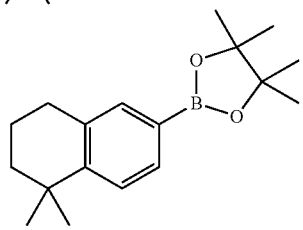

2 g (8.36 mmol) of 6-bromo-1,1-dimethyl-1,2,3,4-tetrahydronaphthalene (preparation see Journal of Medicinal Chemistry, 1998, Vol, 41, 1476-1496) are dissolved in 16 ml of THF, and 2.85 g (11.2 mmol) of bis(pinacolato)diboron and 2.46 g (25.1 mmol) of potassium acetate are added. The reaction mixture is degassed a number of times, 234 mg (0.33 mmol) of bis(triphenylphosphine)-palladium(II) dichloride are added under nitrogen atmosphere, and the mixture is stirred at 70° C. for 20 h. The reaction mixture is filtered and rinsed with 200 ml of ethyl acetate. The filtrate is washed with 50 ml of water, dried over Na$_2$SO$_4$ and evaporated. The crude product is purified by means of flash chromatography on silica gel.

1.53 g oil, Rt.=4.01 min (method B), LCMS: 287 (M+H).

FS802: 2-(8,8-Dimethyl-5,6,7,8-tetrahydronaphthalen-2-yl)-4,4,5,5-tetramethyl-1,3,2-dioxaborolane

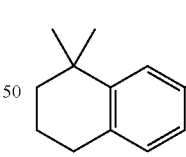

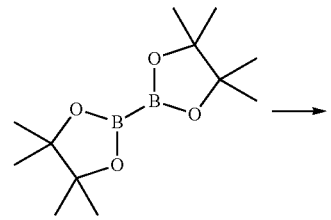

The preparation is carried out analogously to FS801 starting from 7-bromo-1,1-dimethyl-1,2,3,4-tetrahydronaphthalene (preparation see WO2005/66115).

844 mg, yellow oil, Rt.=3.91 min (method B), LCMS: 287 (M+H).

181

FS803: 4,4,5,5-Tetramethyl-2-(1,1,3,3-tetramethylindan-5-yl)-1,3,2-dioxaborolane

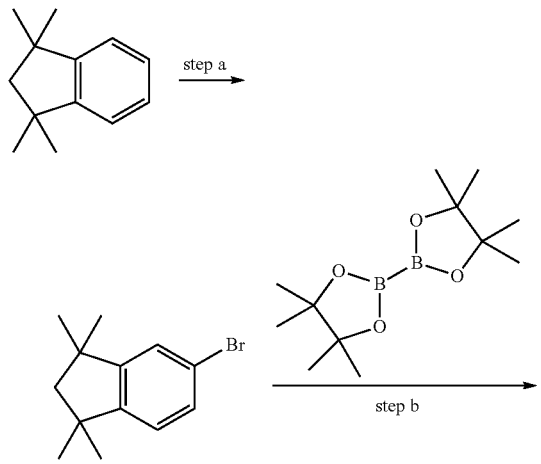

182

-continued

Step a

The bromination of 1,1,3,3-tetramethylindane (see US 2005/148590) is carried out analogously to the procedure in Organic Synthesis, Collective Vol. 3, p. 138.).

732 mg, yellow oil, Rt.=3.97 min (method B).

Step b

The preparation is carried out analogously to FS801 starting from 5-bromo-1,1,3,3-tetramethylindane.

365 mg, yellow oil, Rt.=4.07 min (method B).

$^1$H NMR (400 MHz, DMSO/deuterated TFA) δ 7.57 (dd, J=7.5, 1.0, 1H), 7.50 (s, 1H), 7.17 (d, J=7.2, 1H), 1.90 (s, 2H), 1.31 (s, 12H), 1.30 (s, 6H), 1.28 (s, 6H).

FS804 4-{(2-Hydroxyethyl)-[6'-(5,5,8,8-tetramethyl-5,6,7,8-tetrahydronaphthalen-2-yl)-3,4,5,6-tetrahydro-2H-1,2'-bipyridinyl-4-yl]amino}butan-1-ol

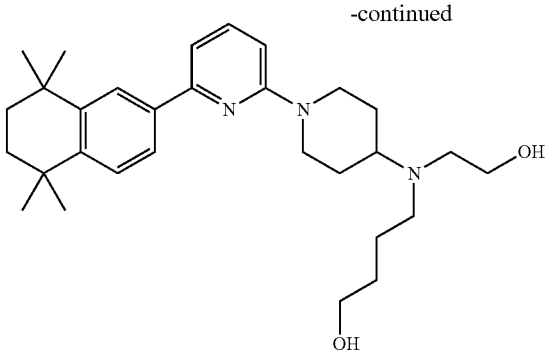

Step 1

400 mg (1.64 mmol) of 4-(2-hydroxyethylamino)piperidine-1-carboxylic acid tert-butyl ester, 1.42 ml (9.82 mmol) of 4-bromobutyl acetate and 1.13 g (8.19 mmol) of potassium carbonate were suspended in 50 ml of acetonitrile and stirred at 70° C. for 3 days. The reaction mixture is filtered, the residue is washed with acetonitrile, and the filtrate was evaporated. The residue was dissolved in 150 ml of dichloromethane, washed with water, the aqueous phase was extracted again with dichloromethane, and the combined organic phases were dried and evaporated. The crude product is reacted further directly.

LCMS: 359 (M+H).

Step 2

The crude product from step 1 is dissolved in dioxane, and 4N HCl in dioxane is added. The reaction mixture is stirred at room temperature for 3 h, where an oily precipitate formed. The supernatant is decanted off, and the residue is dried in vacuo.

LCMS: 359 (M+H).

Step 3

117 mg (0.5 mmol) of 2,6-dibromopyridine, 146 mg (0.5 mmol) of acetic acid 4-[(2-hydroxyethyl)piperidin-4-ylamino]butyl ester hydrochloride and 1981 mg (1.4 mmol) of potassium carbonate are suspended in 4 ml of NMP and stirred at 100° C. for 48 h. The reaction mixture was stirred into water, filtered, and the filtrate is extracted a number of times with ethyl acetate, washed with water, dried and evaporated. The residue is purified by column chromatography on silica gel (eluent dichloromethane/methanol).

38 mg, Rt.=2.10 min (method A), LCMS: 374 (M+H).

Step 4

The reaction is carried out analogously to FS102.

Yield: 10 mg. Rt.=2.76 min (method A), LCMS: 480 (M+H).

FS901: Preparation of 1-[6'-(5,5,8,8-tetramethyl-5,6,7,8-tetrahydronaphthalen-2-yl)-3,4,5,6-tetrahydro-2H-1,2'-bipyridinyl-4-yl]pyrrolidin-3-ylamine

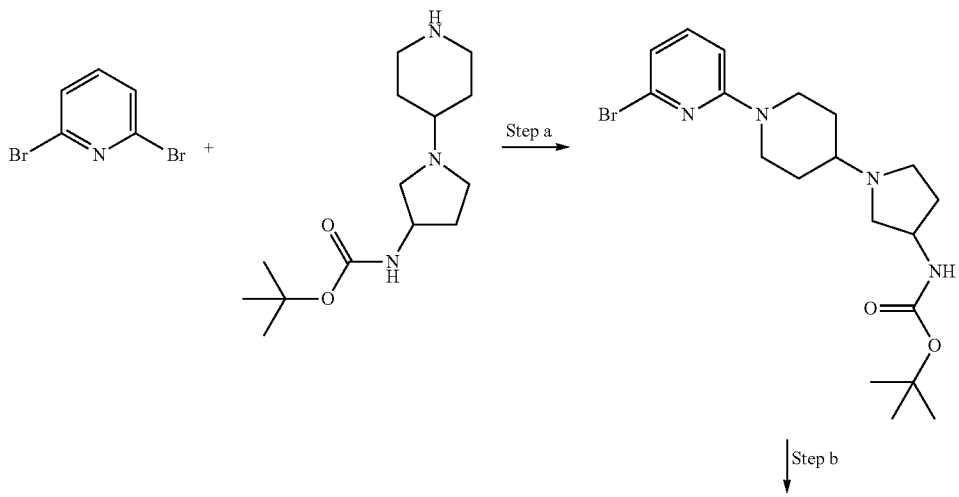

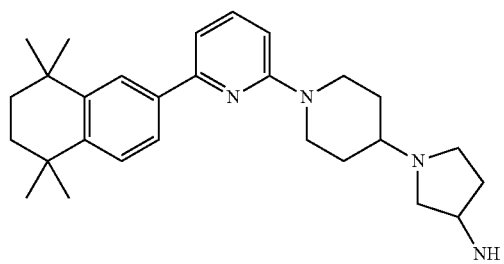

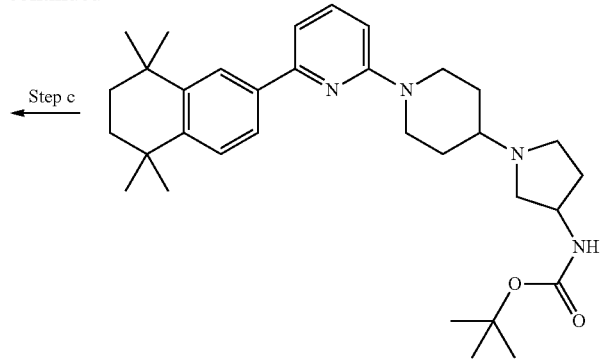

Step c ←

Step a 879 mg (3.71 mmol) of 2,6-dibromoaniline, 1 g (3.71 mmol) of (1-piperidin-4-yl-pyrrolidin-3-yl)carbamic acid tert-butyl ester and 3.65 g (26.4 mmol) of potassium carbonate are suspended in 20 ml of DMSO and stirred at 120° C. for 15 h. Water is added to the reaction mixture, which is then extracted three times with ethyl acetate, dried over $Na_2SO_4$ and evaporated. The crude product is reacted further without further purification.

2.07 g, brown oil, Rt.=2.52 min (method A), LCMS: 426 (M+H).

Step b and c

The further reaction is carried out analogously to FS102 and FS201.
Product:
40 mg, yellow solid, Rt.=2.64 min (method A), LCMS: 433 (M+H).
$^1$H NMR (500 MHz, DMSO/deuterated TFA) δ 7.96 (dd, J=8.9, 7.5, 1H), 7.66 (d, J=1.7, 1H), 7.54-7.44 (m, 2H), 7.27 (d, J=9.1, 1H), 7.13 (d, J=7.3, 1H), 4.38 (d, J=13.3, 2H), 4.09-3.91 (m, 1H), 3.63-3.50 (m, 2H), 3.19 (t, J=12.8, 2H), 2.25-2.16 (m, 2H), 1.77 (d, J=12.1, 2H), 1.67 (s, 4H), 1.26 (d, J=12.9, 12H).

FS902: 6"-(5,5,8,8-Tetramethyl-5,6,7,8-tetrahydronaphthalen-2-yl)-3,4,5,6,3',4',5',6'-octahydro-2H,2'H-[1,4';1',2"]terpyridin-3-ol

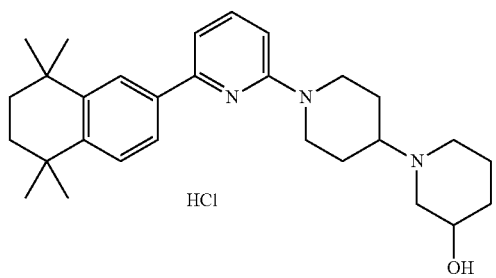 [SMILES: CC1(C)CCC(C)(C)c2cc(-c3cccc(N4CCC(N5CCCC(O)C5)CC4)n3)ccc21 ; Cl]

The preparation is carried out analogously to FS901 (step a and b). The product is in the form of the hydrochloride.
45 mg, yellow solid, Rt.=2.81 min (method A), LCMS: 448 (M+H).
$^1$H NMR (500 MHz, DMSO/deuterated TFA) δ 7.91 (s, 1H), 7.72 (dd, J=8.3, 1.6, 1H), 7.64-7.59 (m, 1H), 7.38 (d, J=8.3, 1H), 7.18 (d, J=7.4, 1H), 6.84 (dd, J=8.4, 5.0, 1H), 5.44 (s, 1H), 4.62-4.53 (m, 2H), 4.08 (s, 2H), 3.75-3.66 (m, 1H), 3.56-3.47 (m, 1H), 3.44-3.23 (m, 3H), 3.07-2.96 (m, 1H), 2.91-2.79 (m, 2H), 2.19-1.84 (m, 3H), 1.76-1.53 (m, 8H), 1.29 (d, J=17.3, 12H).

FS903: 7-{6-[4-(5-Hydroxypentyl)piperazin-1-yl]pyridin-2-yl}-4,4-dimethyl-3,4-dihydro-2H-naphthalen-1-one

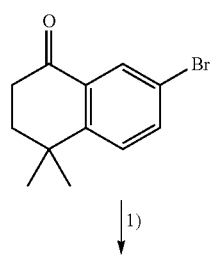

↓ 1)

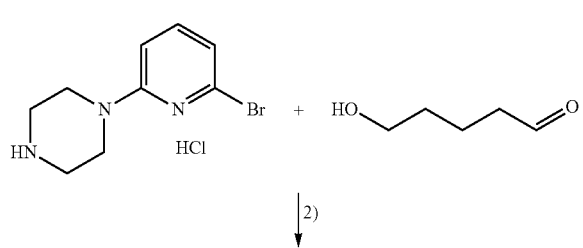

↓ 2)

-continued

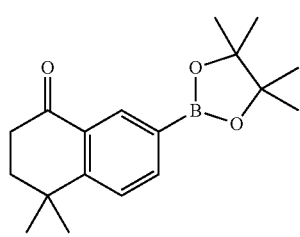
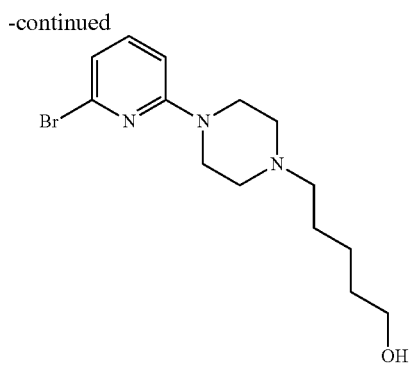

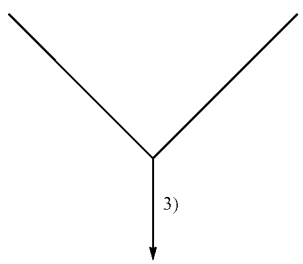

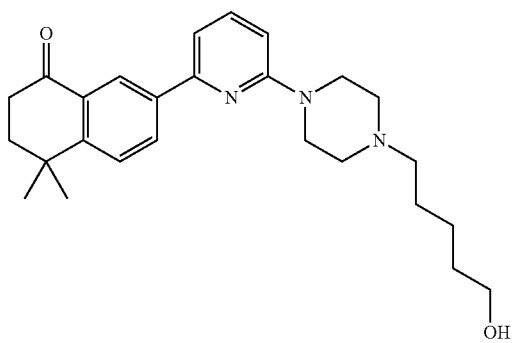

Step 1

97 mg (2.07 mmol) of 7-bromo-4,4-dimethyl-3,4-dihydro-2H-naphthalen-1-one, 685 mg (2.70 mmol) of bis(pinacolato)diboron and 611 mg (6.22 mmol) of potassium acetate are suspended in 10 ml of THF, degassed, and 58 mg (0.08 mmol) of bis(triphenylphosphine)palladium(II) chloride are added under nitrogen atmosphere. The reaction mixture is stirred at 70° C. for 18 h, cooled to RT, water is added, and the mixture is extracted with ethyl acetate. The crude product is purified by means of column chromatography on silica gel.

Yield: 570 mg, yellow solid. Rt.=3.46 min (method A), LCMS: 301 (M+H).

Step 2

The reaction is carried out analogously to FS501.
Yield: 2.1 g, pale-yellow oil. Rt.=1.98 min (method A), LCMS: 328/330 (M+H).

Step 3

The reaction is carried out analogously to FS102.
Yield: 47 mg, pale-yellow oil. Rt.=2.55 min (method A), LCMS: 422 (M+H).
$^1$H NMR (400 MHz, DMSO/deuterated TFA) δ 8.40 (d, J=2.0 Hz, 1H), 8.12 (dd, J=8.3, 2.1 Hz, 1H), 7.77 (dd, J=8.5, 7.6 Hz, 1H), 7.59 (d, J=8.3 Hz, 1H), 7.26 (d, J=7.4 Hz, 1H), 7.01 (d, J=8.7 Hz, 1H), 4.50 (d, J=13.7 Hz, 2H), 3.62 (d, J=11.6 Hz, 2H), 3.48-3.29 (m, 4H), 3.22-3.04 (m, 4H), 1.96 (s, 2H), 1.83-1.63 (m, 3H), 1.53-1.44 (m, 2H), 1.44-1.28 (m, 9H).

FS904: 2-(4-{4-[6-(5,5,8,8-Tetramethyl-5,6,7,8-tet-rahydronaphthalen-2-yl)pyridin-2-yl]-piperazin-1-yl}piperidin-1-yl)ethanol

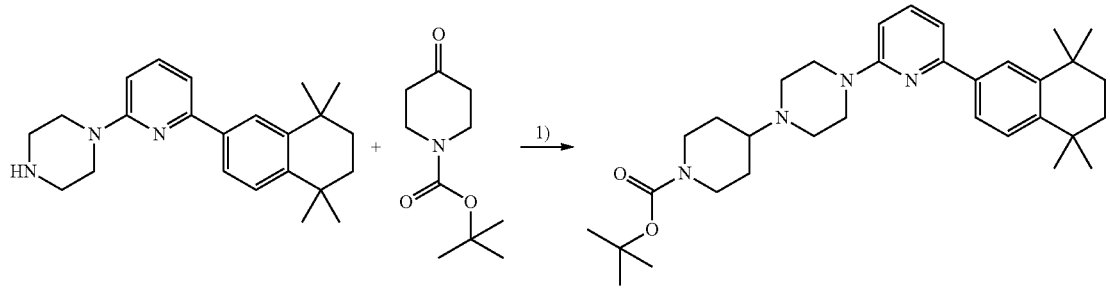

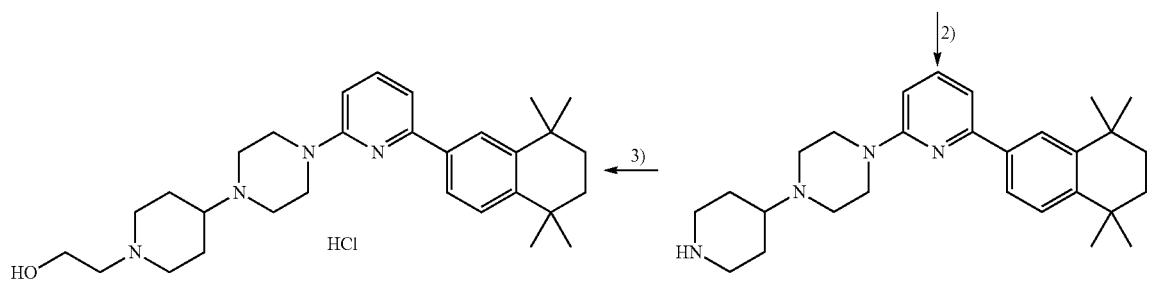

Step 1

The reductive amination is carried out analogously to FS501.

Yield: 420 mg, colourless oil. Rt.=3.32 min (method A), LCMS: 533 (M+H).

Step 2

The Boc protecting group is cleaved off analogously to FS201.

Yield: 350 mg, White solid. Rt.=2.78 min (method A), LCMS: 433 (M+H).

Step 3

The reaction is carried out analogously to FS520. The product is in the form of the hydrochloride.

Yield: 58 mg, white solid. Rt.=2.76 min (method A), LCMS: 477 (M+H).

$^1$H NMR (400 MHz, DMSO/deuterated TFA) δ 7.88-7.80 (m, 2H), 7.65 (dd, J=8.2, 1.9 Hz, 1H), 7.44 (d, J=8.3 Hz, 1H), 7.25 (d, J=7.5 Hz, 1H), 7.09 (d, J=8.7 Hz, 1H), 4.10-3.25 (m, 13H), 3.25-3.14 (m, 2H), 3.07 (t, J=12.1 Hz, 2H), 2.41-2.30 (m, 2H), 2.17-2.02 (m, 2H), 1.68 (s, 4H), 1.28 (d, J=13.9 Hz, 12H).

FS905: 7-{6-[4-(5-Hydroxypentyl)piperazin-1-yl]pyridin-2-yl}-4,4-dimethyl-1,2,3,4-tetrahydronaphthalen-1-ol

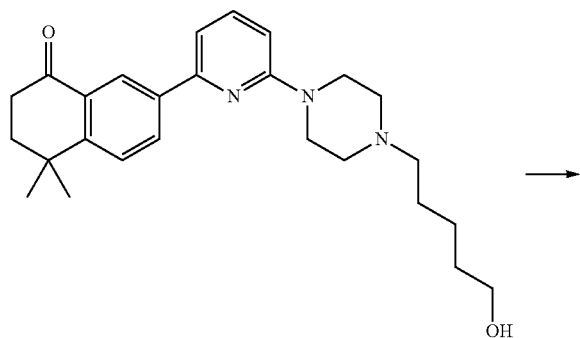

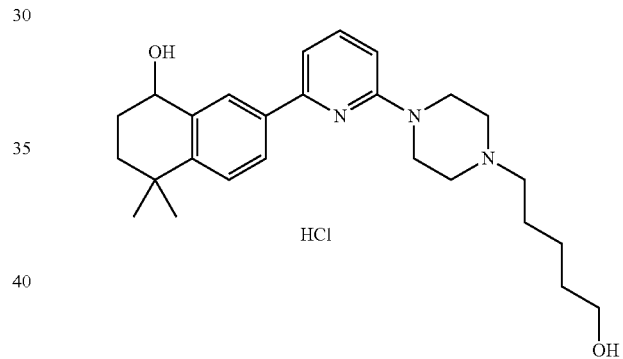

50 mg (0.12 mmol) of 7-{6-[4-(5-hydroxypentyl)piperazin-1-yl]pyridin-2-yl}-4,4-dimethyl-3,4-dihydro-2H-naphthalen-1-one are dissolved in 0.5 ml of THF and 1 ml of methanol, cooled to 0° C., and 4.5 mg (0.12 mmol) of sodium borohydride are added. The reaction mixture is stirred for 30 min, water is added, and the mixture is extracted with ethyl acetate, dried and evaporated. The crude product is purified by means of prep HPLC and subsequently converted into the hydrochloride using methanolic HCl.

Yield: 39 mg, white solid. Rt.=2.45 min (method A), LCMS: 424 (M+H).

$^1$H NMR (400 MHz, DMSO/deuterated TFA) δ 7.94 (d, J=1.8 Hz, 1H), 7.87 (dd, J=8.7, 7.5 Hz, 1H), 7.71 (dd, J=8.2, 2.1 Hz, 1H), 7.44 (d, J=8.3 Hz, 1H), 7.23 (d, J=7.4 Hz, 1H), 7.11 (d, J=8.7 Hz, 1H), 4.62 (t, J=6.0 Hz, 1H), 4.50 (d, J=12.6

Hz, 2H), 3.64 (d, J=10.1 Hz, 2H), 3.45 (t, J=6.2 Hz, 4H), 3.20-3.06 (m, 4H), 2.06-1.68 (m, 6H), 1.52-1.34 (m, 4H), 1.26 (d, J=18.6 Hz, 6H).

FS906: 7-{6-[4-(5-Hydroxypentyl)piperazin-1-yl]pyridin-2-yl}-1,4,4-trimethyl-1,2,3,4-tetrahydronaphthalen-1-ol FS907: 5-{4-[6-(8-Dimethylamino-5,5-dimethyl-5,6,7,8-tetrahydronaphthalen-2-yl)pyridin-2-yl]piperazin-1-yl}pentan-1-ol

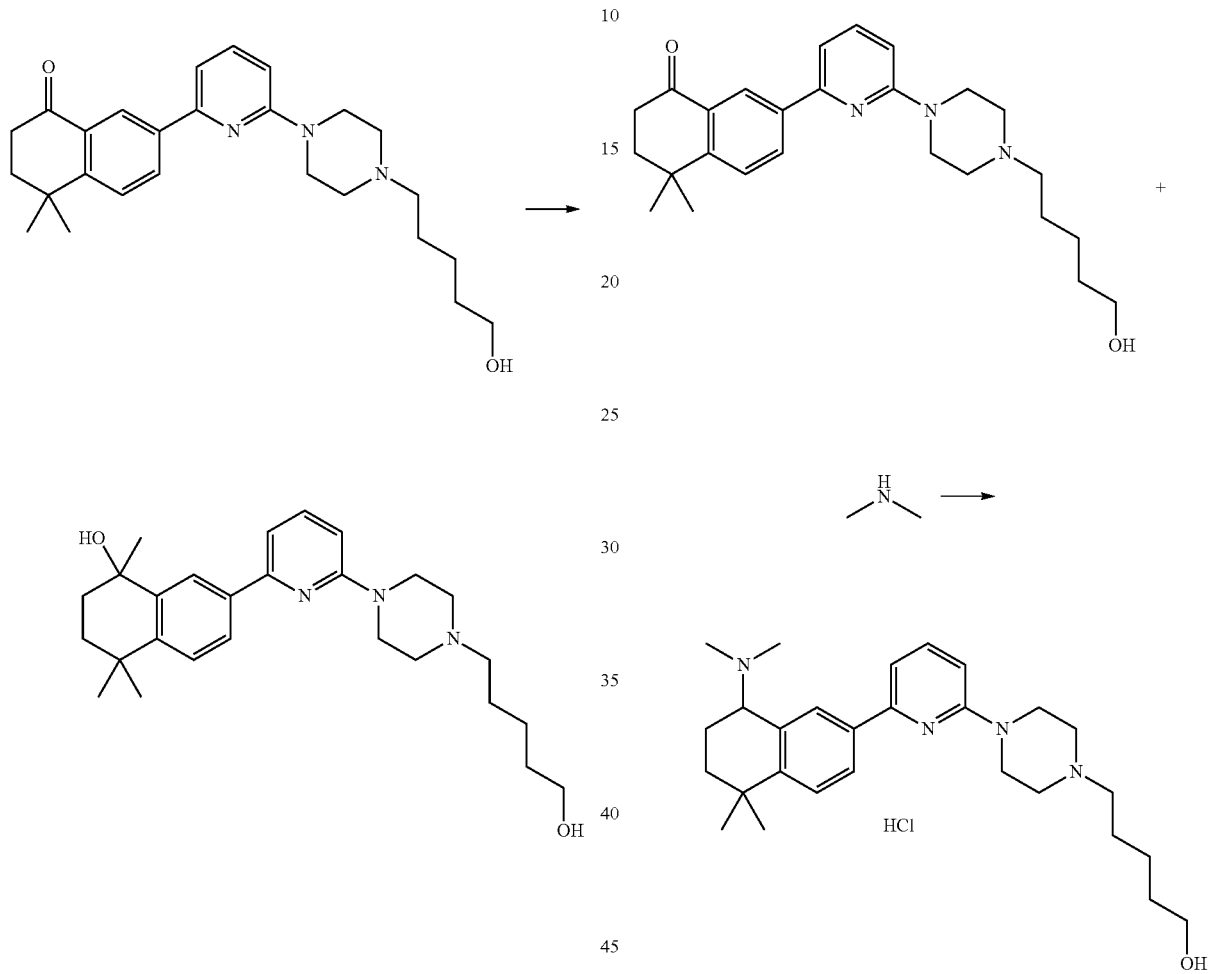

50 mg (0.12 mmol) of 7-{6-[4-(5-hydroxypentyl)piperazin-1-yl]pyridin-2-yl}-4,4-dimethyl-3,4-dihydro-2H-naphthalen-1-one are dissolved in 5 ml of THF, cooled to 0° C., and 224 µl (0.36 mmol) of methyllithium in diethyl ether (5%) are added. The reaction mixture is stirred at 0° C. for 30 min and warmed to room temperature. Water added to the reaction mixture, sodium hydrogencarbonate solution added, and the mixture extracted with ethyl acetate, dried and evaporated. The crude product is purified by means of column chromatography on silica gel.

Yield: 9 mg. Rt.=2.53 min (method A), LCMS: 438 (M+H).

$^1$H NMR (400 MHz, DMSO/deuterated TFA) δ 8.06 (d, J=2.0 Hz, 1H), 7.88-7.81 (m, 1H), 7.69 (dd, J=8.2, 2.1 Hz, 1H), 7.41 (d, J=8.3 Hz, 1H), 7.23 (d, J=7.4 Hz, 1H), 7.10 (d, J=8.8 Hz, 1H), 4.50 (d, J=13.8 Hz, 2H), 3.64 (d, J=9.9 Hz, 2H), 3.52-3.35 (m, 4H), 3.25-3.06 (m, 4H), 2.12-1.64 (m, 6H), 1.55-1.34 (m, 7H), 1.26 (d, J=7.4 Hz, 6H).

50 mg (0.12 mmol) of 7-{6-[4-(5-hydroxypentyl)piperazin-1-yl]pyridin-2-yl}-4,4-dimethyl-3,4-dihydro-2H-naphthalen-1-one are dissolved in 2 ml of 2M dimethylamine in THF, and 15 mg of sodium cyanoborohydride and 38 mg of titanium(IV) isopropoxide are added, and the mixture is stirred in a pressure vessel at 80° C. Water added to the reaction mixture, sodium hydrogencarbonate solution added, and the mixture extracted with ethyl acetate, dried and evaporated. The crude product is purified by means of prep HPLC.

Yield: 5 mg. Rt.=2.14 min (method A), LCMS: 451 (M+H).

$^1$H NMR (500 MHz, DMSO/deuterated TFA) δ 8.12 (d, J=1.3 Hz, 1H), 7.99 (dd, J=8.3, 1.6 Hz, 1H), 7.80-7.74 (m, 1H), 7.57 (d, J=8.4 Hz, 1H), 7.31 (d, J=7.5 Hz, 1H), 6.98 (d, J=8.6 Hz, 1H), 4.77 (t, J=7.0 Hz, 1H), 4.53 (d, J=14.1 Hz, 2H), 3.60 (d, J=11.8 Hz, 2H), 3.48-3.42 (m, 2H), 3.33 (t, J=12.6 Hz, 2H), 3.18-3.06 (m, 4H), 2.94 (s, 3H), 2.57 (s, 3H), 2.18-2.07 (m, 2H), 1.87-1.60 (m, 4H), 1.52-1.44 (m, 2H), 1.44-1.34 (m, 2H), 1.28 (d, J=37.6 Hz, 6H).

FS1001: Aminoacetic acid 5-{4-[3-(5,5,8,8-tetramethyl-5,6,7,8-tetrahydronaphthalen-2-yl)phenyl]piperazin-1-yl}pentyl ester

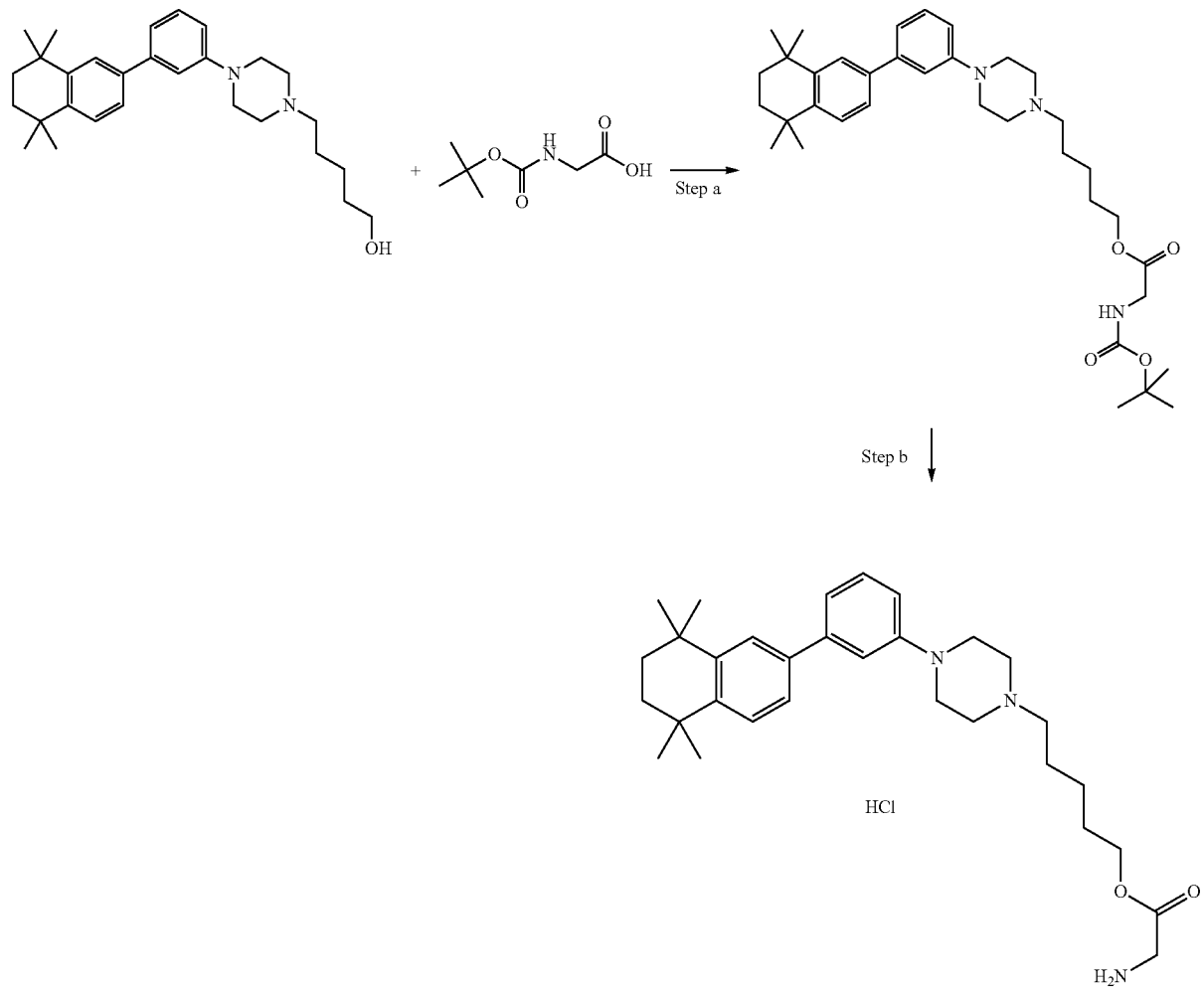 [SMILES: CC1(C)CCC(C)(C)c2cc(-c3cccc(N4CCN(CCCCCO)CC4)c3)ccc21 ; CC(C)(C)OC(=O)NCC(=O)O ; CC(C)(C)OC(=O)NCC(=O)OCCCCCN1CCN(c2cccc(-c3ccc4c(c3)C(C)(C)CCC4(C)C)c2)CC1 ; CC1(C)CCC(C)(C)c2cc(-c3cccc(N4CCN(CCCCCOC(=O)CN)CC4)c3)ccc21 ; Cl]

Step a 40 mg (0.09 mmol) of 5-{4-[3-(5,5,8,8-tetramethyl-5,6,7,8-tetrahydronaphthalen-2-yl)phenyl]piperazin-1-yl}pentan-1-ol and 64 mg (0.37 mmol) of Boc-Gly-OH are dissolved in 5 ml of THF and 1 ml of DCM, and 38 mg (0.18 mmol) of DCC and 1.2 mg of DMAP are added. The reaction mixture is stirred at RT for 1 h and subsequently evaporated to dryness. The crude mixture is reacted further without further purification.

Step b

The protecting group is cleaved off analogously to FS201. The product is in the form of the hydrochloride.

52 mg, yellow solid, Rt.=2.94 min (method A), LCMS: 492 (M+H).

FS1002: 2-(2-{4-[6-(5,5,8,8-Tetramethyl-5,6,7,8-tetrahydronaphthalen-2-yl)pyridin-2-yl]-piperazin-1-yl}ethylamino)ethanol

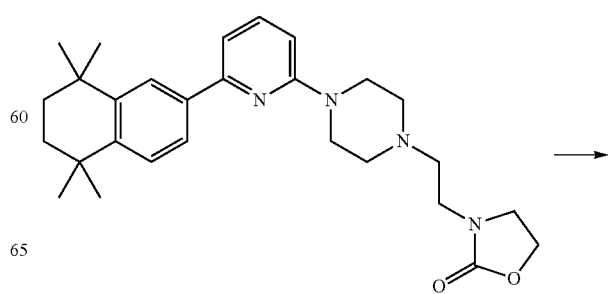

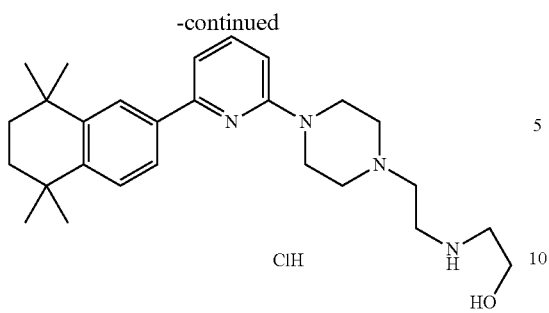

450 µl of 1 N NaOH were added to 70 mg (0.15 mmol) of 3-(2-{4-[6-(5,5,8,8-tetramethyl-5,6,7,8-tetrahydronaphthalen-2-yl)pyridin-2-yl]piperazin-1-yl}ethyl)oxazolidin-2-one in 2 ml of methanol, and the mixture was refluxed for 3 days. The reaction mixture was evaporated, extracted with ethyl acetate, dried and evaporated. The crude product was purified by means of pep. HPLC.

Yield: 50 mg. Rt.=2.68 min (method A), LCMS: 437 (M+H).

$^1$H NMR (500 MHz, DMSO/deuterated TFA) δ 7.87-7.80 (m, 2H), 7.67 (dd, J=8.2, 1.7 Hz, 1H), 7.55-7.48 (m, 1H), 7.43 (d, J=8.3 Hz, 1H), 7.27 (d, J=7.5 Hz, 1H), 7.09 (d, J=8.7 Hz, 1H), 3.74-3.69 (m, 2H), 3.61-3.38 (m, 4H), 4.3-3.8 (b, 6H), 3.25 (t, J=12.2 Hz, 1H), 3.15-3.08 (m, 2H), 1.77-1.62 (m, 4H), 1.36-1.22 (m, 12H).

FS1003 5-{4-[5-(2-Aminoethoxy)-6-(5,5,8,8-tetramethyl-5,6,7,8-tetrahydronaphthalen-2-yl)pyridin-2-yl]piperazin-1-yl}pentan-1-ol 74 mg (0.09 mmol) of 2-{2-[6-[4-(5-hydroxypentyl)piperazin-1-yl]-2-(5,5,8,8-tetramethyl-5,6,7,8-tetrahydronaphthalen-2-yl)pyridin-3-yloxy]ethyl}isoindole-1,3-dione are dissolved in 2 ml of ethanol, and 9 µl of hydrazine hydrate are added. The reaction mixture is stirred at room temperature for 15 h. A precipitate forms, which is filtered off with suction, washed with ethanol and purified by means of column chromatography on silica gel. The product is converted into the hydrochloride using methanolic HCl.

Yield: 21 mg, beige solid. Rt.=2.38 min (method A), LCMS: 495 (M+H).

$^1$H NMR (500 MHz, DMSO/deuterated TFA) δ 7.83 (s, 1H), 7.68 (d, J=9.1 Hz, 1H), 7.62 (d, J=8.3 Hz, 1H), 7.36 (d, J=8.3 Hz, 1H), 6.99 (d, J=9.2 Hz, 1H), 4.32 (d, J=13.5 Hz, 2H), 4.12 (t, J=5.3 Hz, 2H), 3.58 (d, J=11.7 Hz, 2H), 3.42 (t, J=6.3 Hz, 2H), 3.24 (t, J=12.4 Hz, 2H), 3.18-3.05 (m, 6H), 1.77-1.61 (m, 6H), 1.50-1.41 (m, 2H), 1.35 (dt, J=14.9, 7.5 Hz, 2H), 1.25 (d, J=9.0 Hz, 12H).

FS1004: 4-{(4-Aminobutyl)-[6'-(5,5,8,8-tetramethyl-5,6,7,8-tetrahydronaphthalen-2-yl)-3,4,5,6-tetrahydro-2H-1,2'-bipyridinyl-4-yl]amino}butan-1-ol

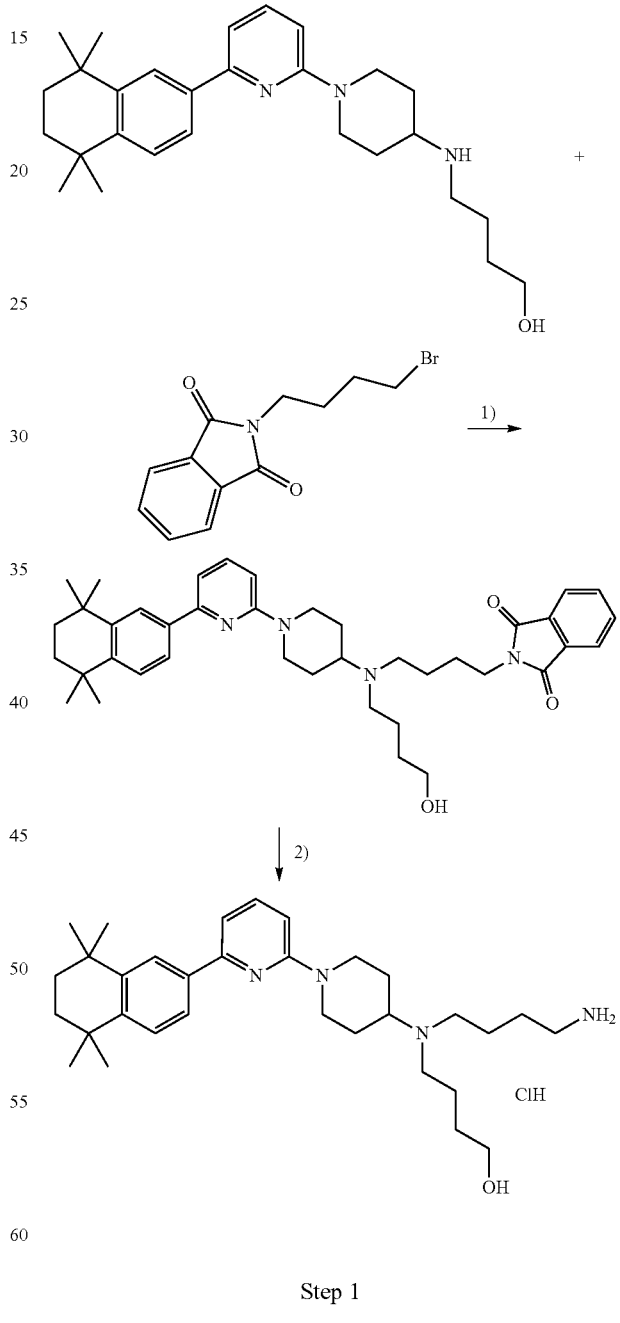

Step 1

The reaction is carried out analogously to FS314.

Yield: 48 mg. Rt.=3.04 min (method A), LCMS: 637 (M+H).

Step 3

The reaction is carried out analogously to FS1002.

Yield: 13 mg. Rt.=2.49 min (method A), LCMS: 507 (M+H).

¹H NMR (400 MHz, DMSO/deuterated TFA) δ 7.98 (dd, J=9.0, 7.4 Hz, 1H), 7.67 (s, 1H), 7.54-7.48 (m, 2H), 7.31 (d, J=9.1 Hz, 1H), 7.12 (d, J=7.3 Hz, 1H), 4.45 (d, J=13.4 Hz, 2H), 3.76-3.66 (m, 1H), 3.48 (t, J=6.0 Hz, 2H), 3.33-3.16 (m, 4H), 3.12-2.97 (m, 2H), 2.86 (t, J=7.4 Hz, 2H), 2.19 (d, J=10.3 Hz, 2H), 1.96-1.84 (m, 2H), 1.84-1.73 (m, 4H), 1.69 (s, 4H), 1.68-1.58 (m, 2H), 1.56-1.46 (m, 2H), 1.29 (d, J=12.2 Hz, 12H).

FS1005 Aminoacetic acid 5-{4-[6-(5,5,8,8-tetramethyl-5,6,7,8-tetrahydronaphthalen-2-yl)pyridin-2-yl]piperazin-1-yl}pentyl ester

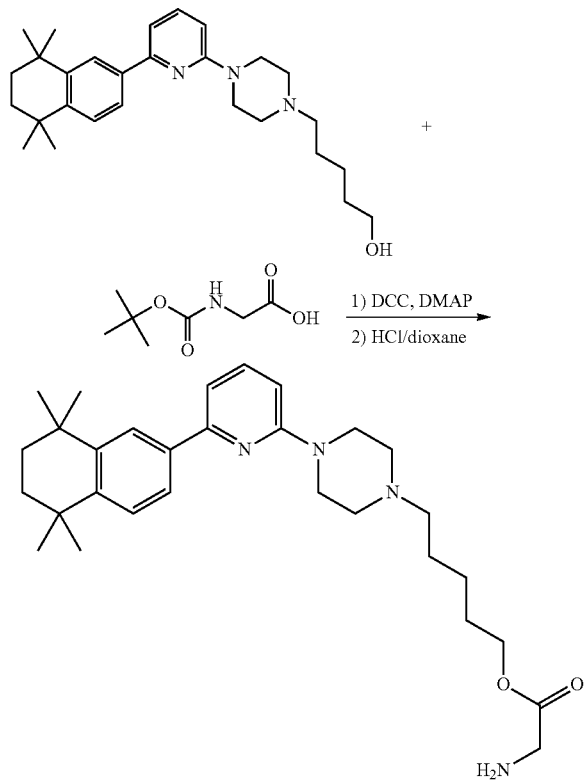

Step 1

30 mg (0.069 mmol) of 5-{4-[6-(5,5,8,8-tetramethyl-5,6,7,8-tetrahydronaphthalen-2-yl)pyridin-2-yl]piperazin-1-yl}pentan-1-ol, 48 mg (0.276 mmol) of Boc-protected glycine and 1 mg of DMAP are dissolved in 2 ml of THF and 0.5 ml of dichloromethane, 28 mg (0.138 mmol) of DCC are added, and the mixture is stirred at room temperature for 18 h. The reaction mixture is diluted with ethyl acetate, extracted with sat. sodium hydrogencarbonate solution and 1 N HCl, dried and evaporated. The product is reacted further directly without further purification

Step 2

The protecting group is cleaved off analogously to FS201. The product is in the form of the hydrochloride.

Yield: 34 mg. Rt.=2.86 min (method A), LCMS: 493 (M+H).

¹H NMR (500 MHz, DMSO/deuterated TFA) δ 7.47 (d, J=1.5 Hz, 1H), 7.38-7.30 (m, 2H), 7.27 (dd, J=8.4, 2.0 Hz, 1H), 7.13 (d, J=1.9 Hz, 1H), 7.05 (d, J=8.5 Hz, 1H), 3.85 (s, 3H), 3.64 (dd, J=34.9, 11.7 Hz, 4H), 3.45 (t, J=6.3 Hz, 2H), 3.31-3.21 (m, 2H), 3.21-3.14 (m, 2H), 3.14-3.03 (m, 2H), 1.77-1.69 (m, 2H), 1.68 (s, 4H), 1.54-1.46 (m, 2H), 1.44-1.34 (m, 2H), 1.28 (d, J=19.2 Hz, 12H).

FS1006 6'-(5,5,8,8-Tetramethyl-5,6,7,8-tetrahydronaphthalen-2-yl)-2,3,5,6-tetrahydro-1,2'-bipyridinyl-4-one

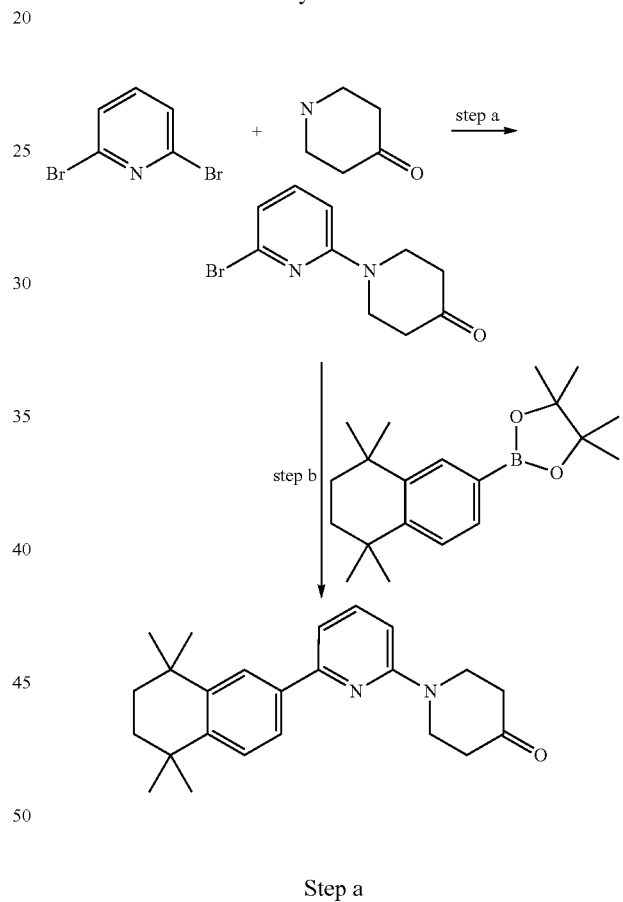

Step a

6'-Bromo-2,3,5,6-tetrahydro-1,2'-bipyridinyl-4-one 5 g (21.11 mmol) of 2,6-dibromopyridine, 2.09 g (21.11 mmol) of piridin-4-one and 7.29 g of potassium carbonate (52.77 mmol) are suspended in 30 ml of DMSO and stirred at 120° C. overnight. Water is then added to the mixture, which is then extracted with EA. The organic phase is washed with a saturated sodium chloride solution, dried over sodium sulfate and evaporated to dryness. The residue formed is purified by means of flash chromatography on silica gel.

2.58 g, yellow oil, Rt.=2.64 min (method A), LCMS: 255 (M+H).

Step b

6'-(5,5,8,8-Tetramethyl-5,6,7,8-tetrahydronaphthalen-2-yl)-2,3,5,6-tetrahydro-1,2'-bipyridinyl-4-one

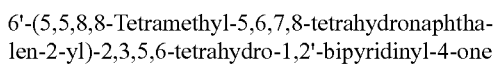

The preparation is carried out analogously to FS102 starting from the product from step a (1 g, 3.92 mmol) and 4,4,5,5-tetramethyl-2-(5,5,8,8-tetramethyl-5,6,7,8-tetrahydronaphthalen-2-yl)-1,3,2-dioxaborolane (1.36 g, 4.31 mmol).

1.04 g, yellow oil, Rt.=3.22 min (method A), LCMS: 363 (M+H).

FS1007 (1R,2S,3R)-3-[6'-(5,5,8,8-Tetramethyl-5,6,7,8-tetrahydronaphthalen-2-yl)-3,4,5,6-tetrahydro-2H-1,2'-bipyridinyl-4-ylamino]cyclopentane-1,2-diol

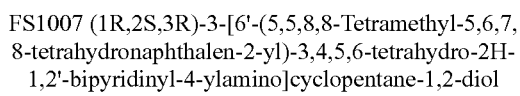

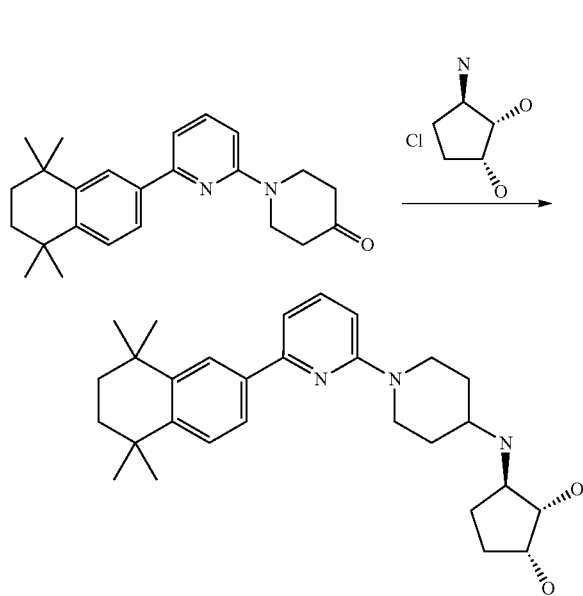

31 mg (0.199 mmol) of (1R,2S,3R)-3-aminocyclopentane-1,2-diol are dissolved in 3.5 ml of THF and 2 ml of DMF, and 33.8 µl of DIPEA are added. 80 mg (0.199 mmol) of 6'-(5,5,8,8-tetramethyl-5,6,7,8-tetrahydronaphthalen-2-yl)-2,3,5,6-tetrahydro-1,2'-bipyridinyl-4-one are added. The mixture is stirred at room temperature for 30 min, 23 µl (0.398 mmol) of glacial acetic acid are added, and the mixture is stirred for a further 10 min. 89 mg (0.398 mmol) of sodium triacetoxyborohydride are subsequently added. The reaction mixture is stirred at room temperature overnight, a concentrated sodium hydrogencarbonate solution is added, and the mixture is extracted twice with EA. The organic phase is dried over sodium sulfate, filtered and evaporated. The residue is purified by means of preparative HPLC. The product is in the form of the hydrochloride.

46 mg, white solid, Rt.=2.54 min (method B), LCMS: 464 (M+H).

$^1$H NMR (500 MHz, DMSO/deuterated TFA) δ=8.09-8.02 (m, 1H), 7.72 (s, 1H), 7.56 (s, 2H), 7.36 (dd, J=9.1, 3.1, 1H), 7.18 (dd, J=7.3, 3.5, 1H), 4.44-4.35 (m, 2H), 4.09-3.96 (m, 2H), 3.70-3.43 (m, 2H), 3.38-3.25 (m, 2H), 2.37-2.22 (m, 2H), 2.07-1.58 (m, 10H), 1.34 (d, J=12.6, 12H).

FS1008 (1S,2R,3S)-3-[6'-(5,5,8,8-Tetramethyl-5,6,7,8-tetrahydronaphthalen-2-yl)-3,4,5,6-tetrahydro-2H-1,2'-bipyridinyl-4-ylamino]cyclopentane-1,2-diol

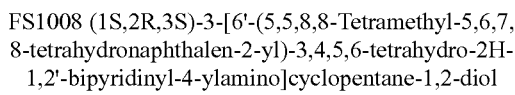

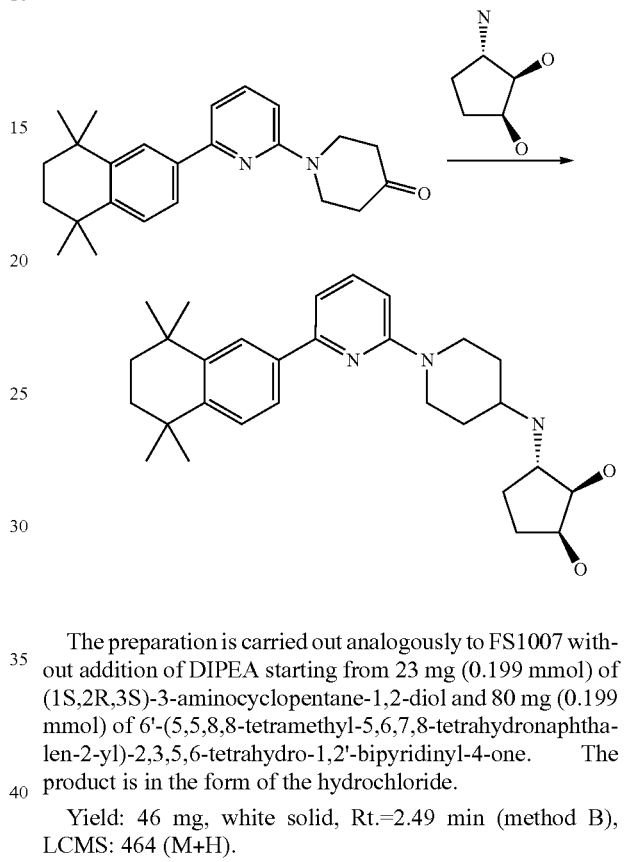

The preparation is carried out analogously to FS1007 without addition of DIPEA starting from 23 mg (0.199 mmol) of (1S,2R,3S)-3-aminocyclopentane-1,2-diol and 80 mg (0.199 mmol) of 6'-(5,5,8,8-tetramethyl-5,6,7,8-tetrahydronaphthalen-2-yl)-2,3,5,6-tetrahydro-1,2'-bipyridinyl-4-one. The product is in the form of the hydrochloride.

Yield: 46 mg, white solid, Rt.=2.49 min (method B), LCMS: 464 (M+H).

$^1$H NMR (500 MHz, DMSO/deuterated TFA) δ=7.91 (d, J=1.8, 1H), 7.71 (dd, J=8.2, 1.8, 1H), 7.65 (t, J=8.0, 1H), 7.40 (d, J=8.3, 1H), 7.17 (d, J=7.4, 1H), 6.88 (d, J=8.5, 1H), 4.50 (d, J=12.7, 2H), 4.01-3.89 (m, 2H), 2.92 (dd, J=27.3, 13.3, 2H), 2.22-2.07 (m, 3H), 1.95-1.84 (m, 1H), 1.68 (s, 4H), 1.65-1.50 (m, 4H), 1.29 (d, J=17.3, 12H).

FS1009 (1S,2R,3R)-3-[6'-(5,5,8,8-Tetramethyl-5,6,7,8-tetrahydronaphthalen-2-yl)-3,4,5,6-tetrahydro-2H-1,2'-bipyridinyl-4-ylamino]cyclopentane-1,2-diol

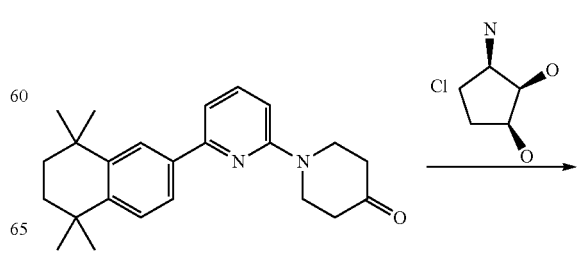

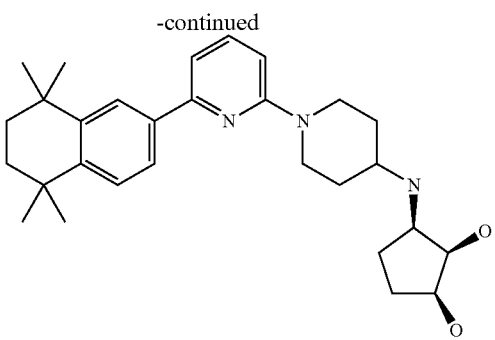

The preparation is carried out analogously to FS1007 starting from 31 mg (0.199 mmol) of (1S,2R,3R)-3-aminocyclopentane-1,2-diol and 80 mg (0.199 mmol) of 6'-(5,5,8,8-tetramethyl-5,6,7,8-tetrahydronaphthalen-2-yl)-2,3,5,6-tetrahydro-1,2'-bipyridinyl-4-one. The product is in the form of the hydrochloride.

Yield: 52 mg, white solid, Rt.=2.54 min (method B), LCMS: 464 (M+H).

$^1$H NMR (400 MHz, DMSO/deuterated TFA) δ=8.04 (dd, J=9.1, 7.4, 1H), 7.72 (s, 1H), 7.55 (s, 2H), 7.35 (d, J=9.0, 1H), 7.18 (d, J=7.2, 1H), 4.39 (d, J=13.4, 2H), 4.09-4.01 (m, 2H), 3.70-3.61 (m, 1H), 3.54-3.43 (m, 1H), 3.30 (t, J=12.0, 2H), 2.29 (dd, J=28.5, 11.2, 2H), 2.06-1.70 (m, 10H), 1.33 (d, J=10.2, 12H).

FS1010 (R)-4-[6'-(5,5,8,8-Tetramethyl-5,6,7,8-tetrahydronaphthalen-2-yl)-3,4,5,6-tetrahydro-2H-1,2'-bipyridinyl-4-ylamino]butane-1,2-diol

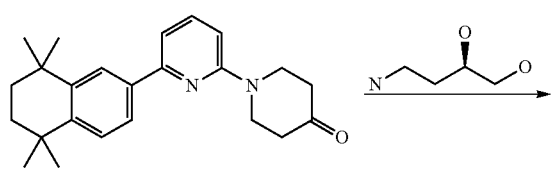

The preparation is carried out analogously to FS1008 starting from 21 mg (0.199 mmol) of (R)-4-aminobutane-1,2-diol and 80 mg (0.199 mmol) of 6-(5,5,8,8-tetramethyl-5,6,7,8-tetrahydronaphthalen-2-yl)-2,3,5,6-tetrahydro-1,2'-bipyridinyl-4-one. The product is in the form of the hydrochloride.

Yield: 29 mg, resin, Rt.=2.43 min (method B), LCMS: 452 (M+H).

$^1$H NMR (400 MHz, DMSO/deuterated TFA) δ=8.04 (dd, J=9.0, 7.4, 1H), 7.72 (s, 1H), 7.60-7.52 (m, 2H), 7.35 (d, J=9.1, 1H), 7.19 (d, J=7.3, 1H), 4.40 (d, J=13.8, 2H), 3.70-3.60 (m, 1H), 3.55-3.42 (m, 2H), 3.41-3.26 (m, 3H), 3.22-3.08 (m, 2H), 2.24 (d, J=10.3, 2H), 1.97-1.86 (m, 1H), 1.84-1.66 (m, 7H), 1.34 (d, J=10.4, 12H).

FS1011 Preparation of (S)-4-[6'-(5,5,8,8-tetramethyl-5,6,7,8-tetrahydronaphthalen-2-yl)-3,4,5,6-tetrahydro-2H-1,2'-bipyridinyl-4-ylamino]butane-1,2-diol

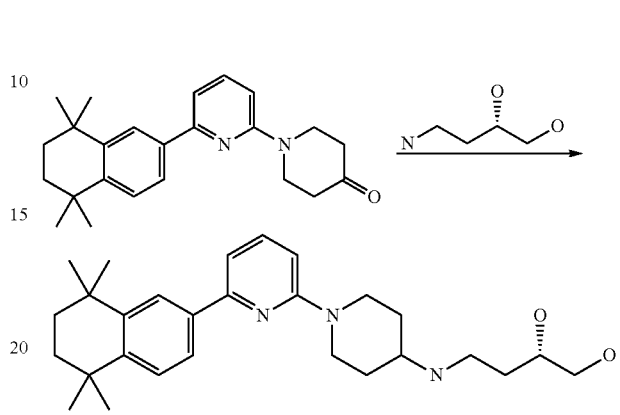

The preparation is carried out analogously to FS1008 starting from 21 mg (0.199 mmol) of (S)-4-aminobutane-1,2-diol and 80 mg (0.199 mmol) of 6'-(5,5,8,8-tetramethyl-5,6,7,8-tetrahydronaphthalen-2-yl)-2,3,5,6-tetrahydro-1,2'-bipyridinyl-4-one. The product is in the form of the hydrochloride.

Yield: 40 mg, resin, Rt.=2.42 min (method B), LCMS: 452 (M+H).

$^1$H NMR (400 MHz, DMSO/deuterated TFA) δ=8.05 (dd, J=9.1, 7.4, 1H), 7.69 (d, J=1.7, 1H), 7.60-7.50 (m, 2H), 7.34 (d, J=9.0, 1H), 7.16 (d, J=7.2, 1H), 4.43-4.34 (m, 2H), 3.73-3.66 (m, 1H), 3.52-3.41 (m, 2H), 3.39-3.28 (m, 2H), 3.24-3.12 (m, 2H), 2.26 (d, J=12.1, 2H), 1.98-1.88 (m, 1H), 1.86-1.78 (m, 2H), 1.75 (s, 4H), 1.34 (d, J=9.3, 12H).

FS1012 ((3aS,4R,7aR)-2,2-Dimethylhexahydrobenzo-1,3-dioxol-4-yl)-[6'-(5,5,8,8-tetramethyl-5,6,7,8-tetrahydronaphthalen-2-yl)-3,4,5,6-tetrahydro-2H-1,2'-bipyridinyl-4-yl]amine

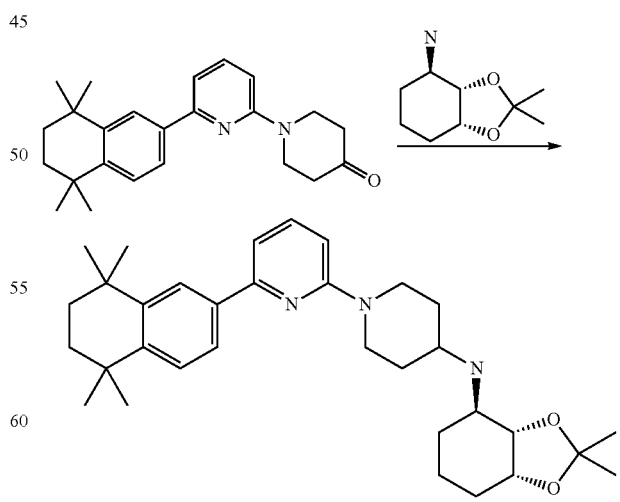

The preparation is carried out analogously to FS1008 in THF starting from 34 mg (0.199 mmol) of (3aS,4R,7aR)-2,2-dimethylhexahydrobenzo-1,3-dioxol-4-yl-amine and 80 mg (0.199 mmol) of 6'-(5,5,8,8-tetramethyl-5,6,7,8-tetrahydronaphthalen-2-yl)-2,3,5,6-tetrahydro-1,2'-bipyridinyl-4-one. The purification is carried out by means of flash chromatography on silica gel.

Yield: 91 mg, yellow resin, Rt.=3.09 min (method B), LCMS: 518 (M+H).

FS1013 (1R,2S,3R)-3-[6'-(5,5,8,8-Tetramethyl-5,6,7,8-tetrahydronaphthalen-2-yl)-3,4,5,6-tetrahydro-2H-1,2'-bi pyridinyl-4-ylamino]cyclohexane-1,2-diol

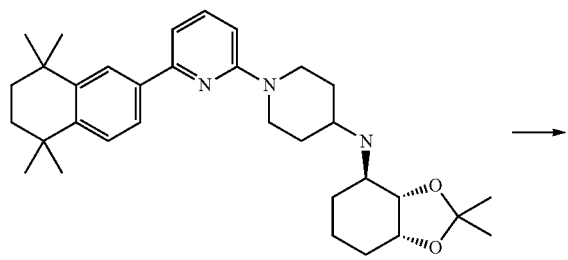

10 ml of 1.25 N HCl in methanol are added to 91 mg of ((3aS,4R,7aR)-2,2-dimethylhexahydrobenzo-1,3-dioxol-4-yl)-[6'-(5,5,8,8-tetramethyl-5,6,7,8-tetrahydronaphthalen-2-yl)-3,4,5,6-tetrahydro-2H-1,2'-bipyridinyl-4-yl]amine, and the mixture is stirred at room temperature overnight. The reaction mixture is evaporated and dried under high vacuum. The product is in the form of the hydrochloride.

Yield: 106 mg, pale solid, Rt.=2.61 min (method B), LCMS: 478 (M+H).

$^1$H NMR (500 MHz, DMSO/deuterated TFA) δ=8.05 (dd, J=9.0, 7.4, 1H), 7.72 (s, 1H), 7.56 (s, 2H), 7.36 (d, J=9.1, 1H), 7.19 (d, J=7.3, 1H), 4.41 (d, J=13.4, 2H), 3.99 (d, J=2.4, 1H), 3.73-3.62 (m, 1H), 3.54-3.49 (m, 1H), 3.37-3.25 (m, 3H), 2.26-2.08 (m, 3H), 2.05-1.93 (m, 1H), 1.86-1.64 (m, 7H), 1.56-1.39 (m, 3H), 1.34 (d, J=13.0, 12H).

FS1014 ((3aR,4S,7aS)-2,2-Dimethylhexahydrobenzo-1,3-dioxol-4-yl)-[6'-(5,5,8,8-tetramethyl-5,6,7,8-tetrahydronaphthalen-2-yl)-3,4,5,6-tetrahydro-2H-1,2'-bipyridinyl-4-yl]amine

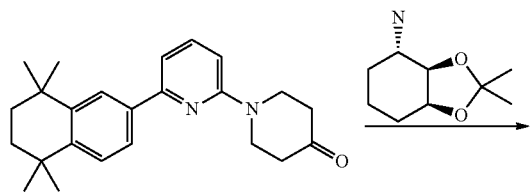

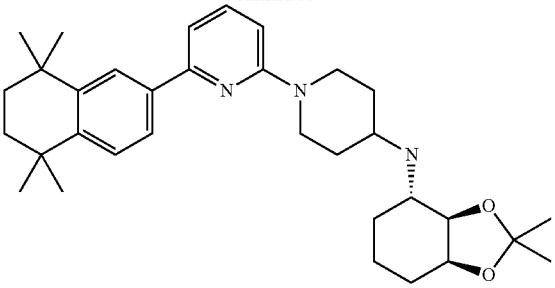

The preparation is carried out analogously to FS1008 in THF starting from 62 mg (0.360 mmol) of (3aR,4S,7aS)-2,2-dimethylhexahydrobenzo-1,3-dioxol-4-ylamine and 145 mg (0.360 mmol) of 6'-(5,5,8,8-tetramethyl-5,6,7,8-tetrahydronaphthalen-2-yl)-2,3,5,6-tetrahydro-1,2'-bipyridinyl-4-one. The purification is carried out by means of flash chromatography on silica gel.

Yield: 168 mg, colourless resin, Rt.=3.58 min (method B), LCMS: 518 (M+H).

FS1015 (1S,2R,3S)-3-[6'-(5,5,8,8-Tetramethyl-5,6,7,8-tetrahydronaphthalen-2-yl)-3,4,5,6-tetrahydro-2H-1,2'-bipyridinyl-4-ylamino]cyclohexane-1,2-diol

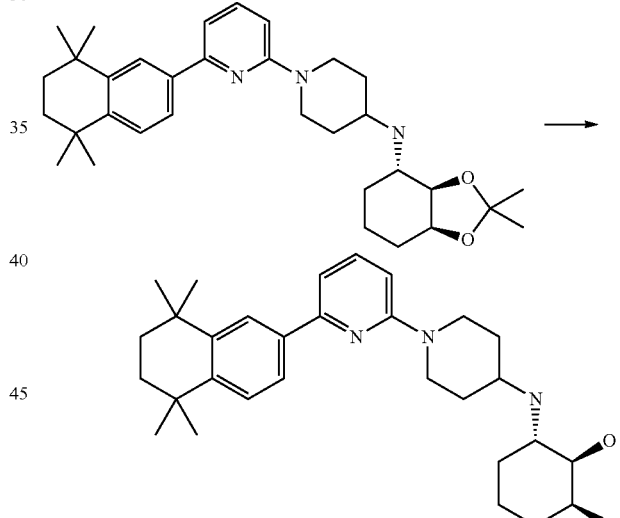

10 ml of 1.25 N HCl in methanol are added to 168 mg of ((3aR,4S,7aS)-2,2-dimethylhexahydrobenzo-1,3-dioxol-4-yl)-[6'-(5,5,8,8-tetramethyl-5,6,7,8-tetrahydronaphthalen-2-yl)-3,4,5,6-tetrahydro-2H-1,2'-bipyridinyl-4-yl]amine, and the mixture is stirred at room temperature overnight. The reaction mixture is evaporated and dried under high vacuum. The product is in the form of the hydrochloride.

Yield: 171 mg, pale solid, Rt.=2.73 min (method B), LCMS: 478 (M+H).

$^1$H NMR (500 MHz, DMSO/deuterated TFA) δ=8.06 (dd, J=9.1, 7.4, 1H), 7.71 (d, J=1.1, 1H), 7.59-7.52 (m, 2H), 7.37 (d, J=9.1, 1H), 7.18 (d, J=7.3, 1H), 4.41 (d, J=13.3, 2H), 4.01 (d, J=2.5, 1H), 3.73-3.64 (m, 1H), 3.56-3.51 (m, 1H), 3.37-3.28 (m, 3H), 2.27-2.10 (m, 3H), 2.07-1.97 (m, 1H), 1.89-1.66 (m, 7H), 1.58-1.29 (m, 15H).

FS1016 Preparation of 4-[1-(6-bromopyridin-2-yl)azepan-4-ylamino]butan-1-ol

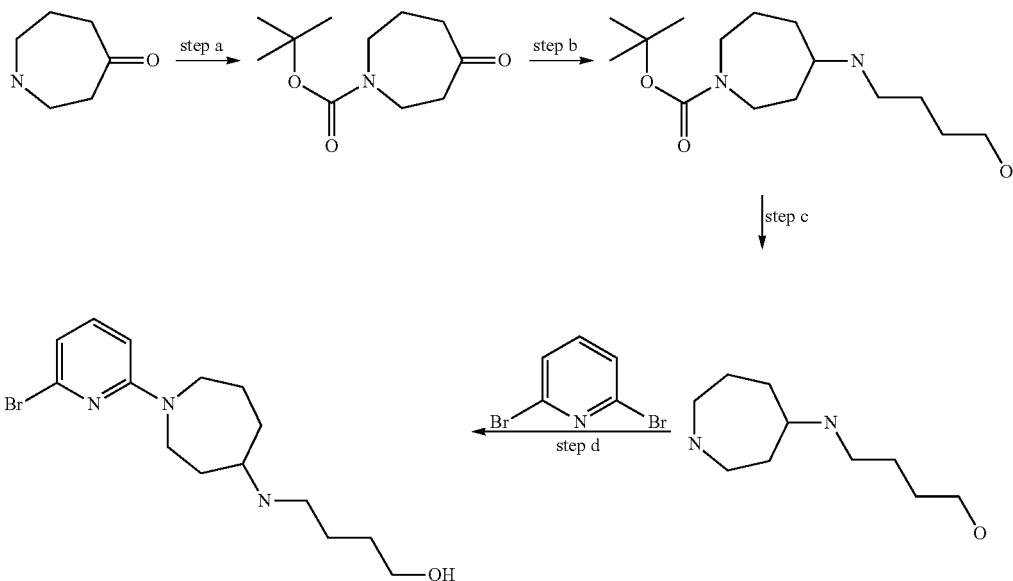

Step a

4-Oxoazepane-1-carboxylic acid tert-butyl ester 1.04 g (6.98 mmol) of azepan-4-one hydrochloride is added to a solution of 1.63 g (15.35 mmol) of sodium carbonate in 10 ml of water. A solution of 1.68 g (7.68 mmol) of di-tert-butyl dicarbonate in 10 ml of THF is slowly added dropwise with vigorous stirring. The reaction mixture is subsequently stirred further at room temperature overnight, evaporated to give an aqueous residue and extracted 3 times with EA. The organic phase is dried over sodium sulfate and evaporated to dryness.

1.62 g, brown oil, Rt.=1.94 min (method B).

Step b 4-(4-Hydroxybutylamino)azepane-1-carboxylic acid tert-butyl ester

The product from step a (1.09 g, 4.65 mmol) is suspended in 10 ml of THF, and 864 µl (9.3 mmol) of 4-amino-1-butanol are added. The mixture is stirred at room temperature for 30 min, 532 µl (9.3 mmol) of glacial acetic acid are added, and the mixture is stirred for a further 10 min. Sodium triacetoxyborohydride (1.97 g, 9.3 mmol) is subsequently added. The reaction mixture is stirred at room temperature overnight, evaporated to dryness, water is added, and the mixture is extracted 3 times with EA. The organic phase is dried over sodium sulfate, filtered and evaporated.

1.39 g, yellow oil, LCMS: 287 (M+H).

Step c 4-(Azepan-4-ylamino)butan-1-ol

The product from step b (1.32 g, 4.65 mmol) is dissolved in 8 ml of dioxane, 16 ml of 4N HCl in dioxane are added, and the mixture is stirred at RT overnight. The reaction mixture is evaporated and dried under high vacuum.

1.09 g, yellow oil, LCMS: 187 (M+H).

Step d

4-[1-(6-Bromopyridin-2-yl)azepan-4-ylamino]butan-1-ol 545 mg (2.3 mmol) of 2,6-dibromopyridine, the product from step c (428 mg, 2.3 mmol) and 954 mg of potassium carbonate (6.9 mmol) are suspended in 20 ml of DMSO and stirred at 120° C. overnight. Water is then added to the mixture, which is then extracted with EA. The organic phase is washed with a saturated sodium chloride solution, dried over sodium sulfate and evaporated to dryness. The residue formed is purified by means of RP flash chromatography on C18 silica gel.

300 mg, colourless oil, Rt.=1.63 min (method B), LCMS: 343 (M+H).

FS1017 Preparation of 4-{1-[6-(5,5,8,8-tetramethyl-5,6,7,8-tetrahydronaphthalen-2-yl)pyridin-2-yl]azepan-4-ylamino}butan-1-ol

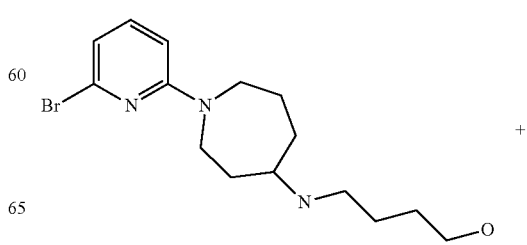

+

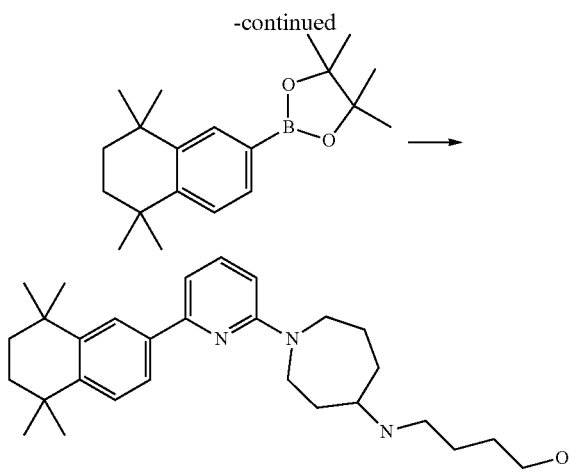

The preparation is carried out analogously to FS102 starting from 106 mg (0.304 mmol) of 4-[1-(6-bromopyridin-2-yl)azepan-4-ylamino]butan-1-ol and 116 mg (0.334 mmol) of 4,4,5,5-tetramethyl-2-(5,5,8,8-tetramethyl-5,6,7,8-tetrahydronaphthalen-2-yl)-1,3,2-dioxaborolane. The crude product is purified by means of RP flash chromatography on C18 silica gel. The product is in the form of the hydrochloride.

68 mg, pale solid, Rt.=2.49 min (method B), LCMS: 450 (M+H).

$^1$H NMR (500 MHz, DMSO/deuterated TFA) δ=7.94 (t, J=8.2, 1H), 7.60 (s, 1H), 7.46 (q, J=8.2, 2H), 7.18 (d, J=9.1, 1H), 7.03 (d, J=7.0, 1H), 3.98-3.87 (m, 1H), 3.84-3.75 (m, 1H), 3.75-3.64 (m, 2H), 3.53-3.38 (m, 2H), 3.34-3.21 (m, 1H), 3.03-2.87 (m, 2H), 2.31 (d, J=12.5, 1H), 2.08 (dd, J=25.8, 14.1, 2H), 1.93-1.43 (m, 11H), 1.33-1.20 (m, 12H).

FS1018 Preparation of 3-[1-(6-bromopyridin-2-yl)azepan-4-ylamino]propan-1-ol

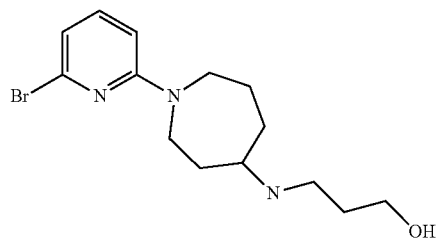 [SMILES: OCCCNC1CCCN(c2cccc(Br)n2)CC1]

The preparation is carried out analogously to 4-[1-(6-bromopyridin-2-yl)azepan-4-ylamino]butan-1-ol starting from 127 μl (1.69 mmol) of 3-amino-1-propanol 524 mg, yellow oil, Rt.=1.59 min (method B), LCMS: 329 (M+H).

FS1019 Preparation of 3-{1-[6-(5,5,8,8-tetramethyl-5,6,7,8-tetrahydronaphthalen-2-yl)pyridin-2-yl]azepan-4-ylamino}propan-1-ol

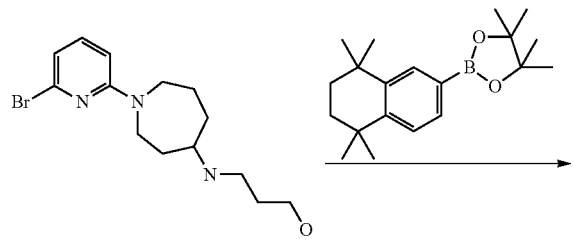

The preparation is carried out analogously to FS102 starting from 107 mg (0.323 mmol) of 3-[1-(6-bromopyridin-2-yl)azepan-4-ylamino]propan-1-ol and 123 mg (0.356 mmol) of 4,4,5,5-tetramethyl-2-(5,5,8,8-tetramethyl-5,6,7,8-tetrahydronaphthalen-2-yl)-1,3,2-dioxaborolane. The crude product is purified by means of RP flash chromatography on C18 silica gel. The product is in the form of the hydrochloride.

84 mg, pale solid, Rt.=2.53 min (method B), LCMS: 436 (M+H).

$^1$H NMR (400 MHz, DMSO/deuterated TFA) δ=8.02 (dd, J=9.1, 7.4, 1H), 7.70 (s, 1H), 7.59-7.51 (m, 2H), 7.26 (d, J=9.2, 1H), 7.12 (d, J=7.3, 1H), 4.08-3.99 (m, 1H), 3.92-3.83 (m, 1H), 3.83-3.71 (m, 2H), 3.57 (t, J=5.9, 2H), 3.41-3.30 (m, 1H), 3.11-3.03 (m, 2H), 2.39 (d, J=13.8, 1H), 2.23-2.04 (m, 2H), 1.98-1.79 (m, 4H), 1.77-1.63 (m, 5H), 1.33 (dd, J=10.0, 7.3, 12H).

FS1020 Preparation of 2-[1-(6-bromopyridin-2-yl)azepan-4-ylamino]ethanol

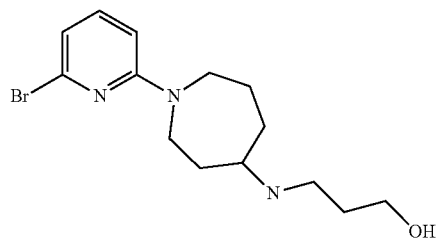 [SMILES: OCCCNC1CCCN(c2cccc(Br)n2)CC1]

The preparation is carried out analogously to 4-[1-(6-bromopyridin-2-yl)azepan-4-ylamino]butan-1-ol starting from 99 μl (1.65 mmol) of ethanolamine 85 mg, colourless oil, Rt.=1.55 min (method B), LCMS: 315 (M+H).

FS1021 Preparation of 2-{1-[6-(5,5,8,8-tetramethyl-5,6,7,8-tetrahydronaphthalen-2-yl)pyridin-2-yl]azepan-4-ylamino}ethanol

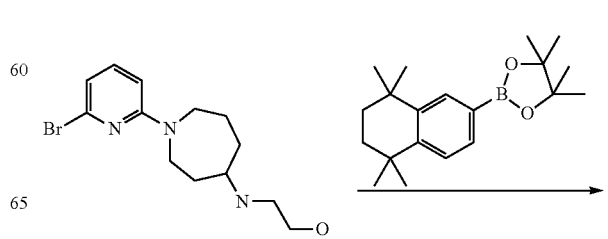

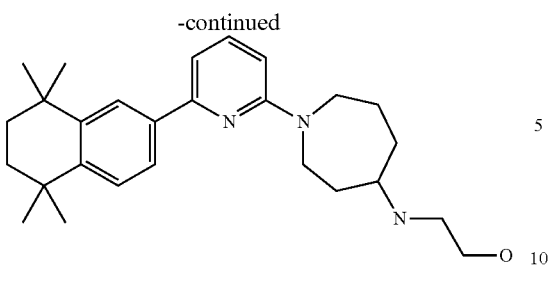

The preparation is carried out analogously to FS102 starting from 79 mg (0.245 mmol) of 2-[1-(6-bromopyridin-2-yl)azepan-4-ylamino]ethanol and 96 mg (0.257 mmol) of 4,4,5,5-tetramethyl-2-(5,5,8,8-tetramethyl-5,6,7,8-tetrahydronaphthalen-2-yl)-1,3,2-dioxaborolane. The product is purified by means of preparative HPLC and converted into the hydrochloride using methanolic HCl.

49 mg, pale solid, Rt.=2.48 min (method B), LCMS: 422 (M+H).

$^1$H NMR (400 MHz, DMSO/deuterated TFA) δ=8.03 (dd, J=9.2, 7.3, 1H), 7.69 (d, J=1.8, 1H), 7.59-7.50 (m, 2H), 7.28 (d, J=9.2, 1H), 7.12 (d, J=7.1, 1H), 4.06-3.96 (m, 1H), 3.94-3.84 (m, 1H), 3.82-3.70 (m, 4H), 3.43-3.34 (m, 1H), 3.13-3.02 (m, 2H), 2.39 (s, 1H), 2.24-2.06 (m, 2H), 2.01-1.83 (m, 2H), 1.78-1.66 (m, 5H), 1.39-1.30 (m, 12H).

FS1022 Preparation of 1-[6-(3,3-dimethylindan-5-yl)pyridin-2-yl]piperazine

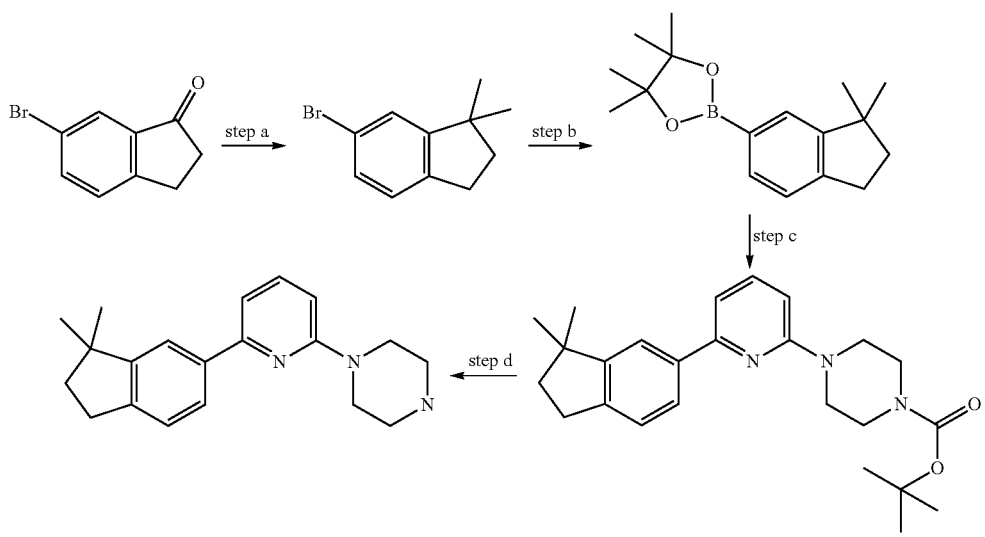

Step a

6-Bromo-1,1-dimethylindane 5.75 ml (52.10 mmol) of titanium(IV) chloride are dissolved in 50 ml of DCM under argon, cooled to −78° C. A 2 M dimethylzinc solution in THF is added dropwise at this temperature (37.22 ml, 74.43 mmol). The mixture is stirred for a further 30 min. A solution of 5.24 g (24.81 mmol) of 6-bromo-1-indanone in 50 ml of DCM is added dropwise at −75° C. The reaction mixture is stirred for a further 45 min, then allowed to come slowly to room temperature, subsequently stirred at room temperature overnight, cooled to 0° C., quenched using MeOH, diluted with water and extracted 3 times with DCM. The org. phase is dried over sodium sulfate, filtered and evaporated. The residue is purified by means of RP flash chromatography on C18 silica gel and subsequently distilled off under reduced pressure.

3.14 g, colourless oil, Rt.=3.64 min (method B)

Step b

2-(3,3-Dimethylindan-5-yl)-4,4,5,5-tetramethyl-1,3,2-dioxaborolane

The preparation is carried out analogously to FS801 starting from the product from step a (1.99 g, 8.85 mmol) and 4,4,5,5-tetramethyl-2-(5,5,8,8-tetramethyl-5,6,7,8-tetrahydronaphthalen-2-yl)-1,3,2-dioxaborolane (2.92 g, 11.50 mmol).

1.34 g, yellow solid, Rt.=3.81 min (method B), LCMS: 273 (M+H).

Step c

4-[6-(3,3-Dimethylindan-5-yl)pyridin-2-yl]piperazine-1-carboxylic acid tert-butyl ester The preparation is carried out analogously to FS 102 starting from 400 mg (1.17 mmol) of 6'-chloro-2,3,5,6-tetrahydro-1,2'-bipyrazinyl-4-carboxylic acid tert-butyl ester and 458 mg (1.26 mmol) of product from step b.

424 mg, white solid, Rt.=3.75 min (method B), LCMS: 408 (M+H).

Step d

1-[6-(3,3-Dimethylindan-5-yl)pyridin-2-yl]piperazine

The compound is prepared analogously to FS201 starting from the product from step c (424 mg, 1.04 mmol). The product is the hydrochloride.

318 mg, white solid. Rt.=2.52 min (method B), LCMS: 308 (M+H).

¹H NMR (400 MHz, DMSO/deuterated TFA) δ=8.01 (dd, J=8.8, 7.6, 1H), 7.69-7.59 (m, 2H), 7.39 (d, J=7.8, 1H), 7.26 (dd, J=8.1, 5.2, 2H), 4.05-3.97 (m, 4H), 3.42-3.34 (m, 4H), 2.98 (t, J=7.2, 2H), 1.99 (t, J=7.2, 2H), 1.32 (s, 6H).

FS1023 5-{4-[6-(3,3-Dimethylindan-5-yl)pyridin-2-yl]piperazin-1-yl}pentan-1-ol

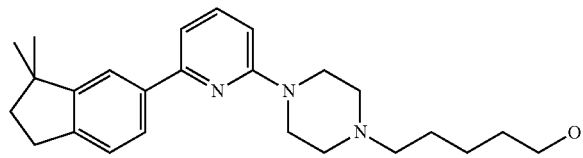 [SMILES: CC1(C)CCc2ccc(-c3cccc(N4CCN(CCCCCO)CC4)n3)cc21]

The preparation is carried out analogously to FS501 starting from 144 mg (0.47 mmol) of 1-[6-(3,3-dimethylindan-5-yl)pyridin-2-yl]piperazine and 96 mg (0.94 mmol) of 5-hydroxypentanal. The product is the hydrochloride.

92 mg, pale solid. Rt.=2.56 min (method B), LCMS: 394 (M+H).

¹H NMR (500 MHz, DMSO/deuterated TFA) δ=7.94 (dd, J=8.6, 7.6, 1H), 7.74-7.68 (m, 2H), 7.36 (d, J=7.8, 1H), 7.30 (d, J=7.4, 1H), 7.19 (d, J=8.8, 1H), 4.54 (d, J=13.8, 2H), 3.70 (d, J=11.9, 2H), 3.50 (t, J=6.3, 3H), 3.25-3.18 (m, 7H), 3.00-2.92 (m, 2H), 1.98 (t, J=7.2, 2H), 1.83-1.74 (m, 2H), 1.59-1.51 (m, 2H), 1.48-1.40 (m, 2H), 1.32 (s, 6H).

FS1024 Acetic acid 4-{4-[6-(3,3-dimethyl indan-5-yl)pyridin-2-yl]piperazin-1-yl}butyl ester

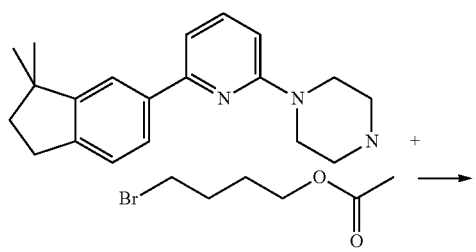

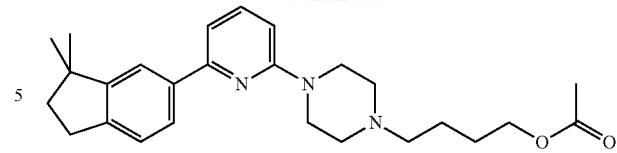

The preparation is carried out analogously to FS401 starting from 142 mg (0.46 mmol) of 1-[6-(3,3-dimethylindan-5-yl)pyridin-2-yl]piperazine and 90 µl of bromobutyl acetate using 2 equiv. of potassium carbonate.

104 mg, yellow oil. Rt.=2.65 min (method B), LCMS: 422 (M+H).

FS1025 4-{4-[6-(3,3-Dimethyl indan-5-yl)pyridin-2-yl]piperazin-1-yl}butan-1-ol

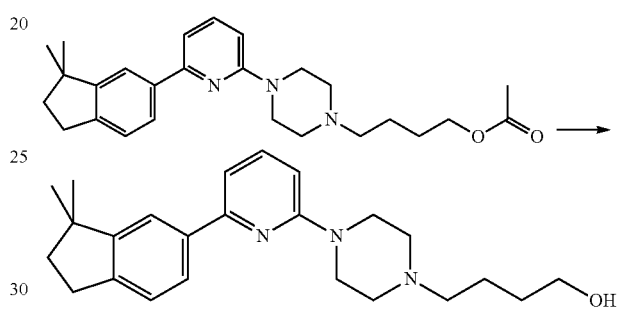

The preparation is carried out analogously to FS402 starting from 104 mg (0.23 mmol) of acetic acid 4-{4-[6-(3,3-dimethylindan-5-yl)pyridin-2-yl]piperazin-1-yl}butyl ester. The product is the hydrochloride.

51 mg, pale solid. Rt.=2.49 min (method B), LCMS: 380 (M+H).

¹H NMR (400 MHz, DMSO/deuterated TFA) δ=7.86 (dd, J=8.6, 7.6, 1H), 7.79-7.72 (m, 2H), 7.32 (t, J=7.8, 2H), 7.10 (d, J=8.6, 1H), 4.54 (d, J=14.0, 2H), 3.68 (d, J=11.6, 2H), 3.48 (dt, J=25.2, 9.2, 4H), 3.29-3.13 (m, 4H), 2.94 (t, J=7.2, 2H), 1.96 (t, J=7.2, 2H), 1.88-1.76 (m, 2H), 1.60-1.49 (m, 2H), 1.31 (s, 6H).

FS1026 Preparation of 6'-(5,5,8,8-tetramethyl-5,6,7,8-tetrahydronaphthalen-2-yl)-3,4,5,6-tetrahydro-2H-1,2'-bipyridinyl-3-ylamine

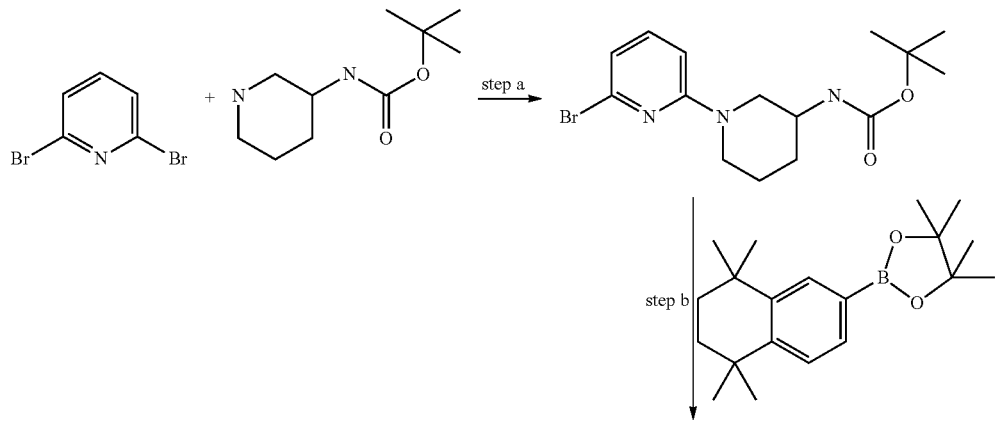

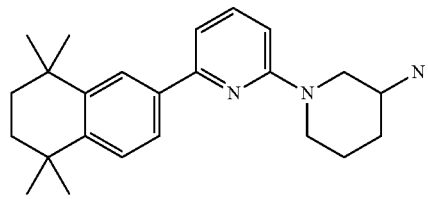
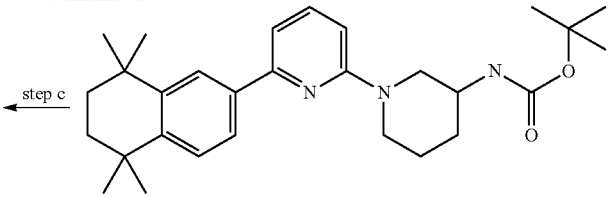

Step a (6'-Bromo-3,4,5,6-tetrahydro-2H-1,2'-bipyridinyl-3-yl)carbamic acid tert-butyl ester The preparation is carried out analogously starting from 1 g (4.23 mmol) of 2,6-dibromopyridine and 845 mg (4.22 mmol) of piperidin-3-ylcarbamic acid tert-butyl ester.
1.28 g, brown oil, Rt.=3.16 min (method B), LCMS: 356 (M+H).

Step b

[6'-(5,5,8,8-Tetramethyl-5,6,7,8-tetrahydronaphthalen-2-yl)-3,4,5,6-tetrahydro-2H-1,2'-bipyridinyl-3-yl]carbamic acid tea-butyl ester The preparation is carried out analogously to FS102 starting from 1.28 g (3.54 mmol) of product from step a and 1.46 g (3.91 mmol) of 4,4,5,5-tetramethyl-2-(5,5,8,8-tetramethyl-5,6,7,8-tetrahydronaphthalen-2-yl)-1,3,2-dioxaborolane.
1.07 g, colourless oil, Rt.=3.61 min (method B), LCMS: 464 (M+H).

Step c

6'-(5,5,8,8-Tetramethyl-5,6,7,8-tetrahydronaphthalen-2-yl)-3,4,5,6-tetrahydro-2H-1,2'-bipyridinyl-3-ylamine The compound is prepared analogously to FS201 starting from the product from step b.
828 mg, yellow solid. Rt.=2.66 min (method B), LCMS: 364 (M+H).
$^1$H NMR (400 MHz, DMSO/deuterated TFA) δ=8.05 (dd, J=9.1, 7.4, 1H), 7.69 (d, J=1.5, 1H), 7.60-7.51 (m, 2H), 7.31 (d, J=9.0, 1H), 7.17 (d, J=7.2, 1H), 4.19 (dd, J=13.5, 3.3, 1H), 4.03-3.93 (m, 1H), 3.66-3.51 (m, 2H), 3.51-3.42 (m, 1H), 2.20-2.10 (m, 1H), 2.00-1.91 (m, 1H), 1.88-1.71 (m, 6H), 1.39-1.30 (m, 12H).

FS1027 Acetic acid 4-[6'-(5,5,8,8-tetramethyl-5,6,7,8-tetrahydronaphthalen-2-yl)-3,4,5,6-tetrahydro-2H-1,2'-bipyridinyl-3-ylamino]butyl ester

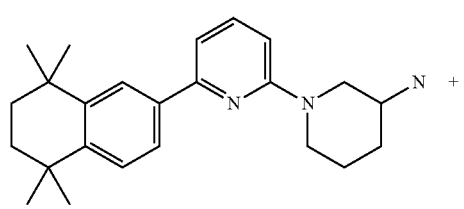

The preparation is carried out analogously to FS401 starting from 94 mg (0.46 mmol) of 6'-(5,5,8,8-tetramethyl-5,6,7,8-tetrahydronaphthalen-2-yl)-3,4,5,6-tetrahydro-2H-1,2'-bipyridinyl-3-ylamine and 45 µl of bromobutyl acetate using 2 equiv. of potassium carbonate.
49 mg, yellow oil. Rt.=2.87 min (method B), LCMS: 478 (M+H).

FS1028 4-[6'-(5,5,8,8-Tetramethyl-5,6,7,8-tetrahydronaphthalen-2-yl)-3,4,5,6-tetrahydro-2H-1,2'-bipyridinyl-3-ylamino]butan-1-ol The preparation is carried out analogously to FS402 starting from 49 mg (0.23 mmol) of acetic acid 4-[6'-(5,5,8,8-tetramethyl-5,6,7,8-tetrahydronaphthalen-2-yl)-3,4,5,6-tetrahydro-2H-1,2'-bipyridinyl-3-ylamino]butyl ester. The product is the hydrochloride.
43 mg, pale solid. Rt.=2.70 min (method B), LCMS: 436 (M+H).
$^1$H NMR (400 MHz, DMSO/deuterated TFA) δ=7.98-7.91 (m, 1H), 7.68 (d, J=1.9, 1H), 7.54-7.43 (m, 2H), 7.23 (dd, J=8.9, 4.3, 1H), 7.14 (d, J=7.3, 1H), 4.42-4.30 (m, 1H), 3.99 (d, J=13.7, 1H), 3.49-3.24 (m, 5H), 3.10-2.97 (m, 2H), 2.19-2.10 (m, 1H), 1.93-1.83 (m, 1H), 1.80-1.60 (m, 8H), 1.54-1.45 (m, 2H), 1.25 (d, J=11.7, 12H).

FS1029 3-[6'-(5,5,8,8-Tetramethyl-5,6,7,8-tetrahydronaphthalen-2-yl)-3,4,5,6-tetrahydro-2H-1,2'-bipyridinyl-3-ylamino]propan-1-ol

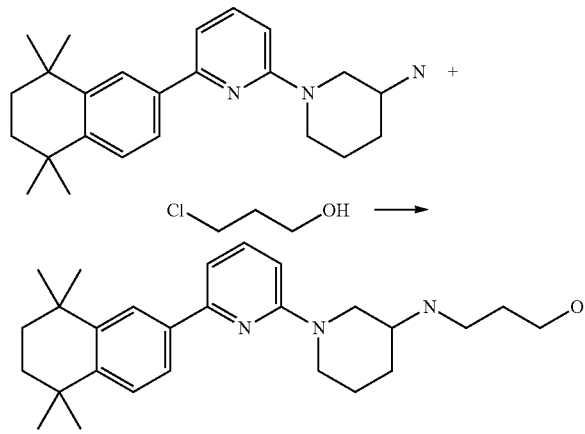

The preparation is carried out analogously to FS301 starting from 73 mg (0.20 mmol) of 6'-(5,5,8,8-tetramethyl-5,6,7,8-tetrahydronaphthalen-2-yl)-3,4,5,6-tetrahydro-2H-1,2'-bipyridinyl-3-ylamine and 33 µl of 3-chloro-1-propanol. The product is the hydrochloride.

75 mg, pale solid. Rt.=3.44 min (method B), LCMS: 422 (M+H).

$^1$H NMR (500 MHz, DMSO/deuterated TFA) δ=7.97 (dd, J=16.5, 8.9, 1H), 7.77 (dd, J=16.4, 1.8, 1H), 7.68-7.59 (m, 1H), 7.52 (dd, J=8.3, 2.8, 1H), 7.27-7.18 (m, 2H), 4.32 (dd, J=100.2, 11.2, 1H), 4.10-3.91 (m, 1H), 3.57 (t, J=5.9, 1H), 3.55-3.30 (m, 3H), 3.24-3.15 (m, 4H), 2.24-2.06 (m, 1H), 1.96-1.68 (m, 8H), 1.37-1.29 (m, 12H).

FS1030 Preparation of 1-[6-(5,5,8,8-tetramethyl-5,6,7,8-tetrahydronaphthalen-2-yl)pyridin-2-yl]-1,4-diazepane

Step a 4-(6-Bromopyridin-2-yl)-1,4-diazepane-1-carboxylic acid tert-butyl ester The preparation is carried out analogously starting from 1.02 g (4.31 mmol) of 2,6-dibromopyridine and 856 mg (4.27 mmol) of azepan-4-ylcarbamic acid tert-butyl ester.

1.17 g, brown oil, Rt.=3.19 min (method B), LCMS: 357 (M+H).

Step b

4-[6-(5,5,8,8-Tetramethyl-5,6,7,8-tetrahydronaphthalen-2-yl)pyridin-2-yl]-1,4-diazepane-1-carboxylic acid tert-butyl ester The preparation is carried out analogously to FS102 starting from 1.13 g (3.18 mmol) of product from step a and 1.46 g (3.49 mmol) of 4,4,5,5-tetramethyl-2-(5,5,8,8-tetramethyl-5,6,7,8-tetrahydronaphthalen-2-yl)-1,3,2-dioxaborolane.

1.01 g, colourless oil, Rt.=3.91 min (method B), LCMS: 464 (M+H).

Step c

1-[6-(5,5,8,8-Tetramethyl-5,6,7,8-tetrahydronaphthalen-2-yl)pyridin-2-yl]-1,4-diazepane The compound is prepared analogously to FS201 starting from the product from step b.

627 mg, white crystals. Rt.=2.71 min (method B), LCMS: 364 (M+H).

$^1$H NMR (400 MHz, DMSO/deuterated TFA) δ=8.00 (dd, J=9.1, 7.4, 1H), 7.70 (s, 1H), 7.54 (s, 2H), 7.21 (dd, J=35.0,

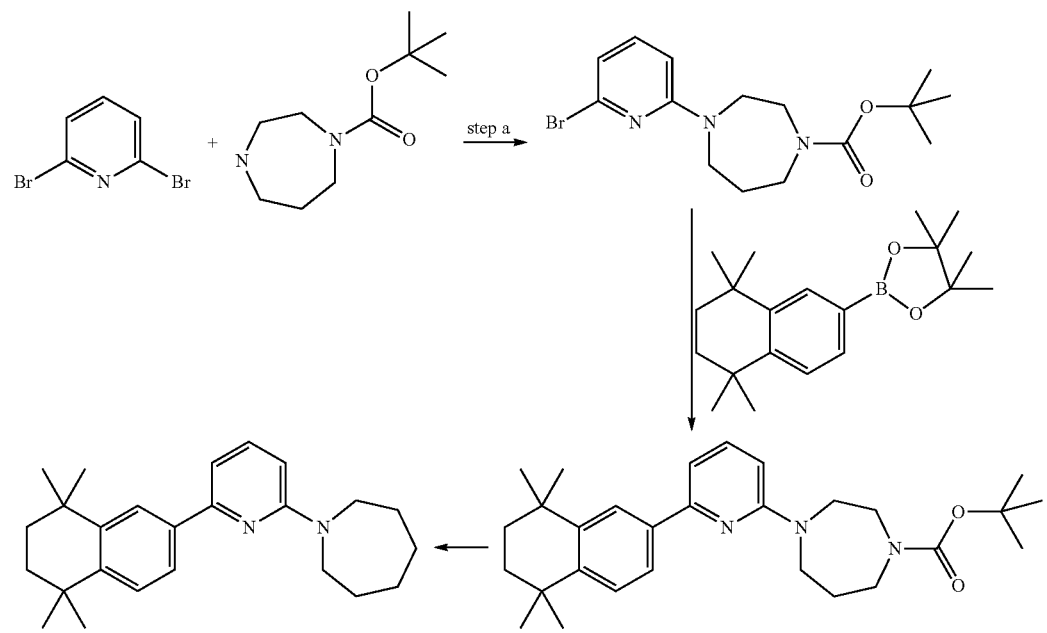

8.2, 2H), 4.15-4.07 (m, 2H), 3.89 (t, J=5.8, 2H), 3.50-3.41 (m, 2H), 3.38-3.30 (m, 2H), 3.23 (s, 2H), 2.28-2.15 (m, 2H), 1.73 (s, 4H), 1.33 (d, J=9.7, 12H).

FS1031 Acetic acid 4-{4-[6-(5,5,8,8-tetramethyl-5,6,7,8-tetrahydronaphthalen-2-yl)-pyridin-2-yl]-1,4-diazepan-1-yl}butylester

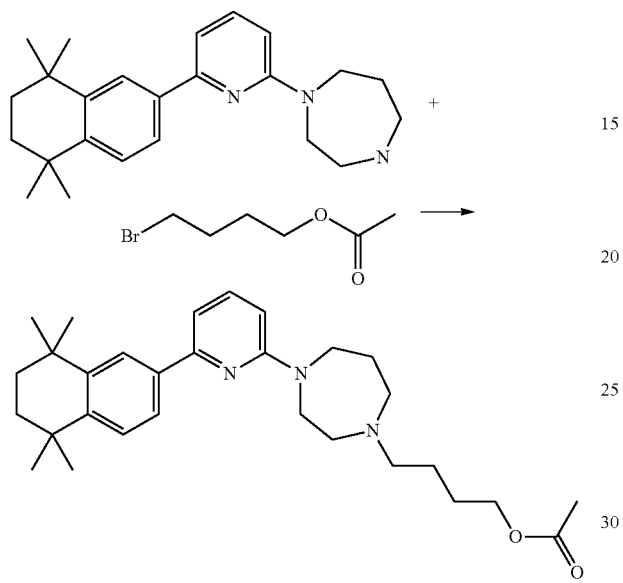

The preparation is carried out analogously to FS401 starting from 68 mg (0.19 mmol) of 1-[6-(5,5,8,8-tetramethyl-5,6,7,8-tetrahydronaphthalen-2-yl)-pyridin-2-yl]-1,4-diazepane and 34 µl of bromobutyl acetate using 2 equiv. of potassium carbonate.

FS1032 4-{4-[6-(5,5,8,8-Tetramethyl-5,6,7,8-tetrahydronaphthalen-2-yl)pyridin-2-yl]-1,4-diazepan-1-yl}butan-1-ol

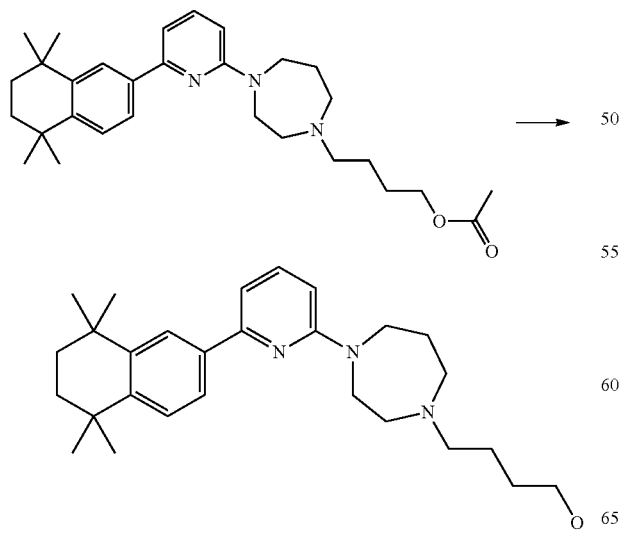

The preparation is carried out analogously to FS402. The product is the hydrochloride.

40 mg, pale solid. Rt.=2.73 min (method B), LCMS: 436 (M+H).

¹H NMR (500 MHz, DMSO/deuterated TFA) δ=7.97-7.89 (m, 1H), 7.60 (s, 1H), 7.51-7.40 (m, 2H), 7.20-7.03 (m, 2H), 4.35 (t, J=5.7, 1H), 4.24-4.14 (m, 1H), 4.05-3.94 (m, 1H), 3.87-3.80 (m, 1H), 3.77-3.61 (m, 2H), 3.60-3.51 (m, 1H), 3.43 (t, J=6.0, 1H), 3.39-3.23 (m, 2H), 3.22-3.10 (m, 2H), 2.40-2.15 (m, 2H), 1.82-1.69 (m, 3H), 1.65 (s, 4H), 1.50-1.41 (m, 1H), 1.25 (d, J=22.4, 12H).

FS1033 3-{4-[6-(5,5,8,8-Tetramethyl-5,6,7,8-tetrahydronaphthalen-2-yl)pyridin-2-yl]-1,4-diazepan-1-yl}propan-1-ol

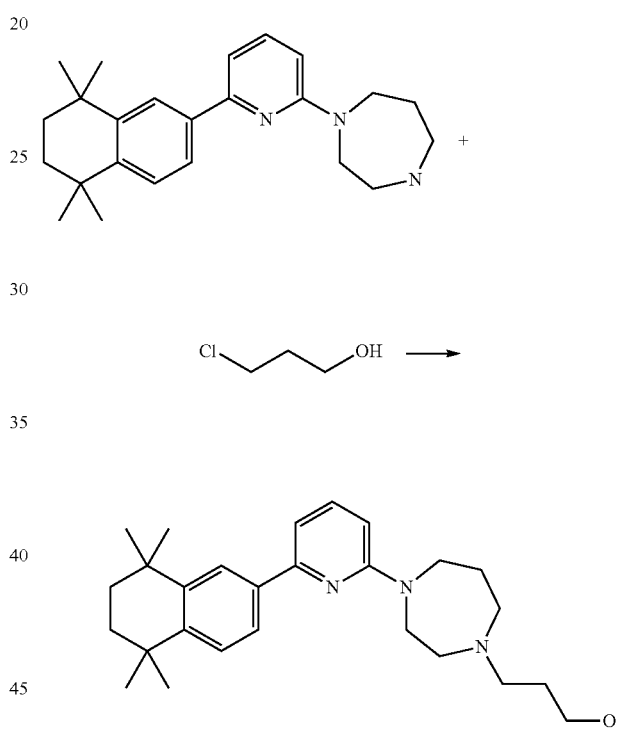

The preparation is carried out analogously to FS301 starting from 66 mg (0.18 mmol) of 1-[6-(5,5,8,8-tetramethyl-5,6,7,8-tetrahydronaphthalen-2-yl)-pyridin-2-yl]-1,4-diazepane and 18 µl of 3-chloro-1-propanol. The product is the hydrochloride.

76 mg, pale solid. Rt.=2.75 min (method B), LCMS: 422 (M+H).

¹H NMR (500 MHz, DMSO/deuterated TFA) δ=8.01 (dd, J=8.9, 7.5, 1H), 7.74 (d, J=1.7, 1H), 7.63-7.50 (m, 2H), 7.26-7.16 (m, 2H), 4.36-4.25 (m, 1H), 4.13-4.00 (m, 1H), 3.95-3.85 (m, 1H), 3.84-3.62 (m, 3H), 3.59-3.54 (m, 2H), 3.47-3.26 (m, 4H), 2.43-2.18 (m, 2H), 1.96-1.86 (m, 2H), 1.74 (s, 4H), 1.39-1.29 (m, 12H).

FS1034 Preparation of (S)-2,2-dimethyl-4-((R)-4-oxo-1-triethylsilanyloxybutyl)oxazolidine-3-carboxylic acid tert-butyl ester and (S)-2,2-dimethyl-4-((S)-4-oxo-1-triethylsilanyloxybutyl)oxazolidine-3-carboxylic acid tert-butyl ester

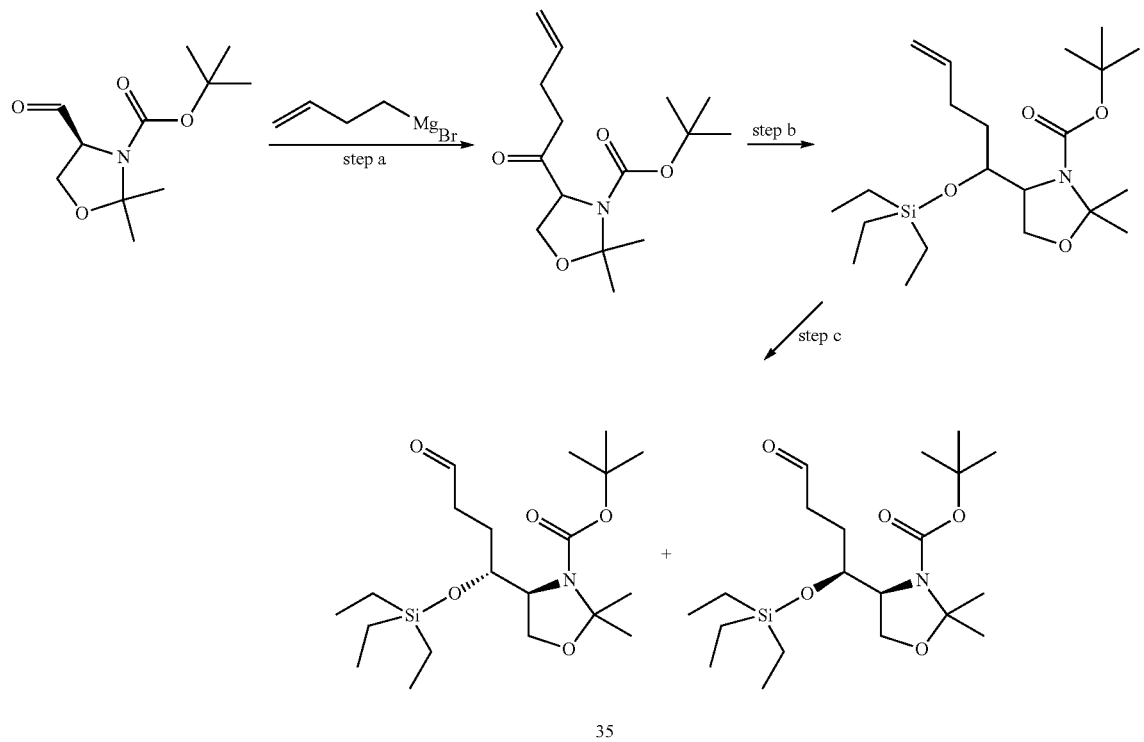

Step a

4-(1-Hydroxypent-4-enyl)-2,2-dimethyloxazolidine-3-carboxylic acid tert-butyl ester 5 g (21.81 mmol) of (S)-4-formyl-2,2-dimethyloxazolidine-3-carboxylic acid tert-butyl ester are dissolved in 33 ml of THF, placed under argon and cooled to −78° C. 43.62 ml (21.81 mmol) of a 0.5 M 3-butenylmagnesium bromide solution in THF are added dropwise. The mixture is stirred further at room temperature overnight. After TLC check, about 90 ml of a saturated $NH_4Cl$ solution are added to the mixture with cooling, the mixture is stirred further overnight and diluted with about 50 ml of water. The phases are separated, and the aqueous phase is extracted a further twice with EA. The combined organic phases are dried over sodium sulfate, filtered and evaporated. The oily residue is subjected to flash chromatography on silica gel.

4.89 g, colourless oil.

Step b

2,2-Dimethyl-4-(1-triethylsilanyloxypent-4-enyl)oxazolidine-3-carboxylic acid tert-butyl ester 4.89 g (17.14 mmol) of product from step a are dissolved in 200 ml of DCM, placed under nitrogen and cooled to 0° C. 2.58 g (17.14 mmol) of chlorotriethylsilane and 209 mg (1.71 mmol) of 4-(dimethylamino)pyridine are added. The reaction solution is stirred at 0° C. for a further 15 min. 4.75 ml (34.27 mmol) of triethylamine are subsequently added. The mixture is allowed to come back to room temperature and is stirred further overnight. After TLC check, about 200 ml of a saturated $NH_4Cl$ solution are added to the reaction mixture. The phases are separated, and the aqueous phase is extracted a further twice with EA. The combined organic phases are dried over sodium sulfate, filtered and evaporated. The residue is subjected to flash chromatography on silica gel.

Clear colourless oil, 5.02 g.

Step c

(S)-2,2-Dimethyl-4-((R)-4-oxo-1-triethylsilanyloxybutyl)oxazolidine-3-carboxylic acid tert-butyl ester and (S)-2,2-dimethyl-4-((S)-4-oxo-1-triethylsilanyloxybutyl)-oxazolidine-3-carboxylic acid tert-butyl ester 5.02 g (12.56 mmol) of product from step b are dissolved in 140 ml of DCM and cooled to −78° C. 2.11 g (25.12 mmol) of sodium hydrogencarbonate are added at this temperature, and ozone is passed through the mixture with stirring for 2.5 h until the solution has a blue coloration. After TLC check, oxygen is then passed through the mixture for 1.5 h until complete decoloration. Triphenylphsophine (3.30 g, 12.56 mmol) is subsequently added. The mixture is stirred at room temperature overnight and then filtered off. The filtrate is evaporated to dryness in a rotary evaporator. The 2 isomers are separated by means of flash chromatography on silica gel.

Isomer c1: clear colourless oil, 1.21 g.
Isomer c2: clear colourless oil, 1.83 g.

FS1035 Preparation of (2S,3R)-2-amino-6-{4-[6-(5,5,8,8-tetramethyl-5,6,7,8-tetrahydronaphthalen-2-yl)pyridin-2-yl]piperazin-1-yl}hexane-1,3-diol

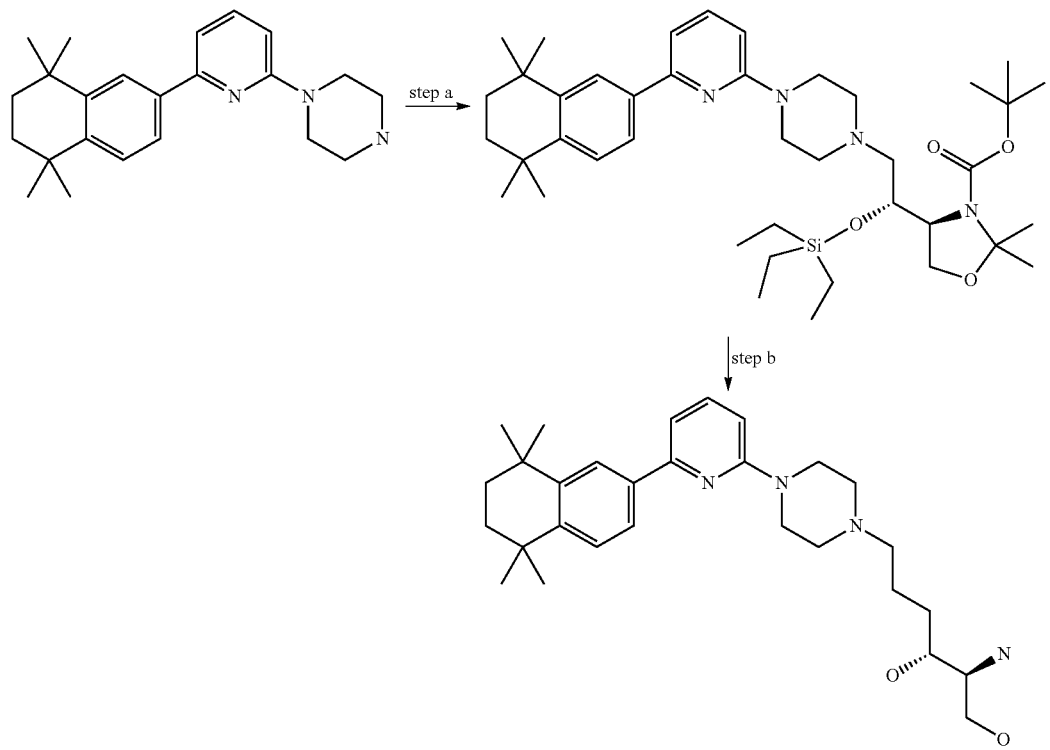

Step a (S)-2,2-Dimethyl-4-((R)-4-{4-[6-(5,5,8,8-tetramethyl-5,6,7,8-tetrahydronaohthalen-2-yl)pyridin-2-yl]piperazin-1-yl}-1-triethylsilanyloxybutyl)oxazolidine-3-carboxylic acid tert-butyl ester 4.3 ml of THF and 175 µl of glacial acetic acid are added to 100 mg (0.29 mmol) of 1-[6-(5,5,8,8-tetramethyl-5,6,7,8-tetrahydronaphthalen-2-yl)pyridin-2-yl]piperazine, and 138 mg (0.34 mmol) of isomer c1 are added. The reaction mixture is stirred at 40° C. for 30 min. 121 mg (0.57 mmol) of sodium triacetoxyborohydride are subsequently added. The reaction mixture is stirred at 40° C. overnight, suspended with 15 ml of EA, washed with 5 ml each of a saturated sodium hydrogencarbonate solution and a saturated sodium chloride solution. The organic phase is dried over sodium sulfate, filtered and evaporated to dryness.

342 mg, clear oil, Rt.=4.00 min (method B), LCMS: 736 (M+H).

Step b (2S,3R)-2-Amino-6-{4-[6-(5,5,8,8-tetramethyl-5,6,7,8-tetrahydronaphthalen-2-yl)-pyridin-2-yl]piperazin-1-yl}hexane-1,3-diol 3 ml of a 1.25 M HCl solution in methanol are added to the intermediate from step a, and the mixture is stirred at room temperature overnight. The reaction mixture is evaporated and separated by means of flash chromatography on C18 silica gel. The product is in the form of the hydrochloride.

31 mg white solid, Rt.=2.32 min (method B), LCMS: 481 (M+H).

$^1$H NMR (400 MHz, DMSO/deuterated TFA) δ=7.96 (dd, J=8.7, 7.6, 1H), 7.82 (d, J=1.9, 1H), 7.65 (dd, J=8.2, 1.9, 1H), 7.51 (d, J=8.3, 1H), 7.29 (d, J=7.4, 1H), 7.22 (d, J=8.8, 1H), 4.63-4.43 (m, 2H), 3.79-3.66 (m, 4H), 3.66-3.49 (m, 4H), 3.29-3.18 (m, 3H), 3.07-2.97 (m, 1H), 2.03-1.81 (m, 2H), 1.74 (s, 4H), 1.69-1.46 (m, 2H), 1.33 (d, J=12.1, 12H).

FS1036 Preparation of (2S,3S)-2-amino-6-{4-[6-(5,5,8,8-tetramethyl-5,6,7,8-tetrahydronaphthalen-2-yl)pyridin-2-yl]piperazin-1-yl}hexane-1,3-diol

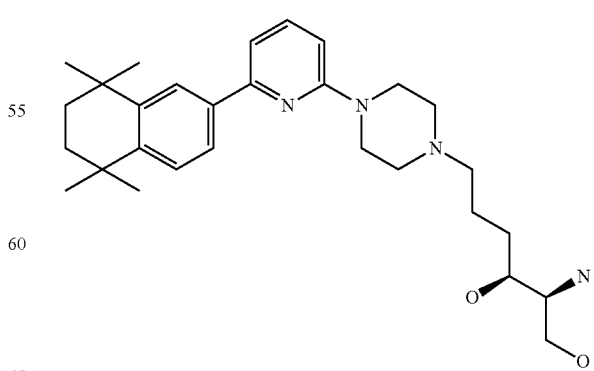

The preparation is carried out analogously starting from 100 mg (0.29 mmol) of 1-[6-(5,5,8,8-tetramethyl-5,6,7,8-tetrahydronaphthalen-2-yl)pyridin-2-yl]piperazine and 138 mg (0.34 mmol) of isomer c2. The product is in the form of the hydrochloride.

44 mg White, Rt.=2.32 min (method B), LCMS: 481 (M+H).

$^1$H NMR (400 MHz, DMSO/deuterated TFA) δ=7.93 (dd, J=8.7, 7.5, 1H), 7.84 (d, J=1.9, 1H), 7.67 (dd, J=8.2, 1.9, 1H), 7.50 (d, J=8.3, 1H), 7.29 (d, J=7.4, 1H), 7.19 (d, J=8.8, 1H), 4.66-4.41 (m, 2H), 3.84-3.64 (m, 5H), 3.60-3.46 (m, 2H), 3.27-3.20 (m, 3H), 3.19-3.10 (m, 1H), 2.05-1.77 (m, 3H), 1.74 (s, 4H), 1.64-1.45 (m, 2H), 1.33 (d, J=12.8, 12H).

FS1101: 1-[3-(2-Methoxyethoxy)-6-(5,5,8,8-tetramethyl-5,6,7,8-tetrahydronaphthalen-2-yl)pyridin-2-yl]piperazine tion mixture is shaken at RT overnight. The reaction mixture is filtered, evaporated to dryness and purified by column chromatography on silica gel.

1.6 g, oil, Rt.=2.86 min (method A), LCMS: 314 (M+H).

Step b

The product from step a and 420 mg (2.23 mmol) of Boc-piperazine are dissolved in 10 ml of DMSO, and 771 mg (5.58 mmol) of potassium carbonate are added. The reaction mixture is stirred at 120° C. for 15 h, water is subsequently added, and the mixture is extracted three times with ethyl acetate,

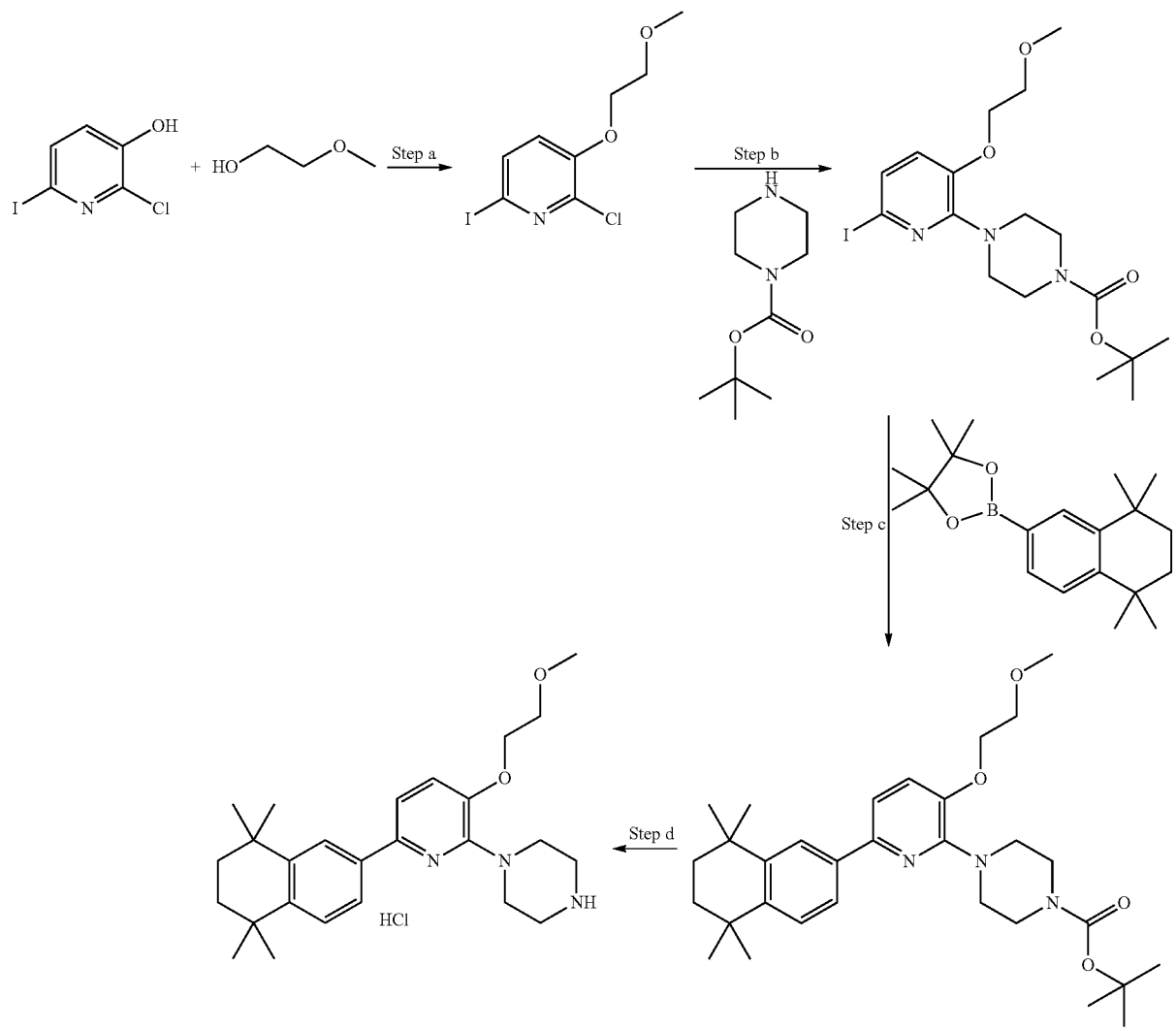

Step a 500 mg (1.96 mmol) of 2-chloro-6-iodopyridin-3-ol are dissolved in 10 ml of DMF, 171 µl (2.15 mmol) of ethylene glycol monomethyl ether, 980 mg (2.94 mmol) of polymer-bound triphenylphosphine (3 mmol/g) and 689 mg (2.94 mmol) of di-tert-butyl azodicarboxylate are added. The reacdried over sodium sulfate and evaporated. The product is reacted further without further purification.

1.3 g, oil, Rt.=3.59 min (method A), LCMS: 464 (M+H).

Step c

The reaction is carried out analogously to FS102.

448 mg, Rt.=4.07 min (method A), LCMS: 524 (M+H).

Step d

The reaction is carried out analogously to FS201.
310 mg, Rt.=3.11 min (method A), LCMS: 424 (M+H).
¹H NMR (500 MHz, DMSO/deuterated TFA) δ 7.90 (d, J=1.9, 1H), 7.68 (dd, J=8.3, 1.9, 1H), 7.48-7.37 (m, 3H), 4.24-4.19 (m, 2H), 3.77-3.70 (m, 6H), 3.58-3.53 (m, 2H), 3.37 (s, 3H), 3.12-3.07 (m, 2H), 1.70 (s, 4H), 1.30 (d, J=19.9, 12H).

The following compounds can be prepared analogously to the compounds described above starting from building blocks which are known from the literature:

| CHEMISTRY | Name | Mass |
|---|---|---|
| Chemistry 0 | 5-{1-[4-(5,5,8,8-Tetramethyl-5,6,7,8-tetrahydro-naphthalen-2-yl)-[1,3,5]triazin-2-yl]-piperidin-4-ylamino}-pentanoic acid amide | 464.66 |
| Chemistry 1 | 2-(2-{1-[4-(5,5,8,8-Tetramethyl-5,6,7,8-tetrahydro-naphthalen-2-yl)-[1,3,5]triazin-2-yl]-piperidin-4-ylamino}-ethyl)-butane-1,4-diol | 481.68 |
| Chemistry 2 | 2-{1-[4-(5,5,8,8-Tetramethyl-5,6,7,8-tetrahydro-naphthalen-2-yl)-[1,3,5]triazin-2-yl]-piperidin-4-ylamino}-pentane-1,5-diol | 467.66 |
| Chemistry 3 | 5-[6'-(5,5,8,8-Tetramethyl-5,6,7,8-tetrahydro-naphthalen-2-yl)-3,4,5,6-tetrahydro-2H-[1,2']bipyridinyl-4-ylamino]-pentanoic acid isopropylamide | 504.76 |
| Chemistry 4 | 5-{1-[4-(5,5,8,8-Tetramethyl-5,6,7,8-tetrahydro-naphthalen-2-yl)-[1,3,5]triazin-2-yl]-piperidin-4-ylamino}-pentanoic acid methylamide | 478.68 |

| CHEMISTRY | Name | Mass |
|---|---|---|
| 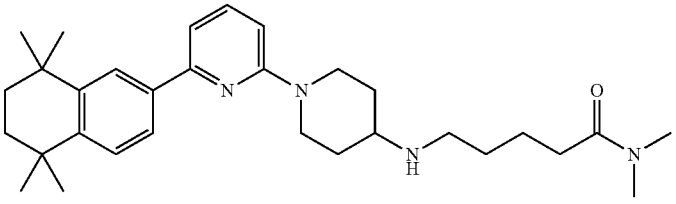<br>Chemistry 5 | 5-[6'-(5,5,8,8-Tetramethyl-5,6,7,8-tetrahydro-naphthalen-2-yl)-3,4,5,6-tetrahydro-2H-[1,2']bipyridinyl-4-ylamino]-pentanoic acid dimethylamide | 490.74 |
| 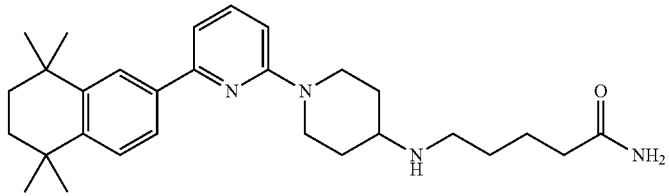<br>Chemistry 6 | 5-[6'-(5,5,8,8-Tetramethyl-5,6,7,8-tetrahydro-naphthalen-2-yl)-3,4,5,6-tetrahydro-2H-[1,2']bipyridinyl-4-ylamino]-pentanoic acid amide | 462.68 |
| 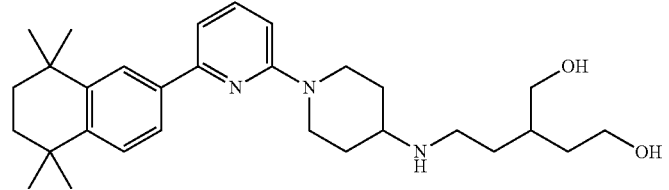<br>Chemistry 7 | 2-{2-[6'-(5,5,8,8-Tetramethyl-5,6,7,8-tetrahydro-naphthalen-2-yl)-3,4,5,6-tetrahydro-2H-[1,2']bipyridinyl-4-ylamino]-ethyl}-butane-1,4-diol | 479.71 |
| 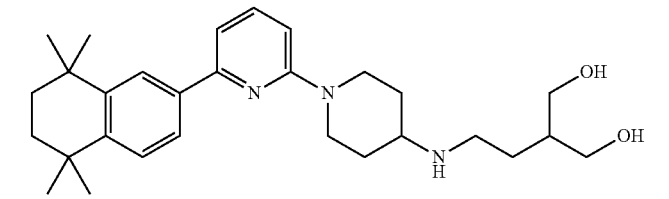<br>Chemistry 8 | 2-{2-[6'-(5,5,8,8-Tetramethyl-5,6,7,8-tetrahydro-naphthalen-2-yl)-3,4,5,6-tetrahydro-2H-[1,2']bipyridinyl-4-ylamino]-ethyl}-propane-1,3-diol | 465.68 |
| 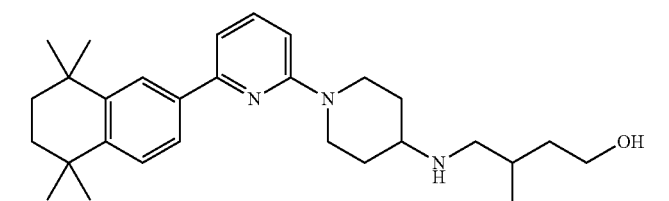<br>Chemistry 9 | 2-{[6'-(5,5,8,8-Tetramethyl-5,6,7,8-tetrahydro-naphthalen-2-yl)-3,4,5,6-tetrahydro-2H-[1,2']bipyridinyl-4-ylamino]-methyl}-butane-1,4-diol | 465.68 |
| 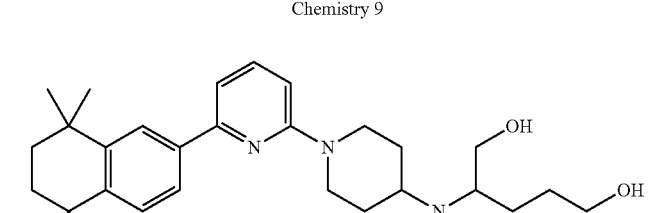<br>Chemistry 10 | 2-[6'-(5,5,8,8-Tetramethyl-5,6,7,8-tetrahydro-naphthalen-2-yl)-3,4,5,6-tetrahydro-2H-[1,2']bipyridinyl-4-ylamino]-pentane-1,5-diol | 465.68 |

-continued

| CHEMISTRY | Name | Mass |
|---|---|---|
| 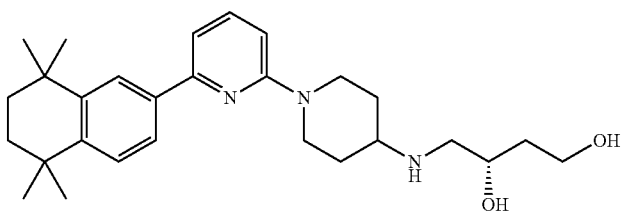<br>Chemistry 11 | (S)-4-[6'-(5,5,8,8-Tetramethyl-5,6,7,8-tetrahydro-naphthalen-2-yl)-3,4,5,6-tetrahydro-2H-[1,2']bipyridinyl-4-ylamino]-butane-1,3-diol | 451.65 |
| 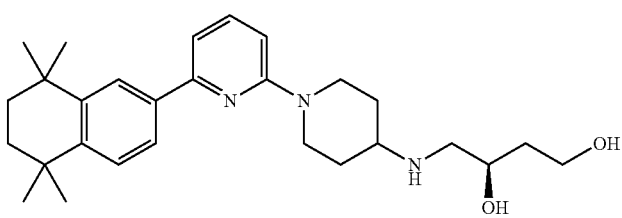<br>Chemistry 12 | (R)-4-[6'-(5,5,8,8-Tetramethyl-5,6,7,8-tetrahydro-naphthalen-2-yl)-3,4,5,6-tetrahydro-2H-[1,2']bipyridinyl-4-ylamino]-butane-1,3-diol | 451.65 |
| 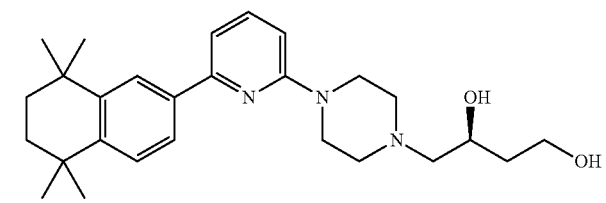<br>Chemistry 13 | (S)-4-{4-[6-(5,5,8,8-Tetramethyl-5,6,7,8-tetrahydro-naphthalen-2-yl)-pyridin-2-yl]-piperazin-1-yl}-butane-1,3-diol | 437.63 |
| 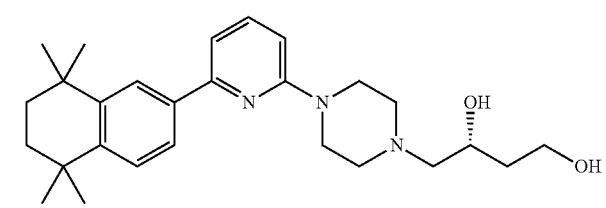<br>Chemistry 14 | (R)-4-{4-[6-(5,5,8,8-Tetramethyl-5,6,7,8-tetrahydro-naphthalen-2-yl)-pyridin-2-yl]-piperazin-1-yl}-butane-1,3-diol | 437.63 |
| 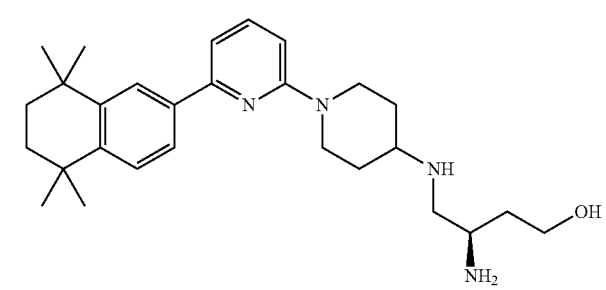<br>Chemistry 15 | (R)-3-Amino-4-[6'-(5,5,8,8-tetramethyl-5,6,7,8-tetrahydro-naphthalen-2-yl)-3,4,5,6-tetrahydro-2H-[1,2']bipyridinyl-4-ylamino]-butan-1-ol | 450.67 |

-continued

| CHEMISTRY | Name | Mass |
|---|---|---|
| 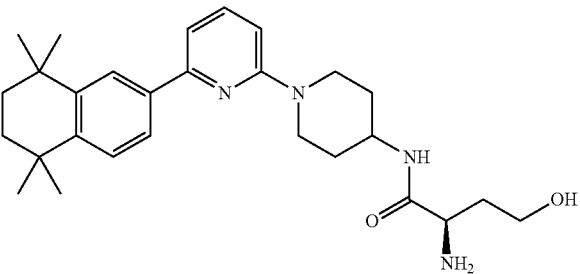<br>Chemistry 16 | (R)-2-Amino-4-hydroxy-N-[6'-(5,5,8,8-tetramethyl-5,6,7,8-tetrahydro-naphthalen-2-yl)-3,4,5,6-tetrahydro-2H-[1,2']bipyridinyl-4-yl]-butyramide | 464.65 |
| 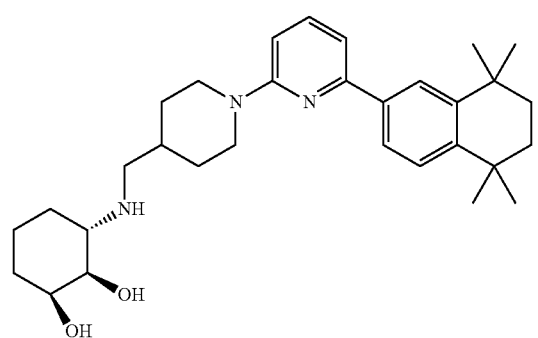<br>Chemistry 19 | (1S,2R,3S)-3-{[6'-(5,5,8,8-Tetramethyl-5,6,7,8-tetrahydro-naphthalen-2-yl)-3,4,5,6-tetrahydro-2H-[1,2']bipyridinyl-4-ylmethyl]-amino}-cyclohexane-1,2-diol | 491.72 |
| 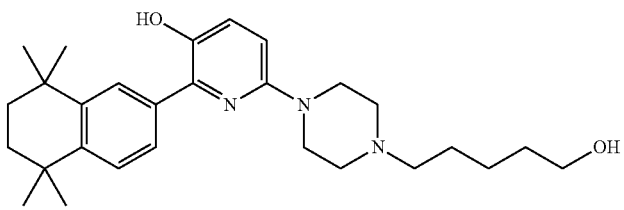<br>Chemistry 20 | 6-[4-(5-Hydroxy-pentyl)-piperazin-1-yl]-2-(5,5,8,8-tetramethyl-5,6,7,8-tetrahydro-naphthalen-2-yl)-pyridin-3-ol | 451.65 |
| 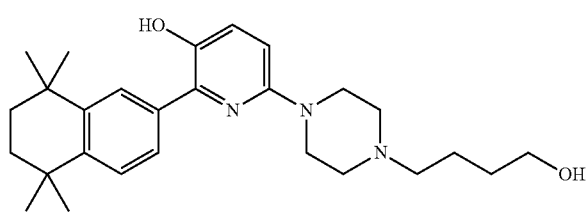<br>Chemistry 21 | 6-[4-(4-Hydroxy-butyl)-piperazin-1-yl]-2-(5,5,8,8-tetramethyl-5,6,7,8-tetrahydro-naphthalen-2-yl)-pyridin-3-ol | 437.63 |
| 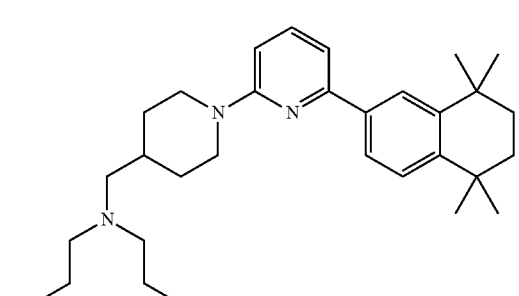<br>Chemistry 22 | 2-{(2-Hydroxy-ethyl)-[6'-(5,5,8,8-tetramethyl-5,6,7,8-tetrahydro-naphthalen-2-yl)-3,4,5,6-tetrahydro-2H-[1,2']bipyridinyl-4-ylmethyl]-amino}-ethanol | 465.68 |

| CHEMISTRY | Name | Mass |
|---|---|---|
| 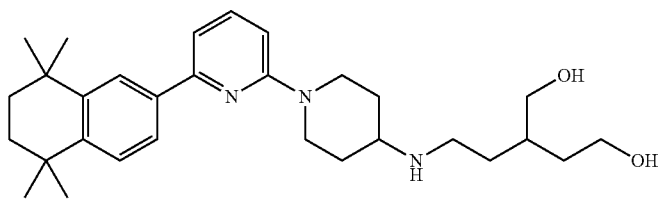<br>Chemistry 23 | 2-{2-[6'-(5,5,8,8-Tetramethyl-5,6,7,8-tetrahydro-naphthalen-2-yl)-3,4,5,6-tetrahydro-2H-[1,2']bipyridinyl-4-ylamino]-ethyl}-butane-1,4-diol | 479.71 |
| 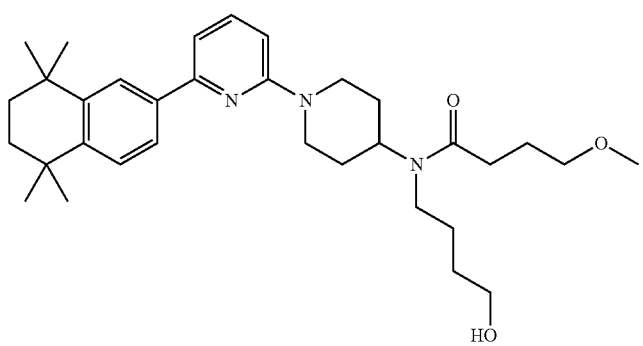<br>Chemistry 24 | N-(4-Hydroxy-butyl)-4-methoxy-N-[6'-(5,5,8,8-tetramethyl-5,6,7,8-tetrahydro-naphthalen-2-yl)-3,4,5,6-tetrahydro-2H-[1,2']bipyridinyl-4-yl]-butyramide | 535.77 |
| 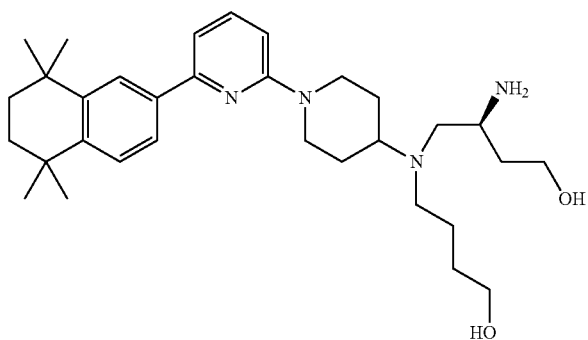<br>Chemistry 25 | (S)-3-Amino-4-{(4-hydroxy-butyl)-[6'-(5,5,8,8-tetramethyl-5,6,7,8-tetrahydro-naphthalen-2-yl)-3,4,5,6-tetrahydro-2H-[1,2']bipyridinyl-4-yl]-amino}-butan-1-ol | 522.78 |
| 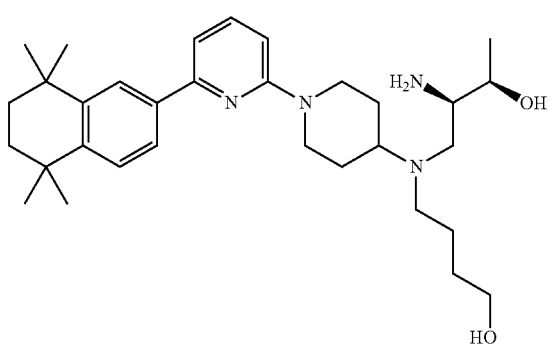<br>Chemistry 27 | 4-{((2R,3R)-2-Amino-3-hydroxy-butyl)-[6'-(5,5,8,8-tetramethyl-5,6,7,8-tetrahydro-naphthalen-2-yl)-3,4,5,6-tetrahydro-2H-[1,2']bipyridinyl-4-yl]-amino}-butan-1-ol | 522.78 |

-continued

| CHEMISTRY | Name | Mass |
|---|---|---|
| 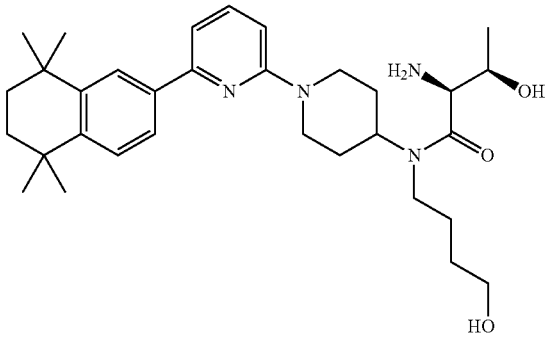<br>Chemistry 28 | (2S,3R)-2-Amino-3-hydroxy-N-(4-hydroxy-butyl)-N-[6'-(5,5,8,8-tetramethyl-5,6,7,8-tetrahydro-naphthalen-2-yl)-3,4,5,6-tetrahydro-2H-[1,2']bipyridinyl-4-yl]-butyramide | 536.76 |
| 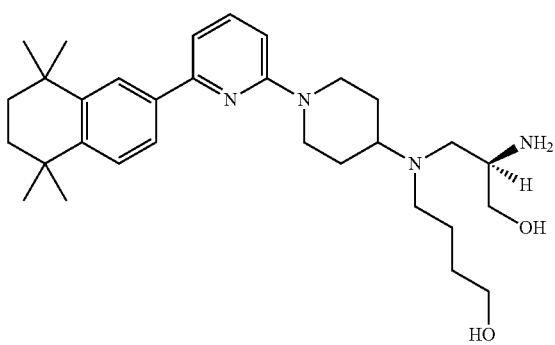<br>Chemistry 29 | 4-{((R)-2-Amino-3-hydroxy-propyl)-[6'-(5,5,8,8-tetramethyl-5,6,7,8-tetrahydro-naphthalen-2-yl)-3,4,5,6-tetrahydro-2H-[1,2']bipyridinyl-4-yl]-amino}-butan-1-ol | 508.75 |
| 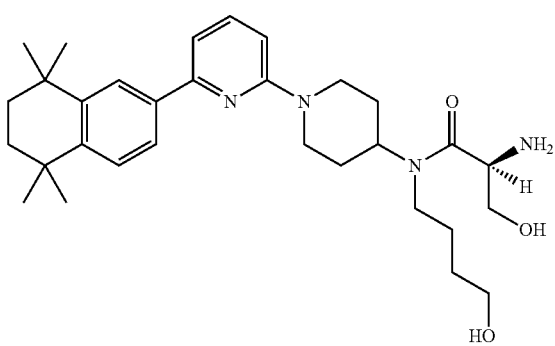<br>Chemistry 30 | (S)-2-Amino-3-hydroxy-N-(4-hydroxy-butyl)-N-[6'-(5,5,8,8-tetramethyl-5,6,7,8-tetrahydro-naphthalen-2-yl)-3,4,5,6-tetrahydro-2H-[1,2']bipyridinyl-4-yl]-propionamide | 522.73 |
| 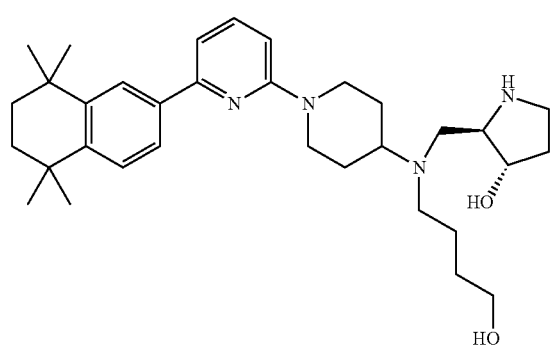<br>Chemistry 31 | (2R,3S)-2-({(4-Hydroxy-butyl)-[6'-(5,5,8,8-tetramethyl-5,6,7,8-tetrahydro-naphthalen-2-yl)-3,4,5,6-tetrahydro-2H-[1,2']bipyridinyl-4-yl]-amino}-methyl)-pyrrolidin-3-ol | 534.79 |

| CHEMISTRY | Name | Mass |
|---|---|---|
| 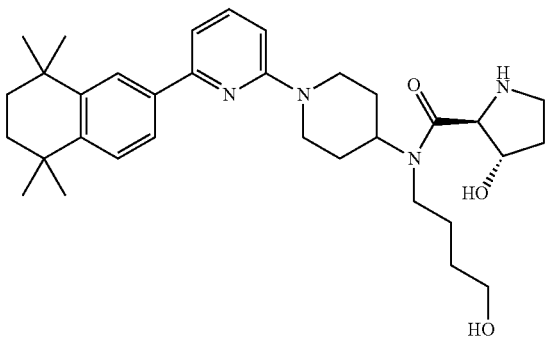<br>Chemistry 32 | (2S,3S)-3-Hydroxy-pyrrolidine-2-carboxylic acid (4-hydroxy-butyl)-[6'-(5,5,8,8-tetramethyl-5,6,7,8-tetrahydro-naphthalen-2-yl)-3,4,5,6-tetrahydro-2H-[1,2']bipyridinyl-4-yl]-amide | 548.77 |
| 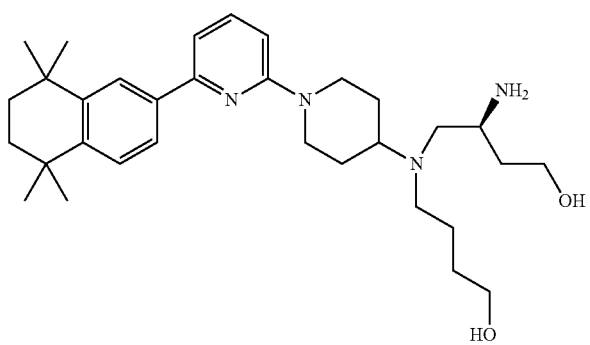<br>Chemistry 33 | (S)-3-Amino-4-{(4-hydroxy-butyl)-[6'-(5,5,8,8-tetramethyl-5,6,7,8-tetrahydro-naphthalen-2-yl)-3,4,5,6-tetrahydro-2H-[1,2']bipyridinyl-4-yl]-amino}-butan-1-ol | 522.78 |

II Biological Assays

The compounds of the formula (I) described in the examples can be tested for a kinase inhibiting activity in by the assays described below. Other assays are known from the literature and could readily be performed by the person skilled in the art (see, for example, Dhanabal et al., *Cancer Res.* 59:189-197; Xin et al., *J. Biol. Chem.* 274:9116-9121; Sheu et al., *Anticancer Res.* 18:4435-4441; Ausprunk et al., *Dev. Biol.* 38:237-248; Gimbrone et al., *J. Natl. Cancer Inst.* 52:413-427; Nicosia et al., *In Vitro* 18:538-549).

Tests for the Inhibition of the SphK1 Activity
Test Description
Biochemical Assay The kinase assay is carried out as a 384-well flashplate assay.

5 nM modified SphK1, 800 nM omega-biotinyl-D-erythro-sphingosine and 1 µM ATP (with 0.3 µCi of $^{33}$P-ATP/well) are incubated in a total volume of 50 µl (25 mM HEPES, 5 mM MgCl$_2$, 1 mM dithiothreitol, 0.01% of Brij35, 0.1% of BSA (fatty acid-free), pH 7.4) without or with test substance (5-10 concentrations) at 30° C. for 120 min. The reaction is terminated using 25 µl of 200 mM EDTA solution, filtered off with suction at room temperature after 30 min, and the cavities are washed 3 times with 100 µl of 0.9% NaCl solution. The non-specific proportion of the kinase reaction (blank) is determined using 0.5 mM NaCl. Radioactivity is measured in topcount. IC$_{50}$ values are calculated using RS1.

Besides checking the activity of the substance for the purified SphK1 enzyme, it is necessary to investigate in the next step whether the substances also inhibit SphK1 in its physiological environment, i.e. in the cytoplasm of the cell.

For this purpose, the formation of S1P in U2OS osteosarcoma cells which have overproduced the enzyme through the introduction of modified SphK1-cDNA is measured using two different methods:

1. The cells are incubated for 1 hour with substances and subsequently for 15 min with tritium-labelled sphingosine. The radioactively labelled sphingosine is taken up by the cells in this time and converted into S1P by SphK1. The cells are then washed and lysed using ammonia solution. In order to separate S1P from unreacted sphingosine, an extraction is carried out by addition of a chloroform/methanol mixture. Whereas the majority of the sphingosine is transferred into the organic phase, S1P accumulates in the aqueous phase and is quantified with the aid of a scintillation counter.

2. The cells are incubated for 1 hour with substances and subsequently for 15 min with sphingosine. The sphingosine is taken up by the cells in this time and converted into S1P by SphK1. The cells are then washed and lysed using methanol. The methanol solution is then evaporated, and the S1P is taken up in lipid-free serum. The quantification of the S1P is carried out using an S1P-specific antibody with the aid of a competitive ELISA assay. The biotin-linked S1P antibody is incubated with the sample solution, and this mixture is transferred into a well whose base has been coated with S1P. Only the antibodies which have not yet bound any S1P from the sample solution bind to the S1P immobilised on the plate and can be quantified, after a washing step, by addition of horseradish peroxidase-coupled streptavidin. To this end, the substrate is added to TMB, which, after conversion by the peroxidase, absorbs at a wavelength of 450 nm and can be measured. A high signal consequently corresponds to a low S1P concentration in the sample solution and a low signal correspondingly to a high S1P concentration.

Pharmacological Data

SphK1 Inhibition ($IC_{50}$ ranges: A: <100 nM, B: 100 nM-1000 nM, C: >1000 nM)

TABLE 2

| Compound according to the invention | $IC_{50}$ |
|---|---|
| Aminoacetic acid 5-{4-[3-(5,5,8,8-tetramethyl-5,6,7,8-tetrahydro-naphthalen-2-yl)phenyl]piperazin-1-yl}pentyl ester | B |
| (S)-3-Methyl-1-[3-(5,5,8,8-tetramethyl-5,6,7,8-tetrahydro-naphthalen-2-yl)phenyl]piperazine | B |
| 1-[2-Methyl-5-(5,5,8,8-tetramethyl-5,6,7,8-tetrahydronaphthalen-2-yl)phenyl]piperazine | C |
| 4-{1-[4-(5,5,8,8-Tetramethyl-5,6,7,8-tetrahydronaphthalen-2-yl)-1,3,5-triazin-2-yl]piperidin-4-ylamino}butan-1-ol | A |
| 1-{1-[4-(5,5,8,8-Tetramethyl-5,6,7,8-tetrahydronaphthalen-2-yl)-1,3,5-triazin-2-yl]piperidin-4-yl}pyrrolidin-3-ylamine | B |
| 5-{4-[3-(2-Methoxyethoxy)-6-(5,5,8,8-tetramethyl-5,6,7,8-tetrahydro-naphthalen-2-yl)pyridin-2-yl]piperazin-1-yl}pentan-1-ol | C |
| 1-[3-(2-Methoxyethoxy)-6-(5,5,8,8-tetramethyl-5,6,7,8-tetrahydro-naphthalen-2-yl)pyridin-2-yl]piperazine | C |
| 1-[4-(5,5,8,8-Tetramethyl-5,6,7,8-tetrahydronaphthalen-2-yl)-1,3,5-triazin-2-yl]piperidin-4-ylamine | A |
| 2-(8,8-Dimethyl-5,6,7,8-tetrahydronaphthalen-2-yl)-4-piperazin-1-yl-1,3,5-triazine | C |
| 1'-[4-(5,5,8,8-Tetramethyl-5,6,7,8-tetrahydronaphthalen-2-yl)-1,3,5-triazin-2-yl]-1,4'-bipiperidinyl-3-ol | B |
| 2-(5,5-Dimethyl-5,6,7,8-tetrahydronaphthalen-2-yl)-4-piperazin-1-yl-1,3,5-triazine | C |
| 5-{4-[4-(5,5,8,8-Tetramethyl-5,6,7,8-tetrahydronaphthalen-2-yl)-1,3,5-triazin-2-yl]piperazin-1-yl}pentan-1-ol | A |
| 5-{4-[3-(5,5,8,8-Tetramethyl-5,6,7,8-tetrahydronaphthalen-2-yl)-phenyl]piperazin-1-yl}pentan-1-ol | A |
| 4-{4-[3-(5,5,8,8-Tetramethyl-5,6,7,8-tetrahydronaphthalen-2-yl)-phenyl]piperazin-1-yl}butan-1-ol | B |
| 1-[3-(5,5,8,8-Tetramethyl-5,6,7,8-tetrahydronaphthalen-2-yl)phenyl]-piperazine | B |
| (R)-2-Amino-3-{4-[6-(5,5,8,8-tetramethyl-5,6,7,8-tetrahydro-naphthalen-2-yl)pyridin-2-yl]piperazin-1-yl}propan-1-ol | C |
| 5-{4-[6-(1,1-Dimethylindan-5-yl)pyridin-2-yl]piperazin-1-yl}pentan-1-ol | C |
| 4-{4-[6-(1,1-Dimethylindan-5-yl)pyridin-2-yl]piperazin-1-yl}butan-1-ol | C |
| 1-[6-(1,1-Dimethylindan-5-yl)pyridin-2-yl]piperazine | C |
| 4-{4-[4-(5,5,8,8-Tetramethyl-5,6,7,8-tetrahydronaphthalen-2-yl)-pyridin-2-yl]piperazin-1-yl}butan-1-ol | B |
| 1-[4-(5,5,8,8-Tetramethyl-5,6,7,8-tetrahydronaphthalen-2-yl)-pyridin-2-yl]piperazine | B |
| 4-{4-[2-(5,5,8,8-Tetramethyl-5,6,7,8-tetrahydronaphthalen-2-yl)-pyridin-4-yl]piperazin-1-yl}butan-1-ol | B |
| 1-[2-(5,5,8,8-Tetramethyl-5,6,7,8-tetrahydronaphthalen-2-yl)-pyridin-4-yl]piperazine | B |
| 4-{4-[4-(5,5,8,8-Tetramethyl-5,6,7,8-tetrahydronaphthalen-2-yl)-1,3,5-triazin-2-yl]piperazin-1-yl}butan-1-ol | A |
| 5-{4-[6-(1,1,3,3-Tetramethylindan-5-yl)pyridin-2-yl]piperazin-1-yl}-pentan-1-ol | B |
| 5-[6'-(5,5,8,8-Tetramethyl-5,6,7,8-tetrahydronaphthalen-2-yl)-3,4,5,6-tetrahydro-2H-1,2'-bipyridinyl-4-ylamino]pentan-1-ol | B |
| 6''-(5,5,8,8-Tetramethyl-5,6,7,8-tetrahydronaphthalen-2-yl)-3,4,5,6,3',4',5',6'-octahydro-2H,2'H-[1,4';1',2'']terpyridin-3-ol | B |
| 1-[6'-(5,5,8,8-Tetramethyl-5,6,7,8-tetrahydronaphthalen-2-yl)-3,4,5,6-tetrahydro-2H-1,2'-bipyridinyl-4-yl]pyrrolidin-3-ylamine | A |
| 5-{4-[6-(8,8-Dimethyl-5,6,7,8-tetrahydronaphthalen-2-yl)pyridin-2-yl]-piperazin-1-yl}pentan-1-ol | C |
| 4-[6'-(5,5,8,8-Tetramethyl-5,6,7,8-tetrahydronaphthalen-2-yl)-3,4,5,6-tetrahydro-2H-1,2'-bipyridinyl-4-ylamino]butan-1-ol | A |
| 4-{4-[6-(1,1,3,3-Tetramethylindan-5-yl)pyridin-2-yl]piperazin-1-yl}-butan-1-ol | B |
| 1-[6-(1,1,3,3-Tetramethylindan-5-yl)pyridin-2-yl]piperazine | B |
| 4-{4-[6-(8,8-Dimethyl-5,6,7,8-tetrahydronaphthalen-2-yl)pyridin-2-yl]piperazin-1-yl}butan-1-ol | C |
| 1-[6-(8,8-Dimethyl-5,6,7,8-tetrahydronaphthalen-2-yl)pyridin-2-yl]-piperazine | C |
| 6'-(5,5,8,8-Tetramethyl-5,6,7,8-tetrahydronaphthalen-2-yl)-3,4,5,6-tetrahydro-2H-1,2'-bipyridinyl-4-ylamine | B |

TABLE 2-continued

| Compound according to the invention | $IC_{50}$ |
|---|---|
| 6-(5,5,8,8-Tetramethyl-5,6,7,8-tetrahydronaphthalen-2-yl)-1',2',3',4',5',6'-hexahydro-2,4'-bipyridinyl | B |
| 2-Piperazin-1-yl-4-(5,5,8,8-tetramethyl-5,6,7,8-tetrahydronaphthalen-2-yl)-1,3,5-triazine | A |
| 6'-(5,5,8,8-Tetramethyl-5,6,7,8-tetrahydronaphthalen-2-yl)-3,4,5,6-tetrahydro-2H-1,2'-bipyrazinyl | C |
| 3-{4-[2-(5,5,8,8-Tetramethyl-5,6,7,8-tetrahydronaphthalen-2-yl)-pyrimidin-4-yl]piperazin-1-yl}propan-1-ol | B |
| 2-Piperazin-1-yl-4-(5,5,8,8-tetramethyl-5,6,7,8-tetrahydronaphthalen-2-yl)pyrimidine | B |
| 4-{4-[6-(5,5-Dimethyl-5,6,7,8-tetrahydronaphthalen-2-yl)pyridin-2-yl]-piperazin-1-yl}butan-1-ol | C |
| 4-Piperazin-1-yl-2-(5,5,8,8-tetramethyl-5,6,7,8-tetrahydronaphthalen-2-yl)pyrimidine | B |
| 5-{4-[6-(5,5-Dimethyl-5,6,7,8-tetrahydronaphthalen-2-yl)pyridin-2-yl]-piperazin-1-yl}pentan-1-ol | B |
| 3-{4-[6-(5,5-Dimethyl-5,6,7,8-tetrahydronaphthalen-2-yl)pyridin-2-yl]-piperazin-1-yl}propan-1-ol | C |
| 1-[6-(5,5-Dimethyl-5,6,7,8-tetrahydronaphthalen-2-yl)pyridin-2-yl]-piperazine | C |
| 4-{4-[6-(5,5,8,8-Tetramethyl-5,6,7,8-tetrahydronaphthalen-2-yl)-pyridin-2-yl]piperazin-1-yl}butan-1-ol | A |
| 5-{4-[6-(5,5,8,8-Tetramethyl-5,6,7,8-tetrahydronaphthalen-2-yl)-pyridin-2-yl]piperazin-1-yl}pentan-1-ol | A |
| 3-{4-[6-(5,5,8,8-Tetramethyl-5,6,7,8-tetrahydronaphthalen-2-yl)-pyridin-2-yl]piperazin-1-yl}propan-1-ol | B |
| 1-[6-(5,5,8,8-Tetramethyl-5,6,7,8-tetrahydronaphthalen-2-yl)-pyridin-2-yl]piperazine | B |

The invention claimed is:

1. A compound of formula (I)

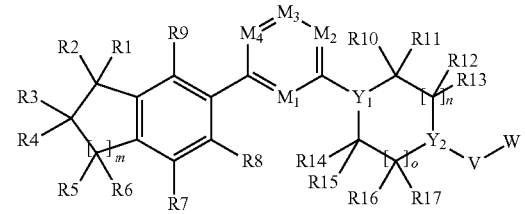

(I)

in which, in each case independently of one another:

$R^1$, $R^2$, $R^5$, $R^6$, $R^{16}$, and $R^{17}$ denote H, A, $OR^{18}$, and $NR^{18}R^{18'}$;

$R^3$, $R^4$, $R^7$, $R^8$, $R^9$, $R^{10}$, $R^{11}$, $R^{12}$, $R^{13}$, $R^{14}$, and $R^{15}$ denote H;

$R^{18}$, and $R^{18'}$ denote H, or A;

$R^{19}$, and $R^{19'}$ denote H, A, $OR^{18}$, $NR^{18}R^{18'}$, or Het;

$M_1$ denotes N;

$M_2$, $M_3$, and $M^4$ denote $CR^{19''}$;

$R^{19''}$ denotes H, O-A, $NR^{18}R^{18'}$ or Het;

$Y_1$, and $Y_2$ denote $CR^{19}$ or N;

V denotes $C(R^{19})(R^{19'})$, $NR^{19}$ or is absent;

W denotes $[C(R^{19})(R^{19'})]_pZ$, CO—$[C(R^{19})(R^{19'})]_pZ$, $[C(R^{19})(R^{19'})]_pN(R^{19})$—Z, CO—N($R^{19}$)—$[C(R^{19})(R^{19'})]_pZ$, N($R^{19}$)—CO—$[C(R^{19})(R^{19'})]_pZ$, CO—O—$[C(R^{19})(R^{19'})]_pZ$, $C(O)OR^{18}$, $OR^{18}$, H or;

Z denotes Het, or A;

A denotes unbranched or branched alkyl having 1, 2, 3, 4, 5, 6, 7, 8, 9 or 10 C atoms, in which 1, 2, 3, 4, 5, 6 or 7 H atoms are optionally replaced by OH, $OR^{19}$, $OC(O)R^{19}$, $NR^{19}C(O)OZ$, $C(O)OR^{19}$, $C(O)N(R^{19})(R^{19'})$ or $N(R^{19})(R^{19'})$, and/or in which one or two $CH_2$ groups are optionally replaced by O, or cyclic alkyl having 3, 4, 5, 6 or 7 C atoms, in which 1, 2, 3, 4, 5, 6 or 7 H atoms are optionally replaced by OH, $OR^{19}$, $OC(O)R^{19}$, $NR^{19}C(O)OZ$, $C(O)OR^{19}$, $C(O)N(R^{19})(R^{19'})$ or $N(R^{19})(R^{19'})$;

Het in each case, independently of one another, denotes a mono-, bi- or tricyclic saturated, unsaturated or aromatic heterocycle having 1 to 4 N, O and/or S atoms, which may be unsubstituted or mono-, di- or trisubstituted by Hal, F, Cl, Br, CN, A, $OR^{18}$, W, $SR^{18}$, $NO_2$, $N(R^{19})(R^{19'})$, $NR^{18}COOZ$, OCONHZ, $NR^{18}SO_2Z$, $SO_2N(R^{18})Z$, $S(O)_mZ$, COZ, CHO, =S, =NH, =NA, oxy (—O⁻) and/or =O (carbonyl oxygen), m denotes 1, or 2, n, and o denote 0, or 1, p denotes 0, 1, 2, 3 or 4, with the proviso that compounds of the formula (I) are excluded in which
(a) V is absent, and
(b) W=C(O)—CH₂-Het;

or a pharmaceutically acceptable salt, solvate, tautomer or stereoisomers thereof.

2. A compound according to claim 1, in which, in each case independently of one another:

$R^1$, $R^2$, $R^5$, $R^6$, $R^{16}$, and $R^{17}$ denote H, A, $OR^{18}$ or $NR^{18}R^{18'}$;

$R^{19}$, and $R^{19'}$ denote H, A, or $OR^{18}$;

$Y_1$, and $Y_2$ denote N,
or
$Y_1$ denotes N, and
$Y_2$ denotes $CR^{19}$,
or
$Y_1$ denotes $CR^{19}$, and
$Y_2$ denotes N;

W denotes $[C(R^{19})(R^{19'})]_pZ$, $CO—[C(R^{19})(R^{19'})]_pZ$, $CO—O—[C(R^{19})(R^{19'})]_pZ$, $[C(R^{19})(R^{19'})]_pN(R^{19})—Z$, $N(R^{19})—CO—[C(R^{19})(R^{19'})]_pZ$, $C(O)OR^{18}$, $OR^{18}$ or H;

Z denotes Het or A;

m denotes 1 or 2;

n, and o denote 0, or 1;

p denotes 0, 1 or 2;

or a pharmaceutically acceptable salt, solvate, tautomer or stereoisomers thereof.

3. A compound, which is one of the following compounds

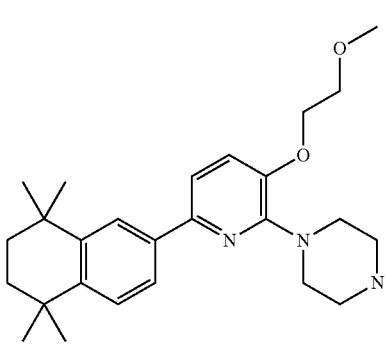

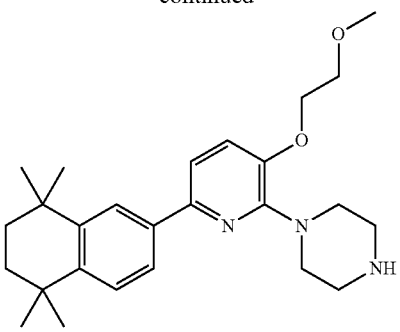

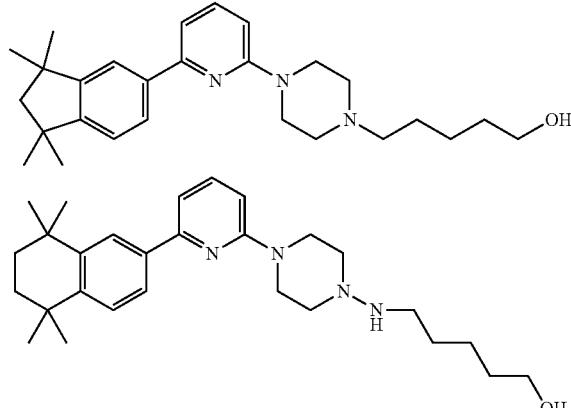

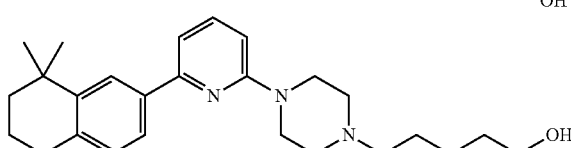

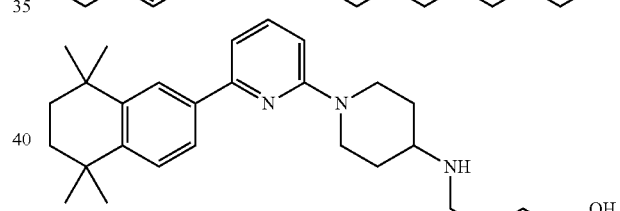

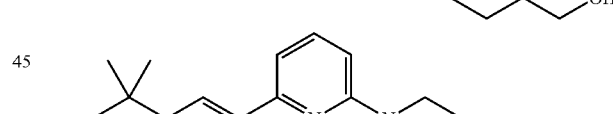

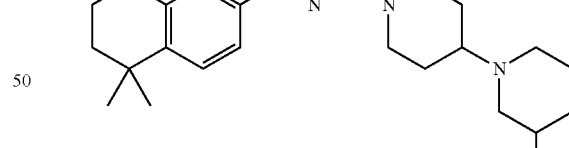

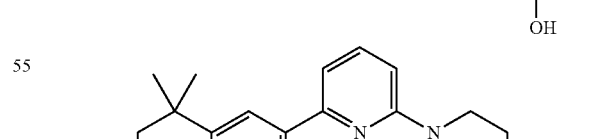

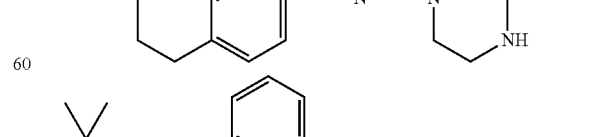

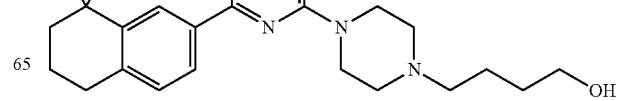

243
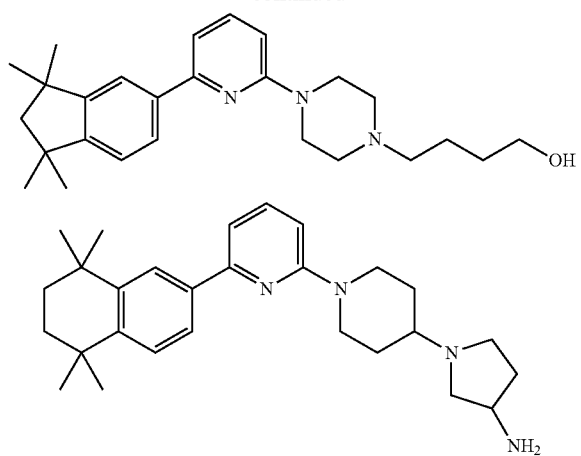
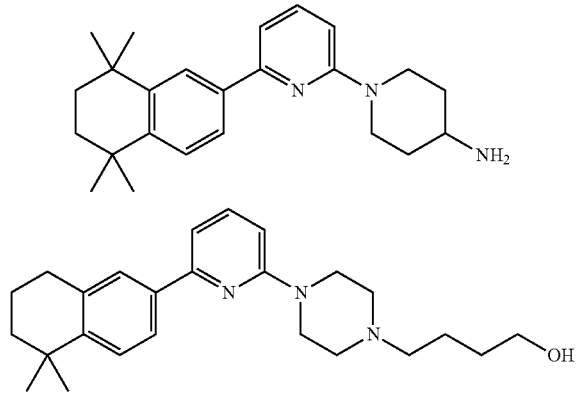
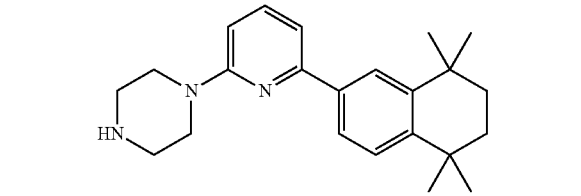
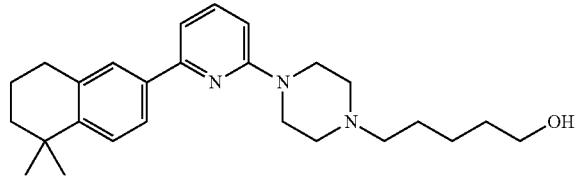
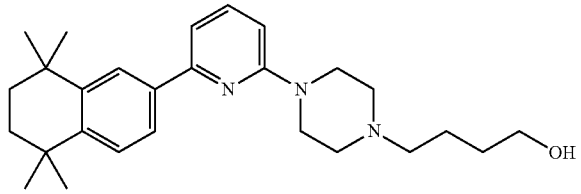
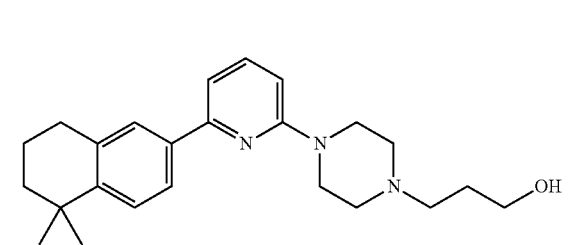
244
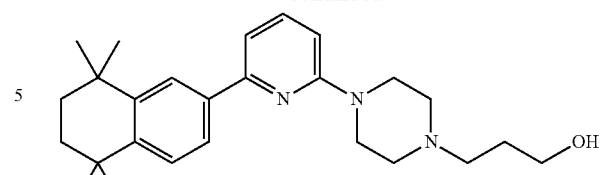
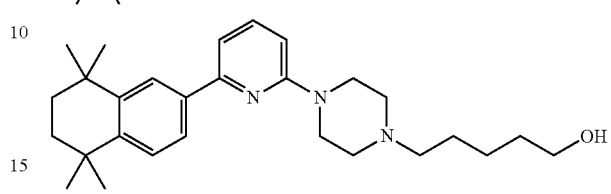
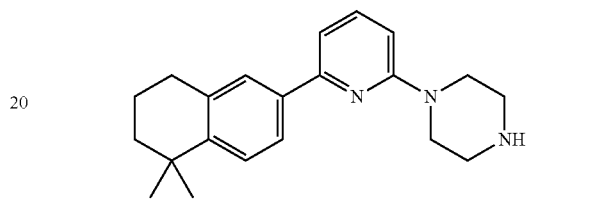
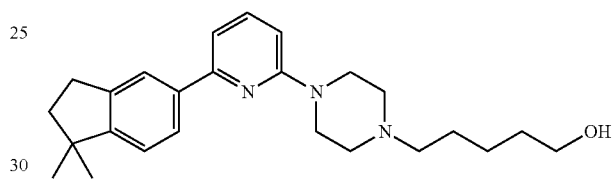
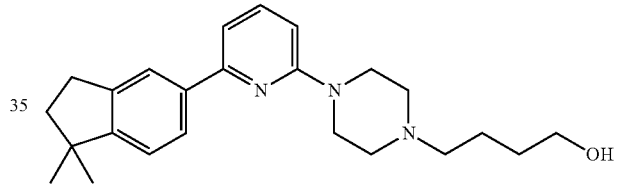
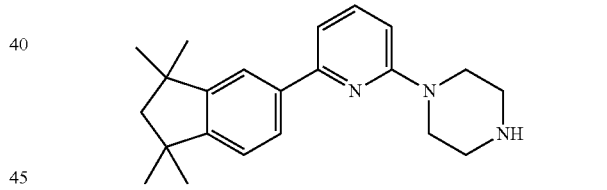
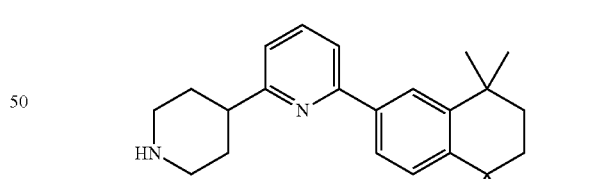
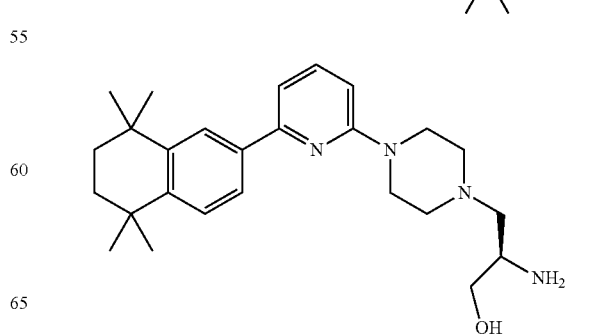

245
-continued
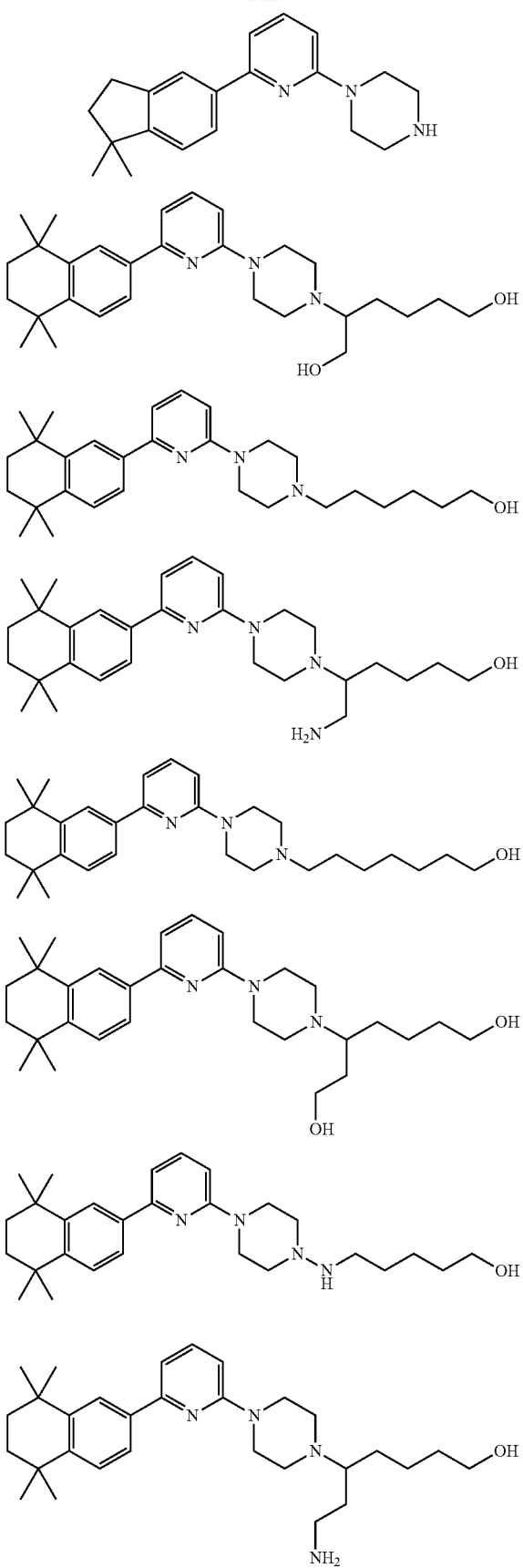
246
-continued
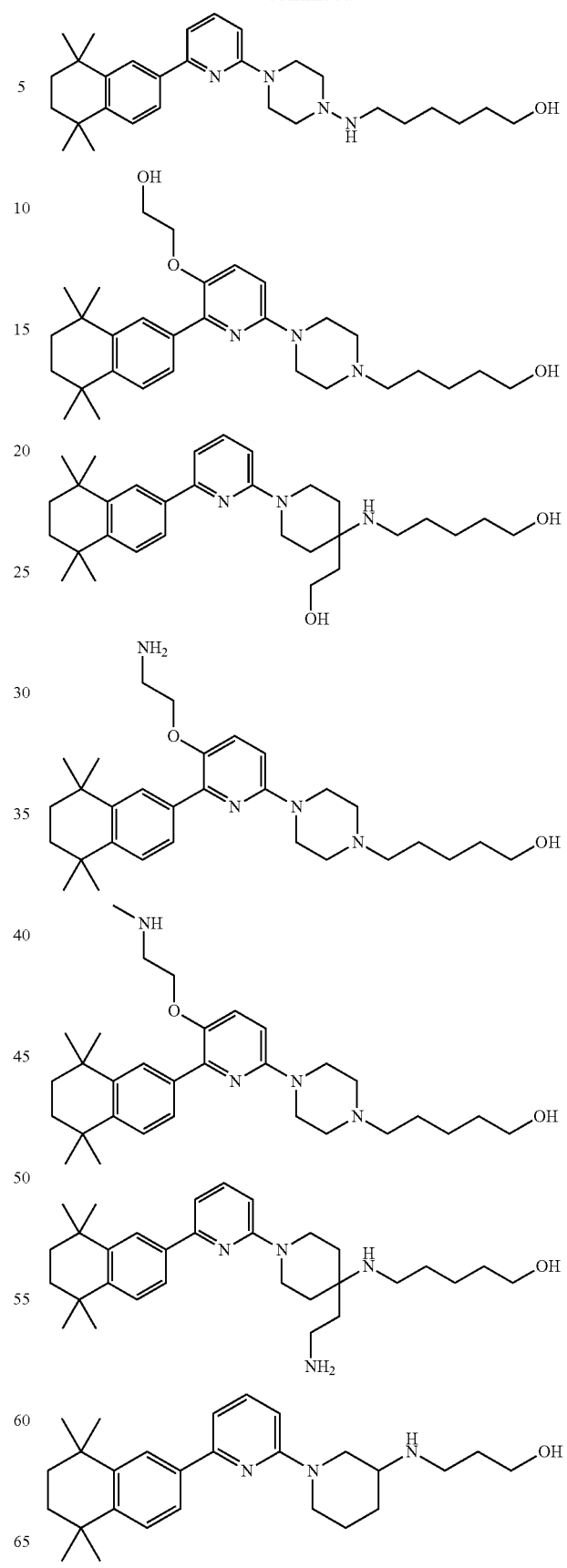

247
-continued
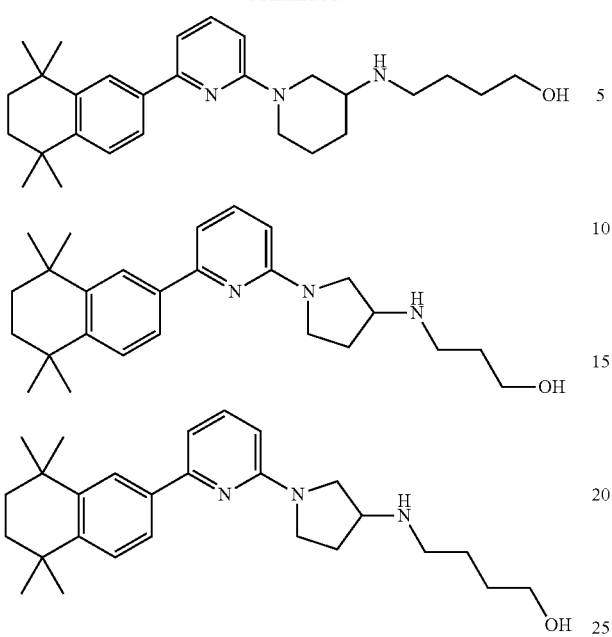
248
-continued
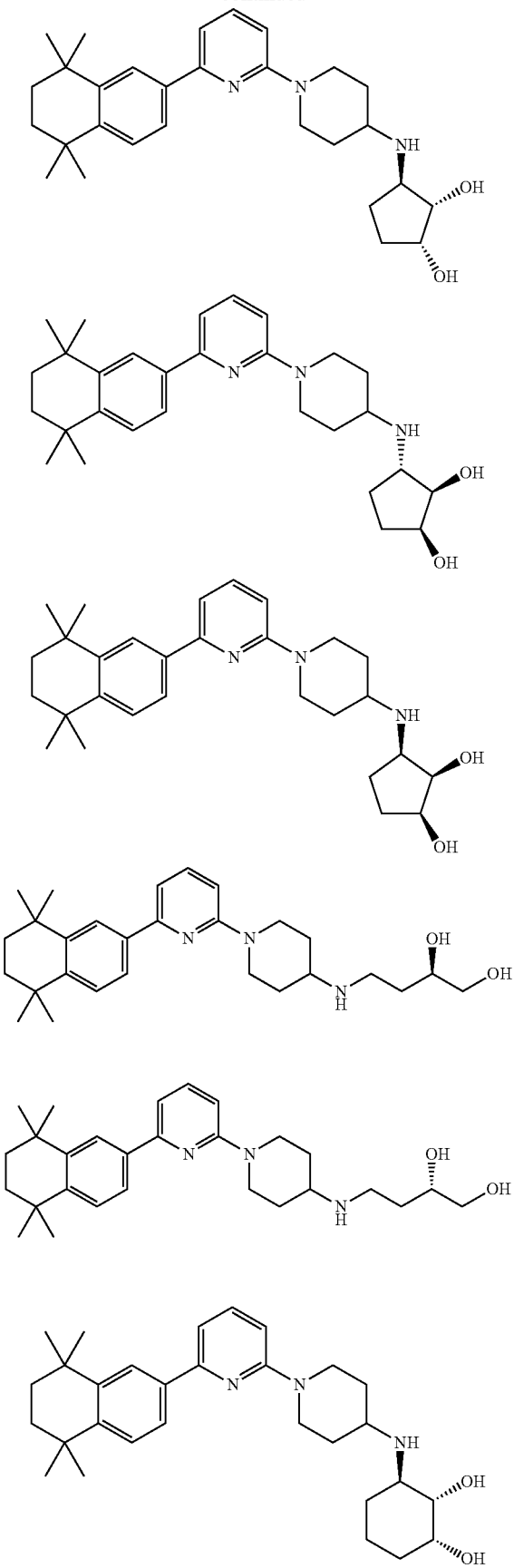

249
-continued
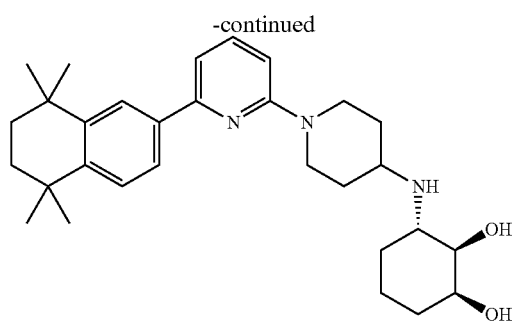
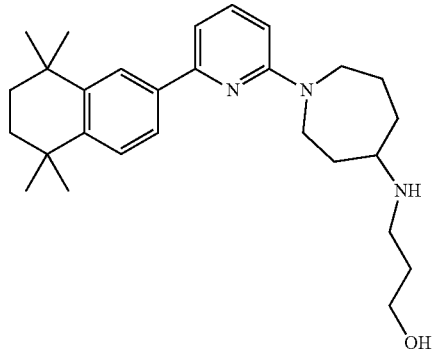
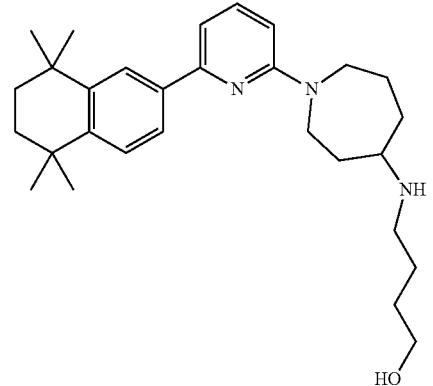
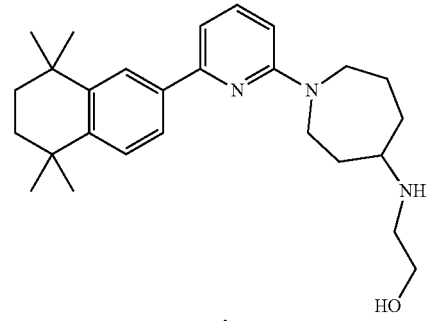
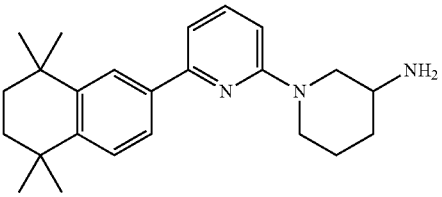
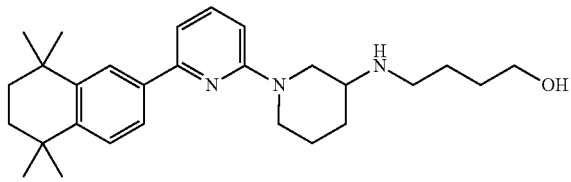
250
-continued
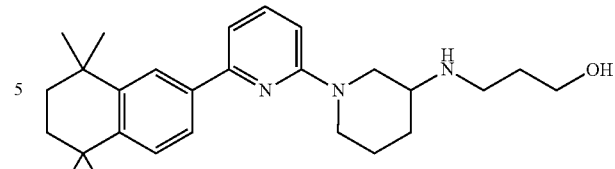
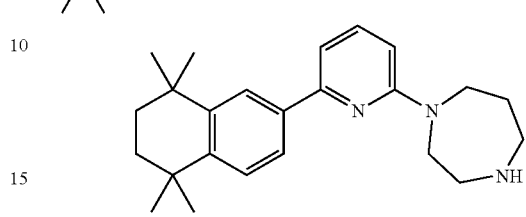
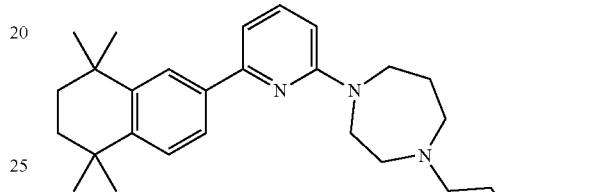
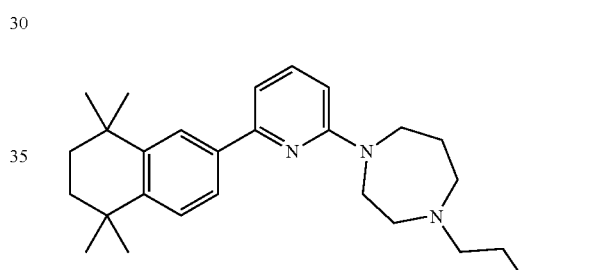
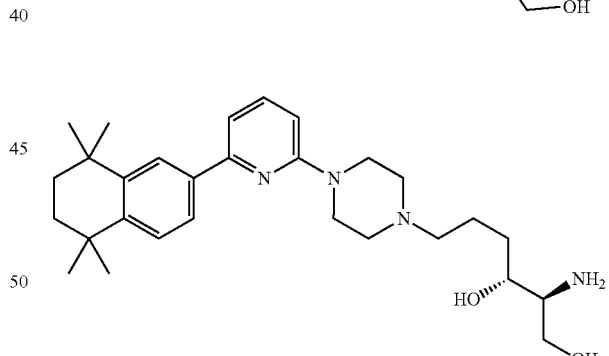
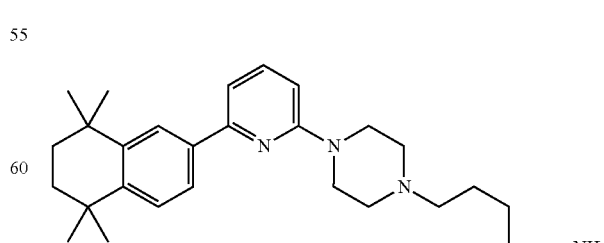

251
-continued
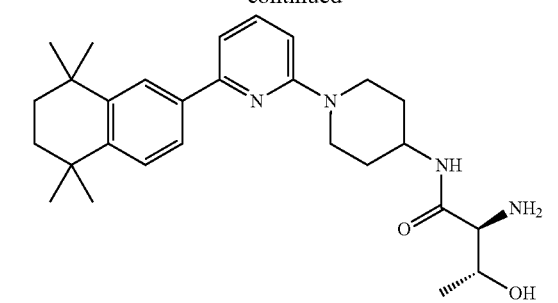
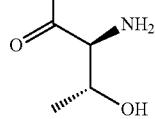
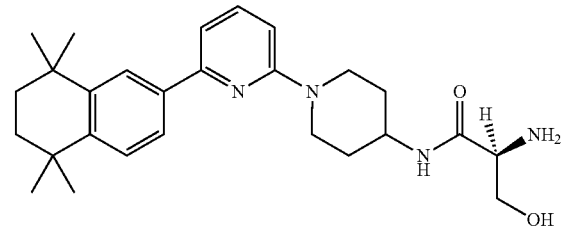
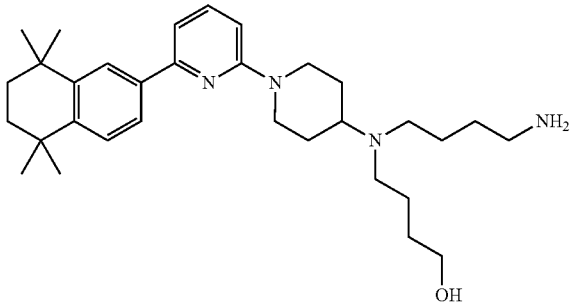
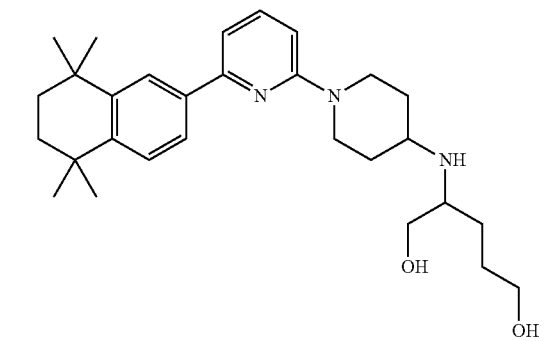
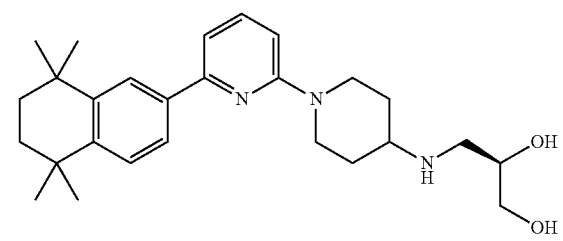
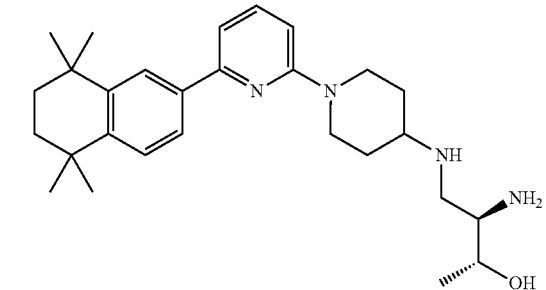
252
-continued
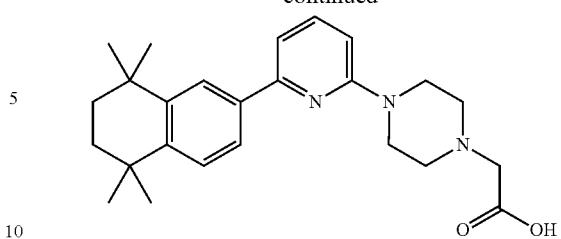
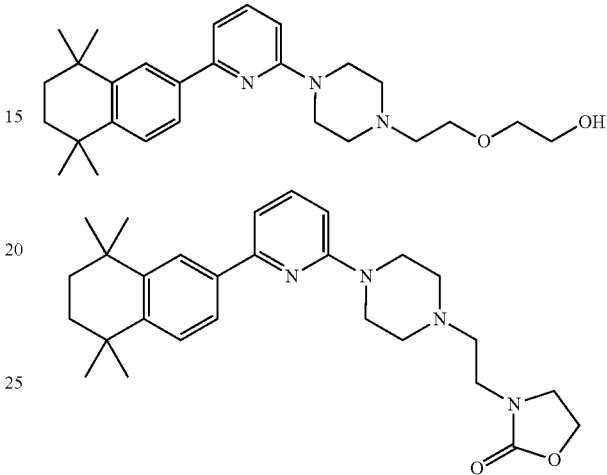
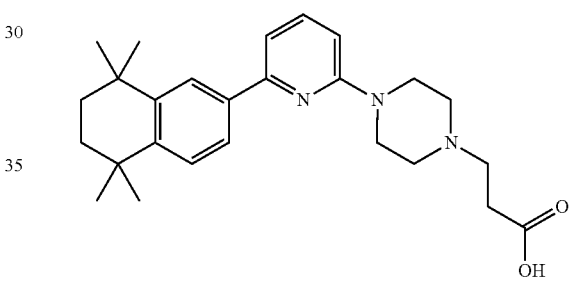
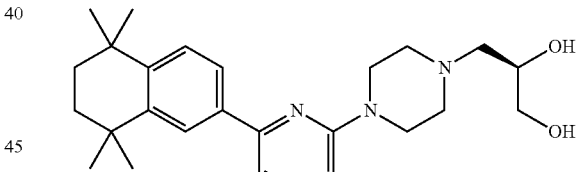
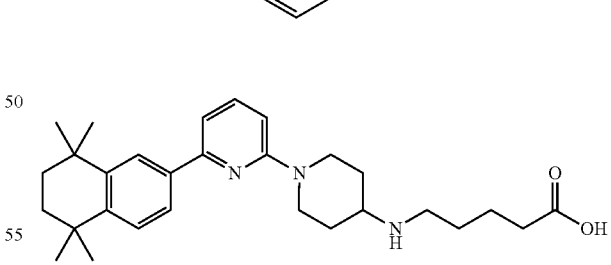
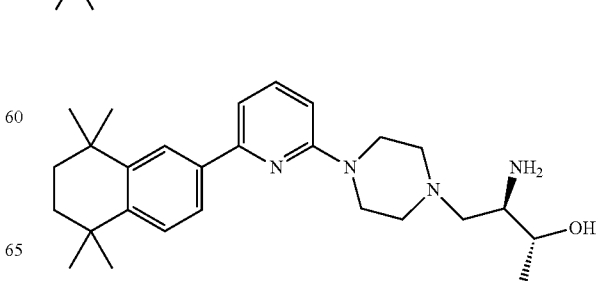

253
-continued
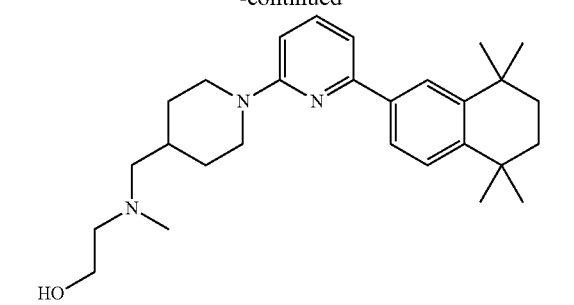
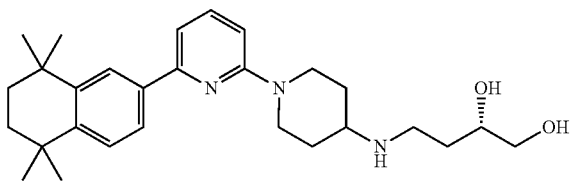
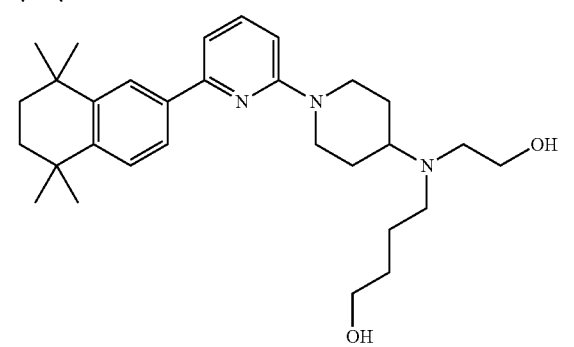
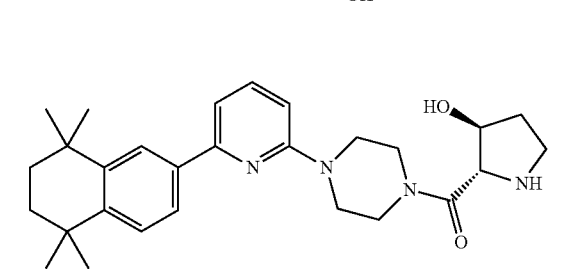
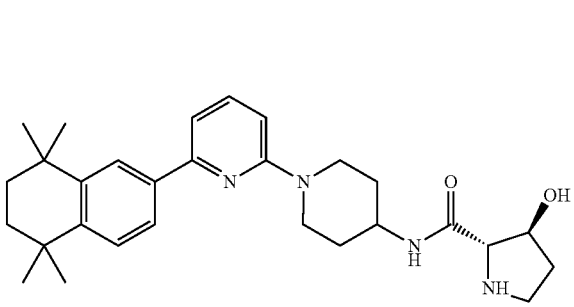
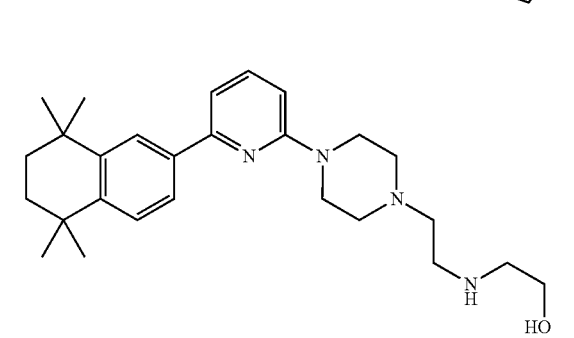
254
-continued
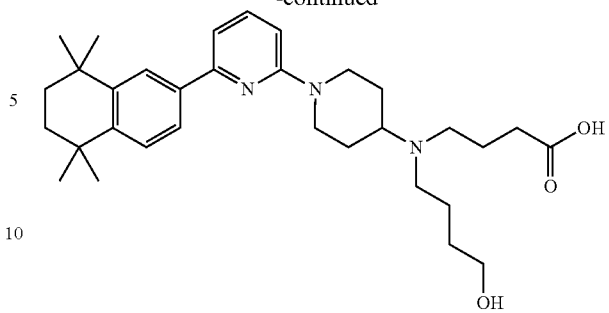
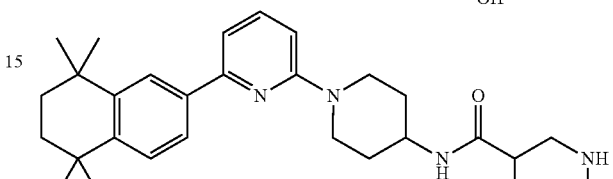
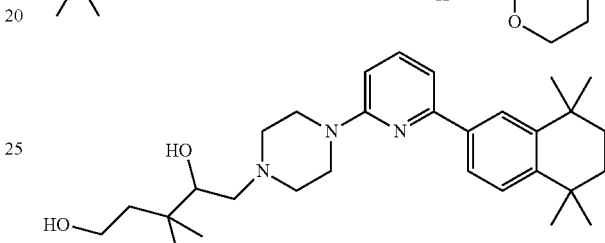
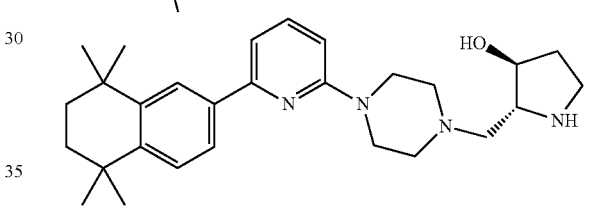
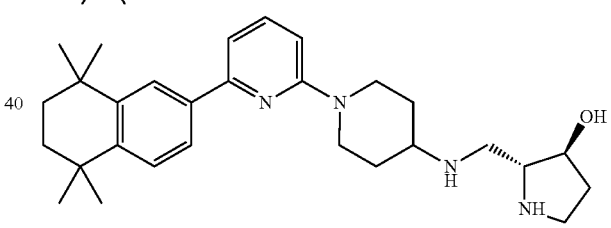
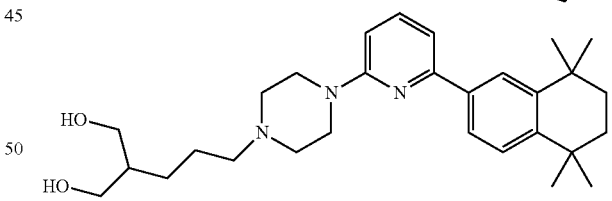
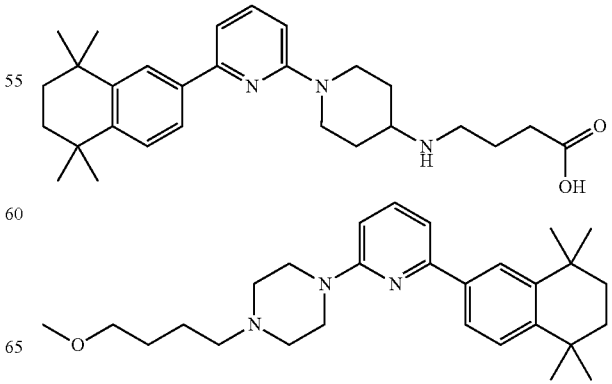

255
-continued
256
-continued
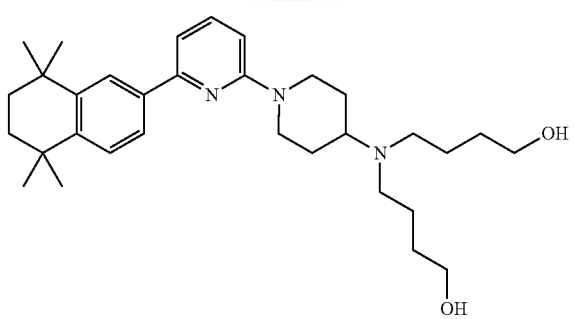
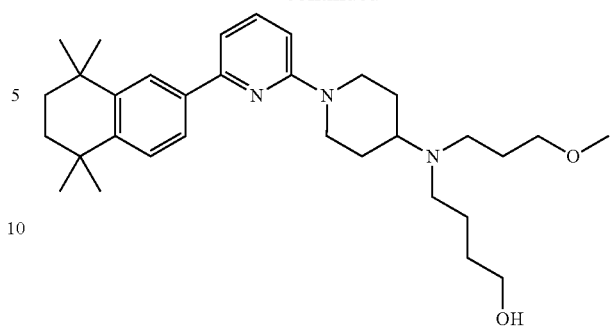
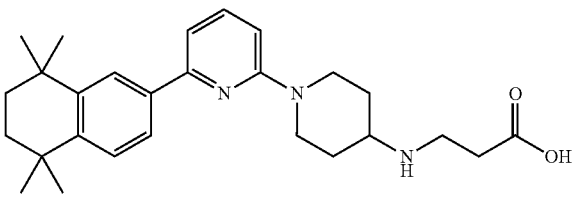
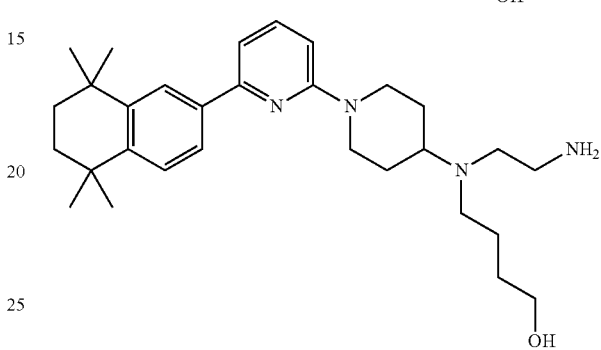
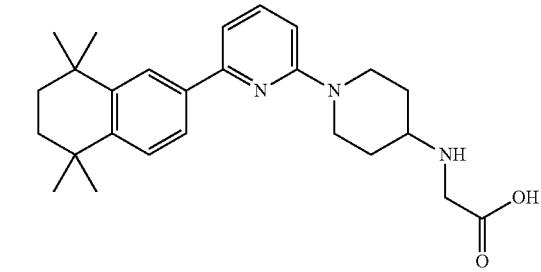
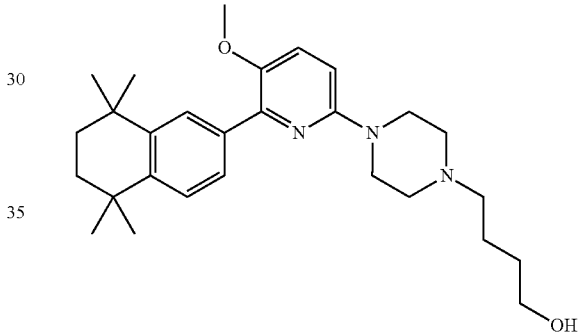
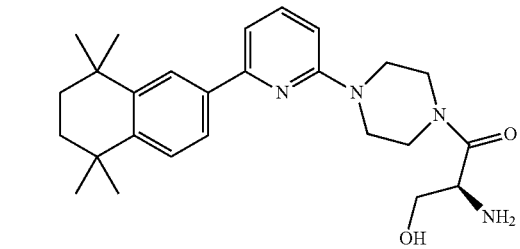
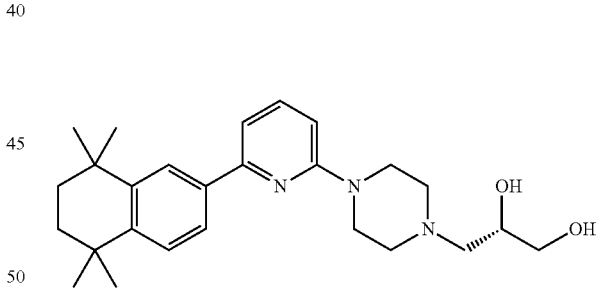
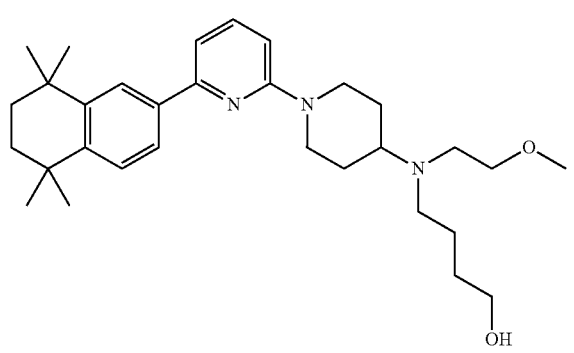
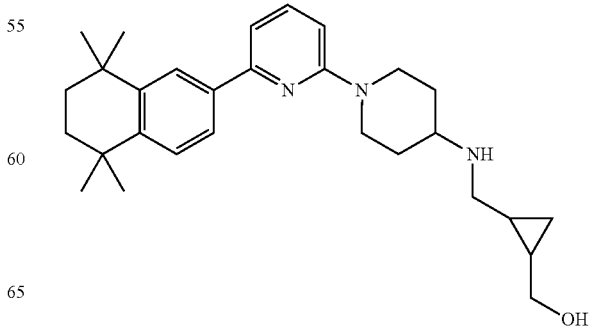

257
-continued
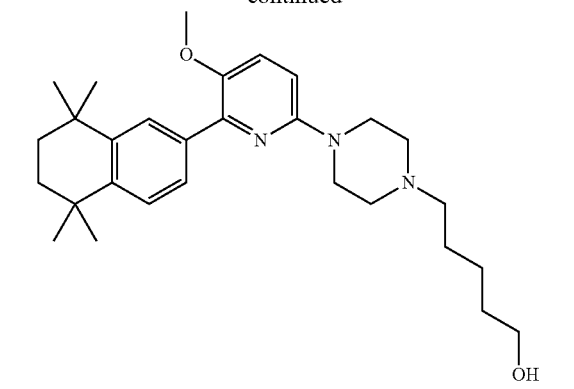
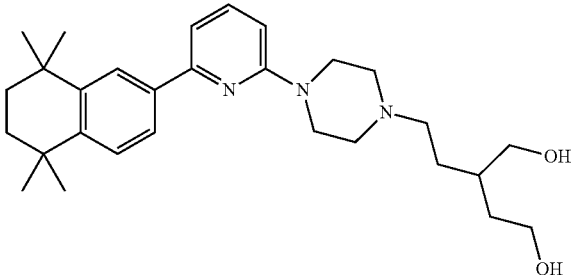
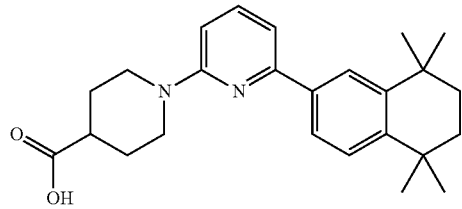
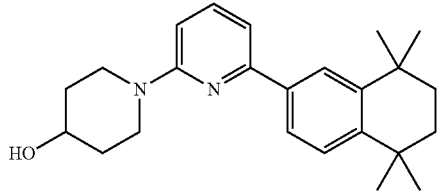
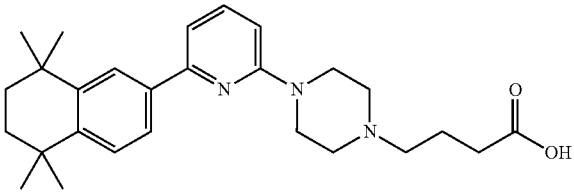
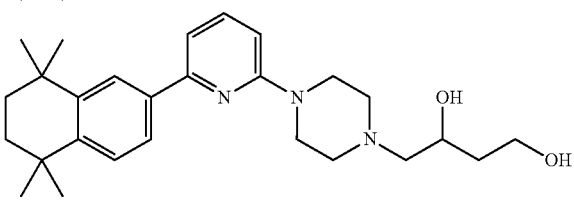
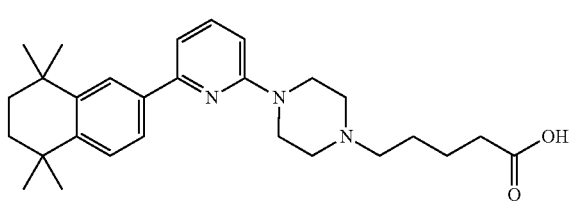
258
-continued
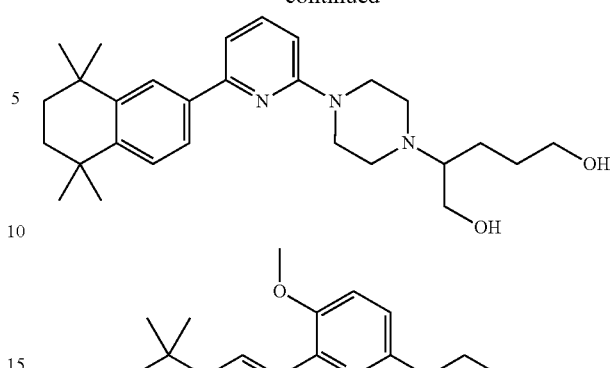
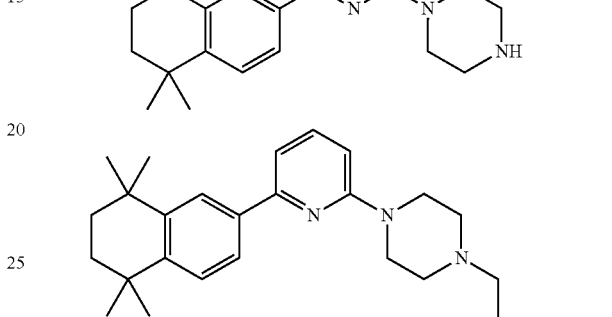
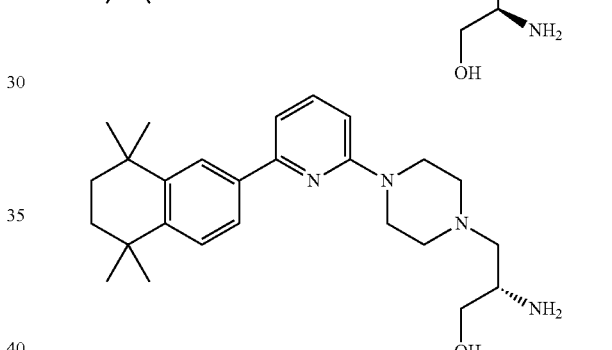
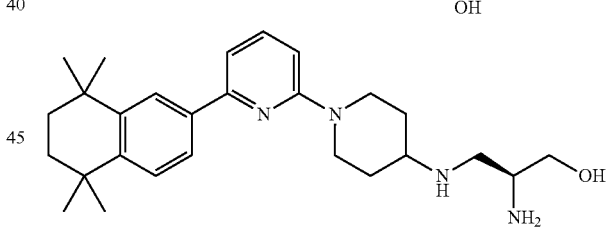
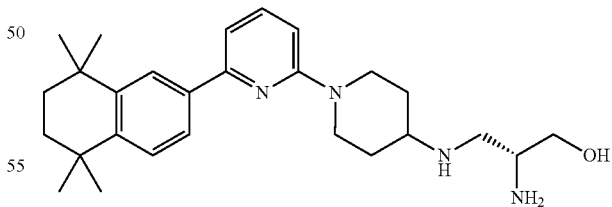
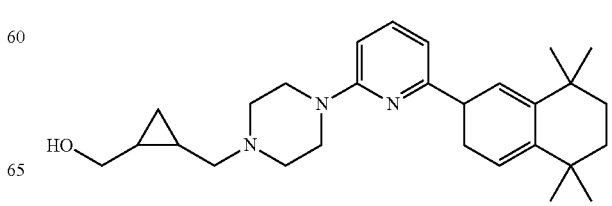

259
-continued
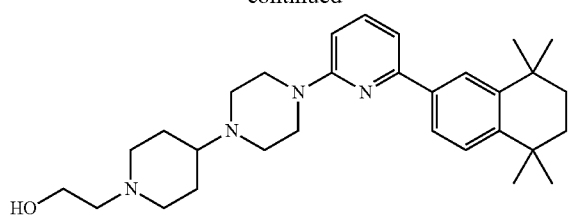
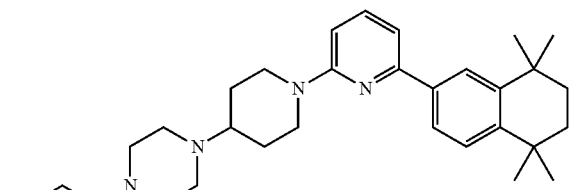
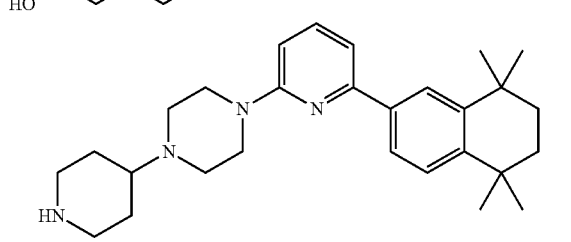
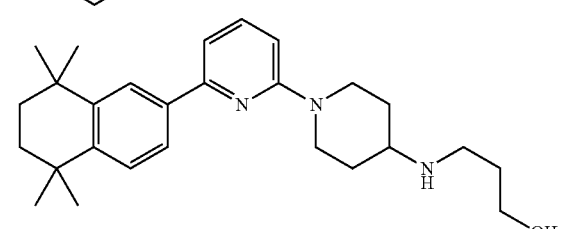
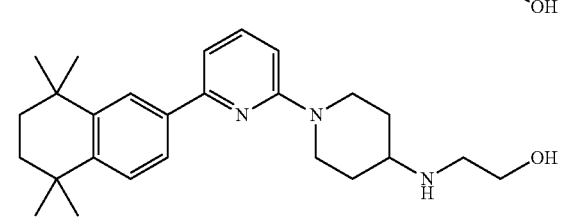
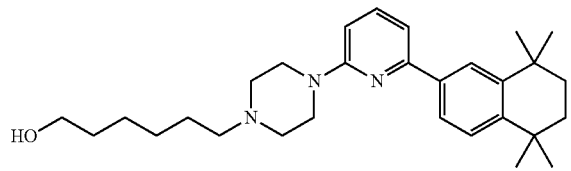
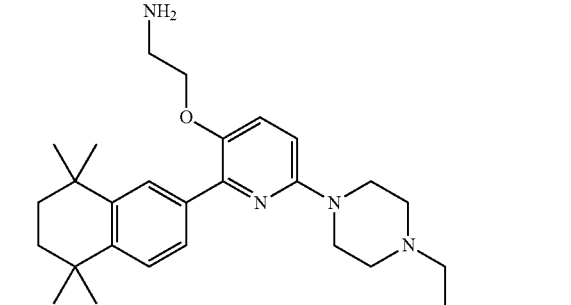
260
-continued
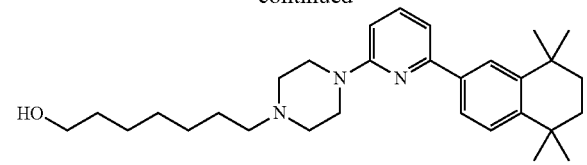
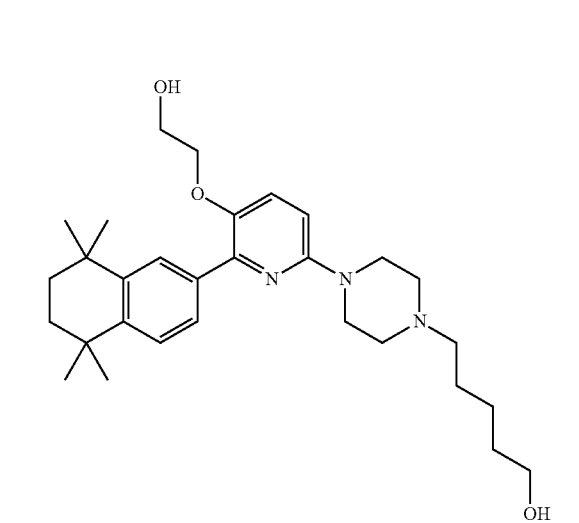
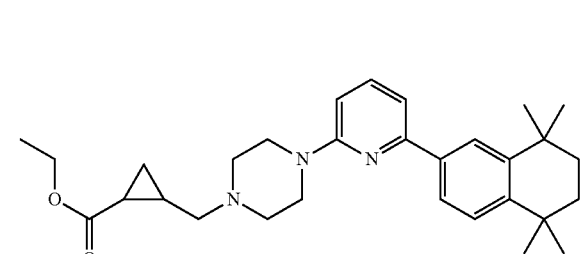
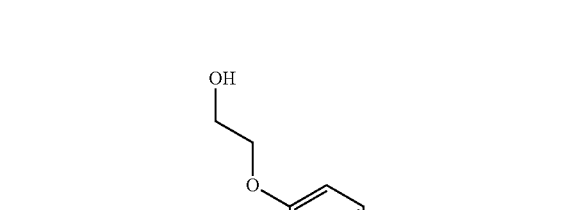
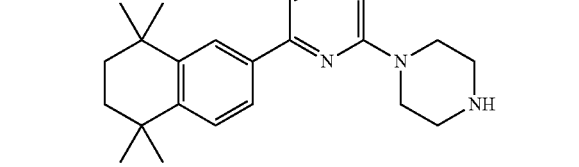

261
-continued
262
-continued
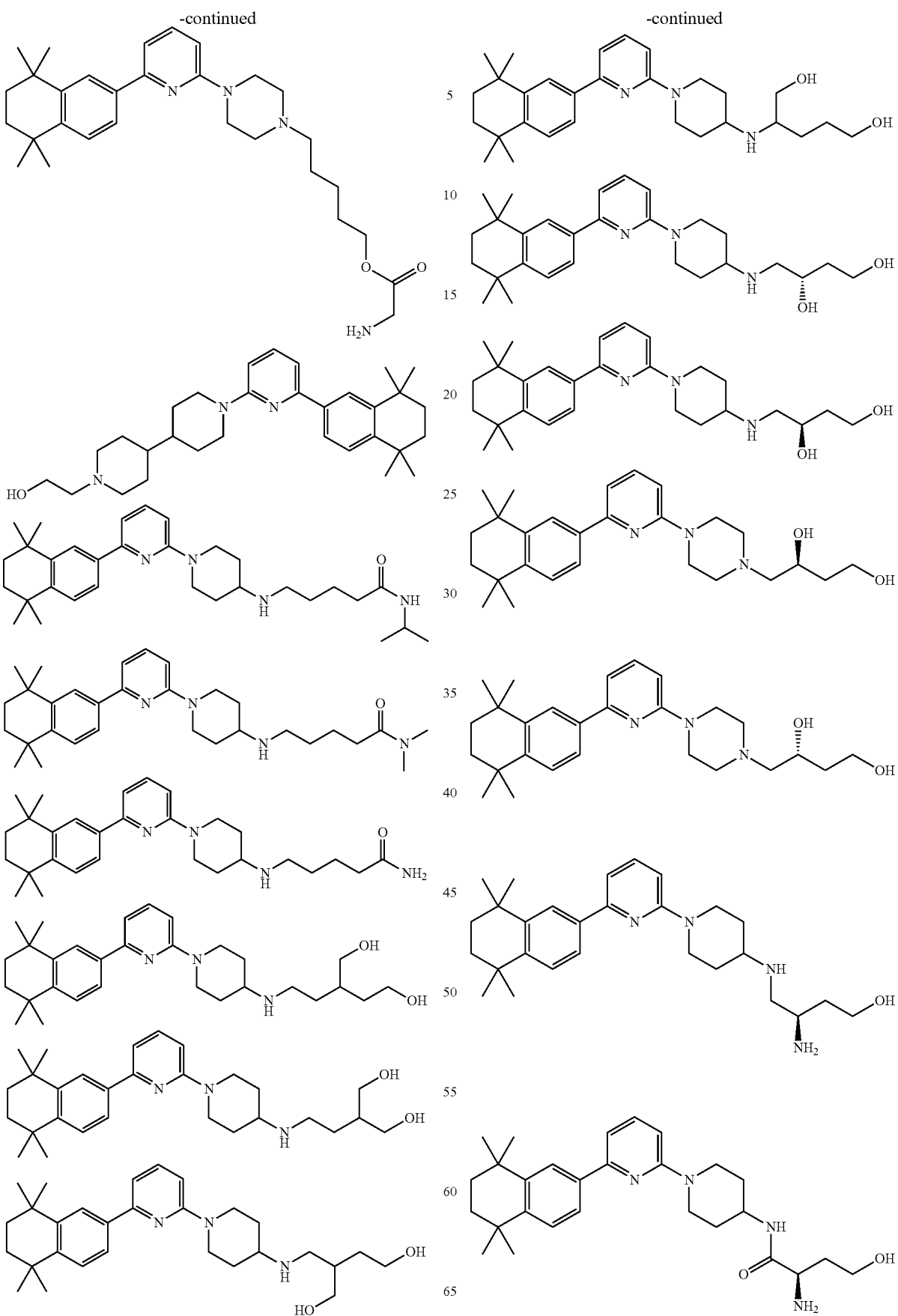

263
-continued
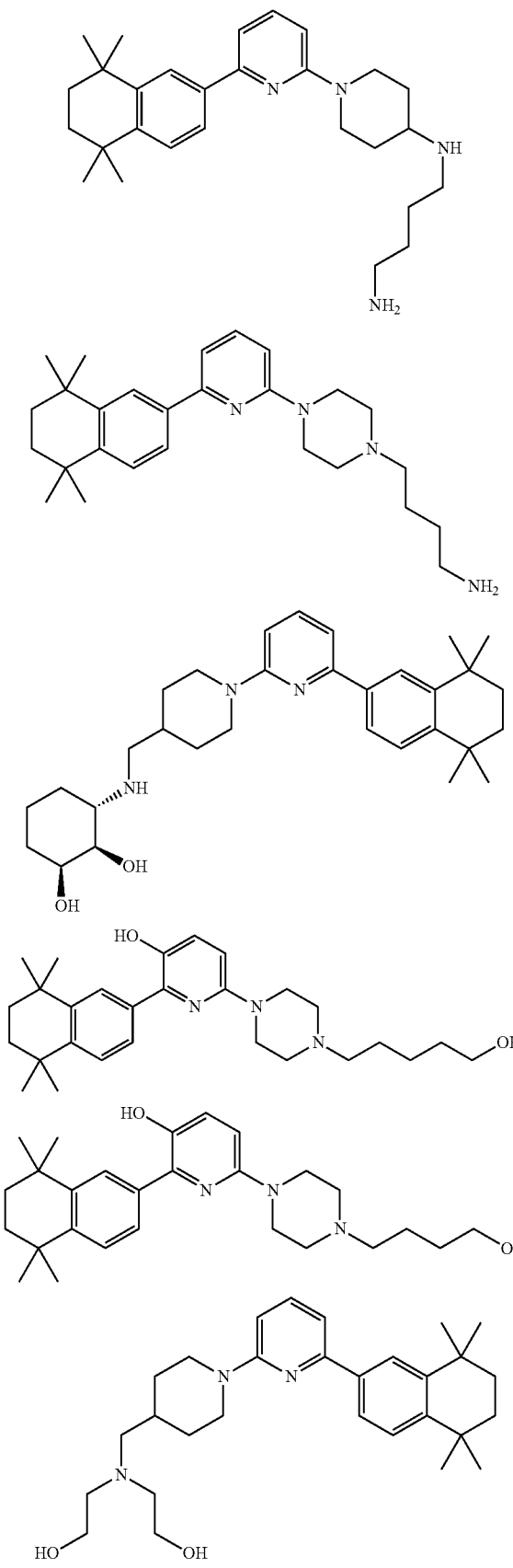
264
-continued
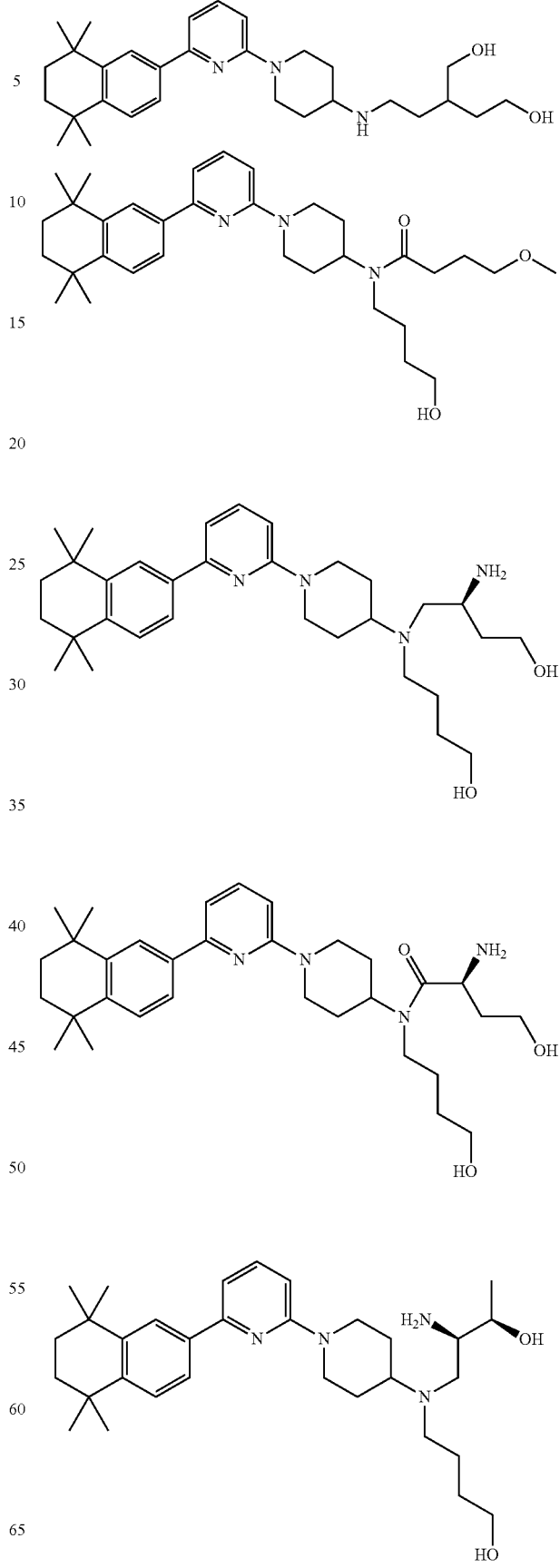

265
-continued

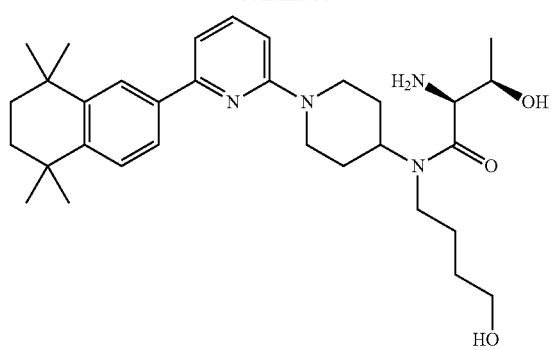

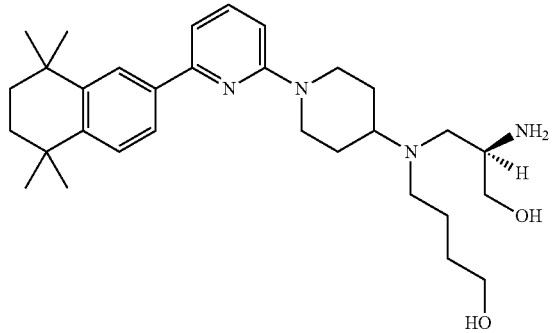

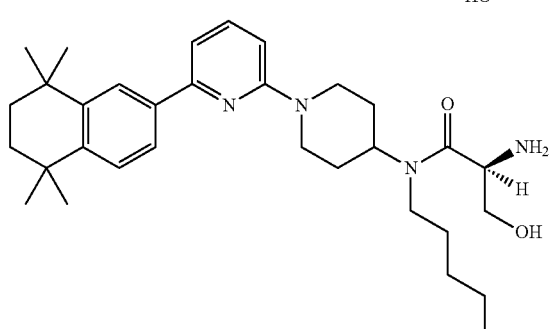

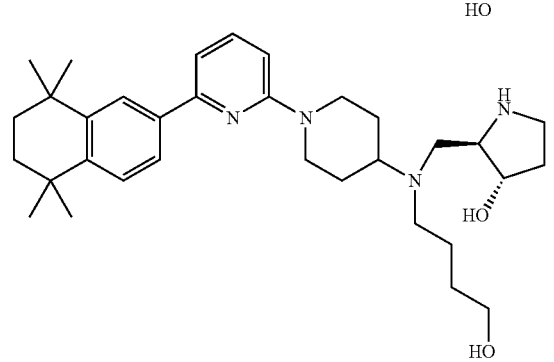

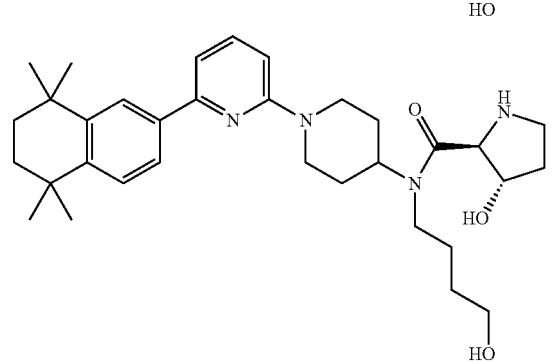

266
-continued

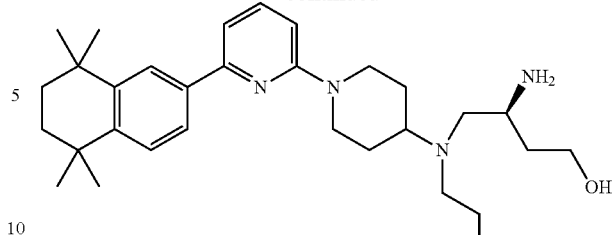

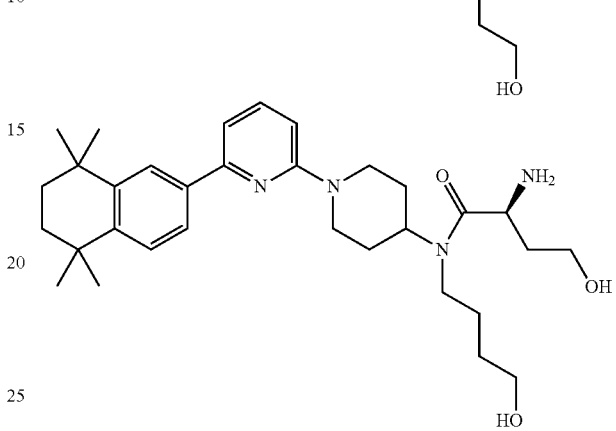

or a pharmaceutically acceptable salt, solvate, tautomer or stereoisomers thereof.

4. A pharmaceutical composition comprising one or more pharmaceutically acceptable carriers and a compound of formula (I)

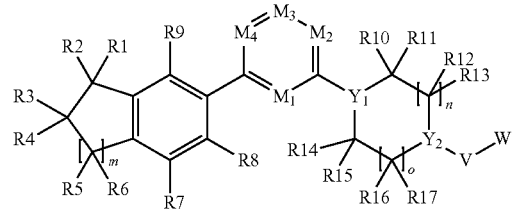

(I)

in which, in each case independently of one another:
$R^1$, $R^2$, $R^5$, $R^6$, $R^{16}$, and $R^{17}$ denote H, A, $OR^{18}$, and $NR^{18}R^{18'}$;
$R^3$, $R^4$, $R^7$, $R^8$, $R^9$, $R^{10}$,
$R^{11}$, $R^{12}$, $R^{13}$, $R^{14}$, and $R^{15}$ denote H;
$R^{18}$, and $R^{18'}$ denote H, or A;
$R^{19}$, and $R^{19'}$ denote H, A, $OR^{18}$, $NR^{18}R^{18'}$, or Het;
$M_1$ denotes N;
$M_2$, $M_3$, and $M_4$ denote $CR^{19''}$;
$R^{19''}$ denotes H, O-A, $NR^{18}R^{18'}$ or Het;
$Y_1$, and $Y_2$ denote $CR^{19}$ or N;
V denotes $C(R^{19})(R^{19'})$, $NR^{19}$ or is absent;
W denotes $[C(R^{19})(R^{19'})]_pZ$, CO—$[C(R^{19})(R^{19'})]_pZ$, $[C(R^{19})(R^{19'})]_pN(R^{19})$—Z, CO—$N(R^{19})$—$[C(R^{19})(R^{19'})]_pZ$, $N(R^{19})$—CO—$[C(R^{19})(R^{19'})]_pZ$, CO—O—$[C(R^{19})(R^{19'})]_pZ$, $C(O)OR^{18}$, $OR^{18}$, H or;
Z denotes Het, or A;
A denotes unbranched or branched alkyl having 1, 2, 3, 4, 5, 6, 7, 8, 9 or 10 C atoms, in which 1, 2, 3, 4, 5, 6 or 7 H atoms are optionally replaced by OH, $OR^{19}$, $OC(O)R^{19}$, $NR^{19}C(O)OZ$, $C(O)OR^{19}$, $C(O)N(R^{19})(R^{19'})$ or $N(R^{19})(R^{19'})$, and/or in which one or two $CH_2$ groups are optionally replaced by O, or cyclic alkyl having 3, 4, 5, 6 or 7 C atoms, in which 1, 2, 3, 4, 5, 6 or 7 H atoms are optionally replaced by OH, $OR^{19}$, $OC(O)R^{19}$, $NR^{19}C(O)OZ$, $C(O)OR^{19}$, $C(O)N(R^{19'})(R^{19'})$ or $N(R^{19})(R^{19'})$;

Het in each case, independently of one another, denotes a mono-, bi- or tricyclic saturated, unsaturated or aromatic heterocycle having 1 to 4 N, O and/or S atoms, which may be unsubstituted or mono-, di- or trisubstituted by Hal, F, Cl, Br, CN, A, $OR^{18}$, W, $SR^{18}$, $NO_2$, $N(R^{19})(R^{19'})$, $NR^{18}COOZ$, OCONHZ, $NR^{18}SO_2Z$, $SO_2N(R^{18})Z$, $S(O)_mZ$, COZ, CHO, =S, =NH, =NA, oxy (—O⁻) and/or =O (carbonyl oxygen), m denotes 1, or 2, n, and o denote 0, or 1, p denotes 0, 1, 2, 3 or 4 or a pharmaceutically acceptable salt, solvate, tautomer or stereoisomers thereof.

5. A method for treating rheumatoid arthritis, comprising administering to a subject in need thereof an effective amount of a compound according to claim 1.

6. A method for treating rheumatoid arthritis, comprising administering to a subject in need thereof an effective amount of a compound according to claim 2.

7. A pharmaceutical composition according to claim 4, further comprising at least one additional pharmacologically active substance.

8. A pharmaceutical composition, comprising one or more pharmaceutically acceptable carriers and at least one compound according to claim 1.

9. A kit comprising apart from each other
at least one compound according to claim 1 and/or at least one pharmaceutical composition comprising said compound; and
at least one further pharmacologically active substance.

10. A compound according to claim 1, wherein $R^{19'''}$ denotes H or O-A.

11. A compound according to claim 1, or a pharmaceutically acceptable salt thereof.

12. A method for treating rheumatoid arthritis, comprising administering to a subject in need thereof an effective amount of a compound according to claim 11.

13. A compound according to claim 3, or a pharmaceutically acceptable salt thereof.

14. A pharmaceutical composition according to claim 4, which contains a compound of formula I or a pharmaceutically acceptable salt thereof.

15. A method for treating rheumatoid arthritis, comprising administering to a subject in need thereof an effective amount of a pharmaceutical composition according to claim 4.

16. A method for treating rheumatoid arthritis, comprising administering to a subject in need thereof an effective amount of a compound according to claim 10.

17. A method for treating rheumatoid arthritis, comprising administering to a subject in need thereof an effective amount of a compound according to claim 13.

18. A method for treating rheumatoid arthritis, comprising administering to a subject in need thereof an effective amount of a compound according to claim 3.

19. A compound according to claim 1, in which, in each case independently of one another:

$R^1$, $R^2$, $R^5$, $R^6$, $R^{16}$, and $R^{17}$ denote H, A, $OR^{18}$, and $NR^{18}R^{18'}$;

$R^3$, $R^4$, $R^7$, $R^8$, $R^9$, $R^{10}$, $R^{11}$, $R^{12}$, $R^{13}$, $R^{14}$, and $R^{15}$ denote H;

$R^{18}$, and $R^{18'}$ denote H, or A;

$R^{19}$, and $R^{19'}$ denote H, A, $OR^{18}$, $NR^{18}R^{18'}$, or Het;

$M_1$ denotes N;

$M_2$, $M_3$, and $M^4$ denote $CR^{19'''}$;

$R^{19}$ denotes H, O-A, $NR^{18}R^{18'}$ or Het;

$Y_1$, and $Y_2$ denote $CR^{19}$ or N;

V denotes $C(R^{19})(R^{19'})$, $NR^{19}$ or is absent;

W denotes $[C(R^{19})(R^{19'})]_pZ$, $CO—[C(R^{19})(R^{19'})]_pZ$, $[C(R^{19})(R^{19'})]_pN(R^{19})—Z$, $CO—N(R^{19})—[C(R^{19})(R^{19'})]_pZ$, $N(R^{19})—CO—[C(R^{19})(R^{19'})]_pZ$, $CO—O—[C(R^{19})(R^{19'})]_pZ$, $C(O)OR^{18}$, $OR^{18}$, or H;

Z denotes Het, or A;

A denotes unbranched or branched alkyl having 1, 2, 3, 4, 5, 6, 7, 8, 9 or 10 C atoms, in which 1, 2, 3, 4, 5, 6 or 7 H atoms are optionally replaced by OH, $OR^{19}$, $OC(O)R^{19}$, $NR^{19}C(O)OZ$, $C(O)OR^{19}$, $C(O)N(R^{19})(R^{19'})$ or $N(R^{19})(R^{19'})$, and/or in which one or two $CH_2$ groups are optionally replaced by O, or cyclic alkyl having 3, 4, 5, 6 or 7 C atoms, in which 1, 2, 3, 4, 5, 6 or 7 H atoms are replaced by OH, $OR^{19}$, $OC(O)R^{19}$, $NR^{19}C(O)OZ$, $C(O)OR^{19}$, $C(O)N(R^{19})(R^{19'})$ or $N(R^{19})(R^{19'})$;

Het in each case, independently of one another, denotes a mono-, bi- or tricyclic saturated, unsaturated or aromatic heterocycle having 1 to 4 N, O and/or S atoms, which may be unsubstituted or mono-, di- or trisubstituted by Hal, F, Cl, Br, CN, A, $OR^{18}$, W, $SR^{18}$, $NO_2$, $N(R^{19})(R^{19'})$, $NR^{18}COOZ$, OCONHZ, $NR^{18}SO_2Z$, $SO_2N(R^{18})Z$, $S(O)_mZ$, COZ, CHO, =S, =NH, =NA, oxy (—O⁻) and/or =O (carbonyl oxygen), m denotes 1, or 2, n, and o denote 0, or 1, p denotes 0, 1, 2, 3 or 4, with the proviso that compounds of the formula (I) are excluded in which
(a) V is absent, and
(b) W=C(O)—$CH_2$-Het;

or a pharmaceutically acceptable salt, solvate, tautomer or stereoisomers thereof.

20. A pharmaceutical composition according to claim 4, in which, in each case independently of one another:

$R^1$, $R^2$, $R^5$, $R^6$, $R^{16}$, and $R^{17}$ denote H, A, $OR^{18}$, and $NR^{18}R^{18'}$;

$R^3$, $R^4$, $R^7$, $R^8$, $R^9$, $R^{10}$, $R^{11}$, $R^{12}$, $R^{13}$, $R^{14}$, and $R^{15}$ denote H;

$R^{18}$, and $R^{18'}$ denote H, or A;

$R^{19}$, and $R^{19'}$ denote H, A, $OR^{18}$, $NR^{18}R^{18'}$ or Het;

$M_1$ denotes N;

$M_2$, $M_3$, and $M^4$ denote $CR^{19'''}$;

$R^{19}$ denotes H, O-A, $NR^{18}R^{18'}$ or Het;

$Y_1$, and $Y_2$ denote $CR^{19}$ or N;

V denotes $C(R^{19})(R^{19'})$, $NR^{19}$ or is absent;

W denotes $[C(R^{19})(R^{19'})]_pZ$, $CO—[C(R^{19})(R^{19'})]_pZ$, $[C(R^{19})(R^{19'})]_pN(R^{19})—Z$, $CO—N(R^{19})—[C(R^{19})(R^{19'})]_pZ$, $N(R^{19})—CO—[C(R^{19})(R^{19'})]_pZ$, $CO—O—[C(R^{19})(R^{19'})]_pZ$, $C(O)OR^{18}$, $OR^{18}$, or H;

Z denotes Het, or A;

A denotes unbranched or branched alkyl having 1, 2, 3, 4, 5, 6, 7, 8, 9 or 10 C atoms, in which 1, 2, 3, 4, 5, 6 or 7 H atoms are optionally replaced by OH, $OR^{19}$, $OC(O)R^{19}$, $NR^{19}C(O)OZ$, $C(O)OR^{19}$, $C(O)N(R^{19})(R^{19'})$ or $N(R^{19})(R^{19'})$, and/or in which one or two $CH_2$ groups are optionally replaced by O, or cyclic alkyl having 3, 4, 5, 6 or 7 C atoms, in which 1, 2, 3, 4, 5, 6 or 7 H atoms are replaced by OH, $OR^{19}$, $OC(O)R^{19}$, $NR^{19}C(O)OZ$, $C(O)OR^{19}$, $C(O)N(R^{19})(R^{19'})$ or $N(R^{19})(R^{19'})$;

Het in each case, independently of one another, denotes a mono-, bi- or tricyclic saturated, unsaturated or aromatic heterocycle having 1 to 4 N, O and/or S atoms, which may be unsubstituted or mono-, di- or trisubstituted by Hal, F, Cl, Br, CN, A, $OR^{18}$, W, $SR^{18}$, $NO_2$, $N(R^{19})(R^{19'})$, $NR^{18}COOZ$, $OCONHZ$, $NR^{18}SO_2Z$, $SO_2N(R^{18})Z$, $S(O)_mZ$, COZ, CHO, =S, =NH, =NA, oxy (—O⁻) and/or =O (carbonyl oxygen), m denotes 1, or 2,
n, and o denote 0, or 1,
p denotes 0, 1, 2, 3 or 4
or a pharmaceutically acceptable salt, solvate, tautomer or stereoisomers thereof.

21. A method for treating rheumatoid arthritis, comprising administering to a subject in need thereof an effective amount of a compound according to claim 19.

22. A method for treating rheumatoid arthritis, comprising administering to a subject in need thereof an effective amount of a compound according to claim 20.

* * * * *